United States Patent
Zerhusen et al.

(10) Patent No.: US 8,334,779 B2
(45) Date of Patent: Dec. 18, 2012

(54) TOUCH SCREEN CONTROL OF A HOSPITAL BED

(75) Inventors: Robert Mark Zerhusen, Cincinnati, OH (US); Ryan A. Reeder, Brookville, IN (US); John D. Vogel, Columbus, IN (US); Michael E. Cerimele, Chardon, OH (US); Carl W. Riley, Milan, IN (US); Timothy D. Wildman, Metamora, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 13/331,148

(22) Filed: Dec. 20, 2011

(65) Prior Publication Data

US 2012/0102434 A1  Apr. 26, 2012

Related U.S. Application Data

(63) Continuation of application No. 13/049,393, filed on Mar. 16, 2011, which is a continuation of application No. 12/710,407, filed on Feb. 23, 2010, now Pat. No. 7,911,349, which is a continuation of application No. 11/611,955, filed on Dec. 18, 2006, now Pat. No. 7,679,520, which is a continuation of application No. 10/211,451, filed on Aug. 2, 2002, now Pat. No. 7,154,397.

(60) Provisional application No. 60/310,092, filed on Aug. 3, 2001.

(51) Int. Cl.
*G08B 23/00* (2006.01)

(52) U.S. Cl. ............... 340/573.1; 340/525; 340/286.07; 715/835; 600/300

(58) Field of Classification Search .................. None
See application file for complete search history.

(56) References Cited

U.S. PATENT DOCUMENTS

| 3,643,219 A | 2/1972 | Heimann |
| 3,910,659 A | 10/1975 | Peterson |
| 3,946,159 A | 3/1976 | Fay |
| 4,356,475 A | 10/1982 | Neumann et al. |
| 4,410,158 A | 10/1983 | Maffei |
| 4,452,499 A | 6/1984 | Verburg |

(Continued)

FOREIGN PATENT DOCUMENTS

EP   0168158   1/1986

(Continued)

OTHER PUBLICATIONS

Pyxis PatientStation .© Bedside Computing System by CardinalHealth, http://www.pyxis.com/prodDetails.aspx?pid=55, last accessed Jan. 18, 2007, original date of publication unknown.

(Continued)

*Primary Examiner* — Eric M Blount
(74) *Attorney, Agent, or Firm* — Barnes & Thornburg LLP

(57) ABSTRACT

A hospital bed includes a frame having at least one movable frame portion and circuitry coupled to the frame. The hospital bed also has a touch screen coupled to the frame and coupled to the circuitry. The touch screen is operable to display a plurality of screens for controlling bed functions, including displaying a frame control screen having at least one icon which is touched by a user to command the circuitry to actuate movement of the movable frame portion of the frame.

23 Claims, 128 Drawing Sheets

U.S. PATENT DOCUMENTS

| | | | |
|---|---|---|---|
| 4,489,454 A | 12/1984 | Thompson | |
| 4,557,453 A | 12/1985 | McCloskey | |
| 4,584,989 A | 4/1986 | Stith | |
| 4,607,897 A | 8/1986 | Schwartz | |
| 4,640,485 A | 2/1987 | Day et al. | |
| 4,687,167 A | 8/1987 | Skalka et al. | |
| 4,708,312 A | 11/1987 | Rohr | |
| 4,715,385 A | 12/1987 | Cudahy et al. | |
| 4,724,555 A | 2/1988 | Poehner et al. | |
| 4,738,369 A | 4/1988 | Desjardins | |
| 4,747,172 A | 5/1988 | Hohol et al. | |
| 4,756,706 A | 7/1988 | Kerns et al. | |
| 4,768,241 A | 9/1988 | Beney | |
| 4,783,036 A | 11/1988 | Vossoughi | |
| 4,835,372 A | 5/1989 | Gombrich et al. | |
| 4,836,478 A | 6/1989 | Sweere | |
| 4,848,710 A | 7/1989 | Newman | |
| 4,852,500 A | 8/1989 | Ryburg et al. | |
| 4,857,713 A | 8/1989 | Brown | |
| 4,872,679 A | 10/1989 | Bohaski et al. | |
| 4,890,856 A | 1/1990 | Murch et al. | |
| 4,934,933 A | 6/1990 | Fuchs | |
| 4,945,592 A | 8/1990 | Sims et al. | |
| 4,981,139 A | 1/1991 | Pfohl | |
| 4,993,683 A | 2/1991 | Kreuzer | |
| 5,023,967 A | 6/1991 | Ferrand | |
| 5,036,852 A | 8/1991 | Leishman | |
| 5,072,906 A | 12/1991 | Foster | |
| 5,077,843 A | 1/1992 | Foster et al. | |
| 5,108,063 A | 4/1992 | Koerber, Sr. et al. | |
| 5,117,521 A | 6/1992 | Foster et al. | |
| 5,177,616 A | 1/1993 | Riday | |
| 5,181,288 A | 1/1993 | Heaton et al. | |
| 5,187,641 A | 2/1993 | Muskatello et al. | |
| 5,246,240 A | 9/1993 | Romich et al. | |
| 5,272,318 A | 12/1993 | Gorman | |
| 5,284,255 A | 2/1994 | Foster et al. | |
| 5,319,816 A | 6/1994 | Ruehl | |
| 5,330,415 A | 7/1994 | Storti et al. | |
| 5,335,651 A | 8/1994 | Foster et al. | |
| 5,337,845 A | 8/1994 | Foster et al. | |
| 5,357,396 A | 10/1994 | Alm | |
| 5,362,021 A | 11/1994 | Phillips | |
| 5,375,604 A | 12/1994 | Kelly et al. | |
| 5,377,371 A | 1/1995 | Foster | |
| 5,396,673 A | 3/1995 | Foster | |
| 5,398,359 A | 3/1995 | Foster | |
| 5,400,991 A | 3/1995 | Werner | |
| 5,403,251 A | 4/1995 | Belsito et al. | |
| 5,407,163 A | 4/1995 | Kramer et al. | |
| 5,417,222 A | 5/1995 | Dempsey et al. | |
| 5,455,975 A | 10/1995 | Foster | |
| 5,457,831 A | 10/1995 | Foster et al. | |
| 5,473,536 A | 12/1995 | Wimmer | |
| 5,473,997 A | 12/1995 | Solomon et al. | |
| 5,494,051 A | 2/1996 | Schneider, Sr. | |
| 5,497,766 A | 3/1996 | Foster et al. | |
| 5,502,480 A | 3/1996 | Kuga et al. | |
| 5,513,406 A | 5/1996 | Foster et al. | |
| 5,527,289 A | 6/1996 | Foster et al. | |
| 5,536,084 A | 7/1996 | Curtis et al. | |
| 5,542,138 A * | 8/1996 | Williams et al. | 5/658 |
| 5,544,649 A | 8/1996 | David et al. | |
| 5,556,065 A | 9/1996 | Wadley | |
| 5,561,412 A | 10/1996 | Novak et al. | |
| 5,562,091 A | 10/1996 | Foster et al. | |
| 5,579,001 A | 11/1996 | Dempsey et al. | |
| 5,579,775 A | 12/1996 | Dempsey et al. | |
| 5,600,311 A | 2/1997 | Rice et al. | |
| 5,611,096 A | 3/1997 | Bartlett et al. | |
| 5,618,090 A | 4/1997 | Montague et al. | |
| 5,623,925 A | 4/1997 | Swenson et al. | |
| 5,630,566 A | 5/1997 | Case | |
| 5,640,953 A | 6/1997 | Bishop et al. | |
| 5,647,491 A | 7/1997 | Foster et al. | |
| 5,651,775 A | 7/1997 | Walker et al. | |
| 5,664,270 A * | 9/1997 | Bell et al. | 5/600 |
| 5,687,717 A | 11/1997 | Halpern et al. | |
| 5,699,038 A | 12/1997 | Ulrich et al. | |
| 5,712,482 A | 1/1998 | Gaiser et al. | |
| 5,713,856 A | 2/1998 | Eggers et al. | |
| 5,715,138 A | 2/1998 | Choi | |
| 5,732,401 A | 3/1998 | Conway | |
| 5,732,712 A | 3/1998 | Adair | |
| 5,738,102 A | 4/1998 | Lemelson | |
| 5,738,316 A | 4/1998 | Sweere et al. | |
| 5,743,503 A | 4/1998 | Voeller et al. | |
| 5,749,374 A | 5/1998 | Schneider, Sr. | |
| 5,752,917 A | 5/1998 | Fuchs | |
| 5,769,440 A | 6/1998 | Jones | |
| 5,771,511 A | 6/1998 | Kummer et al. | |
| 5,772,585 A | 6/1998 | Lavin et al. | |
| 5,772,599 A | 6/1998 | Nevo et al. | |
| 5,788,851 A | 8/1998 | Kenley et al. | |
| 5,791,263 A | 8/1998 | Watt et al. | |
| 5,799,917 A | 9/1998 | Li | |
| 5,820,623 A | 10/1998 | Ng | |
| 5,822,544 A | 10/1998 | Chaco et al. | |
| 5,826,846 A | 10/1998 | Buccieri et al. | |
| 5,831,816 A | 11/1998 | Johns et al. | |
| 5,838,223 A | 11/1998 | Gallant et al. | |
| 5,841,373 A | 11/1998 | Mason | |
| 5,842,672 A | 12/1998 | Sweere et al. | |
| 5,876,008 A | 3/1999 | Sweere et al. | |
| 5,883,370 A | 3/1999 | Walker et al. | |
| 5,883,623 A | 3/1999 | Cseri | |
| 5,889,568 A | 3/1999 | Seraphim et al. | |
| 5,895,354 A | 4/1999 | Simmons | |
| 5,895,571 A | 4/1999 | Utterberg | |
| 5,898,961 A | 5/1999 | Ambach et al. | |
| 5,903,211 A | 5/1999 | Flego et al. | |
| 5,907,291 A | 5/1999 | Chen et al. | |
| 5,918,328 A | 7/1999 | Ramsey | |
| 5,918,331 A | 7/1999 | Hall et al. | |
| 5,918,841 A | 7/1999 | Sweere et al. | |
| 5,924,665 A | 7/1999 | Sweere et al. | |
| 5,944,659 A | 8/1999 | Flach et al. | |
| 5,947,429 A | 9/1999 | Sweere et al. | |
| 5,957,838 A | 9/1999 | Rantala | |
| 5,960,085 A | 9/1999 | de la Huerga | |
| 5,961,448 A | 10/1999 | Swenson et al. | |
| 5,966,760 A | 10/1999 | Gallant et al. | |
| 5,973,598 A | 10/1999 | Beigel | |
| 5,975,081 A | 11/1999 | Hood et al. | |
| 5,978,211 A | 11/1999 | Hong | |
| 5,991,947 A | 11/1999 | Lavin et al. | |
| 5,992,809 A | 11/1999 | Sweere et al. | |
| 5,993,006 A | 11/1999 | Takeuchi et al. | |
| 5,997,147 A | 12/1999 | Tatoian | |
| 6,001,057 A | 12/1999 | Bongiovanni et al. | |
| 6,011,701 A | 1/2000 | Kopp et al. | |
| 6,012,693 A | 1/2000 | Voeller et al. | |
| 6,014,784 A | 1/2000 | Taylor et al. | |
| 6,015,120 A | 1/2000 | Sweere et al. | |
| 6,019,332 A | 2/2000 | Sweere et al. | |
| 6,027,247 A | 2/2000 | Tachi et al. | |
| 6,061,104 A | 5/2000 | Evanicky et al. | |
| 6,064,373 A | 5/2000 | Ditzik | |
| 6,065,732 A | 5/2000 | Cho | |
| 6,073,285 A | 6/2000 | Ambach et al. | |
| 6,089,518 A | 7/2000 | Nilsson | |
| 6,102,476 A | 8/2000 | May et al. | |
| 6,102,855 A | 8/2000 | Kehr et al. | |
| 6,104,443 A | 8/2000 | Adcock et al. | |
| 6,112,182 A | 8/2000 | Akers et al. | |
| 6,125,350 A | 9/2000 | Dirbas | |
| 6,134,103 A | 10/2000 | Ghanma | |
| 6,143,181 A | 11/2000 | Falkvall et al. | |
| 6,144,848 A | 11/2000 | Walsh et al. | |
| 6,146,523 A | 11/2000 | Kenley et al. | |
| 6,150,942 A | 11/2000 | O'Brien | |
| RE36,978 E | 12/2000 | Moscovitch | |
| 6,155,603 A | 12/2000 | Fox | |
| 6,155,975 A | 12/2000 | Urich et al. | |
| 6,168,250 B1 | 1/2001 | Rogov | |
| 6,170,102 B1 | 1/2001 | Kreuzer | |
| 6,175,779 B1 | 1/2001 | Barrett | |

| | | | |
|---|---|---|---|
| 6,175,977 B1 | 1/2001 | Schumacher et al. | |
| 6,176,456 B1 | 1/2001 | Wisniewski | |
| 6,179,260 B1 | 1/2001 | Ohanian | |
| 6,183,417 B1 | 2/2001 | Geheb et al. | |
| 6,189,842 B1 | 2/2001 | Bergeron Gull et al. | |
| 6,202,360 B1 | 3/2001 | Rattner et al. | |
| 6,202,923 B1 | 3/2001 | Boyer et al. | |
| 6,205,601 B1 | 3/2001 | Nessmann et al. | |
| 6,219,587 B1 | 4/2001 | Ahlin et al. | |
| 6,234,172 B1 | 5/2001 | Ausbourne et al. | |
| 6,246,573 B1 | 6/2001 | Khan et al. | |
| 6,260,761 B1 | 7/2001 | Peoples, Jr. | |
| 6,352,504 B1 | 3/2002 | Ise et al. | |
| 6,493,568 B1 | 12/2002 | Bell et al. | |
| 6,510,049 B2 | 1/2003 | Rosen | |
| 6,616,606 B1 | 9/2003 | Petersen et al. | |
| 6,980,111 B2 | 12/2005 | Nolte | |
| 7,032,522 B2 | 4/2006 | George et al. | |
| 7,038,588 B2 | 5/2006 | Boone et al. | |
| 7,154,397 B2 | 12/2006 | Zerhusen et al. | |
| 7,237,287 B2 | 7/2007 | Weismiller et al. | |
| 7,679,520 B2 | 3/2010 | Zerhusen et al. | |
| 7,911,349 B2 | 3/2011 | Zerhusen et al. | |
| 2002/0014951 A1 | 2/2002 | Kramer et al. | |
| 2002/0044059 A1 | 4/2002 | Reeder et al. | |
| 2002/0053086 A1 | 5/2002 | Vanderpohl et al. | |
| 2002/0152211 A1 | 10/2002 | Jam | |
| 2002/0196150 A1 | 12/2002 | Wildman | |
| 2003/0052787 A1 | 3/2003 | Zerhusen et al. | |
| 2006/0180054 A1 | 8/2006 | George et al. | |
| 2007/0120689 A1 | 5/2007 | Zerhusen et al. | |
| 2010/0154124 A1 | 6/2010 | Zerhusen et al. | |

FOREIGN PATENT DOCUMENTS

| | | |
|---|---|---|
| EP | 0 376 066 | 7/1990 |
| GB | 2 218 149 | 8/1989 |
| GB | 2 333 391 | 7/1999 |
| WO | WO 94/13198 | 6/1994 |
| WO | WO 94/22098 | 9/1994 |
| WO | WO 98/02107 | 1/1998 |
| WO | WO 98/08203 | 2/1998 |
| WO | WO 98/29775 | 7/1998 |
| WO | WO 99/42021 | 8/1999 |
| WO | WO 99/52487 | 10/1999 |
| WO | WO 01/57610 | 8/2001 |
| WO | WO 01/97745 | 12/2001 |

OTHER PUBLICATIONS

Tierney et al., "Computerized Display of Past Test Results", Annals of Internal Medicine, vol. 107, No. 4, pp. 569-574, Oct. 1987.

Tierney et al., "Computer Predictions of Abnormal Test Results", JAMA, Feb. 26, 1998, vol. 259, No. 8, pp. 1194-1198.

McDonald et al., "The Regenstrief Medical Records", MD Computing, vol. 5, No. 5, 1988, pp. 34-47.

Tierney et al., "The Effect on Test Ordering of Informing Physicians of the Charges for Outpatient Diagnostic Tests", New England Journal of Medicine, May 24, 1990, pp. 1499-1504.

Tierney et al., Practice Randomization and Clinical Research, Medical Care, Jul. 1991, vol. 29, No. 7, Supplement, pp. JS57-JS64.

McDonald et al., "The Regenstrief Medical Record System: 20 Years of Experience in Hospitals, Clinics, and Neighborhood Health Centers", M.D.Computing, vol. 9, No. 4, 1992, pp. 206-217.

McDonald et al., "The Regenstrief Medical Record System (RMRS): Physician Use for Input and Output and Web Browser Based Computing", JAMIA Symposium Supplement, 1996, one page.

Litzelman et al., "Physicians' Reasons for Failing to Comply with Computerized Preventive Care Guidelines", JGIM, vol. 11, Aug. 1996, pp. 497-499.

Borin, "Harvesting Knowledge Made by Hand", Knowledge Management, Mar. 1999, p. 86.

Thiel, "Convergence in the Post-PC Era", Health Management Technology, 2 pages, Feb. 2000.

* cited by examiner

628

647

PHOTO

PATIENT NAME :

TIME :

MEDS TO GIVE :

DOSE TO GIVE :

METHOD OF ADMIN :

Fig. 49

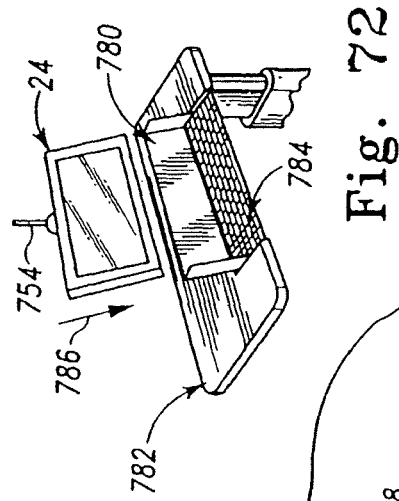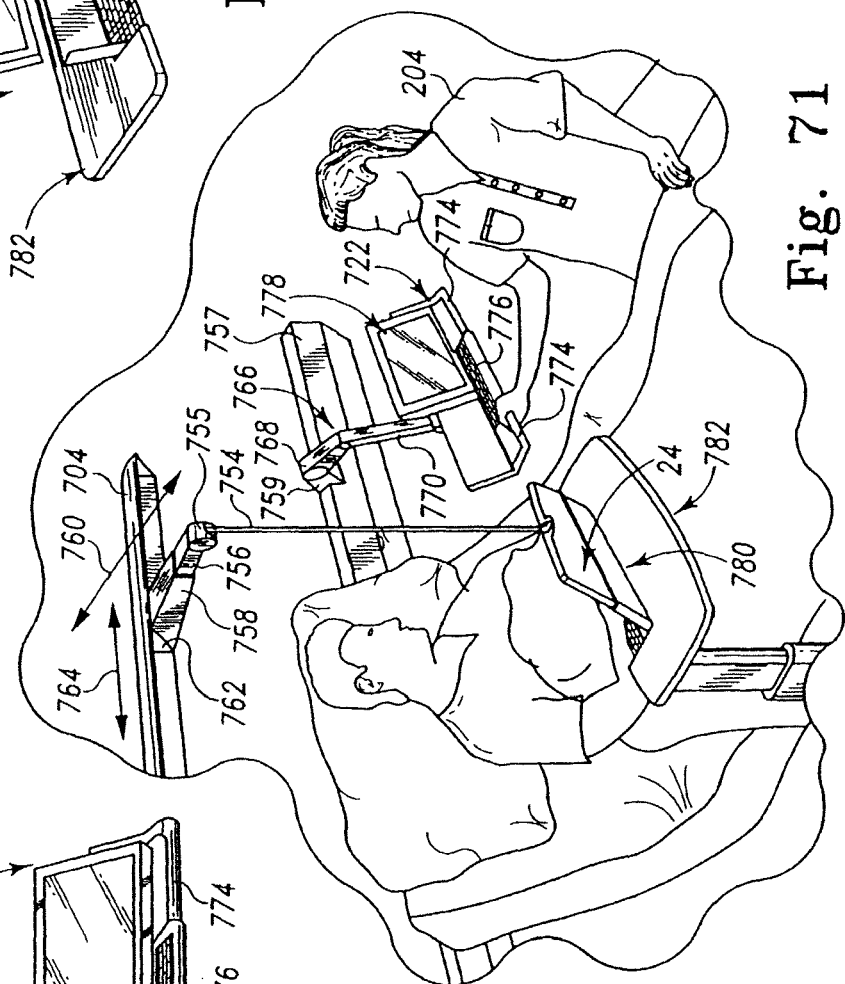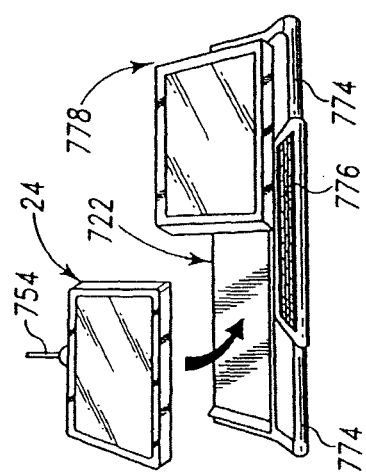

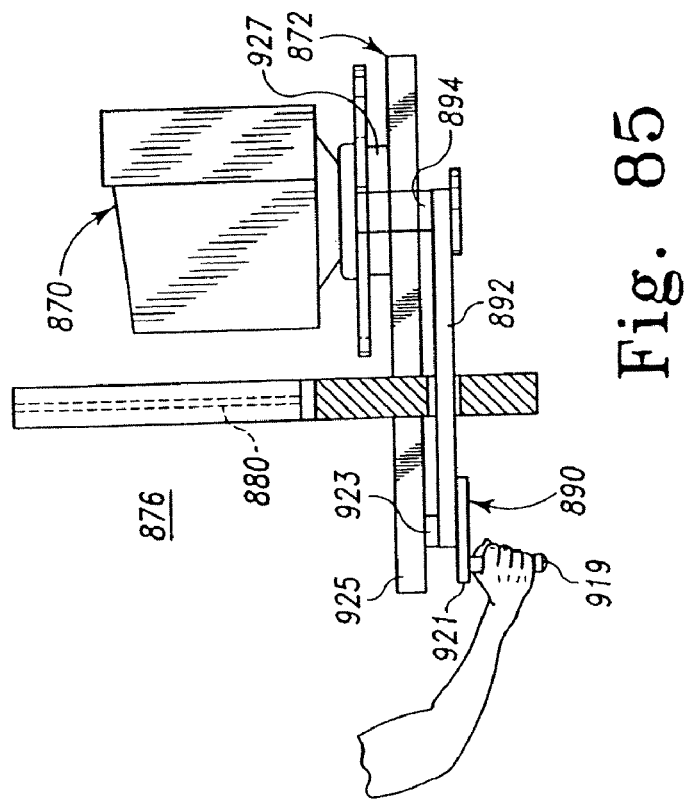
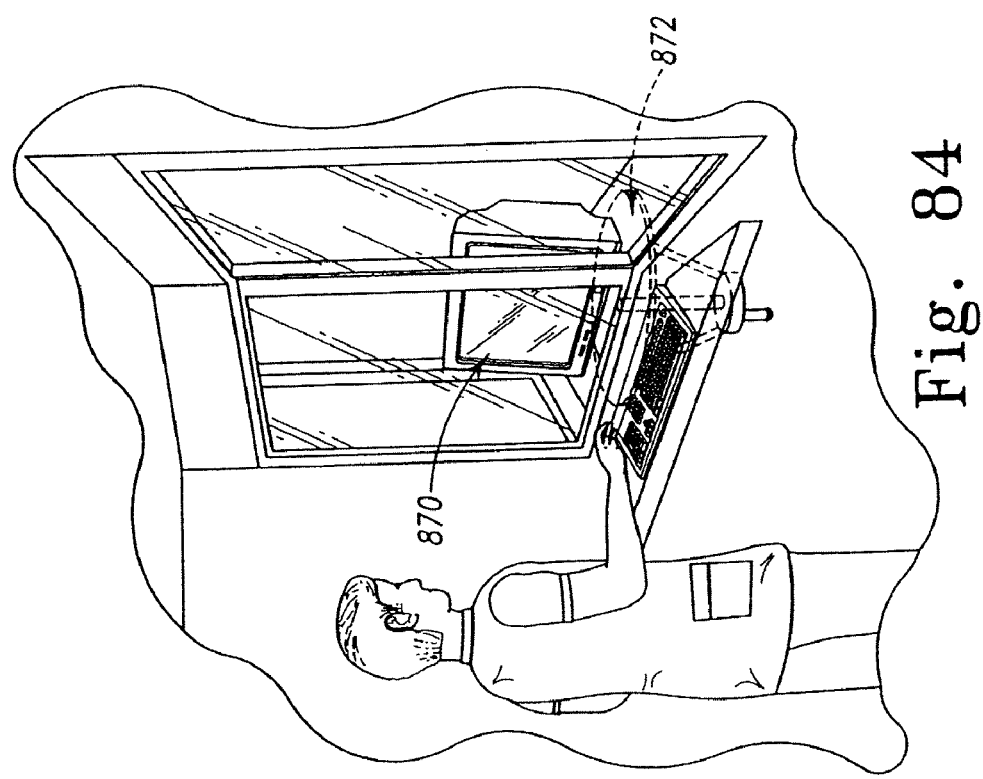
Fig. 85
Fig. 84

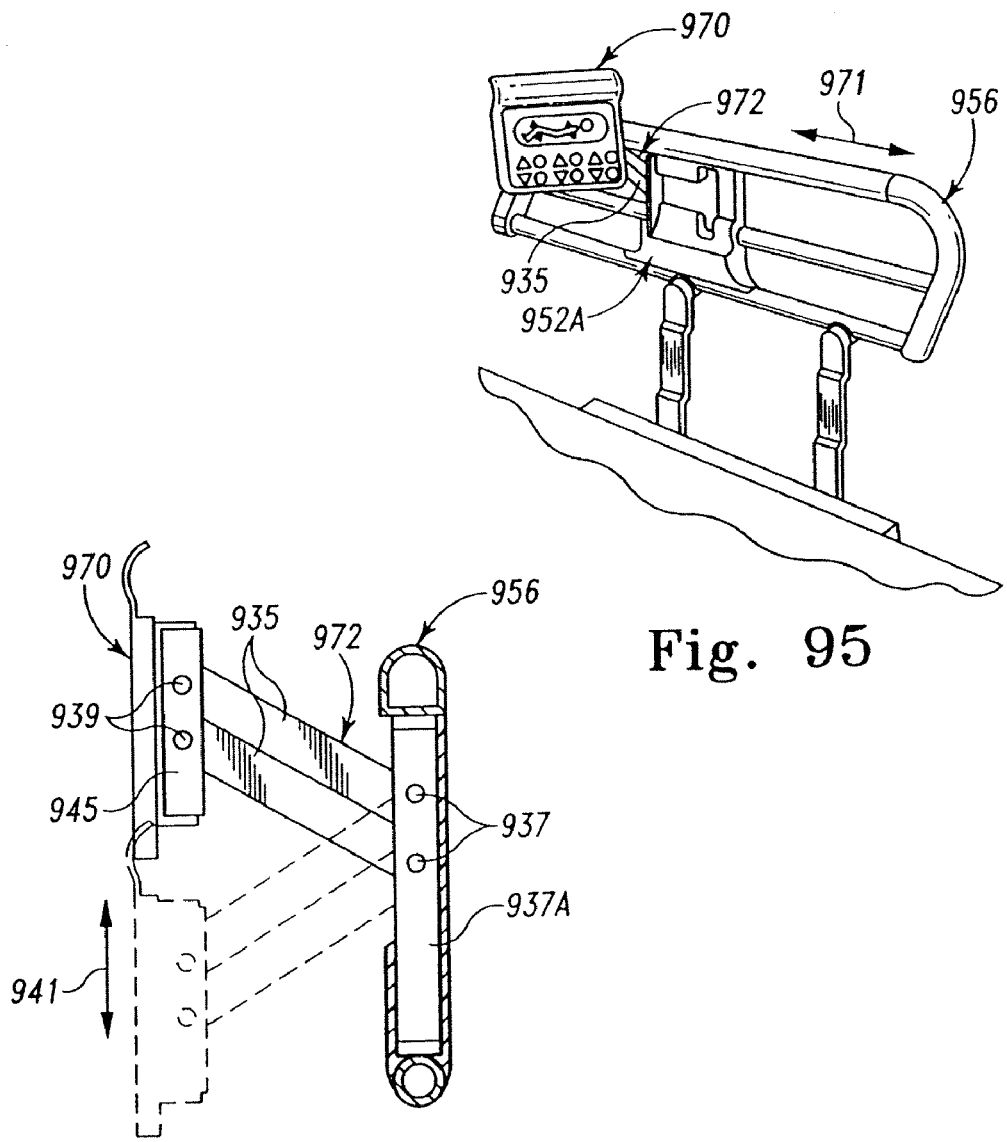
Fig. 95
Fig. 96
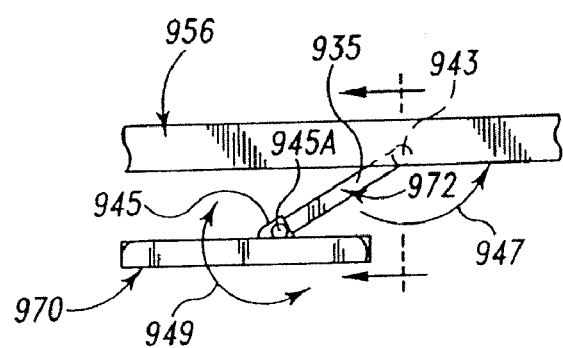
Fig. 97

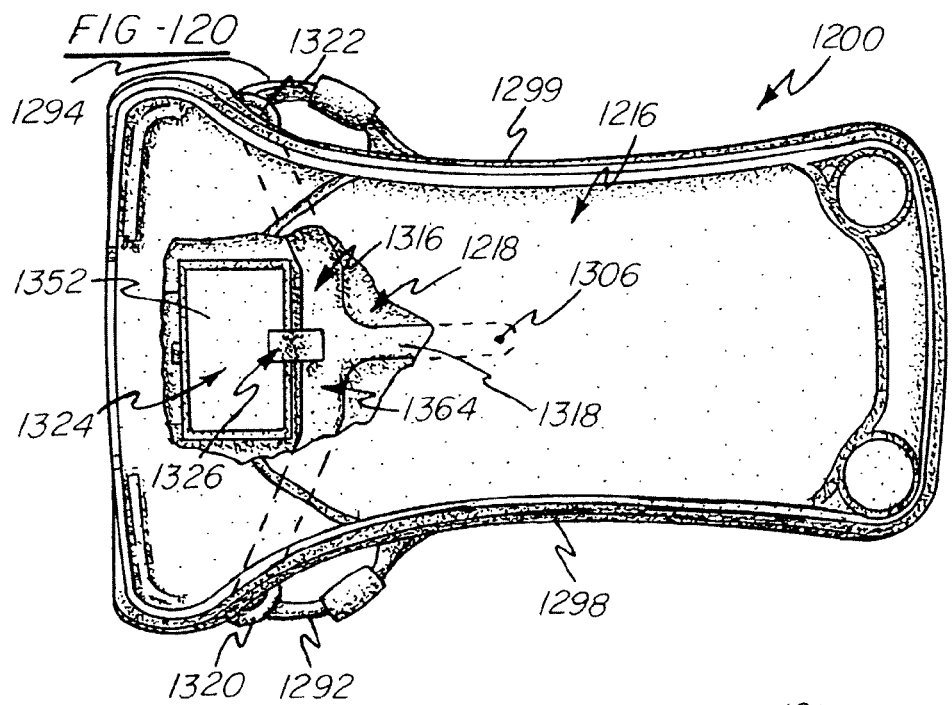
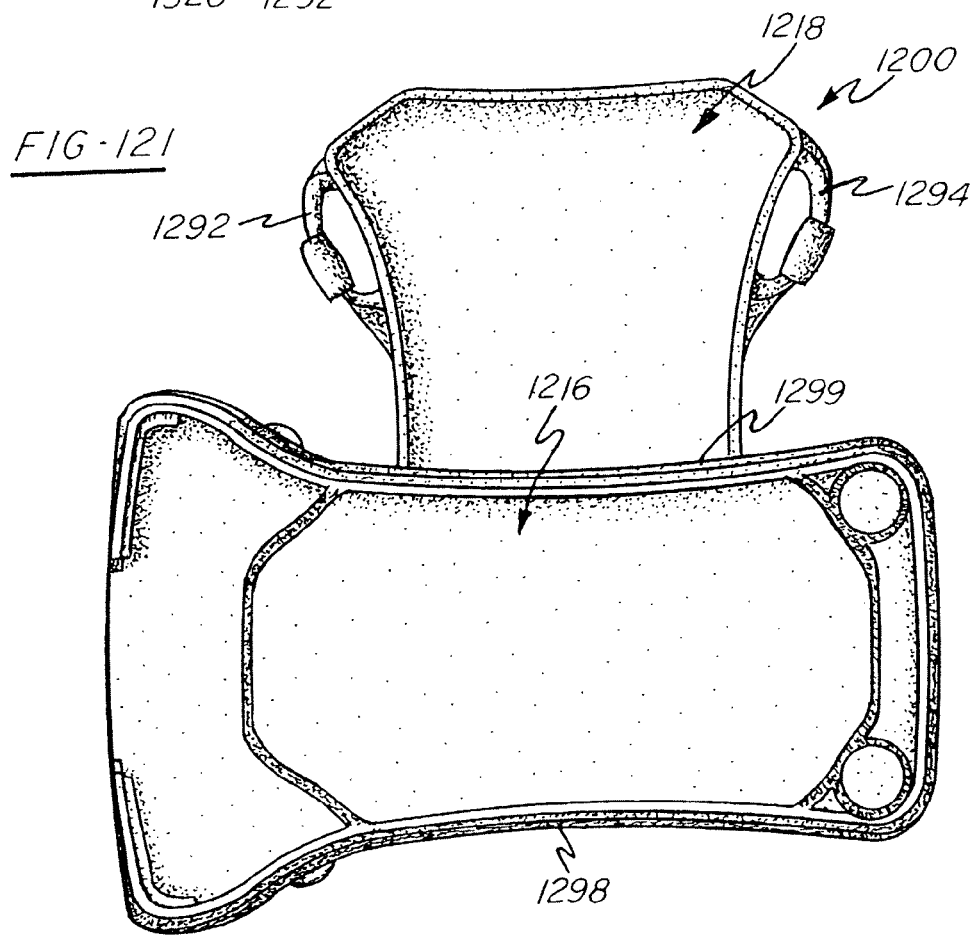

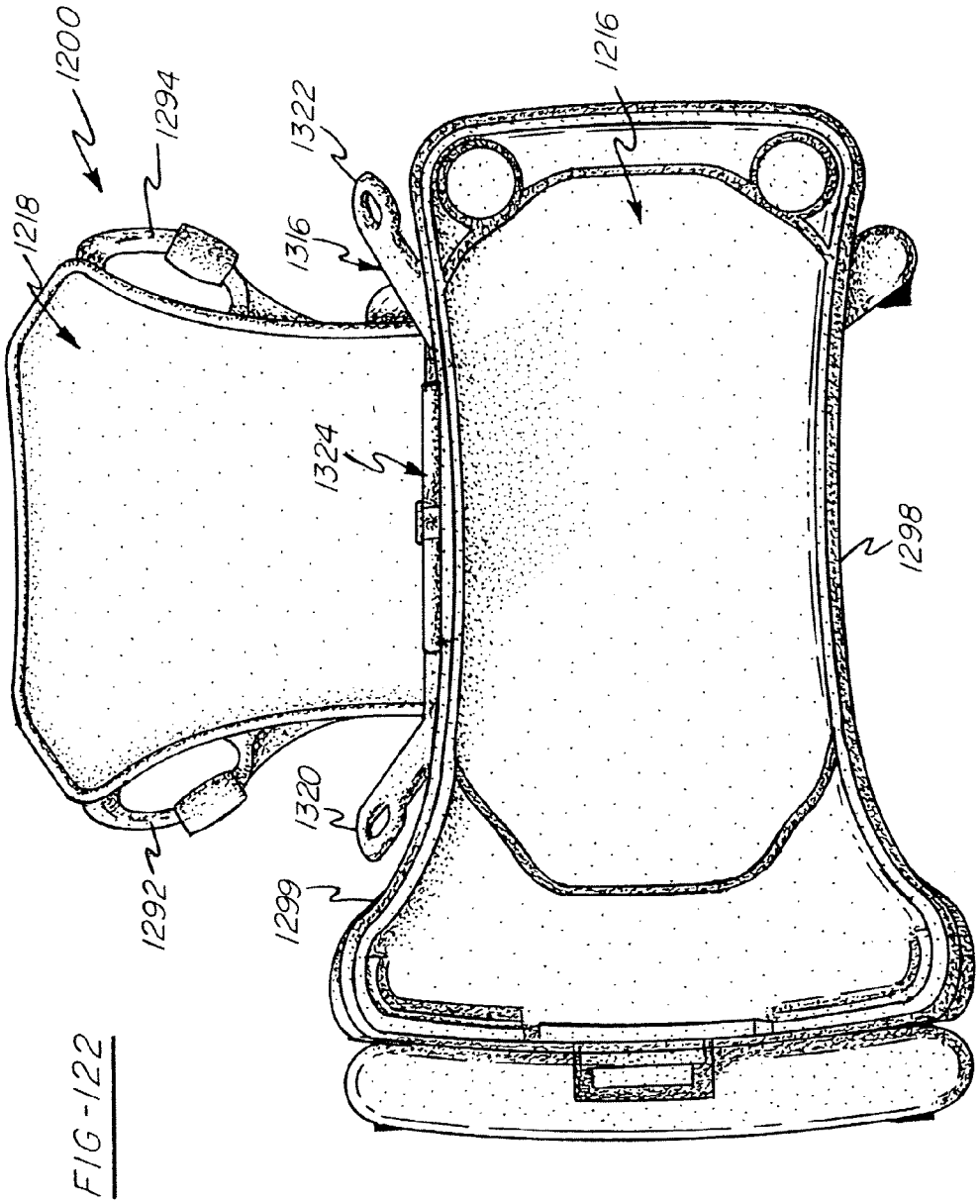

TOUCH SCREEN CONTROL OF A HOSPITAL BED

RELATED APPLICATIONS

This application is a continuation of U.S. application Ser. No. 13/049,393, filed Mar. 16, 2011, which is a continuation of U.S. application Ser. No. 12/710,407, filed Feb. 23, 2010, now U.S. Pat. No. 7,911,349, which is a continuation of U.S. application Ser. No. 11/611,955, filed Dec. 18, 2006, now U.S. Pat. No. 7,679,520, which is a continuation of U.S. application Ser. No. 10/211,451, filed Aug. 2, 2002, now U.S. Pat. No. 7,154,397, which claimed the benefit of U.S. Provisional Patent Application Ser. No. 60/310,092, filed Aug. 3, 2001, which is related to U.S. patent application Ser. No. 09/849,580, filed May 4, 2001 (hereinafter, "the '580 application"), the disclosures of which are hereby expressly incorporated herein by reference.

FIELD OF THE INVENTION

The invention relates to a computer system configured for use at the point of care by a patient and by a caregiver in a hospital or other health care facility in order to care for patients. The present invention facilitates caregiver and patient access to the computer for access to and entry of information at the point of care, provides automatic data capture, provides a computer screen with a flow sheet sized proportion, and provides an interface for other equipment.

BACKGROUND AND SUMMARY OF THE INVENTION

Providing a computer system at the point of care enables access to information from a laboratory, pharmacy, radiology, or other locations away from the point of care where it is needed, at the point of care. The system of the present invention includes both manual and automatic patient data entry at the point of care to create an electronic record. The system permits caregivers to easily input chart data directly into the computer. In addition, the computer receives information automatically from various monitors and medical devices such as vital signs monitors, bed therapy systems, IV pumps, and the like. Therefore, all data related to the patient is captured at a single location (i.e., the point of care). The computer of the present system is designed to remain with the patient in the hospital room and during ambulation or transportation within the hospital. In other words, the computer may follow the patient wherever the patient goes from admit to discharge.

Providing a computer system at the point of care improves communication. Lab and radiology results are presented electronically to the ordering and consulting physicians at the point of care. The system of the present invention facilitates patient care by enabling the creation of virtual teams of caregivers who may never actually meet when caring for the patient. The system instantaneously captures information related to the patient as well as to laboratory and diagnostic procedures ordered for the patient.

In one embodiment, the system provides updated access to information and communication at the point of care. Patient data is stored in a memory of the point-of-care computer or in a main server coupled to the computer by a communication network. Access to all patient information is available to physicians, pharmacy, radiology, lab, cath lab, or any computer connected to the point-of-care computer through a communication network. Doctors or other caregivers at remote locations can view information related to the patient by accessing the computer associated with the patient or the main server through the communication network. In other words, each computer functions as a node on the network, and can access information from other nodes. The present computer system also functions to capture costs of services and supplies, and to transmit the cost information to, for example, a hospital accounting department for billing purposes. Therefore, the system can determine the actual cost of providing services and treatments to the patient, as well as the costs of medication and other supplies used by the patient.

In one embodiment, the computer system of the present invention uses a wireless data receiver to receive signals from badges on the caregiver and the patient and from tags on equipment, medication, a medication lock container located within the hospital room, or other supplies. These signals identify the people or things with which they are associated. The system may also include an input device such as touch sensitive display, a hand pad, a keyboard or a bar code reader to receive these identification signals.

The system of the present invention may be used with the COMposer® communication system available from Hill-Rom Company of Batesville, Ind. Some details of the COMposer® system are disclosed in U.S. Pat. Nos. 5,561,412, 5,699,038, and 5,838,223, all of which are hereby expressly incorporated herein by reference.

In one embodiment of the invention, the computer system is used for monitoring the administration of medication to a patient. The patient prescription information is entered into the hospital communication network. Therefore, the patient's name and associated medication dosage schedule are accessible by the computer in the patient's room. When the pharmacy fills a prescription, the medication is placed in a locked medical container and transported to the patient's room. When the nurse brings the locked medical container to the patient's room, the computer system first identifies the patient by receiving an identification signal from the patient via an RFID tag, a bar code, a transmitter badge, or some other device for providing a unique identification signal associated with the patient. The system then determines whether the patient is due for medication. If so, the system receives identification information from the nurse in a similar manner. If the nurse is not authorized to administer the medication, access to the locked medical container is denied. If the nurse is authorized, then the locked medical container is scanned or otherwise sensed by the computer to determine whether the medication contained therein matches the scheduled medication for the patient. If so, the locked medical container is opened. The medication in the container is then scanned or otherwise sensed by the computer to confirm that the medication is correct. A visual image of the medication is displayed on a display of the point-of-care computer so that the nurse can confirm that the medication is correct. If the medication is correct, then the nurse provides an input to the computer and the computer scans or otherwise senses the medication. The patient is billed for the medication at that time by the computer system. The computer may then prompt the nurse to indicate whether the patient held down the medication. If the patient did not hold down the medication, then the medication is not added to the patient's chart. If the patient held down the medication, then the system automatically adds the medication dosage and time of administration to the patient's chart.

Additional features of the invention will become apparent to those skilled in the art upon consideration of the following drawings in conjunction with the detailed description of the illustrated embodiments exemplifying the best mode of carrying out the invention as presently perceived.

BRIEF DESCRIPTION OF THE DRAWINGS

The detailed description particularly refers to the accompanying figures in which:

FIGS. 43-63 depict various screens generated on a touch screen display of the present invention;

FIGS. 71-73 are perspective views of another embodiment of a mounting configuration;

FIG. 84 is a perspective view of another embodiment of a mounting configuration of a point-of-care computer system of the present invention;

FIG. 85 is a side elevational view, partly in section, of the mounting configuration of FIG. 84;

FIG. 95 is a perspective view of another embodiment of a mounting configuration;

FIG. 96 is a side elevation view, partly in section, of the mounting configuration of FIG. 95;

FIG. 97 is a top plan view of the mounting configuration of FIG. 95;

FIGS. 120-122 are top plan views of the overbed table of FIG. 119;

DETAILED DESCRIPTION OF EMBODIMENTS OF THE INVENTION

The embodiments described below are merely exemplary and are not intended to limit the invention to the precise forms disclosed. Instead, the embodiments were selected for description to enable one of ordinary skill in the art to practice the invention.

Figure 1:
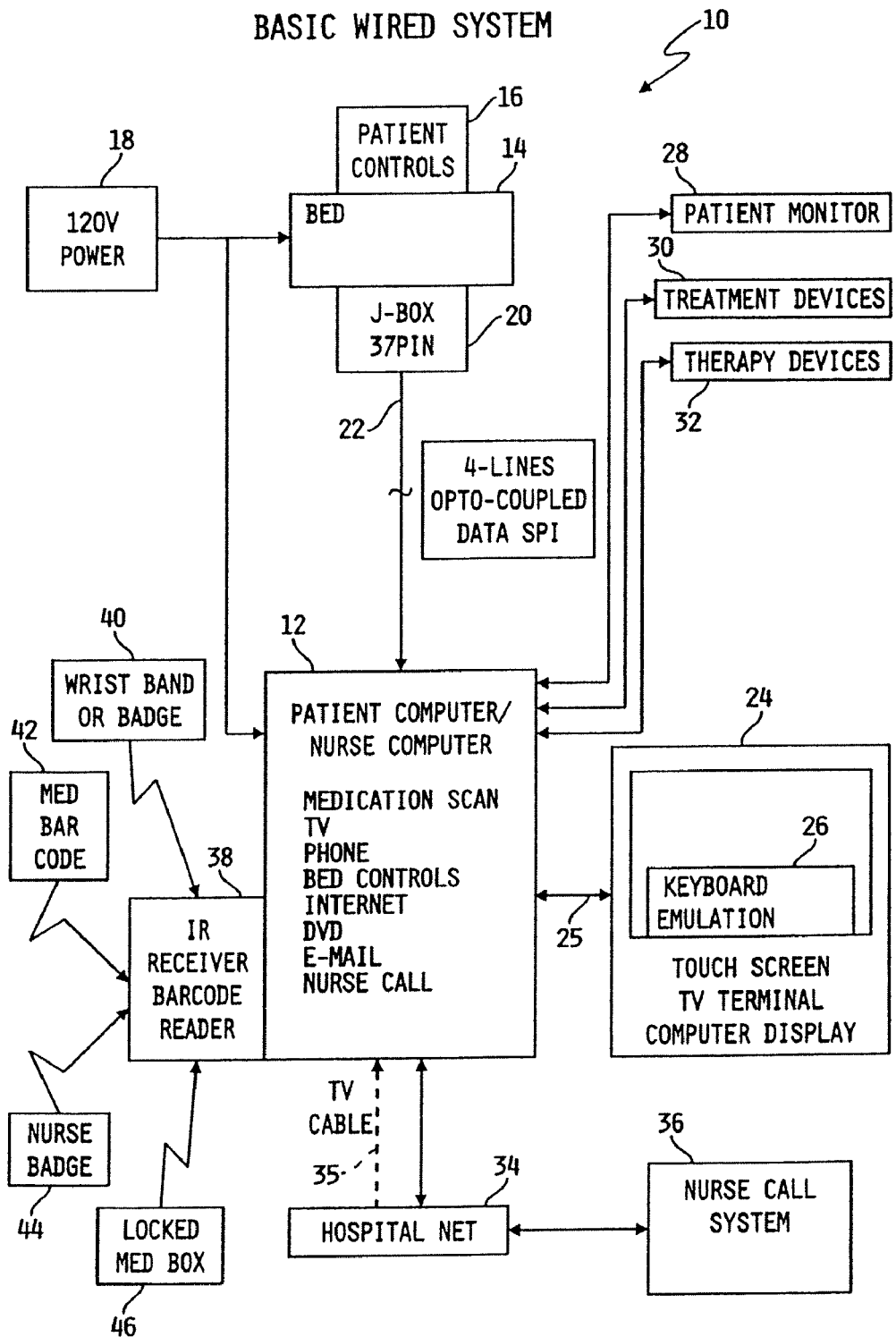
FIG. 1 is a block diagram illustrating components of a wired computer system and medication dispenser of the present invention.

Referring now to the drawings, FIG. 1 is a block diagram illustrating components of a patient and nurse point-of-care computer system 10 according to the present invention. System 10 generally includes a computer 12 that is electrically coupled to a display 24, a bed 14, a nurse call system 36, and an input device 38. Computer 12 illustratively has a processor, a memory, and a plurality of input and output ports. Computer 12 is coupled to bed 14 either by a wired connection shown in FIG. 1, or by a wireless connection discussed below in connection with FIG. 2.

Bed 14 illustratively includes a plurality of patient controls 16 to control various bed functions such as movement of bed deck sections, mattress controls, entertainment controls, or other controls. A power supply 18 is configured to supply power to bed 14. Bed 14 illustratively includes a 37 pin J-Box connector 20. Connector 20 includes a plurality of lines which indicate various conditions of bed 14, such as the location of deck sections, the status of bed functions, the status of caster locks, and the like. Connector 20 is coupled to computer 12 by a data link 22 which illustratively includes four lines that are opto-coupled to computer 12 using, for example, a Serial Peripheral Interface (SPI) Motorola® data standard. Data link 22 permits two-way communication between computer 12 and bed 14. In other words, bed status conditions and patient data can be transmitted from bed 14 through data link 22 to computer 12. In addition, control signals for bed 14 can be transmitted from computer 12 through data link 22 to bed 14.

In one embodiment, computer 12 is used to provide controlled medication administration, television, radio/audio, telephone, and bed controls, internet access, e-mail functions, and nurse call functions. Illustratively, display 24 is a touch screen display that can be used as both a television terminal and a computer display. Software operated by computer 12 may provide a keyboard emulation 26 on display 24 to permit a user to enter information into computer 12 using touch screen display 24. It is understood that any suitable input device such as a hand pad (described below), a pen or stylus based input device, a keyboard, a mouse, a joy stick, a voice recognition interface, or other such device may be used to enter information into computer 12.

Patient monitors 28, treatment devices 30, and therapy devices 32 are also coupled to computer 12 as discussed in detail in the '580 application. Computer 12 is also coupled to a hospital communication network 34 which is coupled to nurse call communication system 36 such as, for example, the COMposer® or COMLinx communication systems mentioned above.

Input device 38 may include an IR or RF receiver, a bar code reader, a smart card reader, a magnetic stripe reader or other suitable input device. Input device 38 is configured to receive information from a bar-coded tag, RFID tag, or other transmitter on a wristband or badge 40 located on a patient, on medication 42 to be given to the patient, on a nurse badge 44, on a locked medication box 46, or on other objects. In one embodiment, device 38 is an RFID sensor for receiving identification information from RFID tags associated with a caregiver, a patient, medication 42, locked medication box 46, or other equipment or supplies.

Hospital network 34 provides a television input signal on line 35 to computer 12. Therefore, computer 12 is used to provide television signals to display 24. Computer 12 is illustratively coupled to display 24 using a low Voltage Differential Signaling (LVDS) interface 25.

Figure 2:
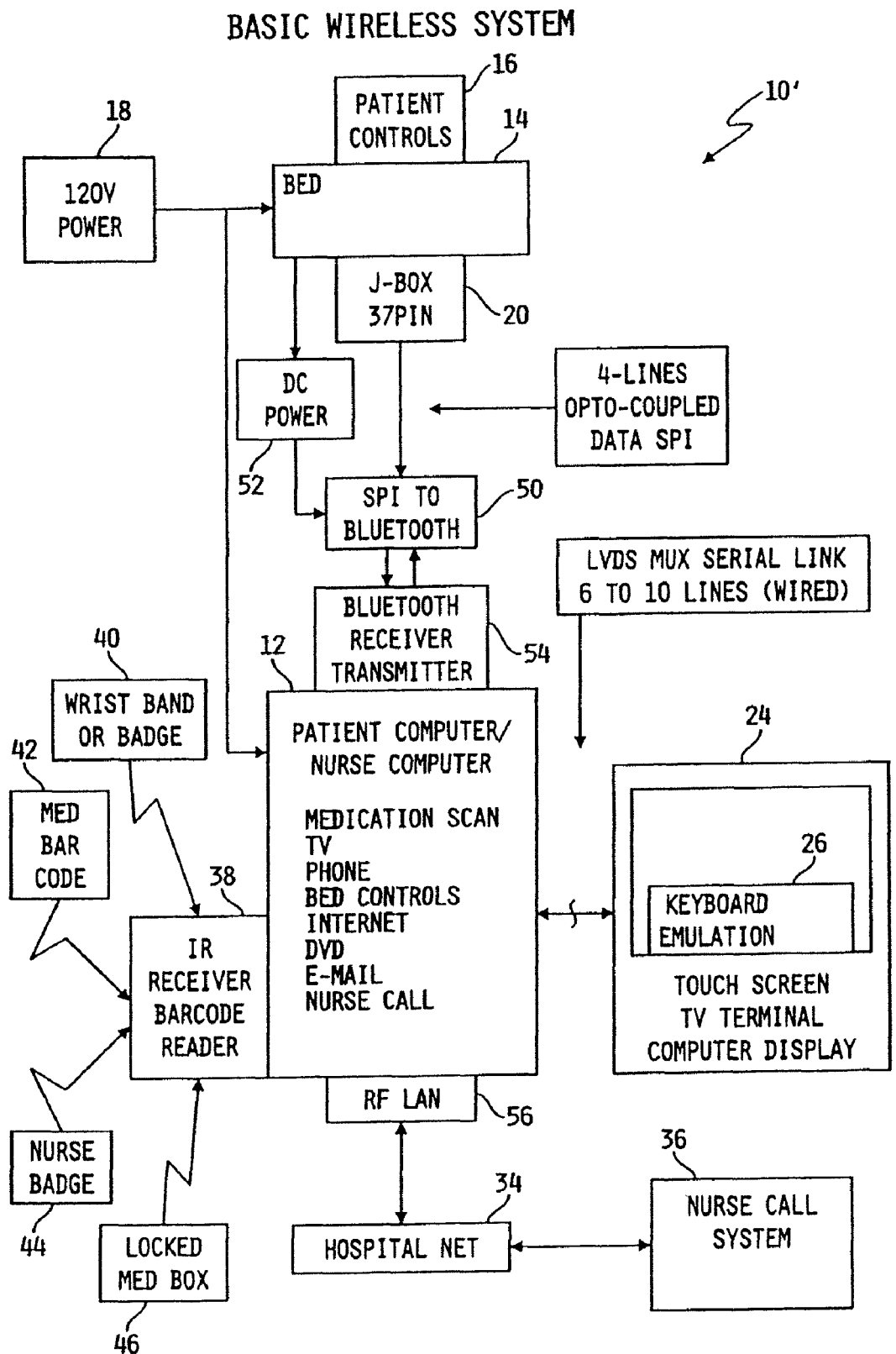
FIG. 2 is a block diagram illustrating components of a wireless computer system and medication dispenser of the present invention.

A wireless computer system 10' of the present invention is illustrated in FIG. 2. Those elements referenced by numbers the same as those used in FIG. 1 perform the same or similar function. In FIG. 2, J-Box connector 20 is illustratively coupled to a SPI-to-Bluetooth converter 50. It should be understood that any type of suitable wireless data transmitter/receiver and converter can be used. Converter 50 is coupled to a DC power supply 52 connected to bed 14. Converter 50 illustratively transmits an RF signal to a transceiver 54 coupled to computer 12. Converter 50 and transceiver 54 may employ RF, IR, or other suitable communication technique. Illustratively, the Bluetooth protocol is used for RF transmissions. Also illustratively, computer 12 is coupled to hospital communication network 34 by a wireless RF LAN Ethernet connection 56 that illustratively provides a 1-10 GHz data transmission rate. Therefore, television or voice IP signals can be transmitted between network 34 and computer 12.

Figure 3A:
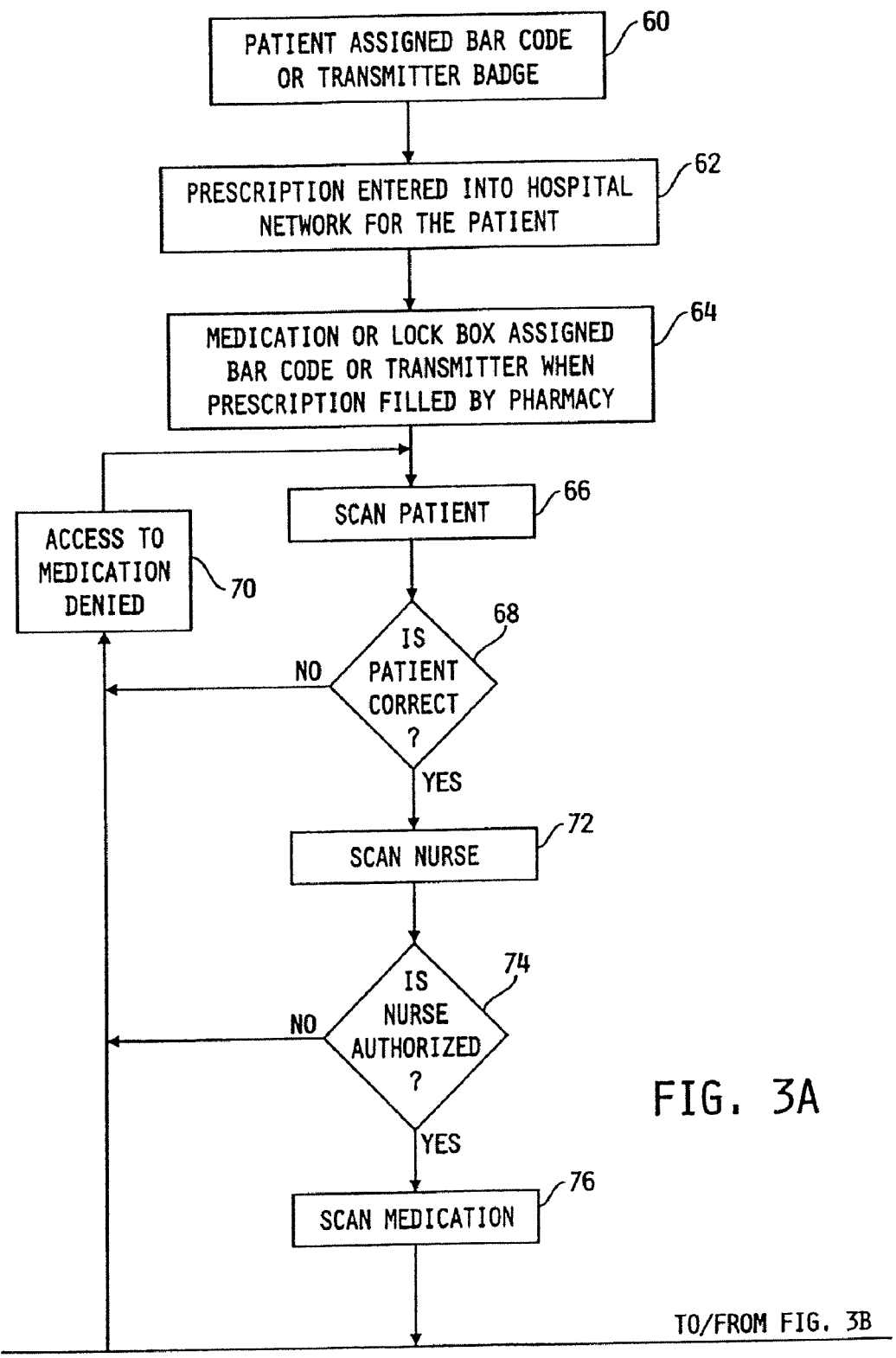
FIGS. 3A and 3B are flow charts illustrating the steps performed by the system to monitor administration of medication to a patient.
Figure 3B:
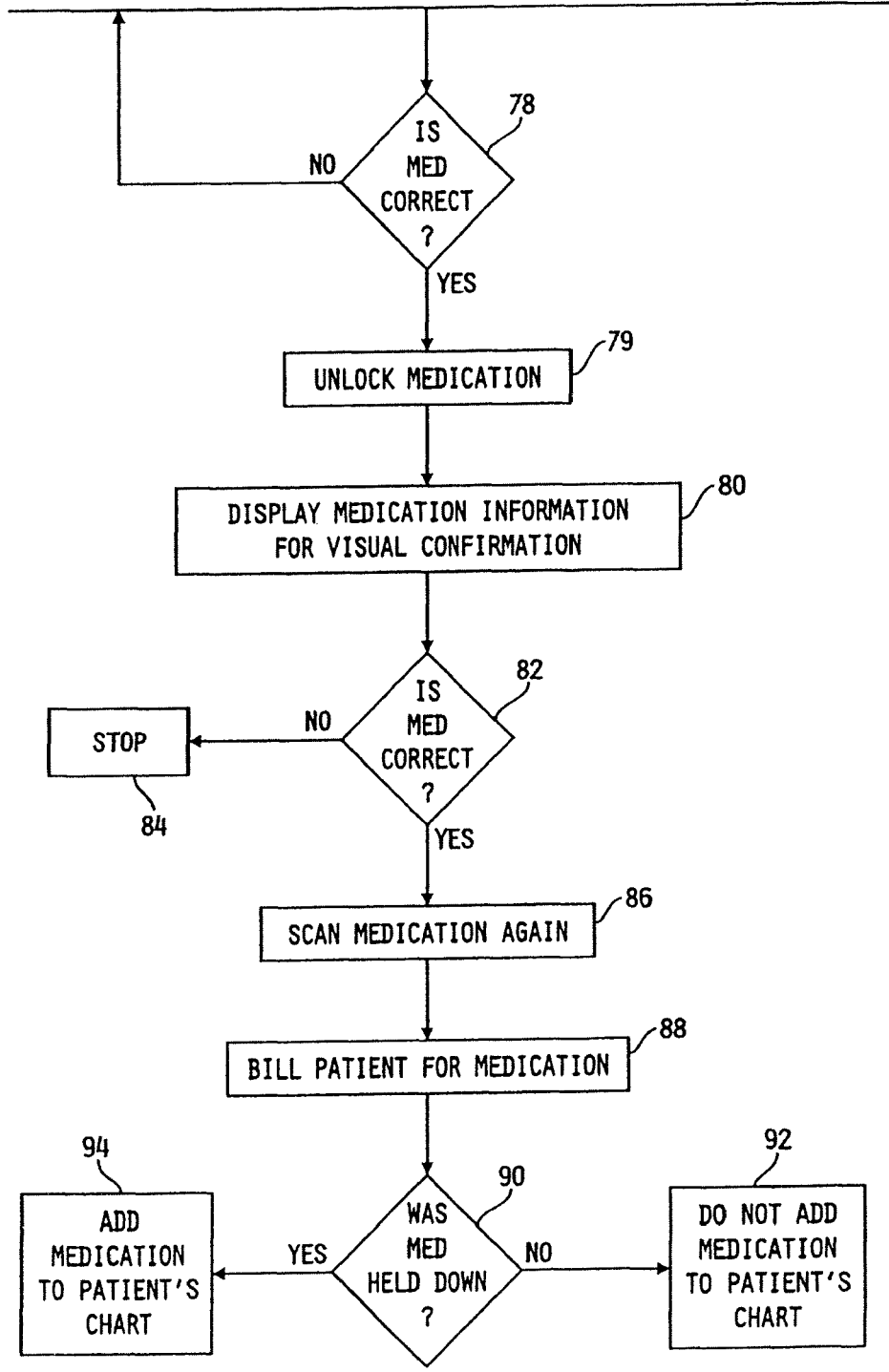
Figure 4:
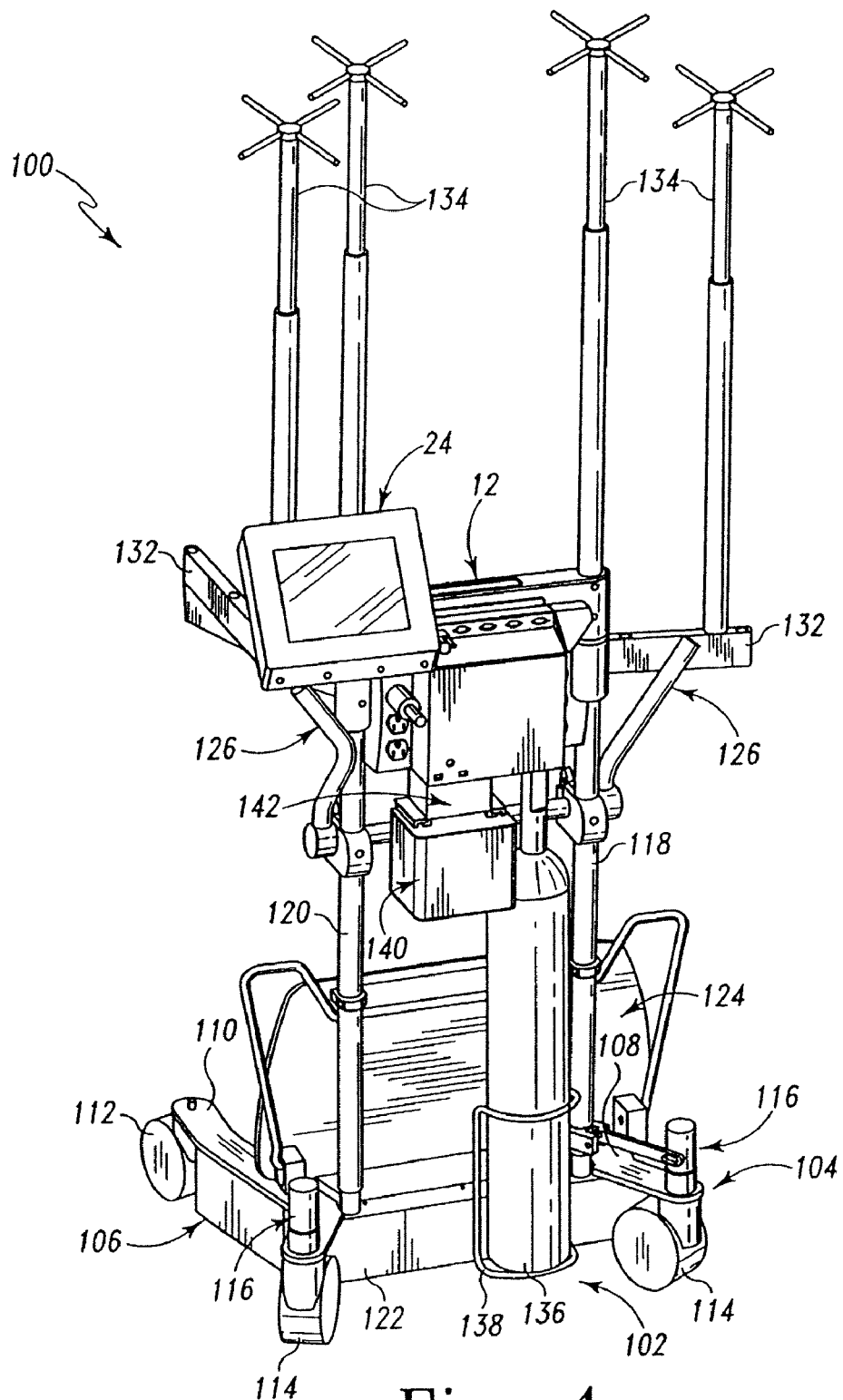
FIGS. 4-7 are perspective views of another embodiment of the present invention including a patient assist cart having a computer and display mounted thereon and a locked medication box in accordance with one embodiment of the present invention.

FIGS. 3A and 3B illustrate steps performed by system 10 (or system 10') to monitor administration of patient medication and to unlock locked medication box 46 to provide access to medication 42 for a patient. As illustrated in FIG. 3A, a patient is assigned a unique bar code identification or a transmitter badge (for example, having an RFID tag) which transmits a unique identification signal corresponding to the patient as indicated at block 60. When a doctor prescribes a certain medication for the patient, the prescription is entered into hospital network 34 as indicated at block 62. Network 34 then provides a dosage schedule and medication type corresponding to the patient.

When a prescription is filled by the pharmacy, medication 42 or a locked medication box 46 containing medication 42 is assigned a bar code, a transmitter badge, or other device that transmits a unique identification signal. The signal may either correspond to the particular patient for which medication 42 was prescribed, or to the particular type of medication 42 in locked medication box 46. This step is illustrated in block 64. Details of an embodiment providing medication containers with unique transmitters are illustrated in co-pending U.S. Provisional Patent Application Ser. No. 60/309,963, filed Aug. 3, 2001, entitled "MEDICATION TRACKING SYS- TEM," and owned by the assignee of the present application, the disclosure of which is hereby expressly incorporated herein by reference.

Next, a caregiver delivers medication 42 located in locked medication box 46 or other medication container to the patient's room. Computer 12 first receives patient identification information as illustrated at block 66. Patient identification information is entered into computer 12 through input device 38 using, for example, a bar code reader which reads a bar code on a patient wristband or other location, or an RFID receiver which receives a signal from a badge or tag on the patient as illustrated at block 66. Computer 12 then determines whether the correct patient has been located for receipt of medication 42 by accessing the hospital records via network 34 as illustrated at block 68. Computer 12 receives the prescription schedule via network 34 to determine whether the patient is due for medication 42. An image of the patient may be displayed on display 24 to permit the nurse to verify the patient's identity. If an incorrect patient is identified, or the patient is not due for medication 42, then access to medication 42 in locked medication box 46 is denied as illustrated at block 70.

If, at block 68, the correct patient is identified and is due for medication 42, computer 12 receives nurse identification information as illustrated at block 72. Input device 38 scans a bar code tag associated with the nurse or automatically detects a unique identification signal from a badge or RFID tag assigned to the nurse. Computer 12 then determines whether the nurse is an authorized caregiver for administering medication 42 by comparing the signal received at block 72 to a database of authorized caregivers available from hospital network 34 as illustrated at block 74. If the nurse is not authorized to administer medication 42, then access to medication 42 in locked medication box 46 is denied at block 70. If the nurse is authorized, then computer 12 opens locked medication box 46 and receives identification information from medication 42 as illustrated at block 76. Medication 42 is illustratively scanned using a bar code reader. In addition, computer 12 may identify medication 42 or locked medication box 46 by detecting a unique identification signal transmitted by a badge or RFID tag associated with medication 42, locked medication box 46, or other medication container.

Referring now to FIG. 3B, computer 12 determines whether medication 42 detected at block 76 is correct by comparing the received identification signal to information received from hospital network 34. If medication 42 is not correct, access to medication 42 is denied at block 70. If medication 42 is correct, computer 12 displays information related to medication 42 on display 24. In an illustrated embodiment, computer 12 displays an image of the particular pill or other type of medication on display 24 for visual confirmation of medication 42 by the nurse as illustrated by block 80. Upon reviewing the displayed image, the nurse confirms that medication 42 is correct as illustrated at block 82. If medication 42 is not correct, then the nurse stops the administration of medication 42 as illustrated at block 84. If the nurse confirms that medication 42 is correct at block 82, then computer 12 scans or otherwise receives identification information from medication 42 again at block 86. Computer 12 then automatically bills the patient for medication 42 as illustrated at block 88. Computer 12 then prompts the nurse at block 90 to indicate whether or not the patient held down medication 42. If medication 42 was not held down, computer 12 does not add medication 42 to the patient's medical chart as illustrated at block 92. If medication 42 was held down, computer 12 adds medication 42 to the patient's chart including dosage amount and time of administration as illustrated at block 94.

Another embodiment of the present invention is illustrated in FIGS. 4-7. A patient assist cart 100 includes a base 102 having opposite side supports 104, 106. Side supports 104, 106 include elongated support plates 108, 110, respectively. Casters 112 (one shown) are coupled to one end of plates 108, 110. Casters 112 illustratively include self-contained actuatable locks. Locking casters 114 are coupled to opposite ends of plates 108, 110. Brake mechanisms 116 are coupled to casters 114. Break mechanisms 116 are actuated by weight applied to cart 100. Cart 100 further includes upwardly extending support tubes 118, 120 coupled to a central portion 122 of base 102, a foldable seat 124, moveable patient and caregiver handles 126, a computer 12 mounted between support tubes 118 and 120, a display 24 coupled to cart 100 by an arm assembly, moveable support arms 132 that support IV poles 134, and an oxygen or air tank 136 coupled to cart 100 by a support bracket 138, all of which are described in further detail in the '580 application. Finally, cart 100 further includes a med bank or locked medication box 140 that is removably coupled to a coupler 142 on patient assist cart 100. Medication box 140 may function as medication box 46 of FIGS. 1-3B.

Figure 5A:
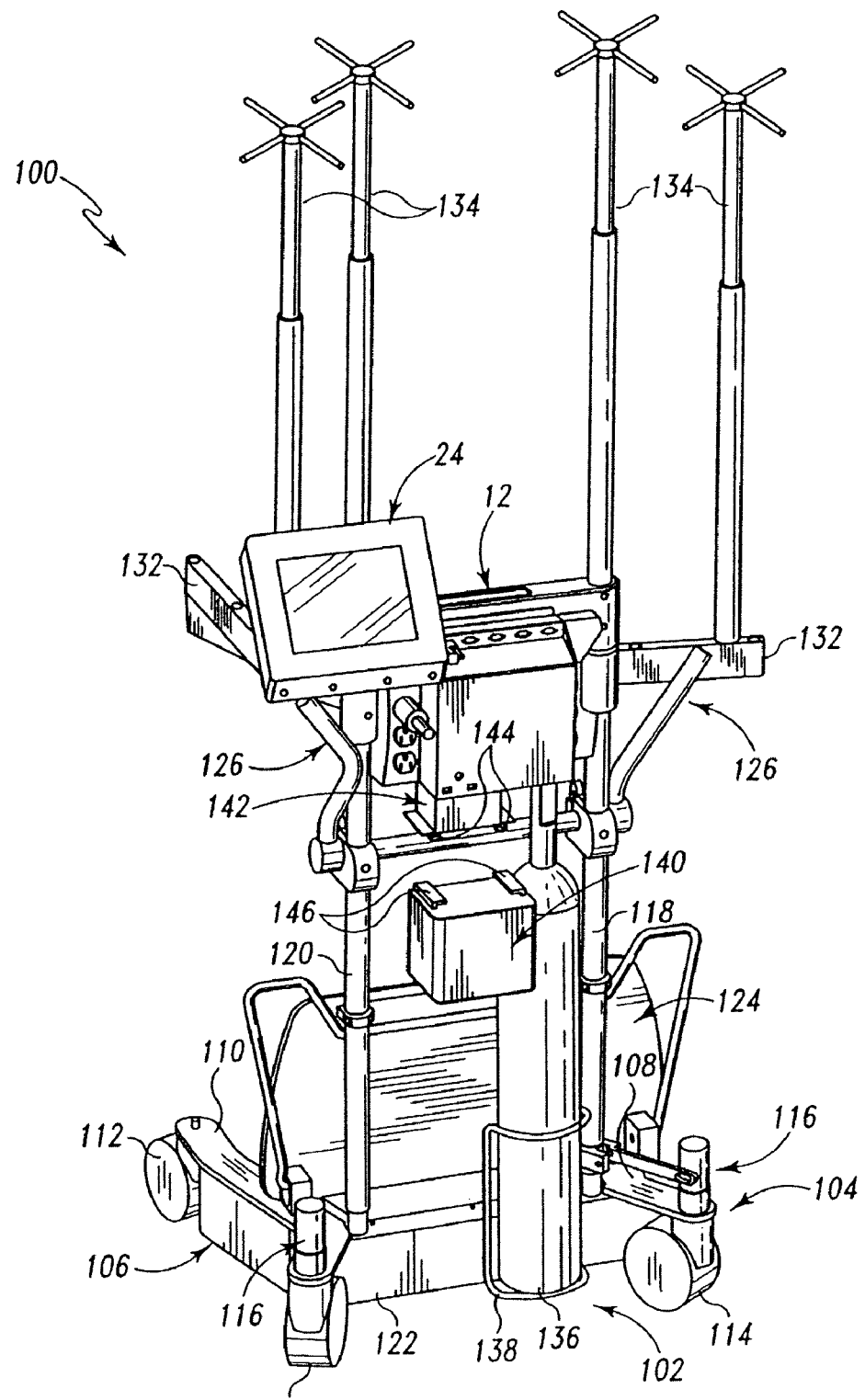
Figure 6:
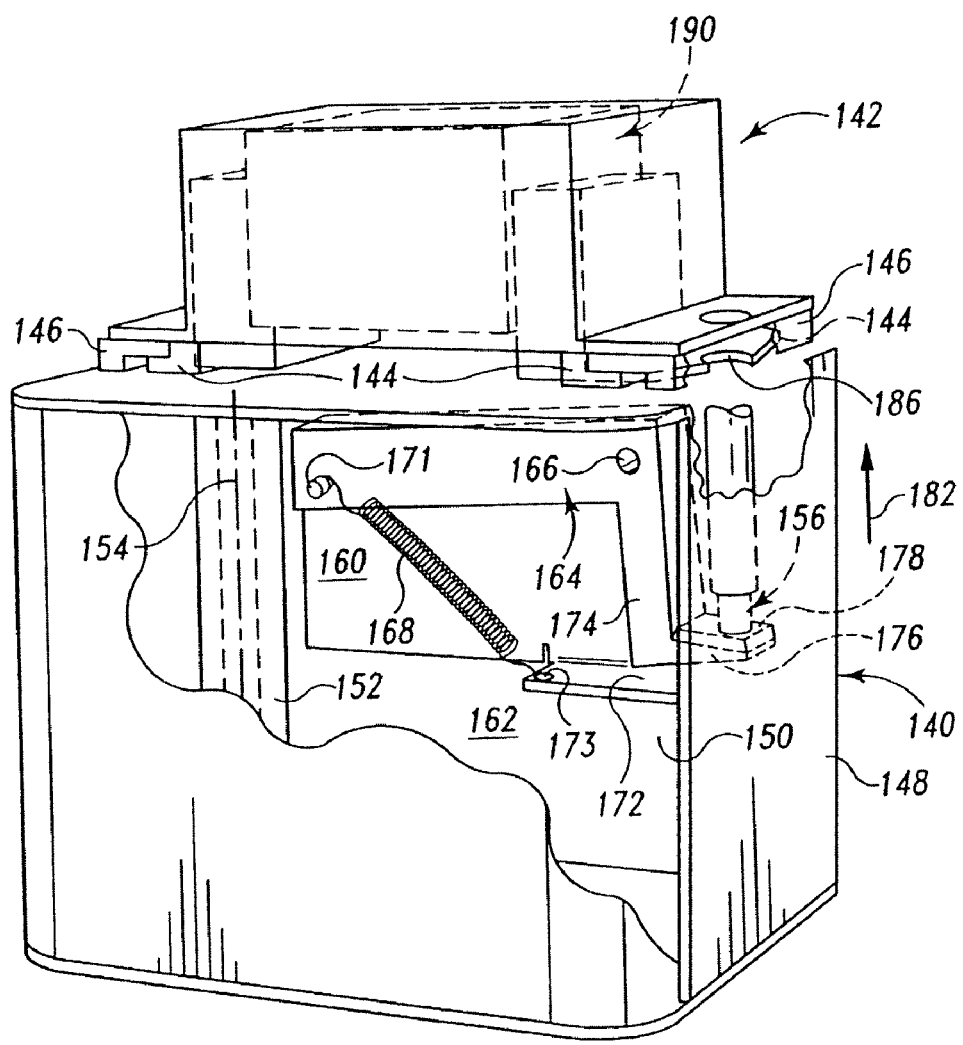
Figure 7:
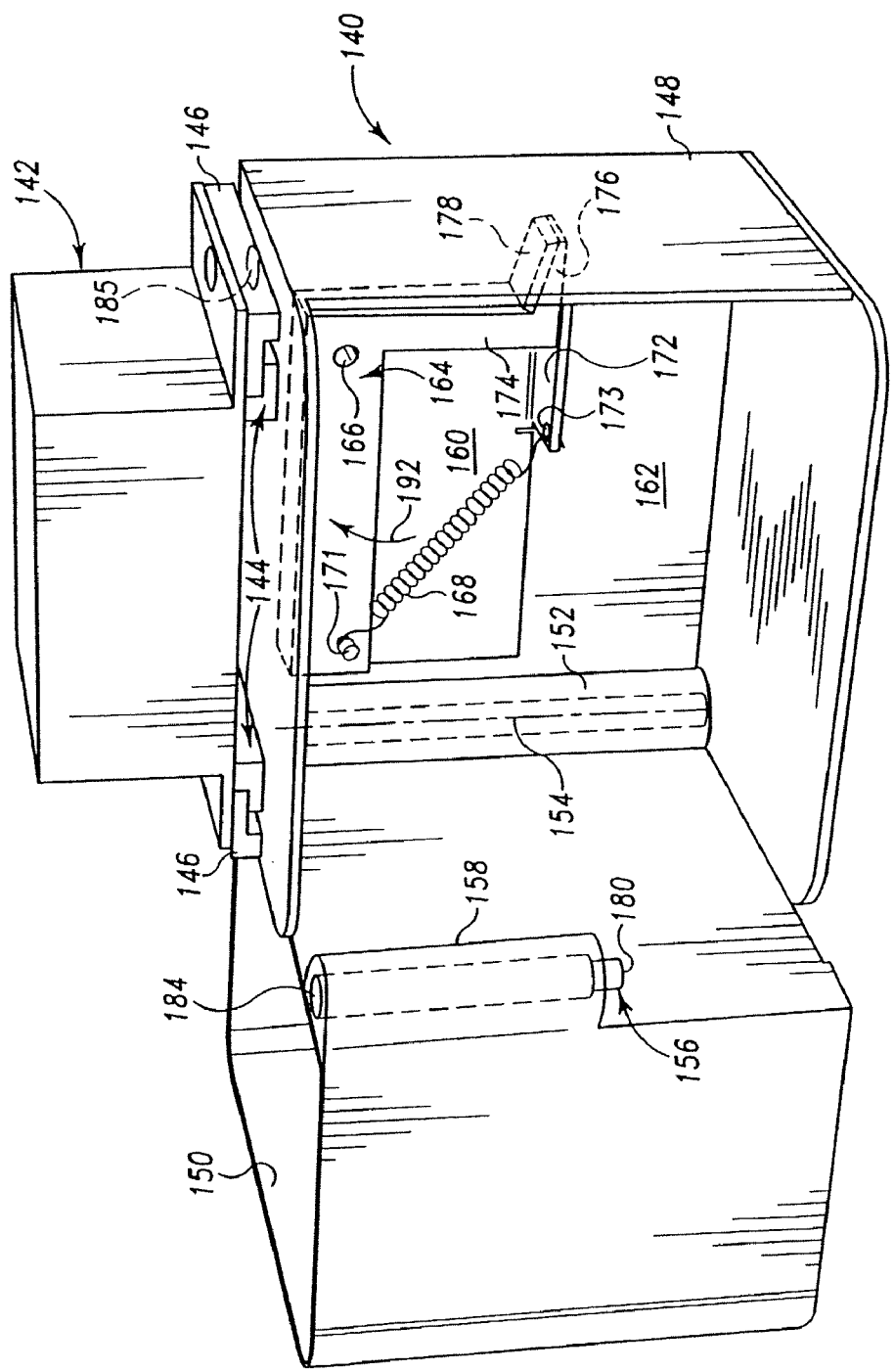
Figure 8:
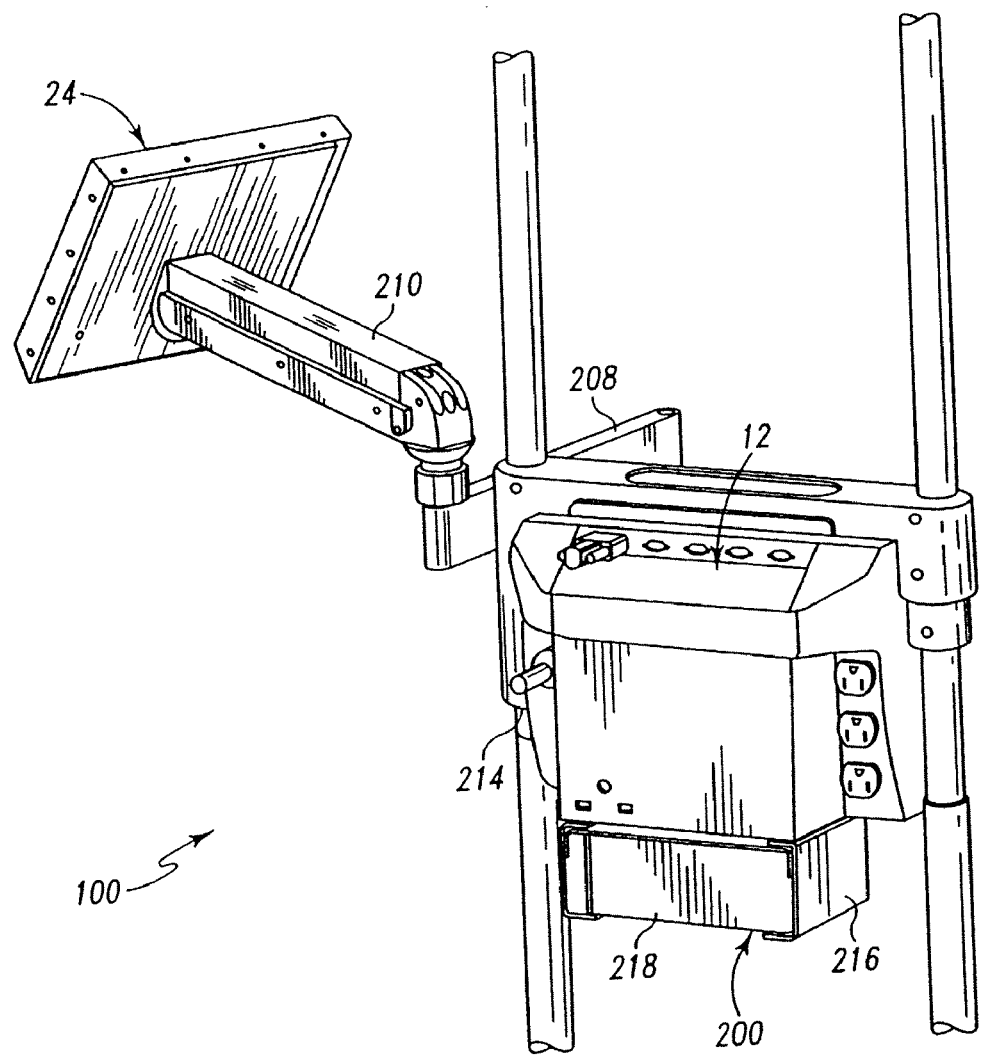
FIGS. 8-12 are perspective views of another embodiment of a patient assist cart and locked medication box of the present invention.

FIG. 5A illustrates medication box 140 removed from coupler 142. Medication box 140 can then be transported to a pharmacy for refilling or loaded into a receptacle in a patient's room or other location. FIGS. 6 and 7 illustrate details of medication box 140 and coupler 142. Coupler 142 illustratively includes a pair of tracks 144 configured to receive first and second flanges 146 coupled to medication box 140. Medication box 140 includes an outer housing 148 and an internal compartment 150 which is coupled to housing 148 by pivot connector 152 for pivotal movement about pivot axis 154. A locking plunger 156 is configured to lock compartment 150 in a closed position as shown in FIG. 6 and to lock medication box 140 to coupler 142 as described below.

As best shown in FIG. 7, plunger 156 is located in a housing 158 of compartment 150. Plunger 156 normally moves due to gravity to the lowered position shown in FIG. 7. A support plate 160 is coupled to a rear wall 162 of housing 148. An L-shaped lock arm 164 is pivotably coupled to plate 160 by pivot connection 166. A spring 168 is coupled between a post 171 on lock arm 164 and an aperture 173 formed in a flange 172 of plate 160 to bias lock arm 164 to the position shown in FIG. 6. Arm 174 of lock arm 164 includes a head 176 having a ramp surface 178 configured to engage a bottom surface 180 of plunger 156 as compartment 150 is closed. When ramp surface 178 engages bottom surface 180 of plunger 156, the biasing force of spring 168 on lock arm 164 causes ramp surface 178 to lift plunger 156 upwardly in the direction of arrow 182 in FIG. 6 to lock compartment 150 to housing 148. A top surface 184 of plunger 156 moves through an aperture 185 of housing 148. In addition, top surface 184 of plunger 156 moves into a notch or aperture 186 formed in track 144 to lock housing 148 to coupler 142 which is secured to cart 100.

Figure 5B:
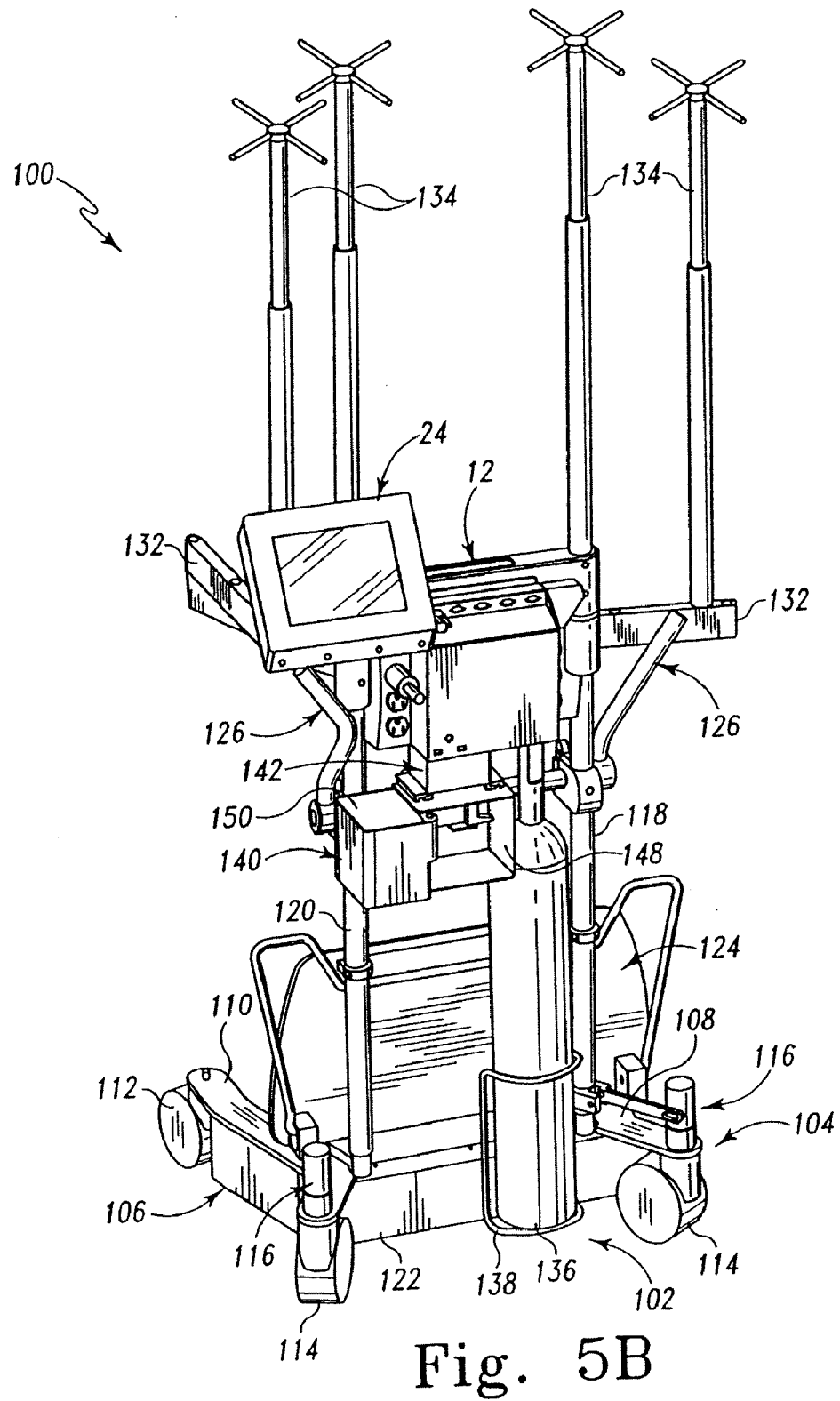

When it is desired to open compartment 150, a magnetic actuator 190 (FIG. 6) on cart 100 is actuated by computer 12 to rotate lock arm 164 clockwise about pivot connection 166 as indicated by arrow 192 in FIG. 7. This causes lock arm 164 to move to the position shown in FIG. 7 which, in turn, permits plunger 156 to drop into housing 158 of compartment 150. Therefore, compartment 150 can be pivoted to an opened position as shown in FIGS. 5B and 7, or medication box 140 can be removed from tracks 144 as shown in FIG. 5A. Once medication box 140 is removed from cart 100, spring 168 biases lock arm 164 (no longer influenced by magnetic actuator 190) to the position of FIG. 7. Therefore, if medication box 140 is removed from cart 100 while compartment 150 is in a closed position within housing 148, plunger 156 is pushed upwardly into aperture 185 of housing 148 by head 176 of lock arm 164 to lock compartment 150 in the closed position.

Another embodiment of a locked medication box 200 according to the present invention is illustrated in FIGS. 8-11. Those elements referenced by numbers from previous figures perform the same or similar function. Medication box 200 is coupled to patient assist cart 100, which includes a display 24 shown oriented for use by a caregiver in FIG. 8. It should be understood that arms 206 (not shown), 208 and 210 that support display 24 may be pivoted so that a patient has access to display 24. Arm 206 (not shown) is coupled to cart 100 by pivot connection 214. Details of components of the display support arms are included in the '580 application.

Figure 9:
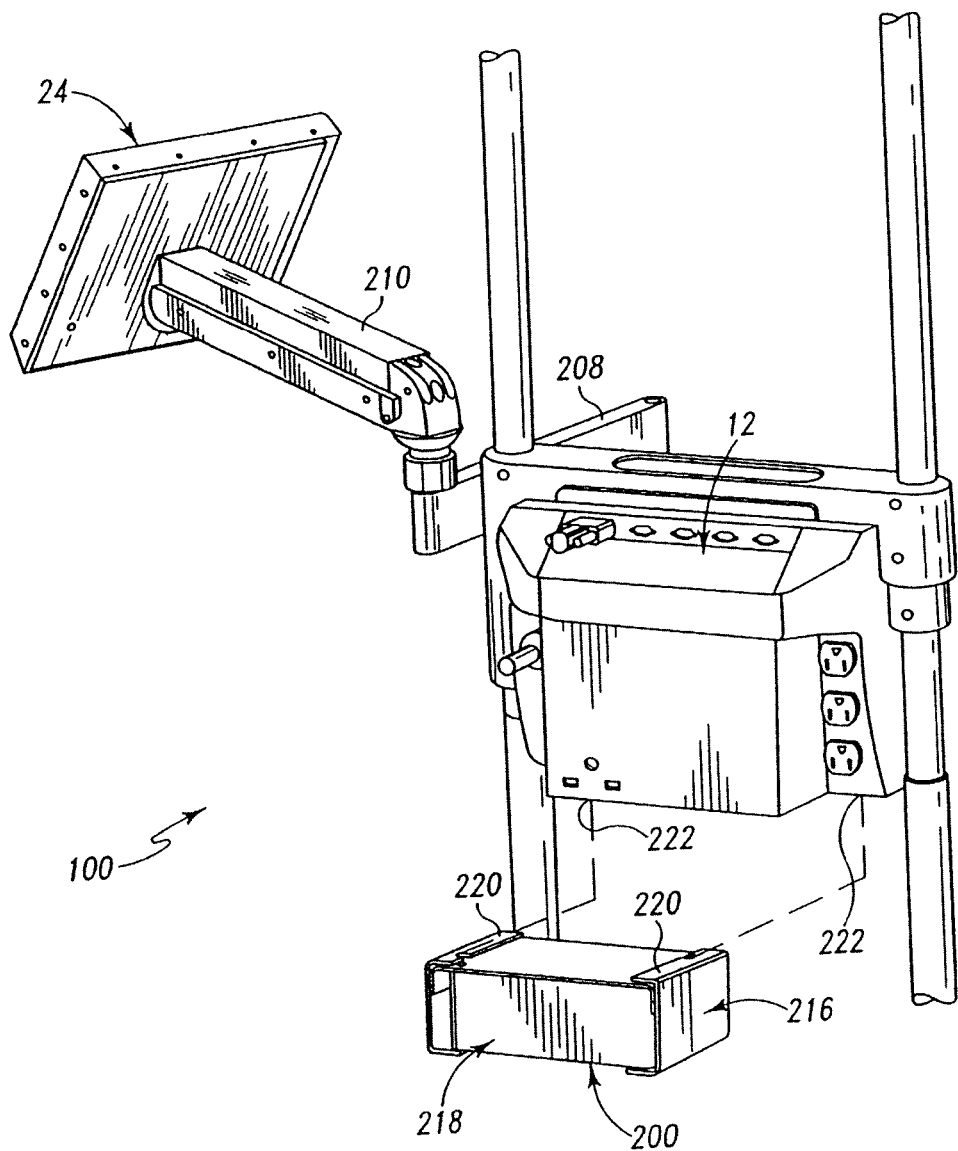
Figure 10:
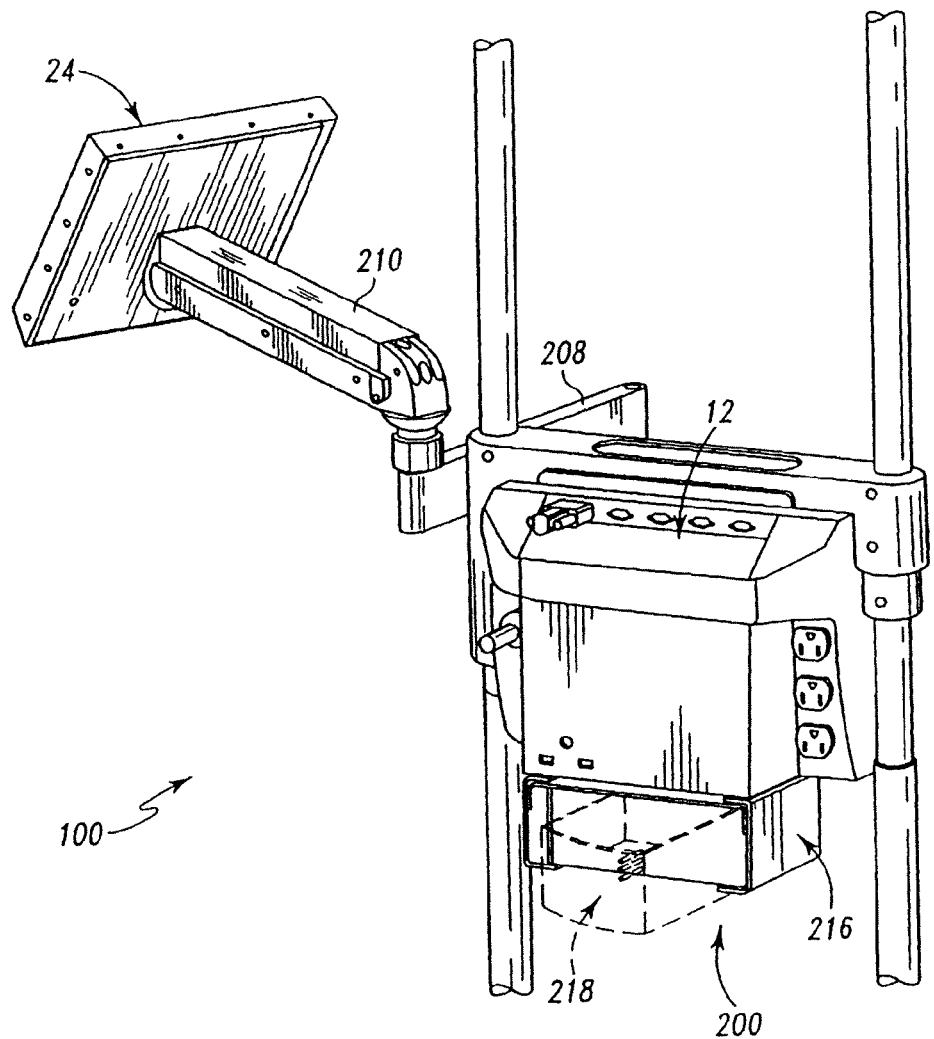

As shown in the figures, medication box 200 is coupled to cart 100 and includes an outer housing 216 and an internal pivotable compartment 218. FIG. 9 shows medication box 200 removed from cart 100. Illustratively, medication box 200 includes tracks 220 formed on outer housing 216 configured to slide into mating tracks 222 formed on cart 100. FIG. 10 shows internal compartment 218 (in dashed lines) in a fully open position.

Figure 11:
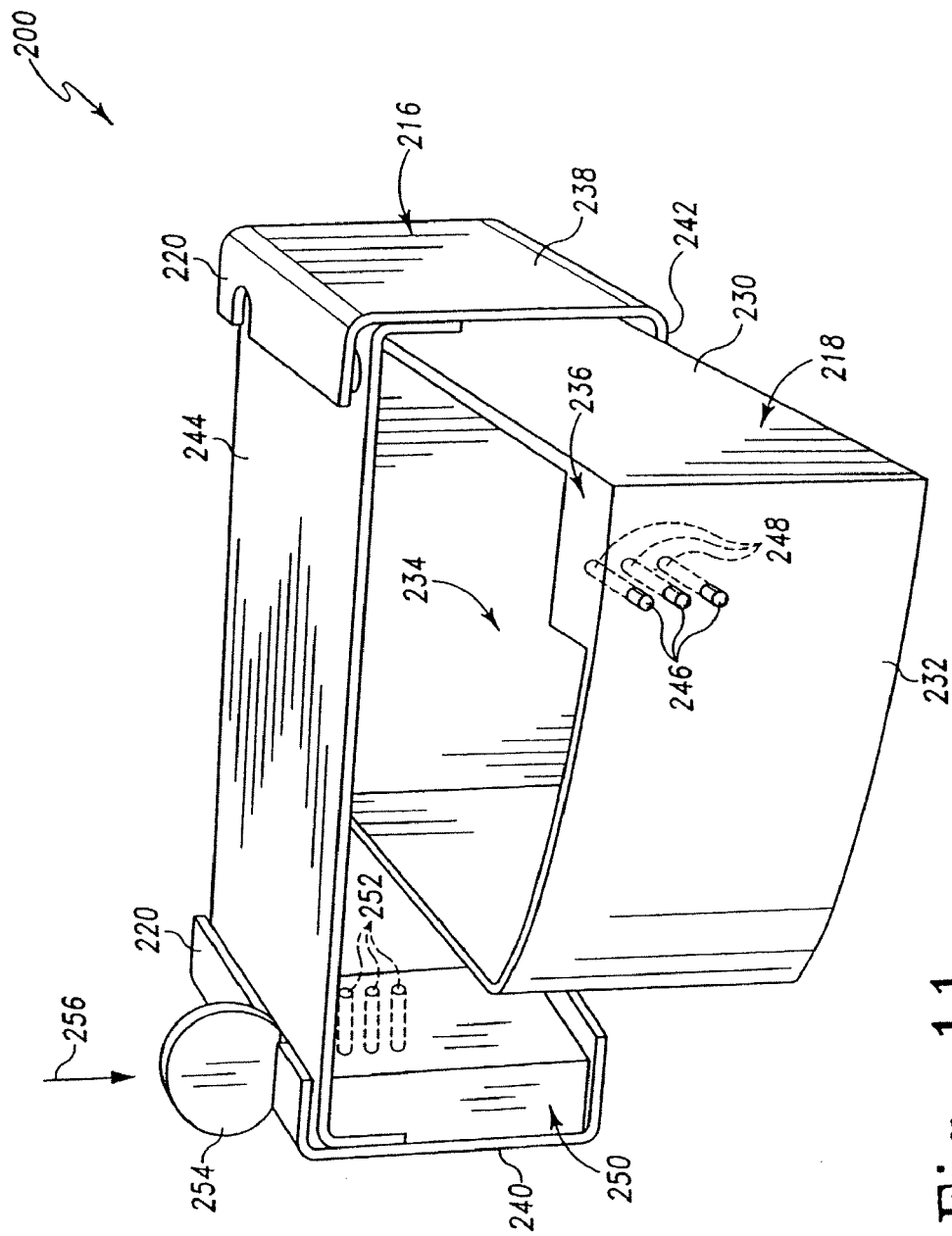

Referring now to FIG. 11, compartment 218 of medication box 200 includes a front panel 230, a curved side wall 232 and an interior region 234 for holding medication 42. Compartment 218 includes a locking portion 236 which holds locking components as described below. Housing 216 includes opposite sidewalls 238, 240, a bottom surface 242, and a top surface 244. Tracks 220 extend above top surface 244. Lock pins 246 extend into apertures 248 formed in sidewall 232 of locking portion 236. Pins 246 are biased by springs (not shown) to extend outwardly from apertures 248.

Housing 216 is formed to include a locking portion 250 that also includes a plurality of pins 252 spaced to align with lock pins 246 when compartment 218 is in a closed position. A key 254 configured for insertion into an aperture (not shown) of track 220, top surface 244, and locking portion 250 in the direction of arrow 256 moves pins 252 from locking portion 250 so that pins 252 move pins 246 into apertures 248, thereby releasing compartment 218. Thus, the normally locked medication box 200 may be unlocked by key 254 when sent to a pharmacy for filling. The nurse may also have a key 254 to unlock compartment 218.

Figure 12:
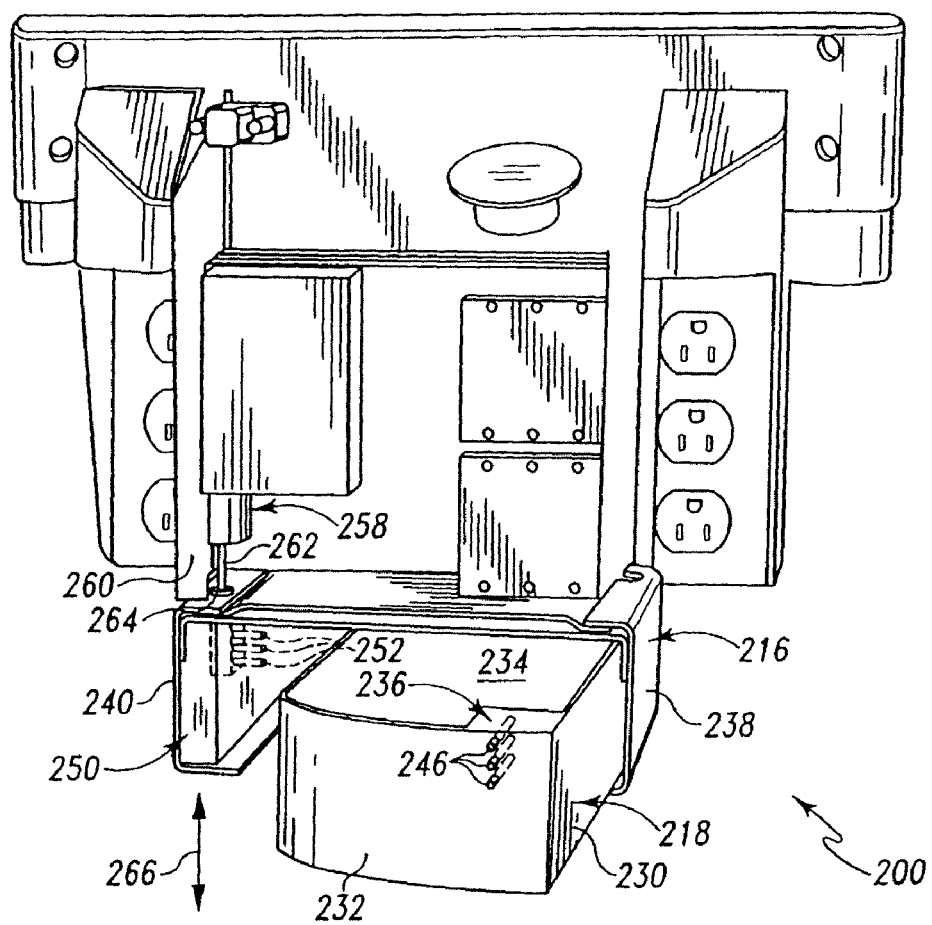
Figure 13:
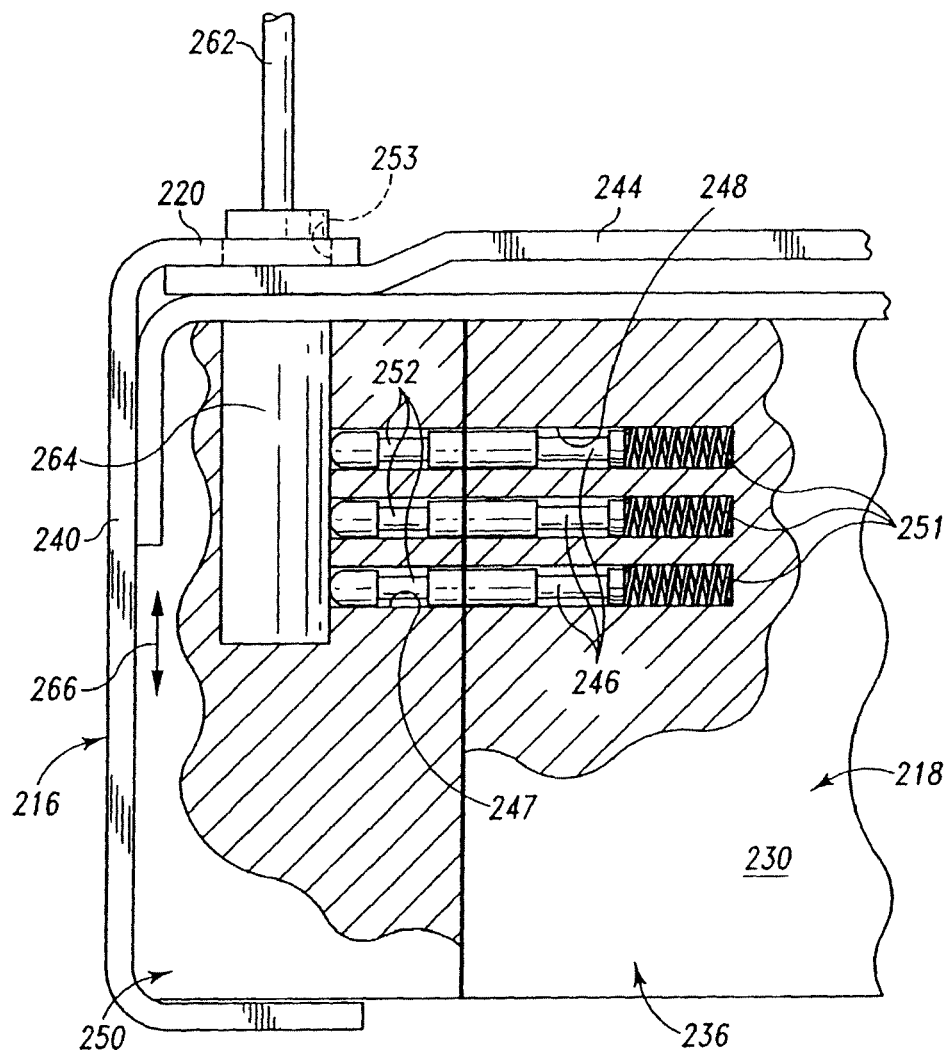
FIGS. 13 and 14 are side elevational views, partly in section, of components of the locked medication box depicted in FIGS. 8-12.
Figure 14:
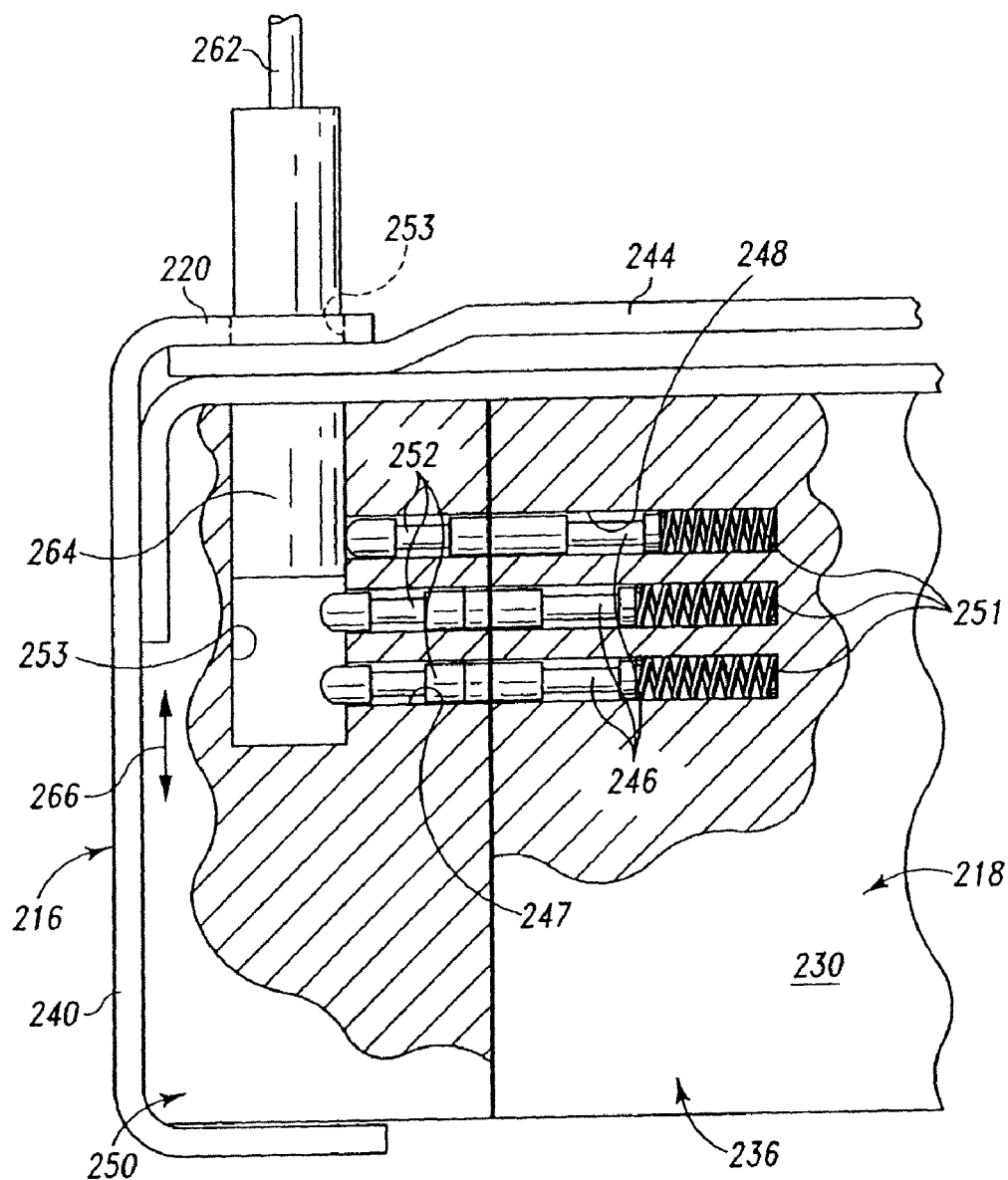

Referring now to FIGS. 12-14, in an alternate embodiment similar to that of FIGS. 8-11, a linear actuator 258 is coupled to a support 260 on cart 100. Actuator 258 is coupled to a stem 262 and key 264 that moves pins 252 in a manner similar to key 254. Illustratively, actuator 258 is a stepper motor that moves key 264 up and down in the direction of double headed arrow 266. Key 264 extends through an aperture 253 (FIGS. 13, 14) of housing 216 to secure housing 216 of medication box 200 to support 260 of cart 100. Key 264 is designed to move pins 252 against the biasing force of springs 251 in apertures 248 of locking portion 236 to a proper location so that pins 246 are retracted from apertures 247 to release compartment 218 for pivotable movement. FIG. 13 shows pins 246 in unlocked positions in which pins 246 are located within apertures 248 of locking portion 236 (flush with the interface between locking portion 250 and locking portion 236) and pins 252 are within locking portion 250. Therefore, compartment 218 can be pivoted to an open position. FIG. 14 shows compartment 218 in a locked position. As shown, key 264 is partially retracted from aperture 253 and two of pins 246 extend into apertures 247 of locking portion 250 on housing 216, thereby preventing compartment 218 from being pivoted to an open position.

Figure 15:
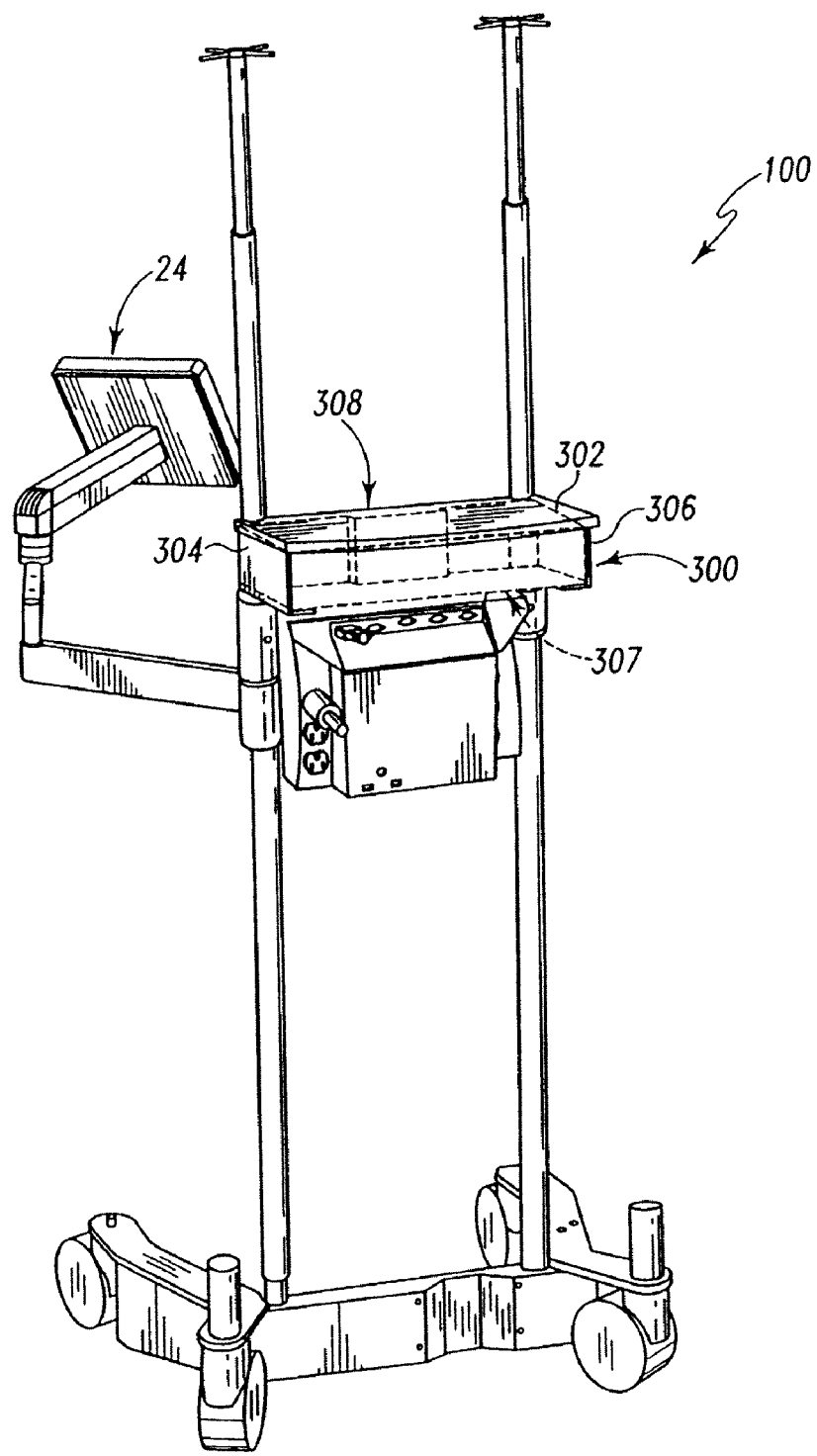
FIGS. 15-18 are perspective views of yet another embodiment of a patient assist cart and locked medication box of the present invention.

Another embodiment of the present invention is illustrated in FIGS. 15-18. In this embodiment, a sliding medical box 300 is coupled to patient assist cart 100. FIG. 15 illustrates cart 100 with display 24 positioned for viewing by, for example, a patient. A work surface 302 is rigidly coupled to patient assist cart 100. Surface 302 provides an area on which a caregiver can work when dispensing medication from medication box 300. Medication box 300 also includes sidewalls 304, 306 which are rigidly coupled to patient assist cart 100.

Figure 16:
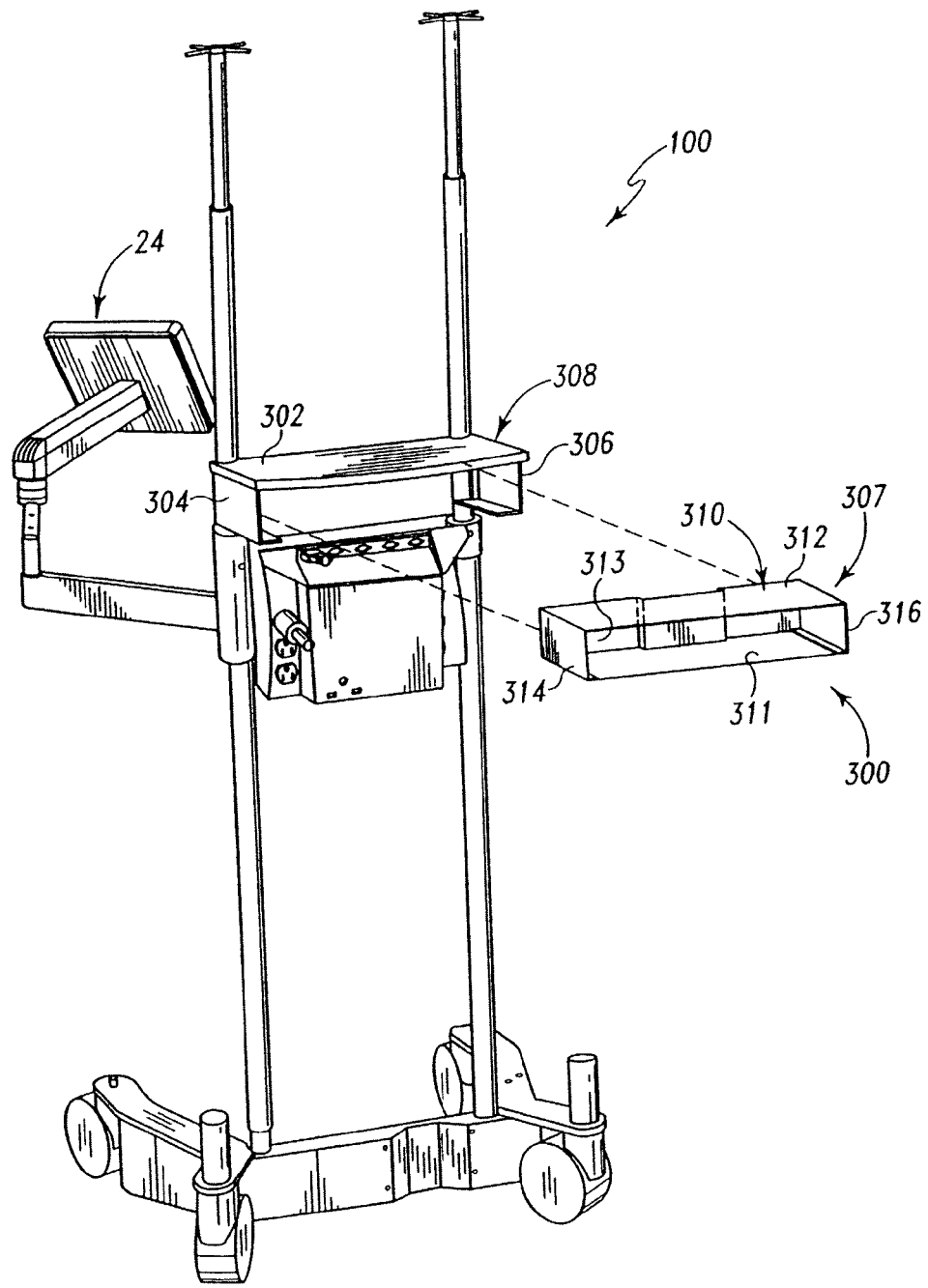
Figure 17:
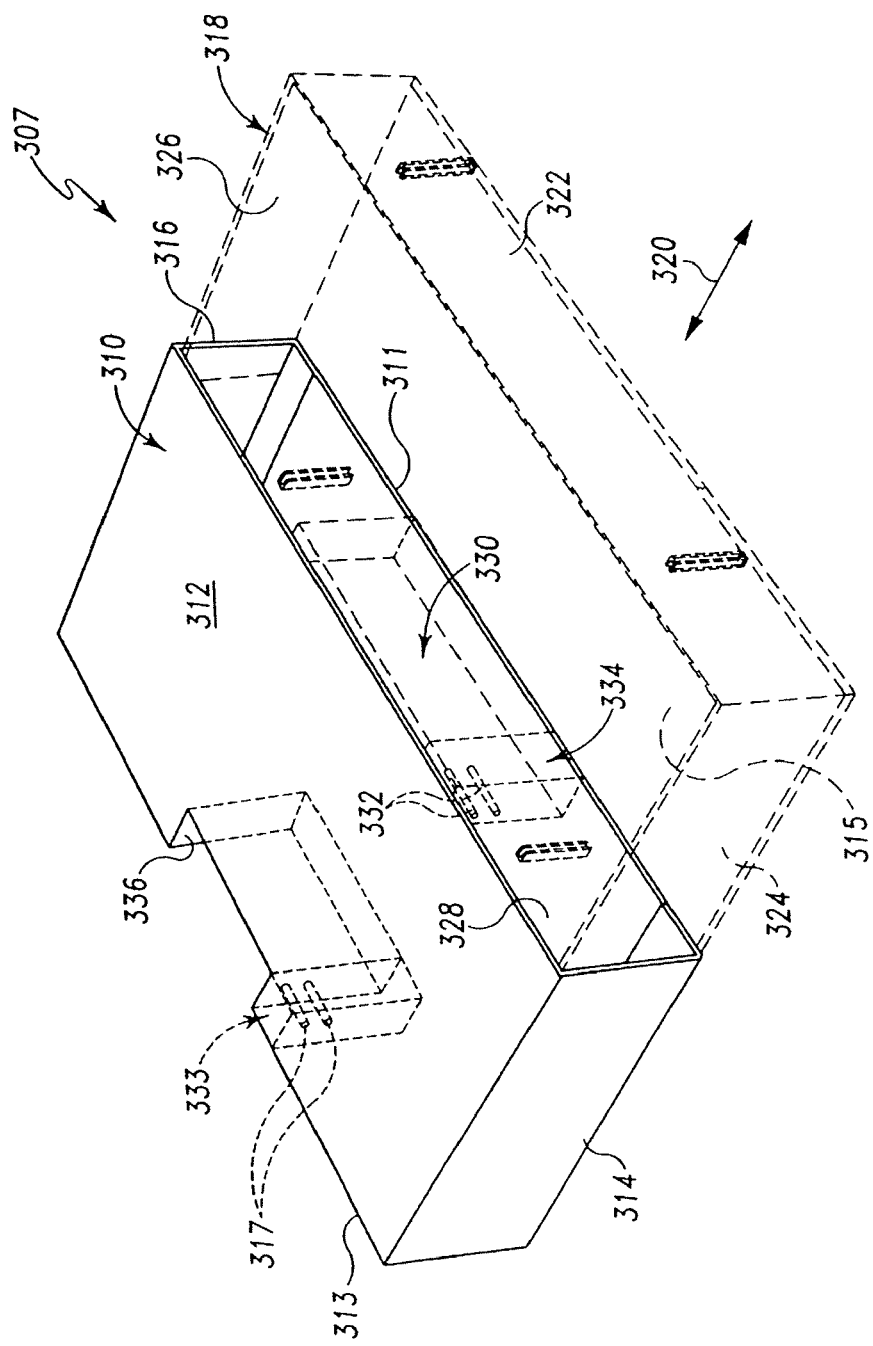

A sliding compartment 307 is removable from a housing 308 defined by work surface 302 and sidewalls 304, 306. As shown in FIG. 16, compartment 307 includes an outer lid or cover 310 having a top wall 312, a bottom wall 311, a rear wall 313, and sidewalls 314, 316. As best shown in FIG. 17, compartment 307 also includes a drawer or tray 318 (shown in dashed lines) that is moveable into and out of cover 310 in the direction of double headed arrow 320. Tray 318 includes a front wall 322, sidewalls 324, 326, a bottom wall 315, and a rear wall 328. Tray 318 also includes a recessed portion 330. Locking pins 332 are located in a locking portion 334 of tray 318 located adjacent recessed portion 330. Cover 310 includes a corresponding notched portion 336 that permits access to recessed portion 330 of tray 318 through cover 310.

Figure 18:
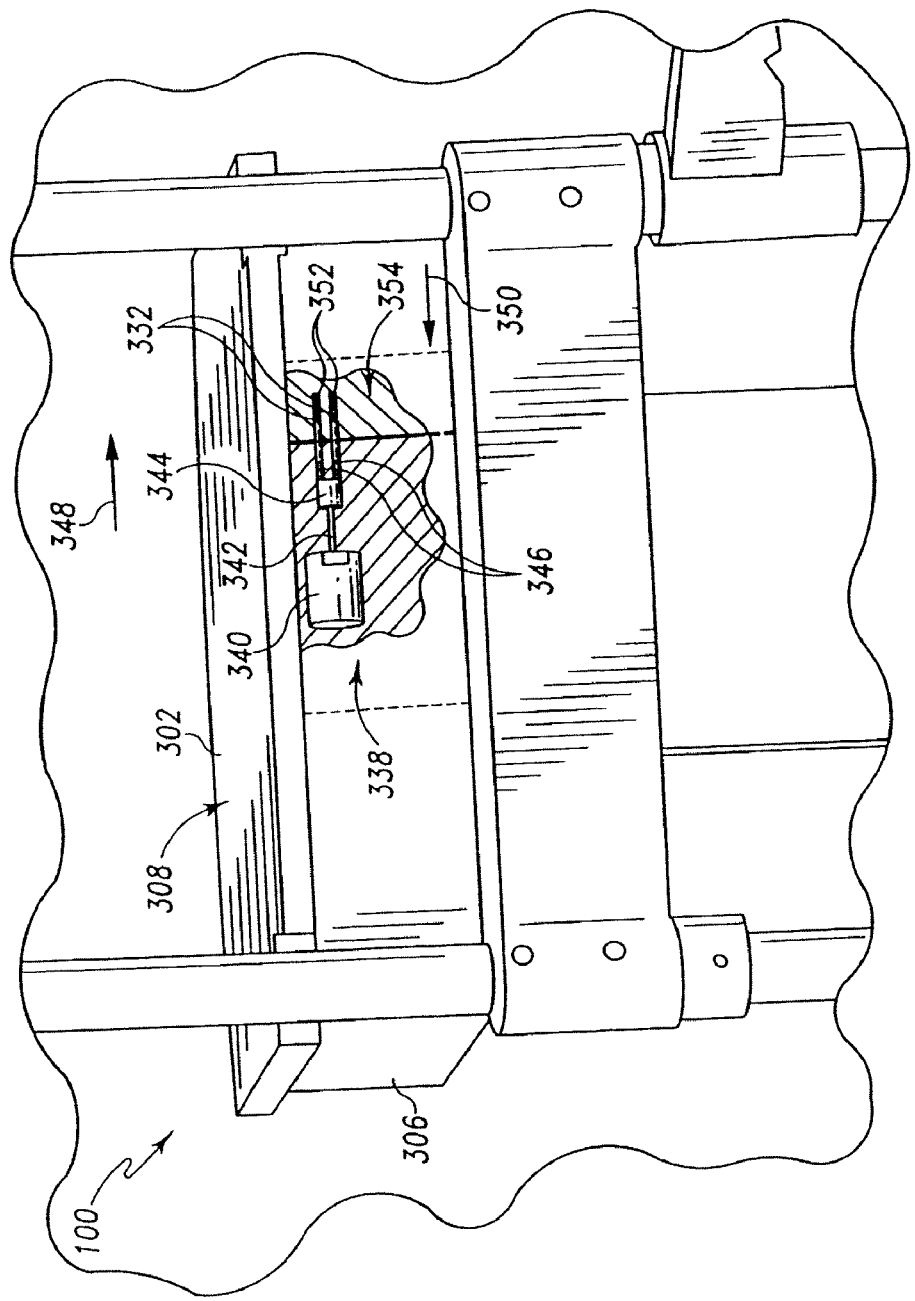

As shown in FIG. 18, a linear motor lock mechanism 338 is coupled to cart 100. Mechanism 338 includes a linear motor 340 coupled to a stem 342. Stem 342 is coupled to a key 344 configured to move pins 346 as motor 340 moves stem 342 and key 344 in the direction of arrow 348 in FIG. 18. Key 344 and pins 346 remain with cart 100. Pins 332 of tray 318 are spring biased in the direction of arrow 350 by springs 352. When tray 318 is fully inserted into cover 310 and housing 308 on cart 100, pins 332 enter locking apertures that also contain pins 346. Pins 332 also pass through apertures 317 formed through a portion 333 (FIG. 17) of rear wall 313 of cover 310 to secure tray 318 to cover 310. When linear motor lock mechanism 338 is operated to move key 344 to a first position, pins 346 urge pins 332 to the right as viewed in FIG. 18 against the biasing force of springs 352 to unlock tray 318 from cover 310 to permit sliding movement of tray 318 relative to cover 310 in the direction of arrow 320 (FIG. 17). Pins 346 retain cover 310 in position relative to housing 308 of cart 100. When linear actuator 340 is actuated to retract key 344, cover 310 and tray 318 are removable as a unit from cart 100. Pins 332 still engage cover 310 so that tray 318 is locked inside cover 310 even when cover 310 is removed from cart 100.

Figure 19:
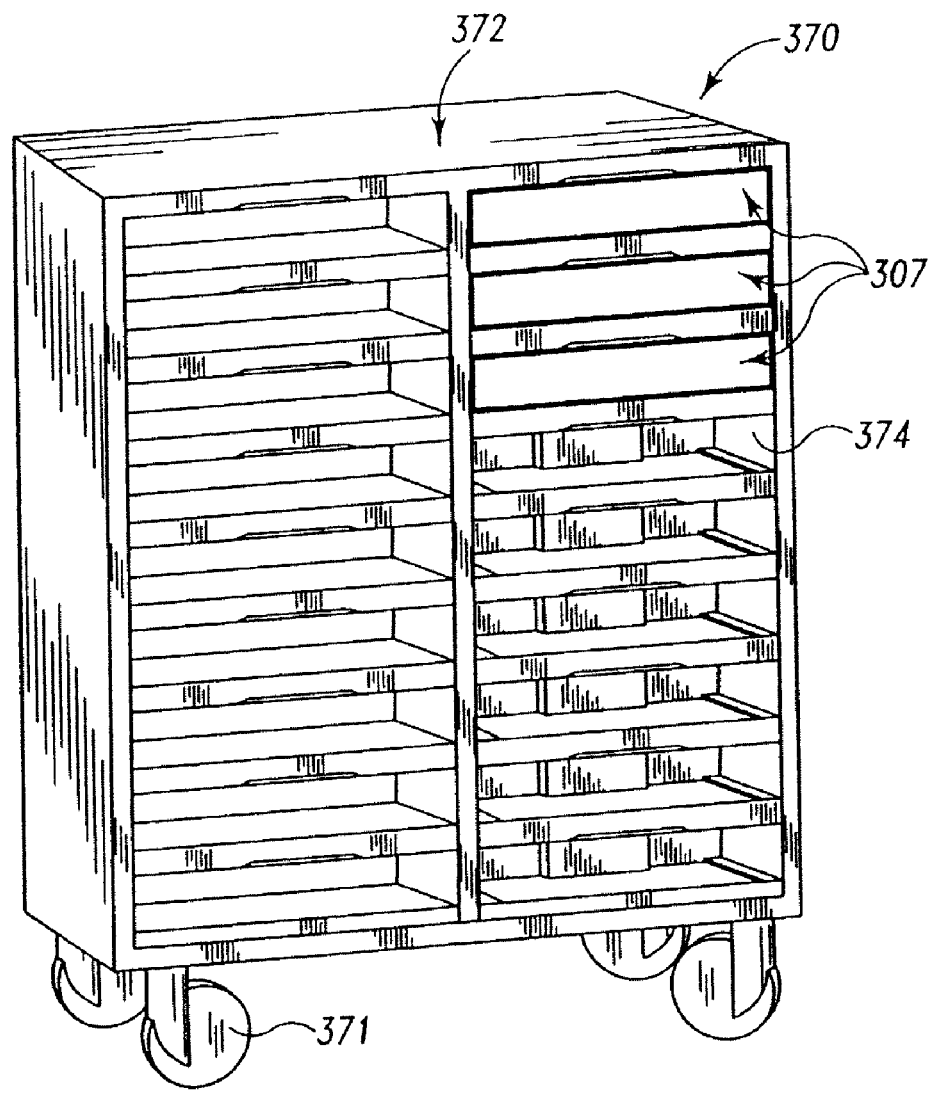
FIGS. 19 and 20 are perspective views of a transport cart for transporting medication boxes.
Figure 20:
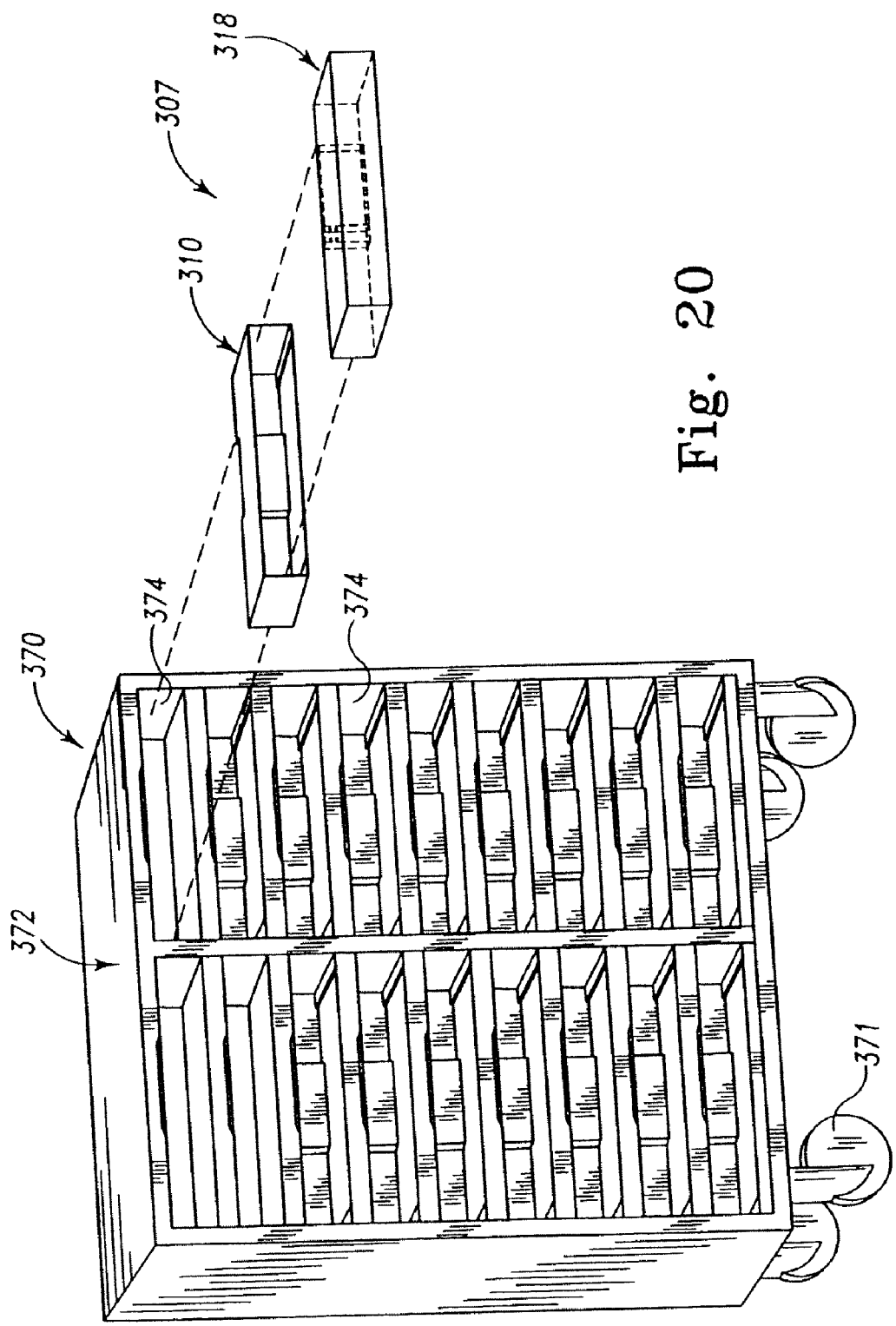
Figure 21:
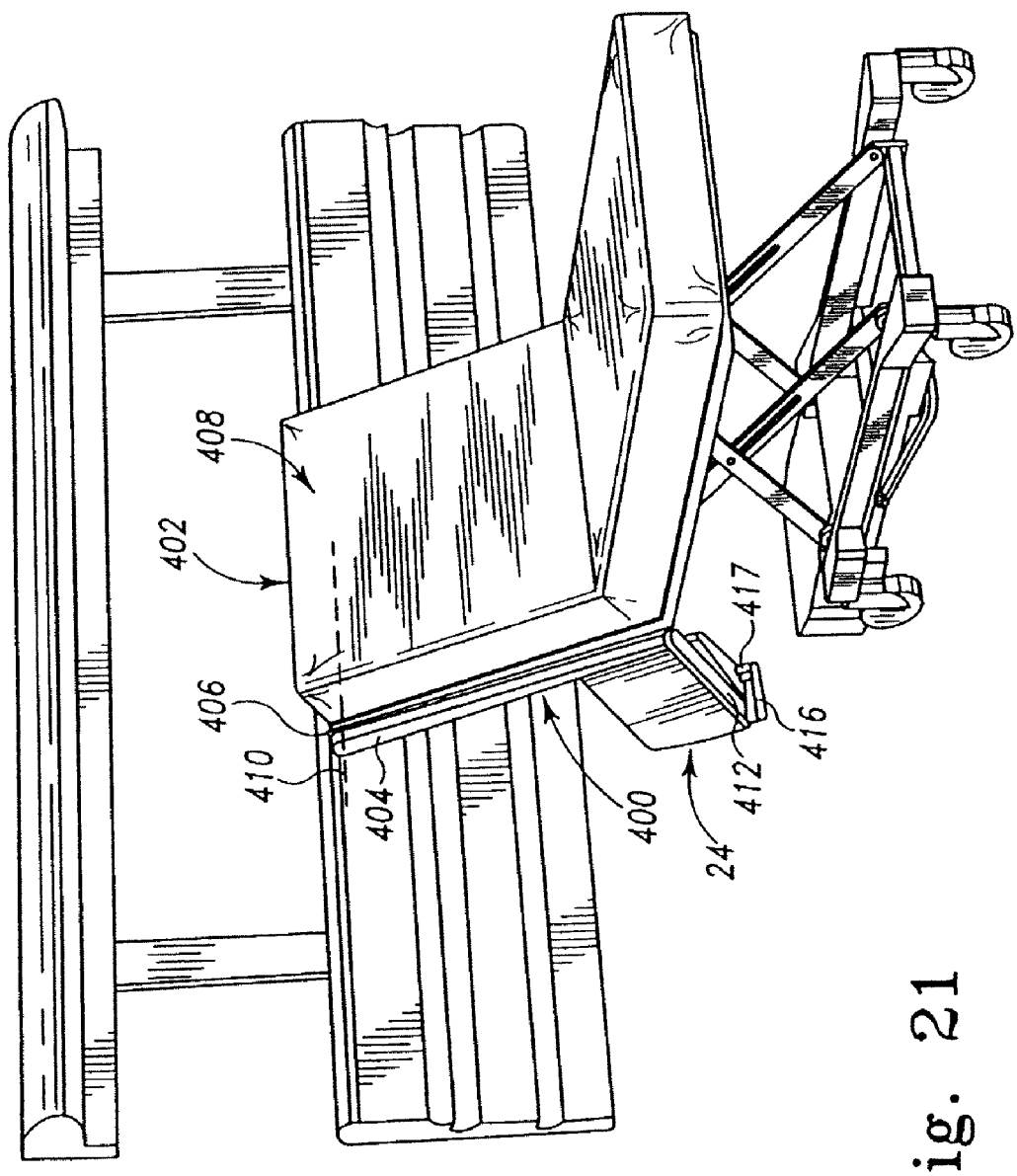
FIGS. 21-24 are perspective views of one mounting configuration of a point-of-care computer display of the present invention.
Figure 22:
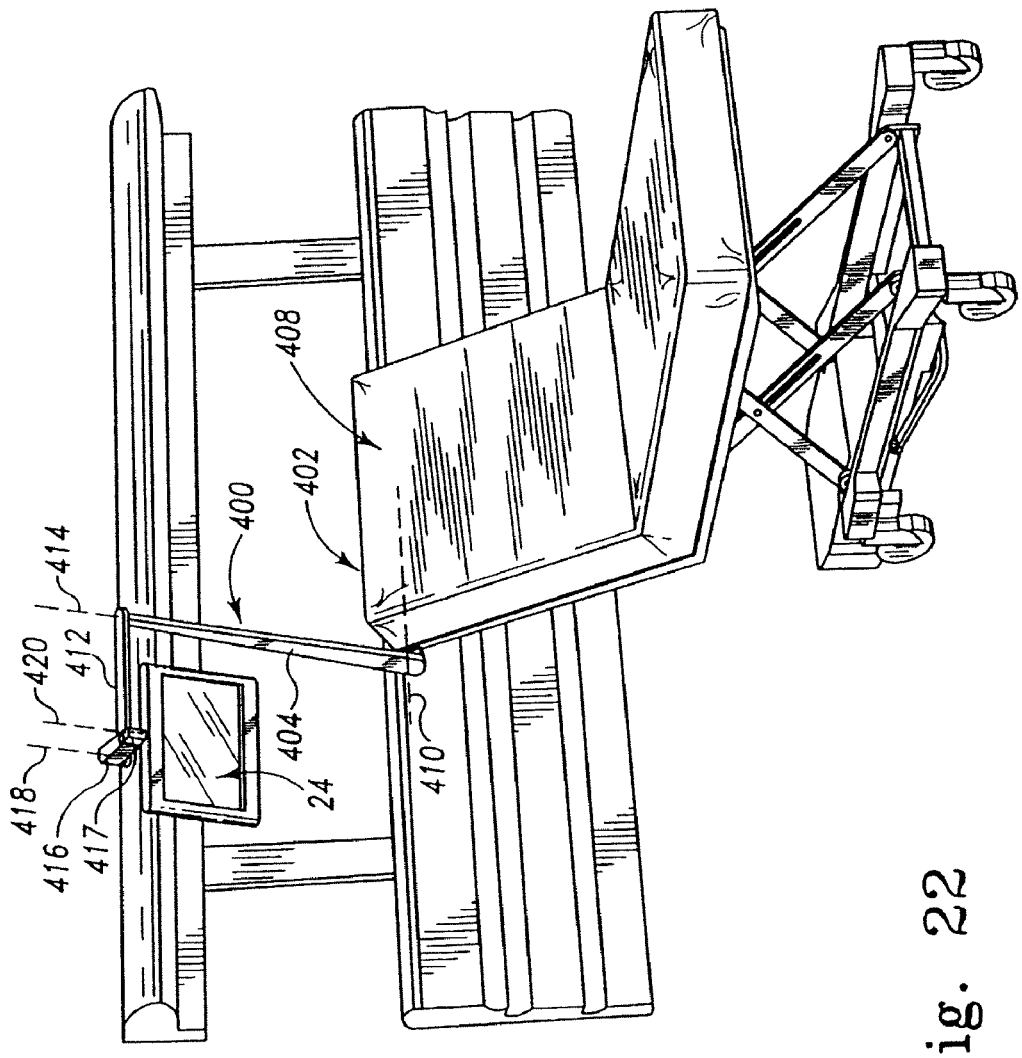

Locked compartments 307 can be loaded into a transport cart 370 as shown in FIGS. 19 and 20. Cart 370 includes a housing 372 having a plurality of receptacles 374 configured to receive compartments 307. Cart 370 may further include wheels or casters 371 so that cart 370 can be transported to and from a pharmacy for loading trays 318 with appropriate medication for each patient. Cart 100 may also include locks such as the locking mechanisms discussed above with reference to cart 100. FIG. 20 shows the entire cover 310 and tray 318 removed from a receptacle 374.

In another embodiment of the present invention, tray 318 does not include pins 332. Instead, key 344 or another latch mechanism enters an aperture or receptacle formed in tray 318 to lock tray 318 in a closed position on cart 100 when desired. When the actuator removes key 344 or latch from the receptacle in tray 318, cover 310 and tray 318 are removable from cart 100. In this embodiment, tray 318 is not locked to cover 310 when medication box 300 is removed.

Another embodiment of the present invention is illustrated in FIGS. 21-24. Display 24 discussed above with reference to FIGS. 4, 5A, and 5B is coupled to an arm assembly 400 secured to a bed 402. Arm assembly 400 includes a first arm 404, a second arm 412, a third arm 416, and a coupler 417 connected to display 24. Arm 404 is pivotally coupled to a frame 406 of bed 402 adjacent a head end 408 of bed 402. Arm 404 is pivotable about a transverse axis 410 from a storage position illustrated in FIG. 21 to an elevated position illustrated in FIG. 22. Arm 412 is coupled to arm 404 for rotation about axis 414. Arm 416 is coupled to arm 412 for rotation about axis 418. Coupler 417 is coupled to an opposite end of arm 416 for rotation about axis 420. Finally, coupler 417 is coupled to display 24. Therefore, arm assembly 400 can be moved to position display 24 in a plurality of different positions relative to bed 402 for viewing by a caregiver and/or a patient, and for entering information into computer 12 via display 24 by the caregiver and/or patient.

Figure 23:
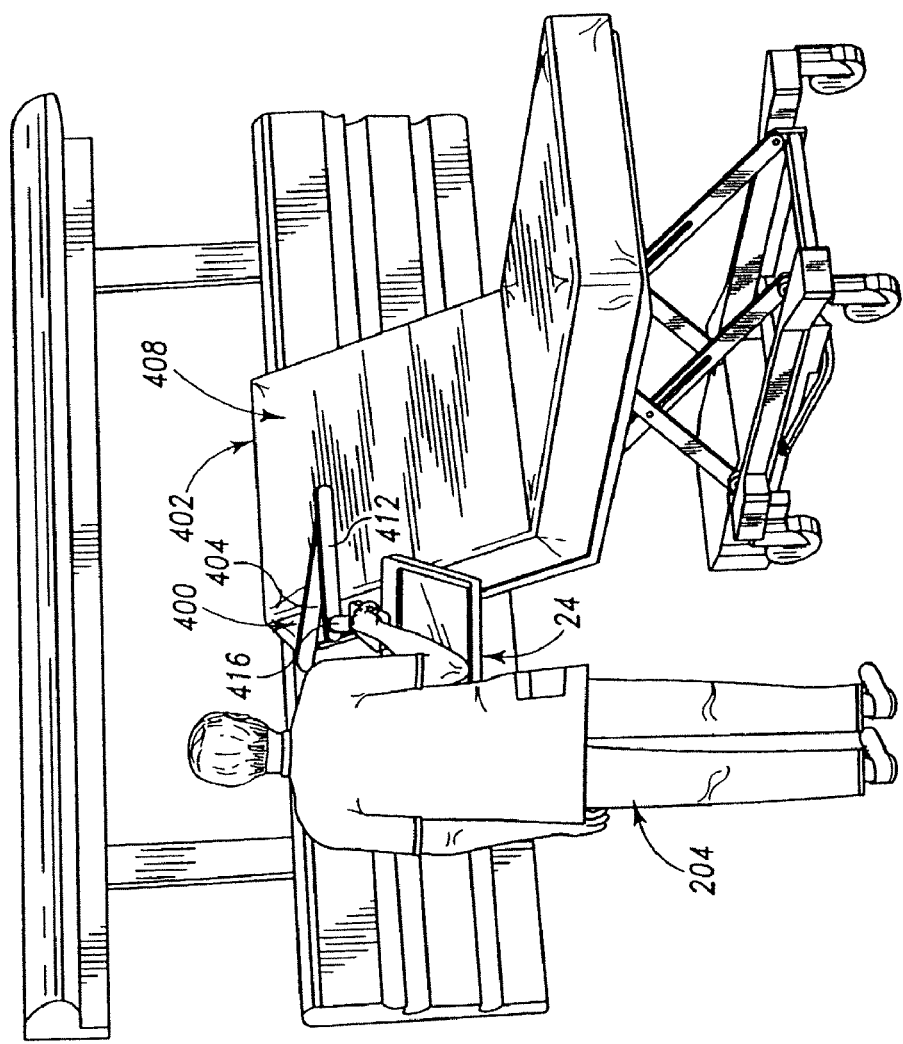
Figure 24:
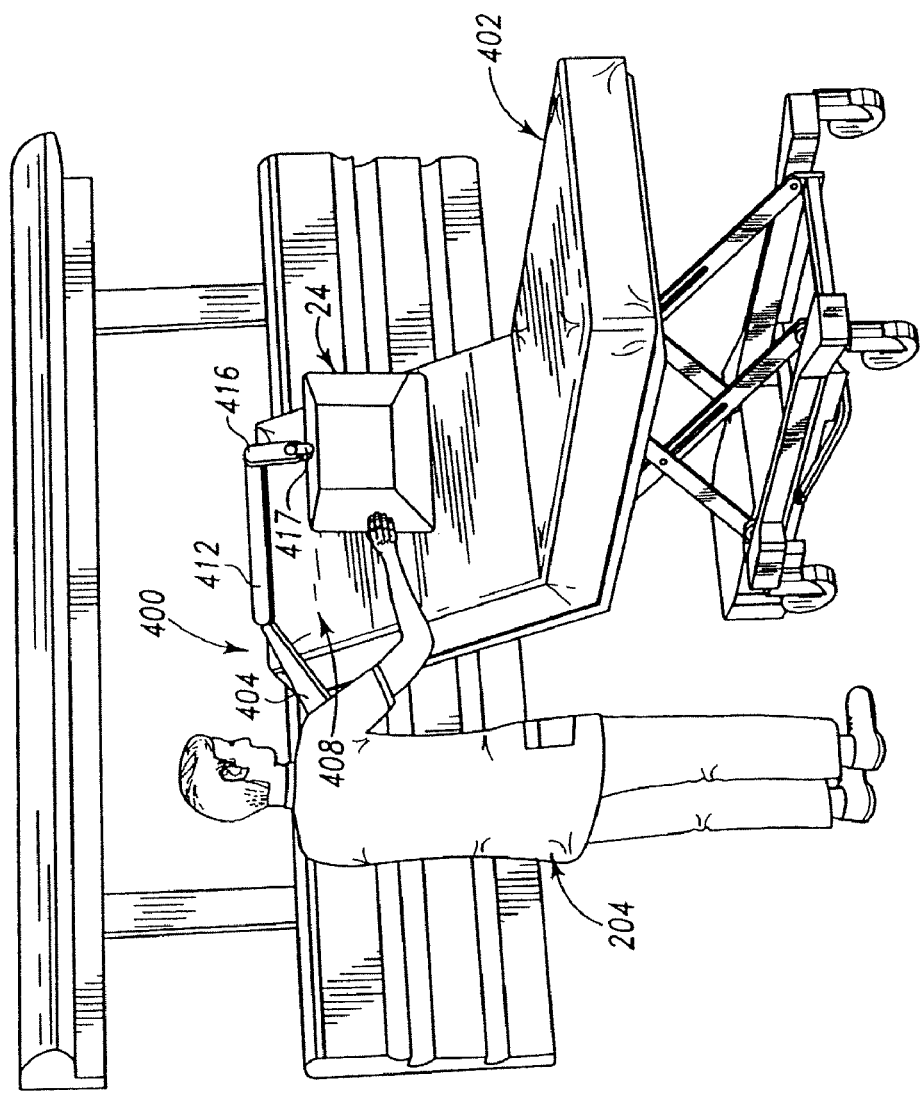

FIG. 23 illustrates arm 404 pivoted to a substantially horizontal position, arm 412 pivoted outwardly from bed 402, arm 416 pivoted downwardly, and display 24 angled for viewing and facilitating entry of information into computer 12 by a caregiver 204 using display 24. FIG. 24 illustrates arm assembly 400 positioned so that display 24 is accessible by a patient. Therefore, the patient can view display 24 for information or entertainment and can also enter information into computer 12 via display 24.

Figure 25:
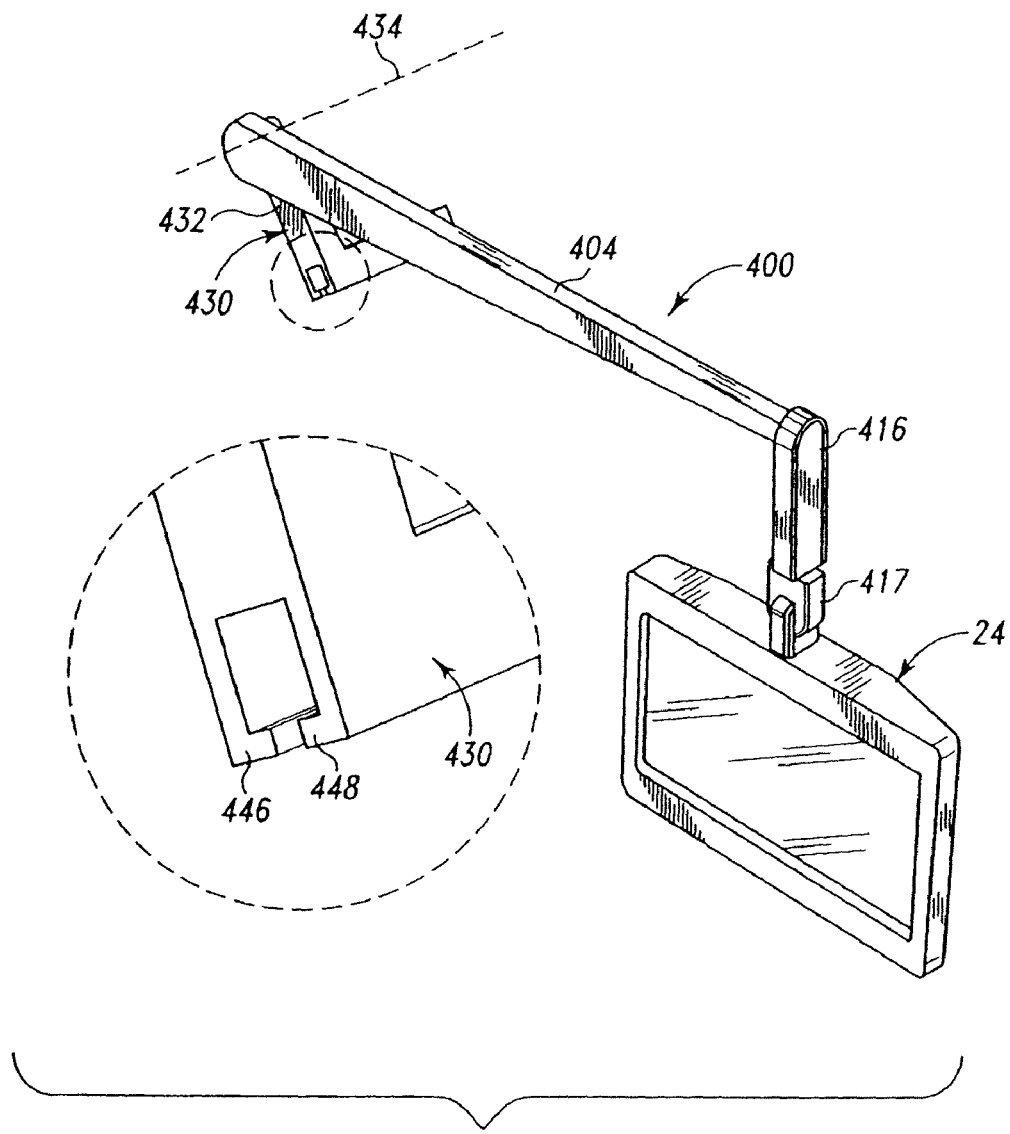
FIGS. 25-27 are perspective views of another embodiment of a mounting configuration.
Figure 26:
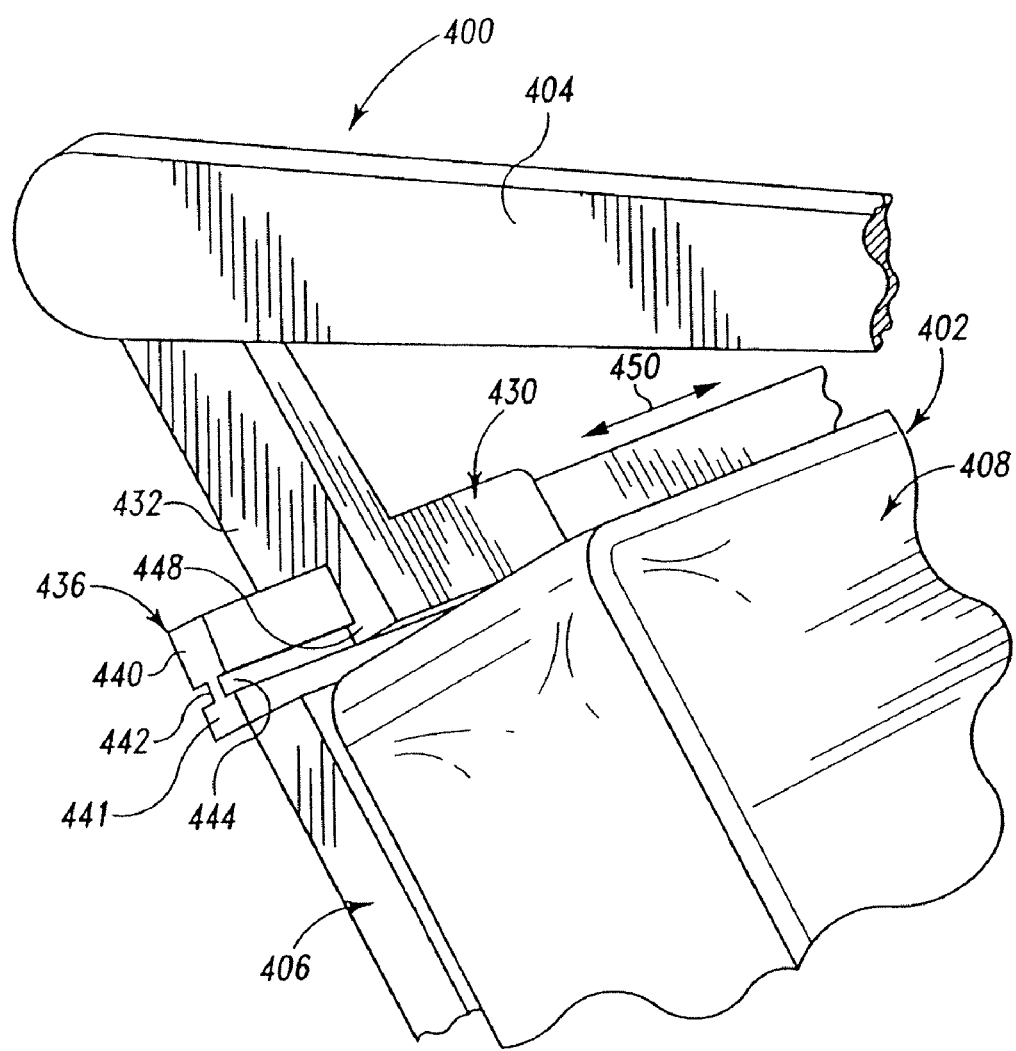
Figure 27:
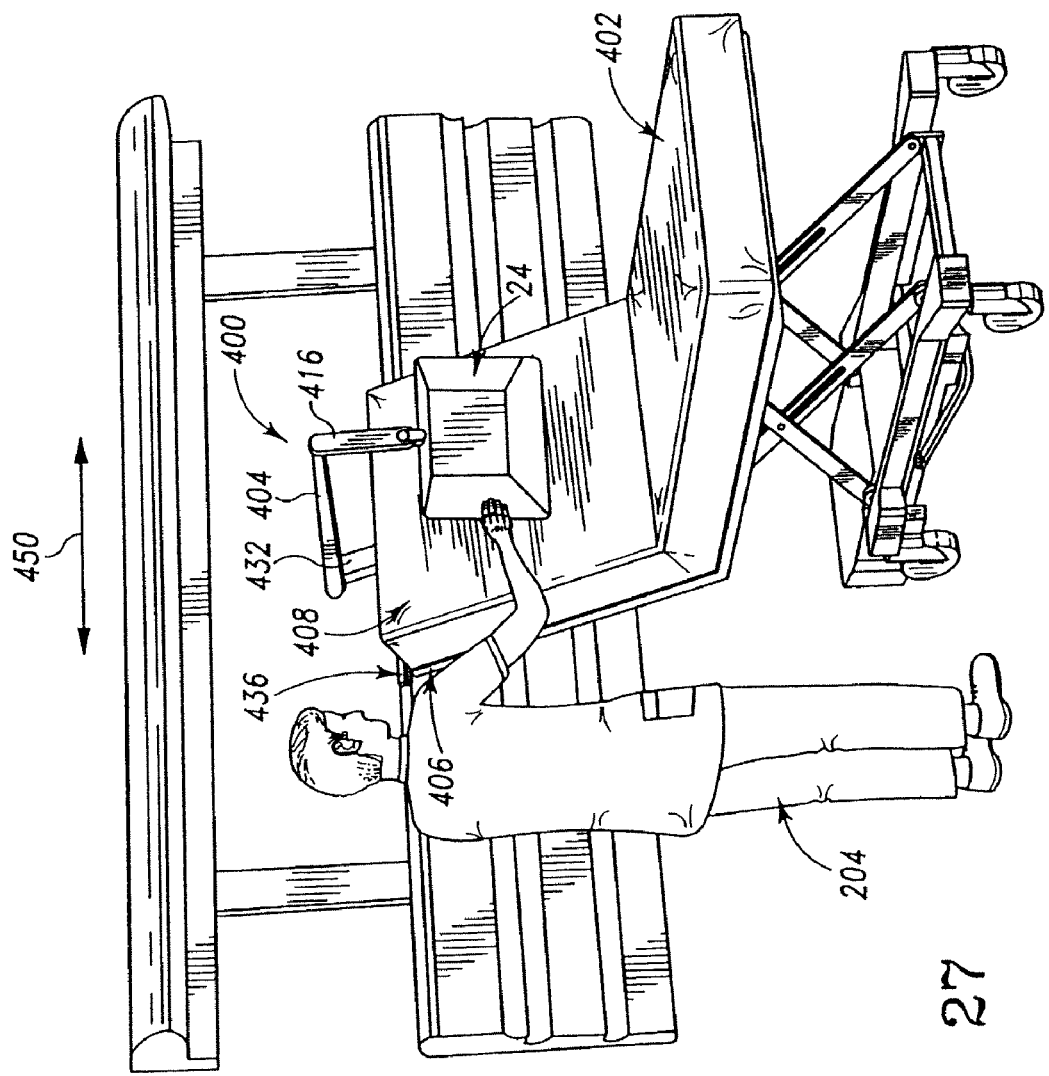

Another embodiment of the present invention is illustrated in FIGS. 25-27. In this embodiment, arm 404 is pivotally coupled to a sliding member 430 for rotation about an axis 434. Sliding member 430 includes an arm 432 coupled to arm 404. Sliding member 430 is formed to slide onto a track member 436 connected to a head end 408 of bed frame 406 as best shown in FIG. 26. Track member 436 illustratively includes a head portion 440, notches 442, 444, and a foot portion 441 connected to bed frame 406. Flanges 446, 448 on sliding member 430 enter notches 442, 444, respectively, to movably couple sliding member 430 to track member 436 on bed 402. Sliding member 430 is slideable back and forth in the direction of double headed arrow 450 shown in FIGS. 26 and 27. Therefore, arm assembly 400 can be positioned at a plurality of desired positions along head end 408 of bed 402. In another embodiment, sliding member 430 is slideable on a track extending around the entire outer periphery of bed 402 to position arm assembly 400 in any of a plurality of desired locations around bed 402.

Figure 28:
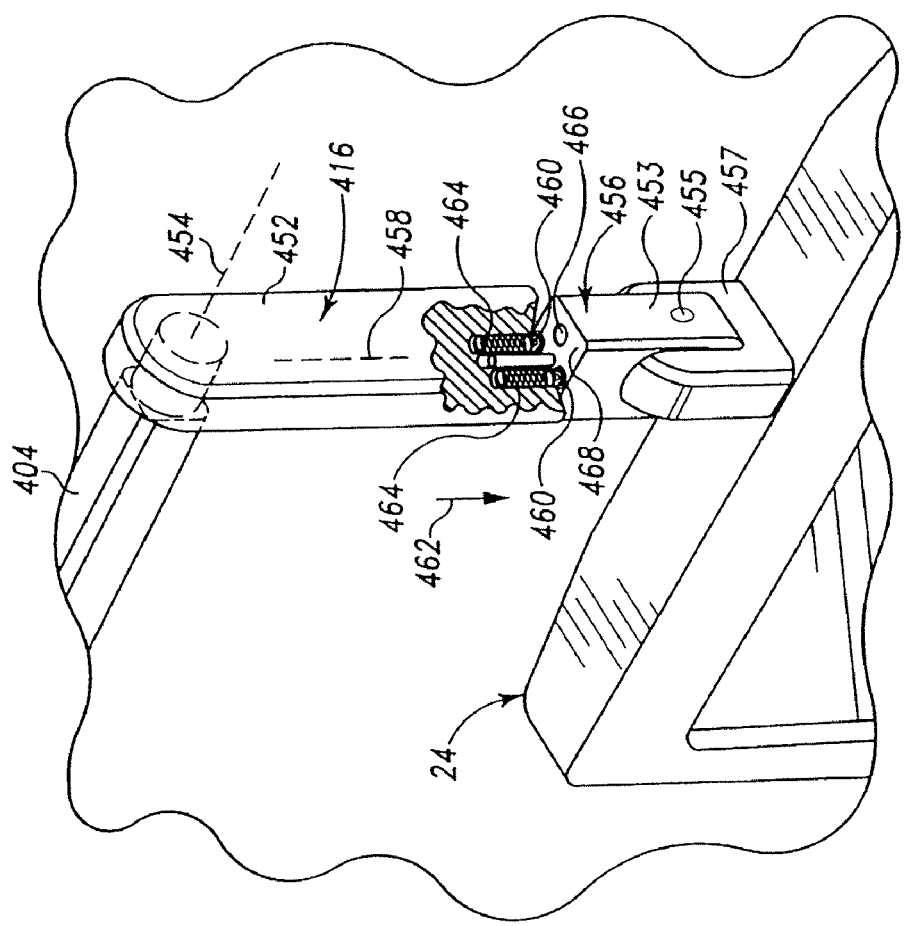
FIGS. 28 and 29 are perspective views of a detent coupling mechanism for use in the various disclosed mounting configurations.
Figure 29:
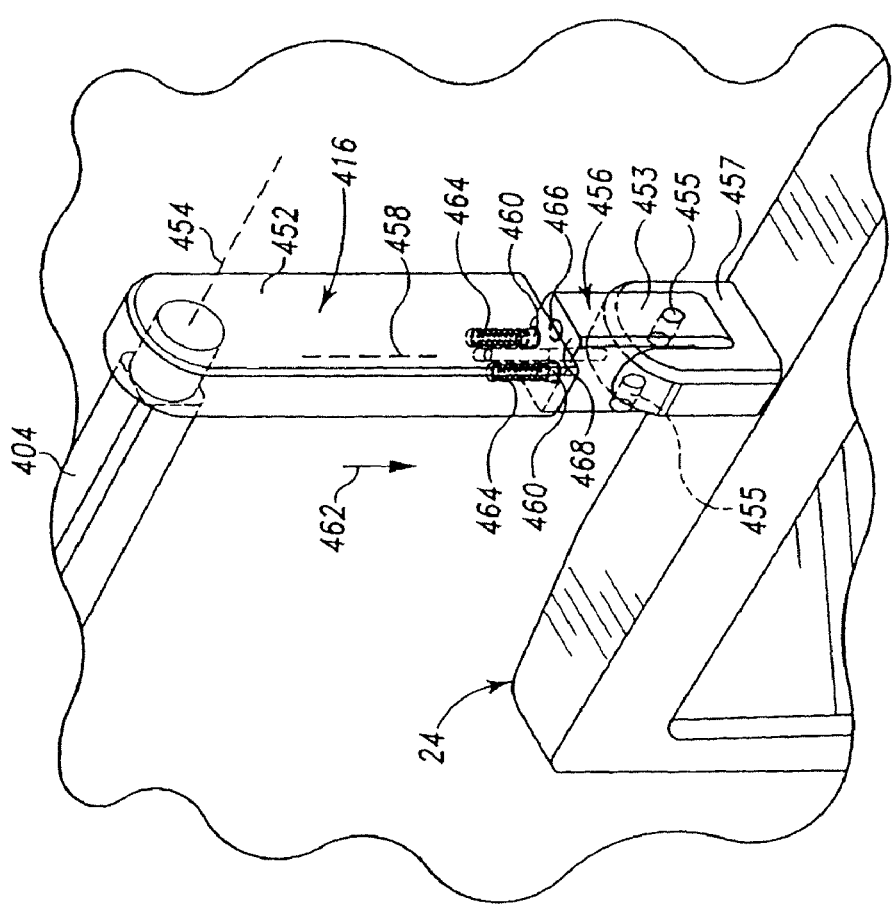
Figure 30:
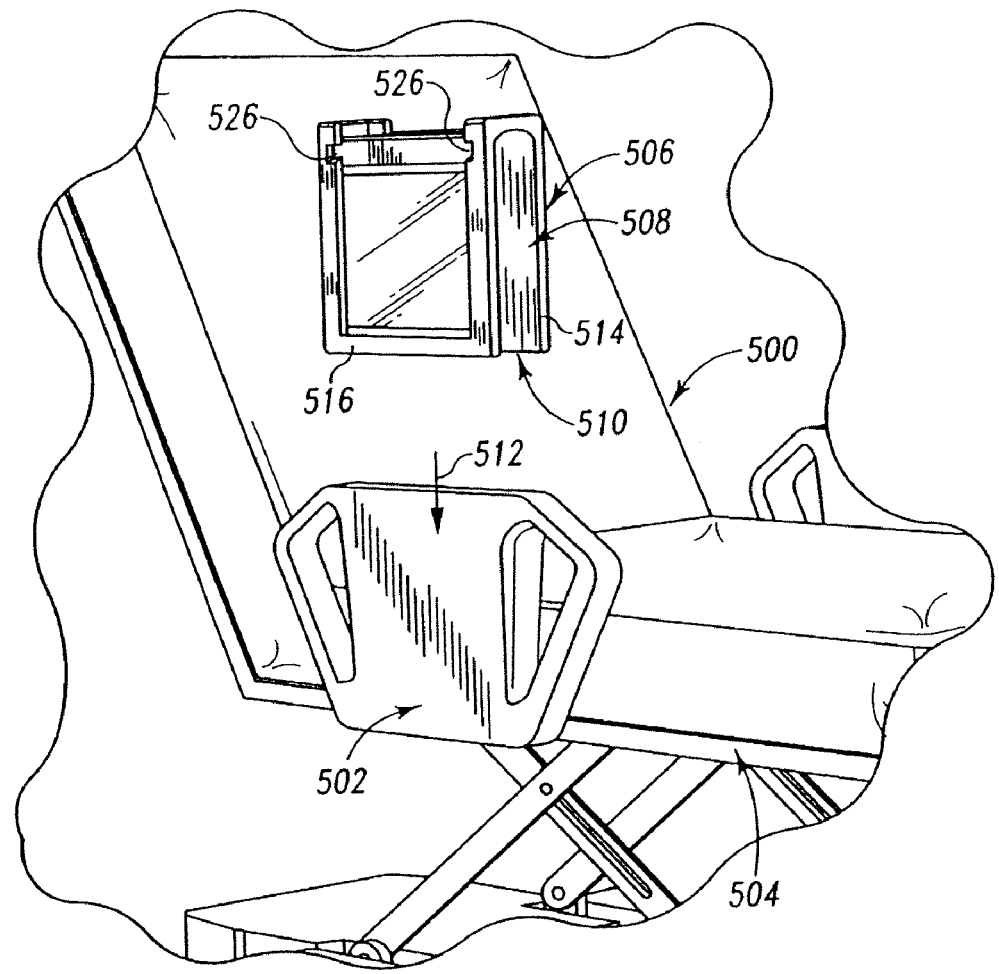
FIGS. 30-34 are perspective views of a display carrier mounting configuration.

In the illustrated embodiment, arms 432, 404, 412, and 416 are coupled together by a plurality of detents to hold the arms at desired locations relative to each other. It is understood that other types of locking mechanisms and clutch mechanisms can be used to hold the arms in desired relative positions. FIGS. 28 and 29 illustrate a first connector 452 of arm 416 pivotably coupled to arm 404 for rotation about axis 454. Arm 416 is coupled to another arm 456 for rotation about a longitudinal axis 458. Detent balls 460 are spring biased downwardly in the direction of arrow 462 by springs 464. Balls 460 enter recesses 466 formed in top surface 468 of arm 456 to hold arms 416 and 456 in selected orientations relative to each other. Arm 456 also includes a pair of extensions 453 that each include a pin 455 for extending into openings formed in a coupler 457 connected to display 24 as best shown in FIG. 29. Coupler 457 and display 24 can thus be rotated about pins 455.

Figure 31:
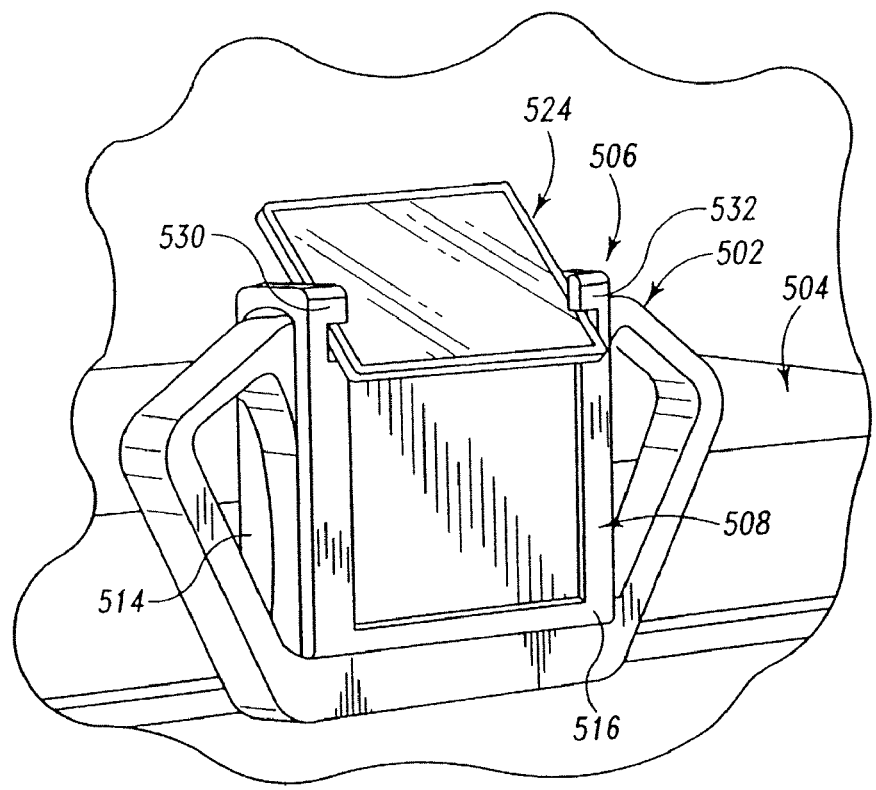
Figure 32:
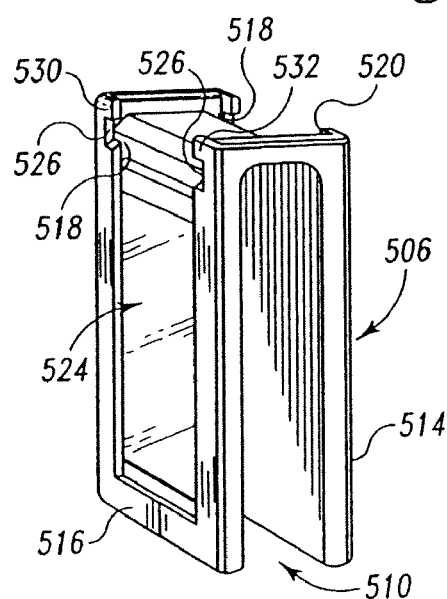
Figure 33:
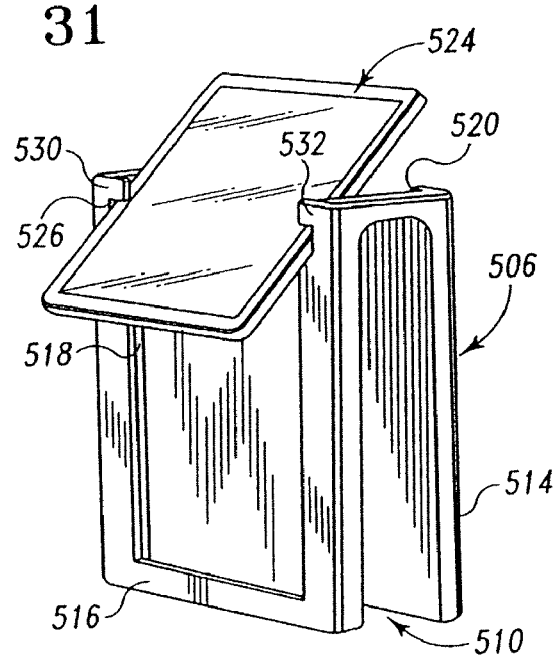

Another embodiment of the present invention is illustrated in FIGS. 30-34. In this embodiment, a bed 500 includes siderails 502 mounted on opposite sides of bed frame 504. A display carrier 506 includes a U-shaped body portion 508 including an open end 510 slideable over siderail 502 in the direction of arrow 512 shown in FIG. 30. FIG. 31 illustrates carrier 506 installed on siderail 502. As best shown in FIGS. 32 and 33, carrier 506 includes first and second side portions 514, 516. Each side portion 514, 516 includes spaced apart tracks 518, 520 configured to receive a removable display 524 which functions in the same manner as display 24 discussed above with reference to FIGS. 4, 5A, and 5B.

Display 524 is slideably inserted into tracks 518, 520 on either side portion 514, 516 of carrier 506. Display 524 is also moveable to an angled position (shown in FIGS. 31 and 33) extending through slots 526, 528 formed in tracks 518, 520 of side portion 516, respectively, and held in place by tabs 530, 532 which engage opposite sides of display 524. Therefore, a caregiver can view display 524 and enter information using display 524 as discussed above.

Figure 34:
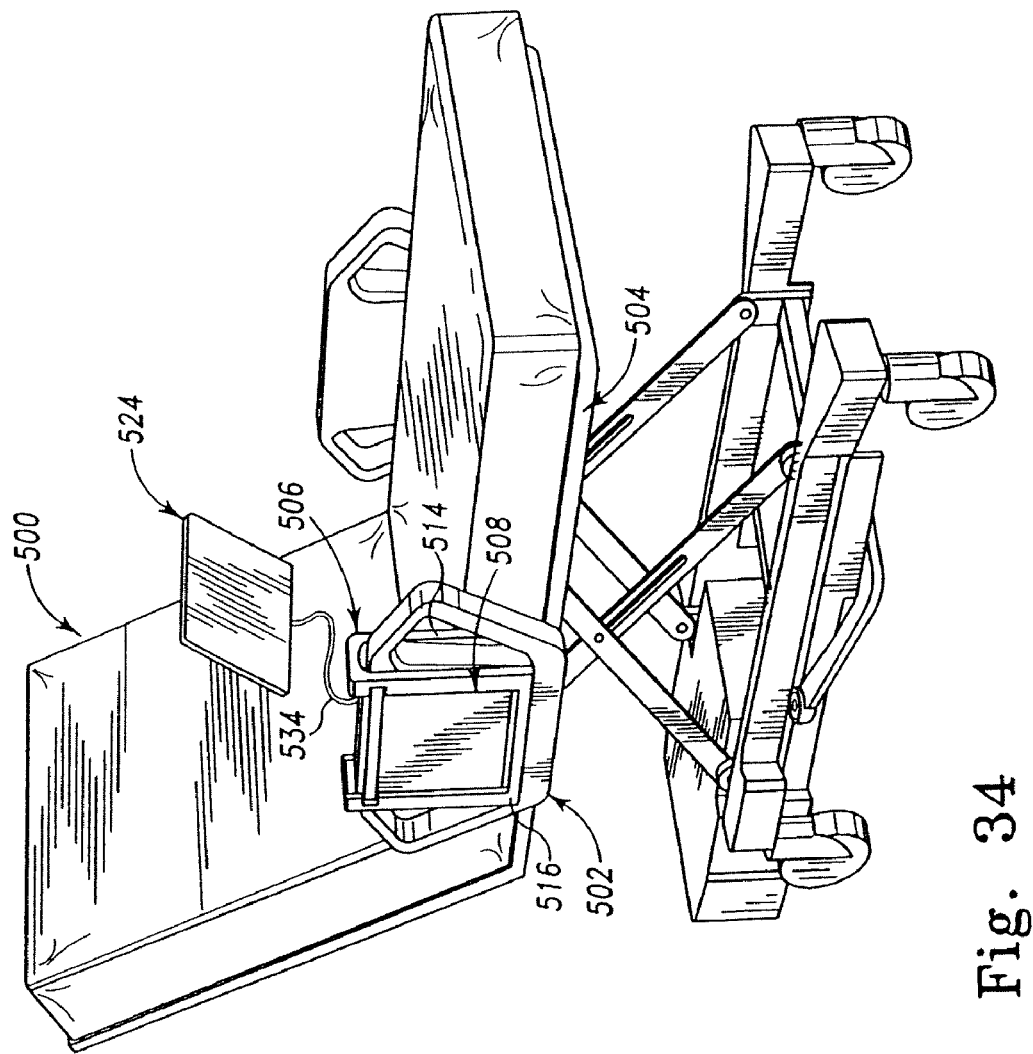

In operation, carrier 506 is installed on siderail 502 on either side of bed 500. If desired, a suitable fastener such as a screw, bolt, strap, or Velcro® fastener may be used to attach carrier 506 to siderail 502. Display 524 is then removable from tracks 518, 520 so that display 524 is accessible to the patient or caregiver. FIGS. 31 and 33 illustrate display 524 accessible by caregiver 204. As shown in FIG. 34, display 524 may also be removed from carrier 506. In this variation of the described embodiment, a cable 534 is coupled to display 524 and to computer 12 as discussed above. A patient can then orient display 524 in a desired manner to position and utilize display 524 for viewing information or entertainment programs and/or entering information and commands, accessing and creating messages, or using the Internet as discussed herein.

Figure 35:
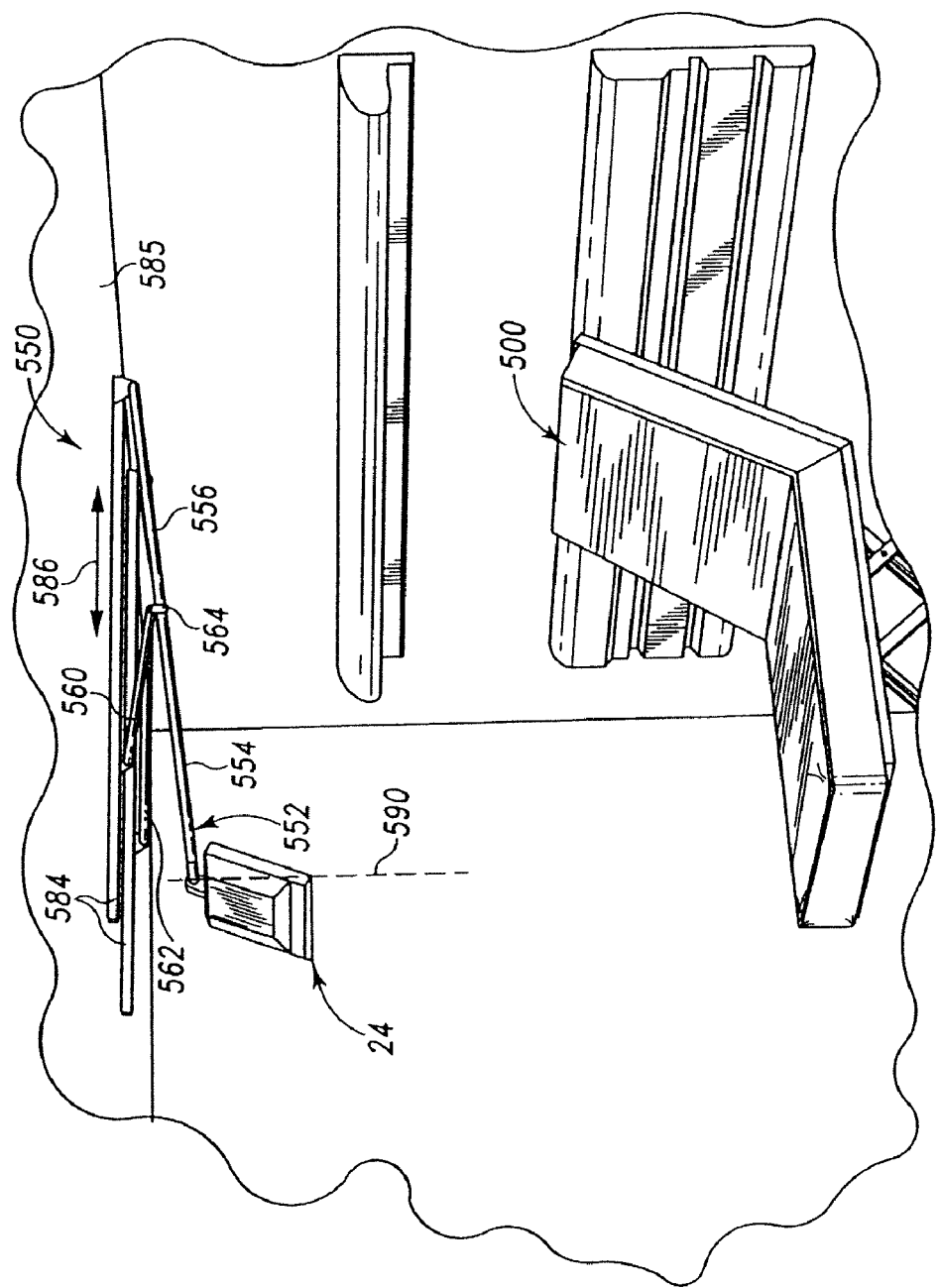
FIGS. 35 and 36 are perspective views of another mounting configuration of the present invention.
Figure 36:
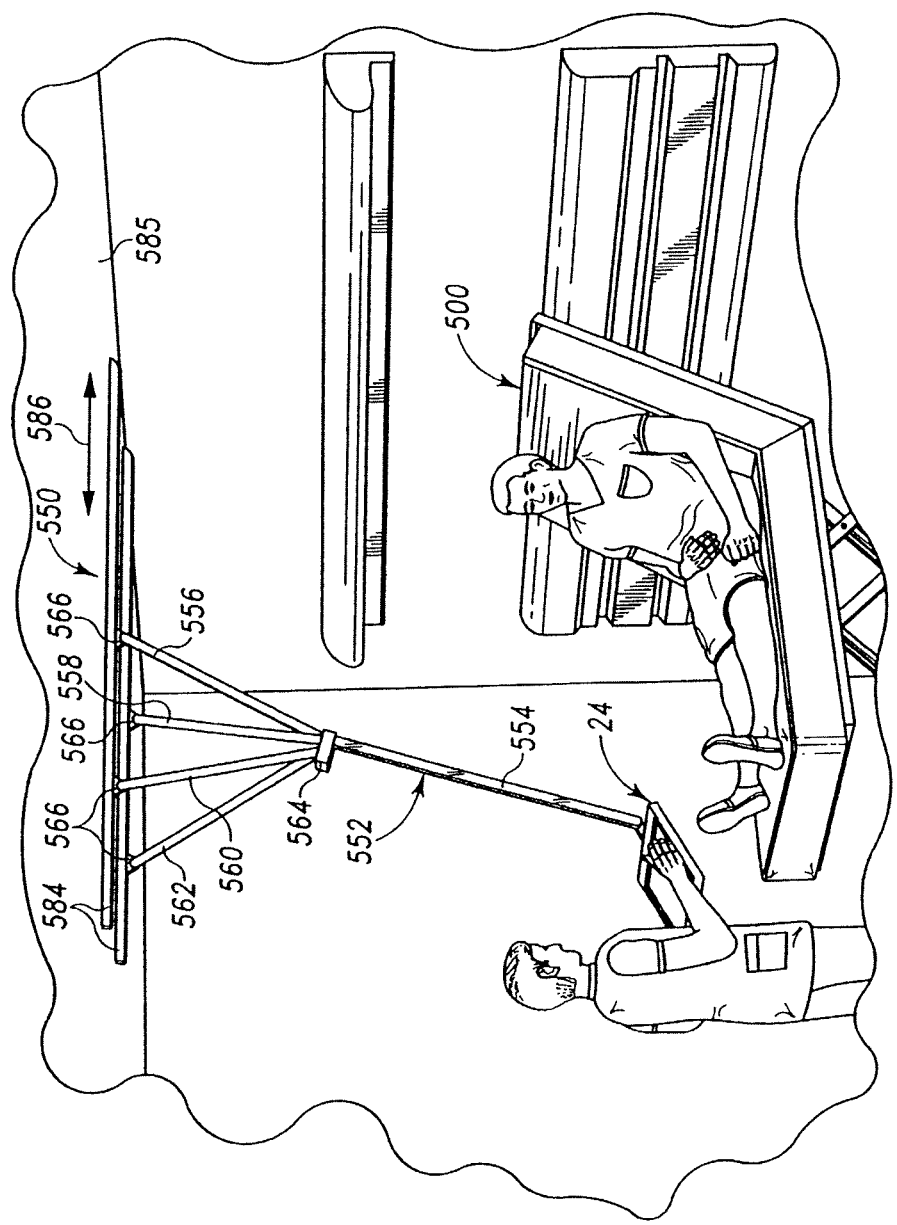

FIGS. 35-39 illustrate another embodiment of the present invention. In this embodiment, display 24 is mounted to an overhead arm assembly 550. Arm assembly 550 includes a Y-shaped arm 552 having a central portion 554 and arms 556, 558 extending from central portion 554. Arms 556, 558 cannot move relative to central portion 554. As best shown in FIG. 36, arm assembly 550 further includes arms 560, 562 which are pivotably coupled at one end to arm 552 adjacent the junction between central portion 554 and arms 556, 558 by pivot connection 564. Arms 556, 558 and the other ends of arms 560, 562 are movably connected to tracks 584 mounted to ceiling 585. Each of arms 556, 558, 560, and 562 are coupled to tracks 584 by drive assemblies 566.

Figure 37:
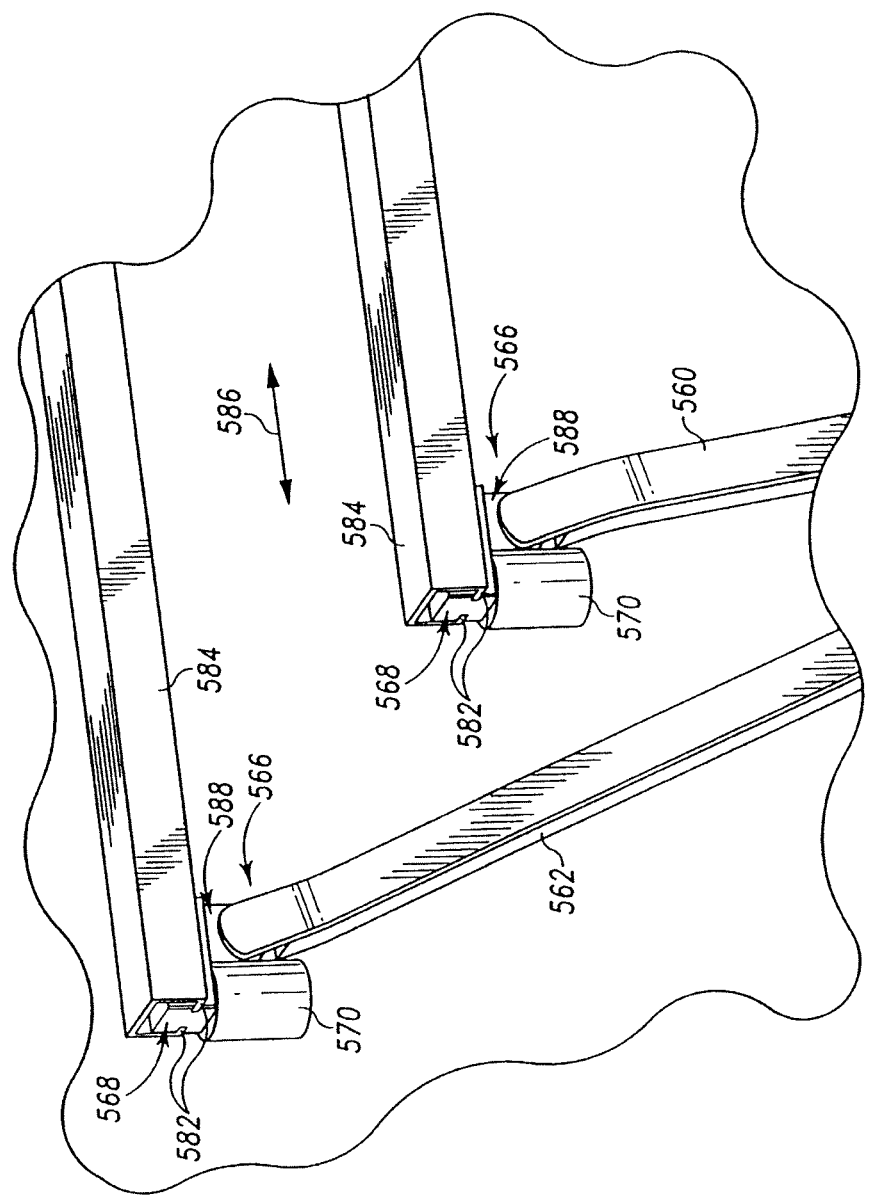
FIGS. 37-39 are perspective views of components of the mounting configuration of FIGS. 35 and 36.
Figure 38:
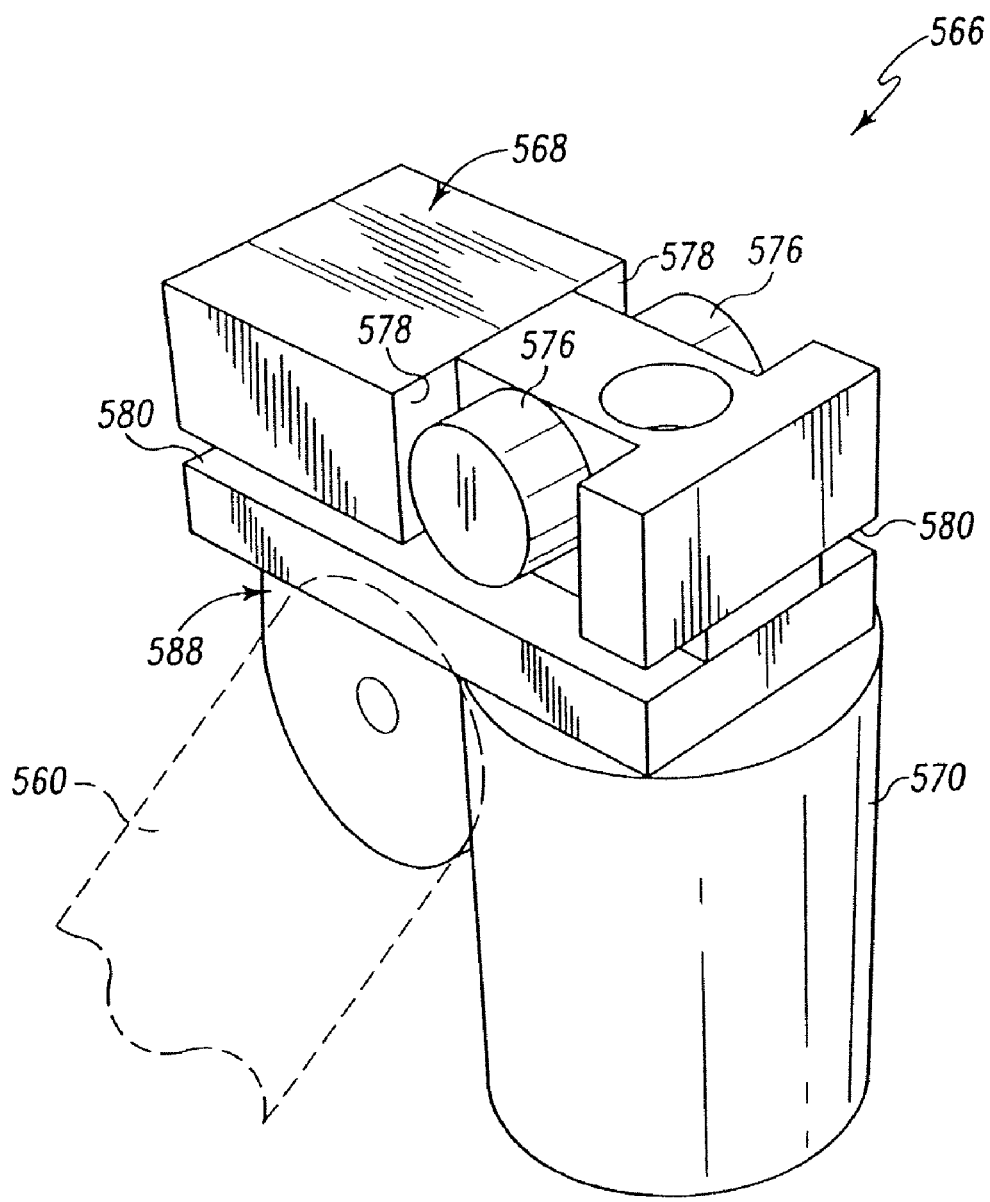
Figure 39:
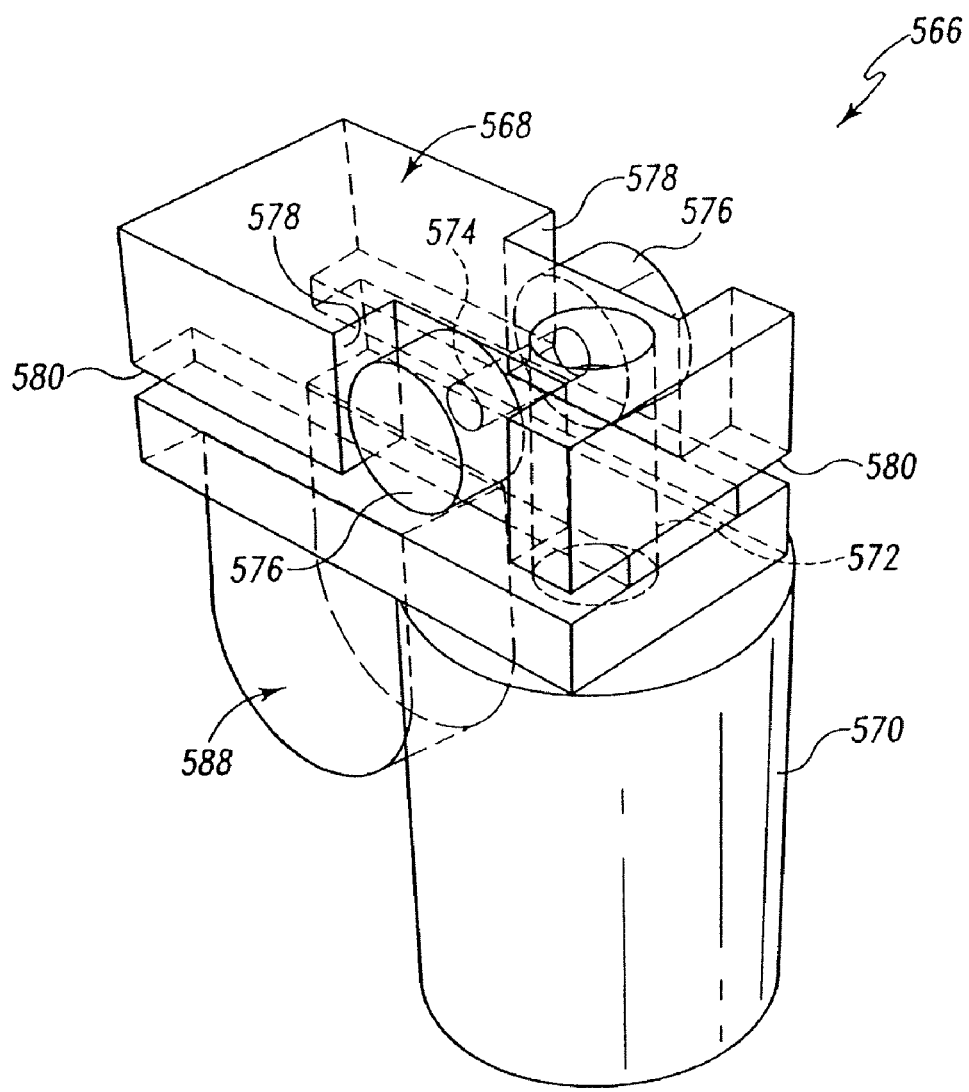

Referring now to FIGS. 37-39, drive assemblies 566 include a body portion 568 and a motor 570 coupled to body portion 568. As shown in FIG. 39, motor 570 is configured to rotate a shaft 572 which, via gears, threads, or other interface (not shown), rotates a drive shaft 574. Drive shaft 574 rotates drive wheels 576 located in recesses 578 of body portion 568. It is understood that other suitable drive linkages may be used to rotate wheels 576. Wheels 576 are also in communication with elongated slots 580 formed on opposite sides of body portion 568. As best shown in FIG. 37, slots 580 are sized to receive flanges 582 of tracks 584. Wheels 576 engage flanges 582 to move body portions 568 back and forth within tracks 584 in the direction of double headed arrow 586 in FIG. 37. Body portion 568 further includes a mounting section 588 configured to be coupled to arms 556, 558, 560 and 562 to permit rotation of arms 556, 558, 560, and 562 relative to mounting section 588 as best illustrated in FIGS. 37 and 38.

Referring back to FIGS. 35 and 36, a controller (not shown) is configured to control motors 570 to move drive assemblies 566 within tracks 584, thereby moving the upper ends of arms 556, 558, 560 and 562 along tracks 584. As should be apparent from the figures, as the upper ends of arms 556, 558, 560, and 562 move along tracks 584, display 24 is moved toward and away from bed 500 in the direction of double headed arrow 586. Additionally, as drive assemblies 566 move the upper ends of arms 560, 562 toward and away from the upper ends of arms 556, 558, display 24 is moved up and down relative to ceiling 585. FIG. 35 illustrates arm assembly 550 (and display 24) located adjacent ceiling 585 in a raised position. In FIG. 35, a patient in bed 500 can view display 24. Display 524 can also be rotated about axis 590 so that the caregiver can view display 24. FIG. 36 illustrates the orientation of arm assembly 550 to lower display 24 for use by the caregiver. It should be understood that display 24 may also be positioned in the lowered position for use by the patient.

Figure 41:
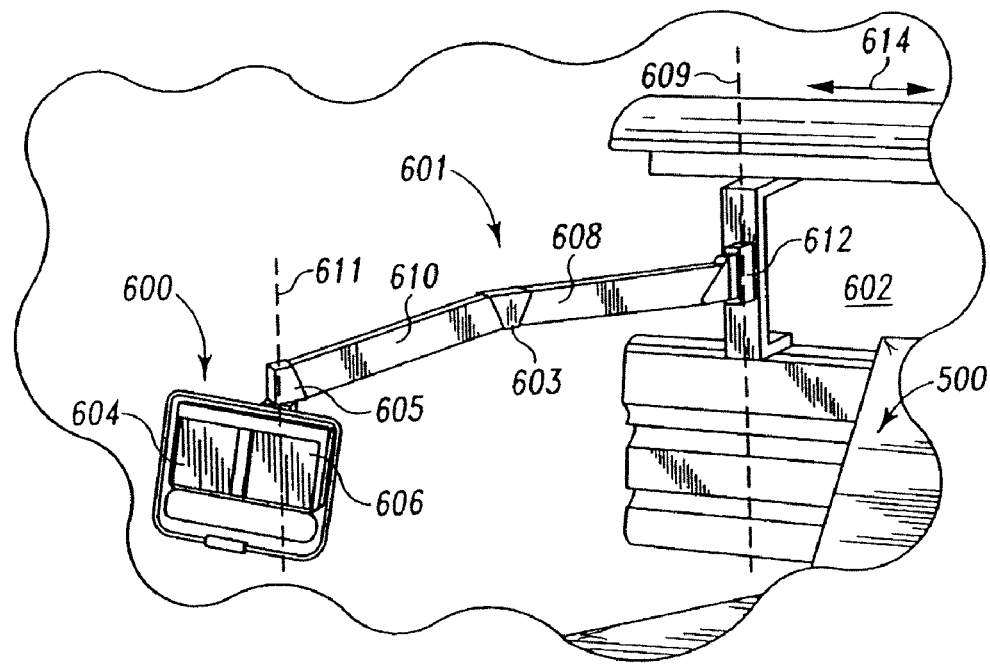
FIGS. 40 and 41 are perspective views of another embodiment of a mounting configuration supporting a dual screen display.
Figure 40:
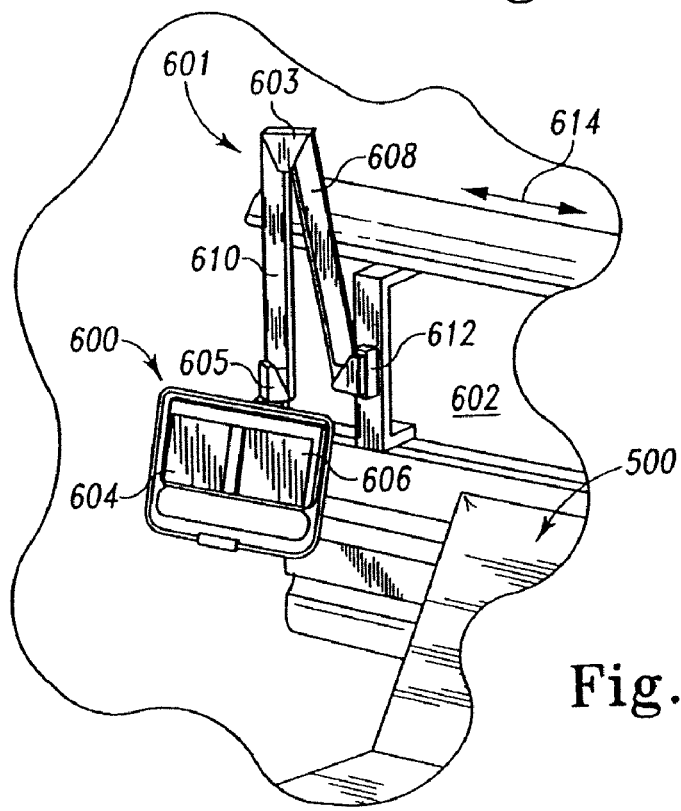

Another embodiment of the present invention is illustrated in FIGS. 40 and 41. In this embodiment, a display 600 is mounted on wall 602 adjacent bed 500, and supported by arm assembly 601. Illustratively, display 600 includes first and second screens 604, 606. Dual display screens 604, 606 are described in detail in the '580 application. Arm assembly includes a bracket 612 coupled to wall 602, a first arm 608 coupled to bracket 612 for rotation about an axis 609, a second arm 610 movably coupled to arm 608 by coupler 603, and a display coupler 605 connected between arm 610 and display 600 to permit movement of display 600 about axis 611. FIG. 40 illustrates display 600 oriented for use by a caregiver in a retracted position adjacent wall 602 for viewing information on screens 604, 606. In FIG. 41, first and second arms 608, 610 are extended. In this extended position, arm 608 may be pivoted about axis 609 at bracket 612 and display 600 may be pivoted about axis 611 at display coupler 605 to position display 600 for use by the patient. Bracket 612 may be pivotably coupled to wall 602 or may be slideably coupled to wall 602 to move back and forth in the direction of double headed arrow 614.

Figure 42:
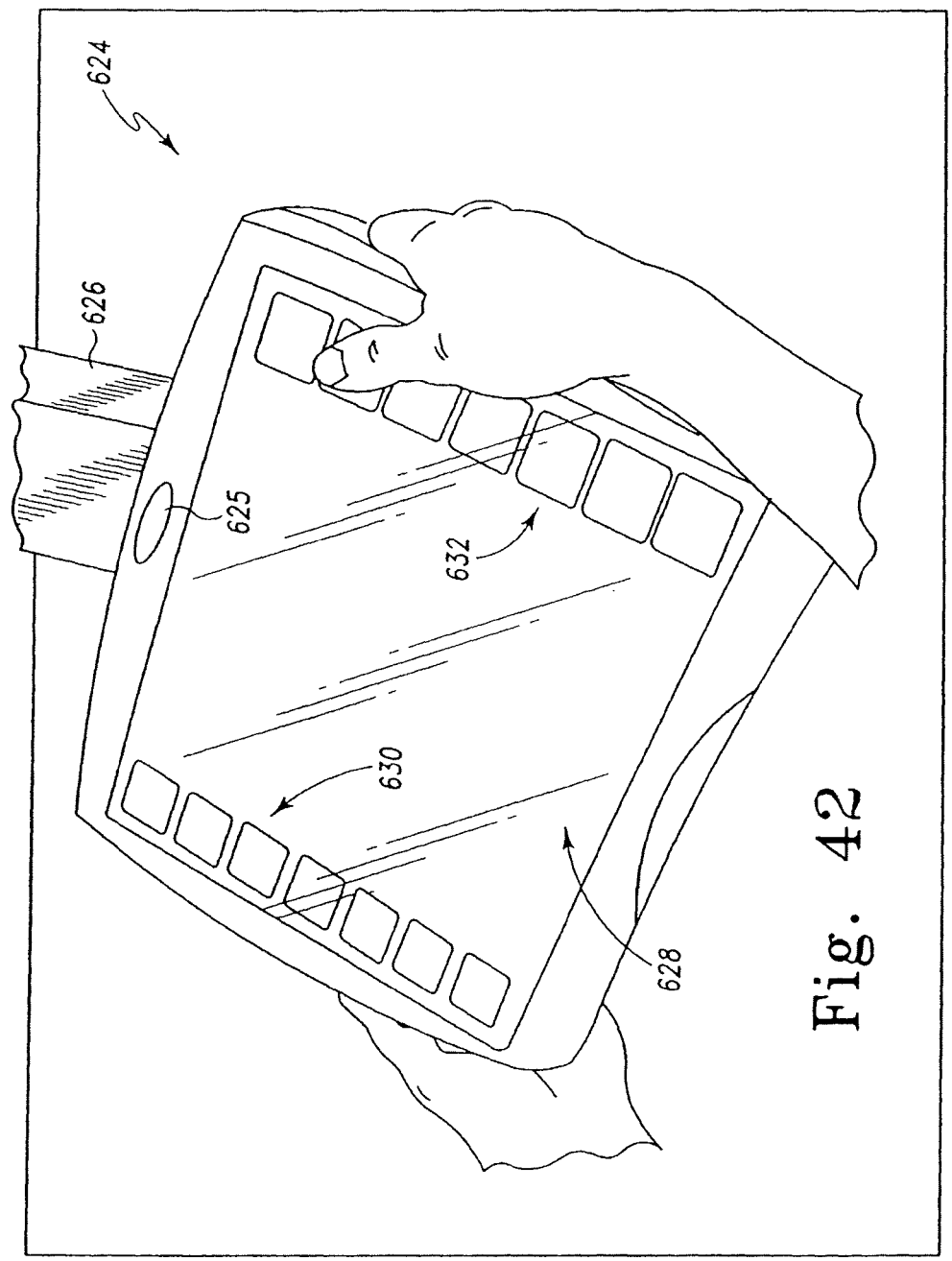
FIG. 42 is a perspective view of a display according to the present invention.

FIGS. 42-63 illustrate another embodiment of the present invention. A display 624 similar to display 24 discussed above is shown in FIG. 42. Display 624 is mounted on an arm 626. It should be understood, however, that display 24 may be mounted to any of the equipment described herein, and supported by any of the arm assemblies or other display supports described herein. Display 624 includes a touch screen control panel 628 that displays a plurality of caregiver icons 630 and a plurality of patient icons 632. By activating one of the icons, menus are called up and displayed on touch screen 628. It should be understood that touch screen control panel 628 may employ any of a variety of conventional touch screen technologies and be embodied as a touch screen that is pressure sensitive, or activated by changes in magnetic field, capacitance, resistance, or optical interference. For convenience, this description will refer to icons on screens of touch screen control panel 628 as being "activated" or "touched."

Illustratively, patient control icons 632 are always displayed. Caregiver icons 630 may only be displayed when an authorized caregiver is in the room. Computer 12 (not shown in FIG. 42) can receive information from a nurse tracking system to automatically display caregiver icons 630 when a caregiver enters the room. More specifically, display 624 may include, for example, an RFID sensor 625 that detects an RFID tag worn by a nurse, and display caregiver icons 630 upon determining from identification information transmitted by the tag that the nurse is an authorized caregiver.

Figure 43:
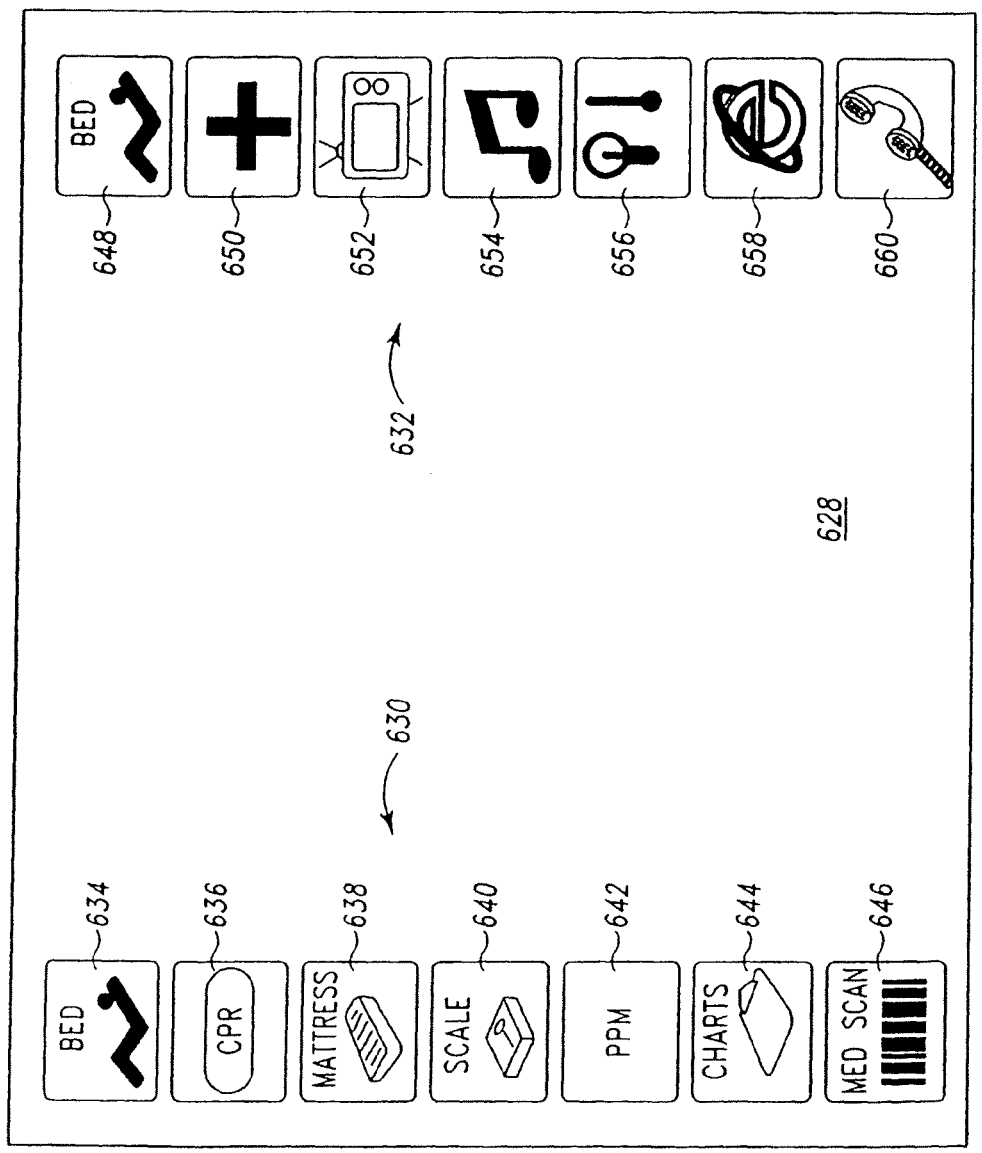

FIG. 43 illustrates caregiver icons 630 and patient icons 632 in more detail. Caregiver icons 630 illustratively include a bed control icon 634, a CPR icon 636, a mattress control icon 638, a scale control icon 640, a patient position monitoring (PPM) icon 642, a charting icon 644, and a med scan icon 646. Patient icons 632 illustratively include a bed control icon 648, a nurse call icon 650, a television control icon 652, a music control icon 654, an environment control icon 656, an Internet icon 658, and a telephone control icon 660.

Figure 44:
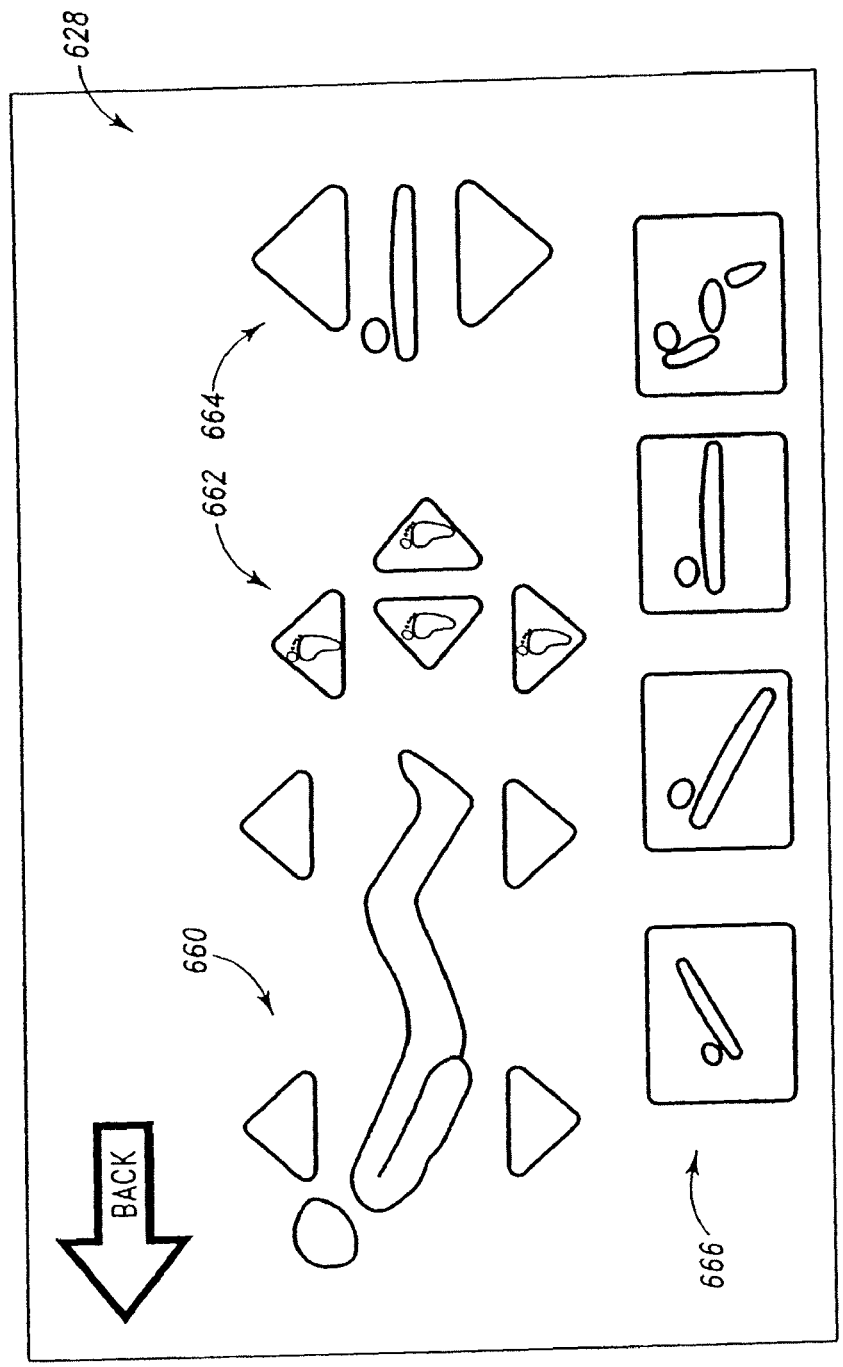
Figure 45:
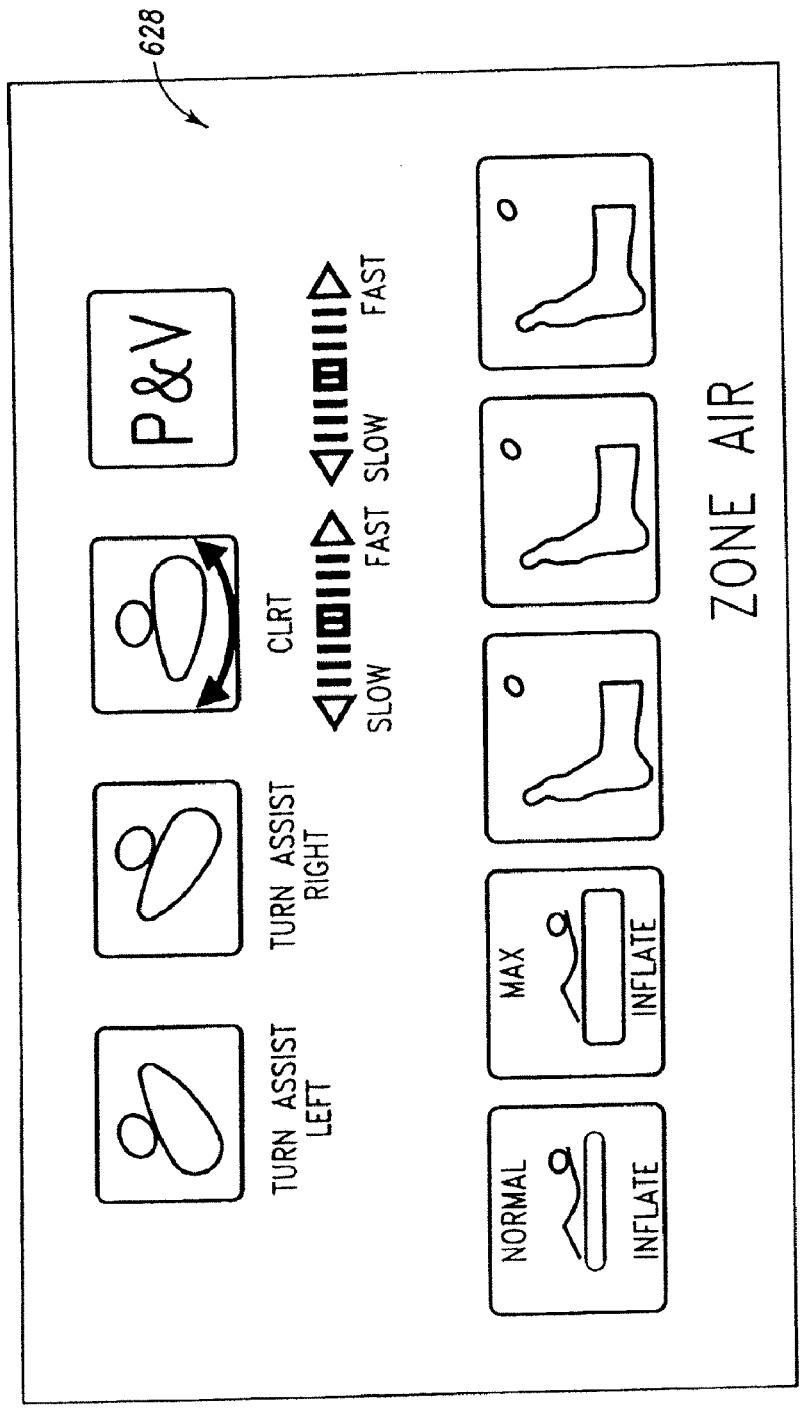
Figure 55:
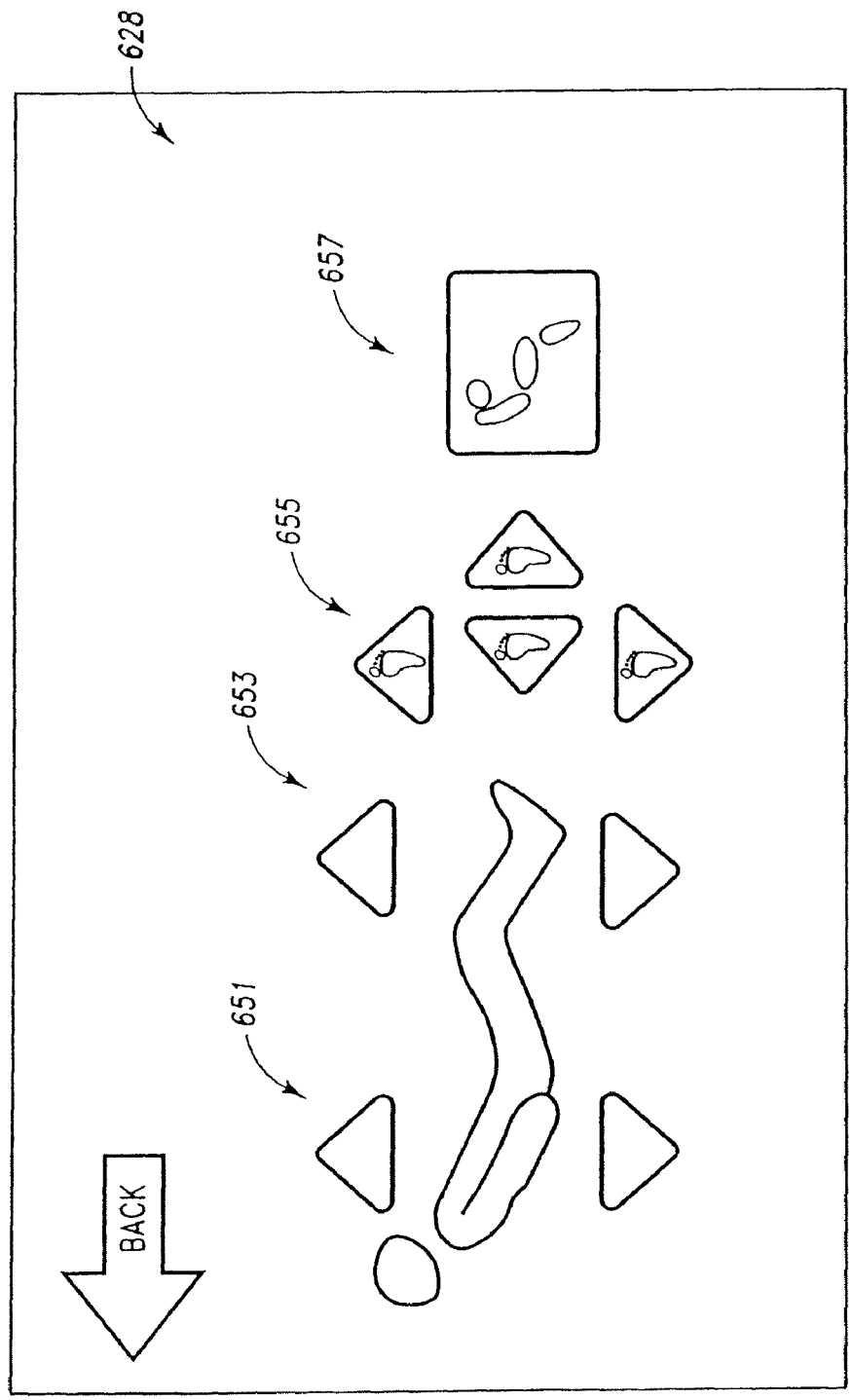

FIG. 44 illustrates a sample bed control screen displayed on touch screen 628 when caregiver bed control icon 634 is pressed. The illustrated bed control screen includes controls 660 for moving various deck sections of a bed (not shown), controls 662 for moving the bed foot sections, hi/lo controls 664 for raising and lowering the bed, and additional deck adjustment controls 666 for tilting the bed or positioning the bed in a flat or chair position. Typically, a bed control screen displayed upon activation of patient bed control icon 648 (as opposed to caregiver bed control icon 634) will include head up/down, knee up/down, chair, and vascular controls. FIG. 55 illustrates sample patient bed controls displayed on screen 628 when patient bed control icon 648 is activated. These controls include head up/down controls 651, knee up/down controls 653, foot controls 655, and chair position controls 657. Caregiver bed controls will typically include bed hi/lo, head up/down, knee up/down, Trendelenburg and reverse Trendelenburg positions, foot adjust, chair, and vascular controls.

CPR icon 636 automatically activates a code blue condition. Activation of mattress control icon 338 illustratively results in the screen shown in FIG. 45. In an illustrated embodiment, the caregiver can control a mattress controller (not shown) coupled to computer 12 that provides turn assist, continuous lateral rotation therapy, percussion and vibration therapy, normal inflation, max inflation, and heel suspension using, for example, a Zone Air® mattress available from Hill-Rom Company of Batesville, Ind.

Figure 46:
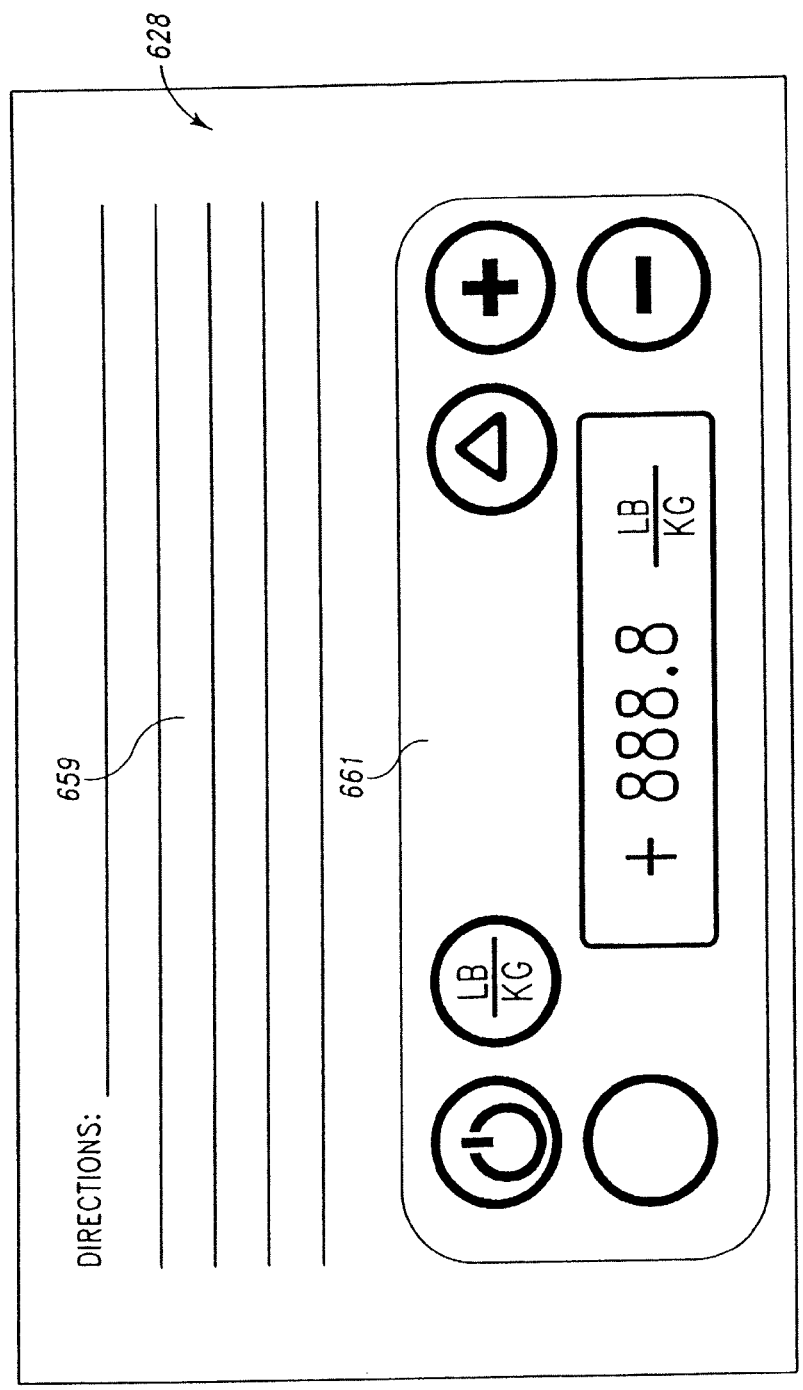

Activation of scale icon 640 illustratively results in the screen shown in FIG. 46 which displays operating instructions in directions area 659 and control functions for a bed scale in control area 661.

Figure 47:
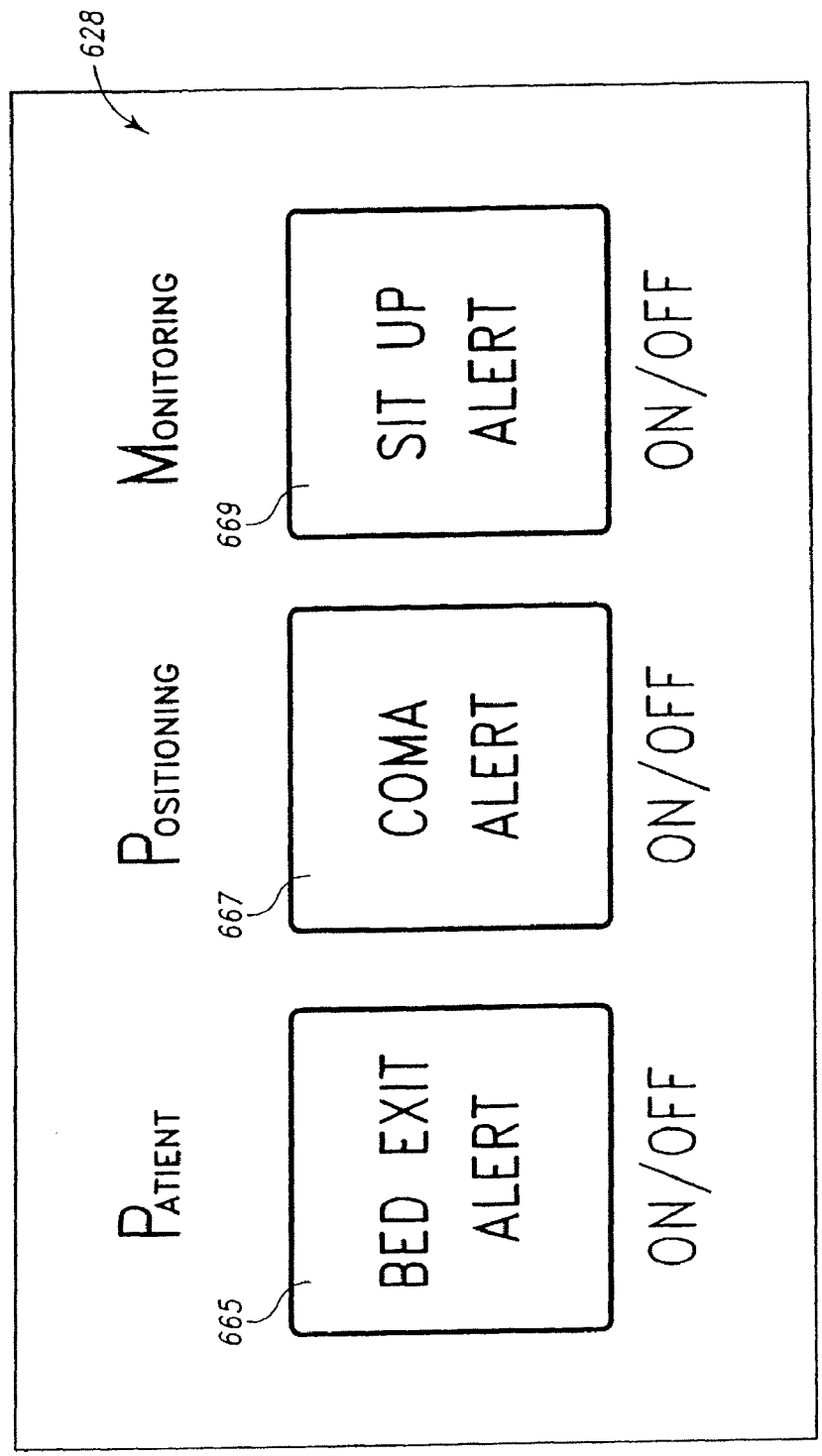

If the patient positioning monitoring icon 642 is touched, then the screen shown in FIG. 47 is displayed on screen 628. The caregiver can activate features of a patient position monitoring system (not shown) coupled to computer 12 by activating the icons on screen 628. The caregiver can enable the bed exit alert by touching icon 665, the coma alert by touching icon 667, and the sit up alert by touching icon 669.

When charting icon 644 is touched, an overall chart is displayed on screen 628. A nurse can enter information into the chart. In addition, a MAR and lab menu may be displayed on screen 628.

Figure 48:
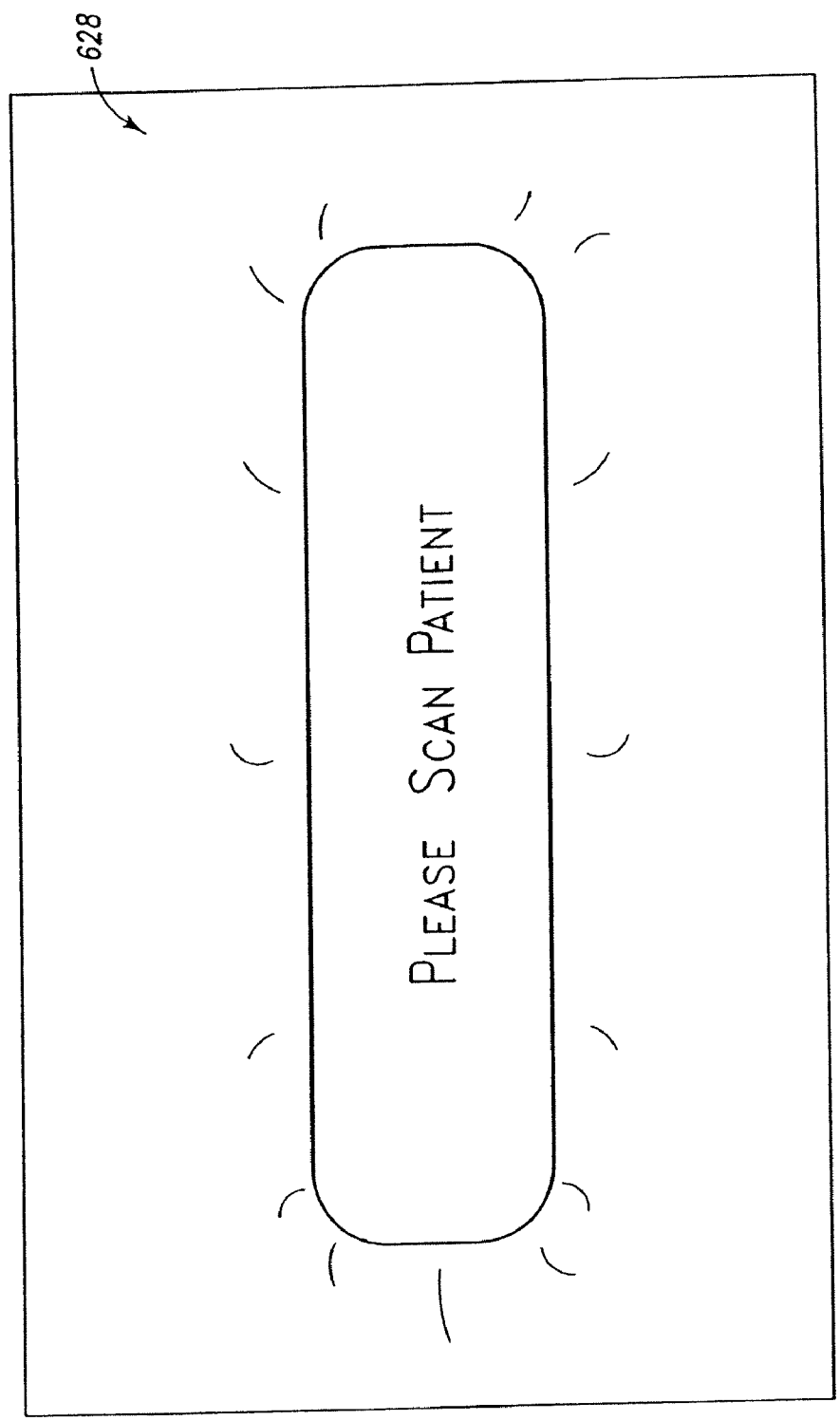

When med scan icon 646 is touched, screens are displayed on screen 628 to perform the functions discussed above in connection with FIGS. 3A and 3B. First, an image similar to that shown in FIG. 48 is displayed on screen 628 advising the caregiver to scan the patient or otherwise enter patient identification information into computer 12. As explained above, the caregiver either uses a bar code scanner to scan a bar code on a patient wristband or other location or a receiver automatically receives a transmission from a badge or tag associated with the patient. Computer 12 then generates the screen shown in FIG. 49 that includes the patient's name, time, scheduled medications to give, scheduled dose to give, and methods of administration. An image or photo 647 of the patient is also illustratively displayed to confirm that the patient is the correct patient.

Figure 50:
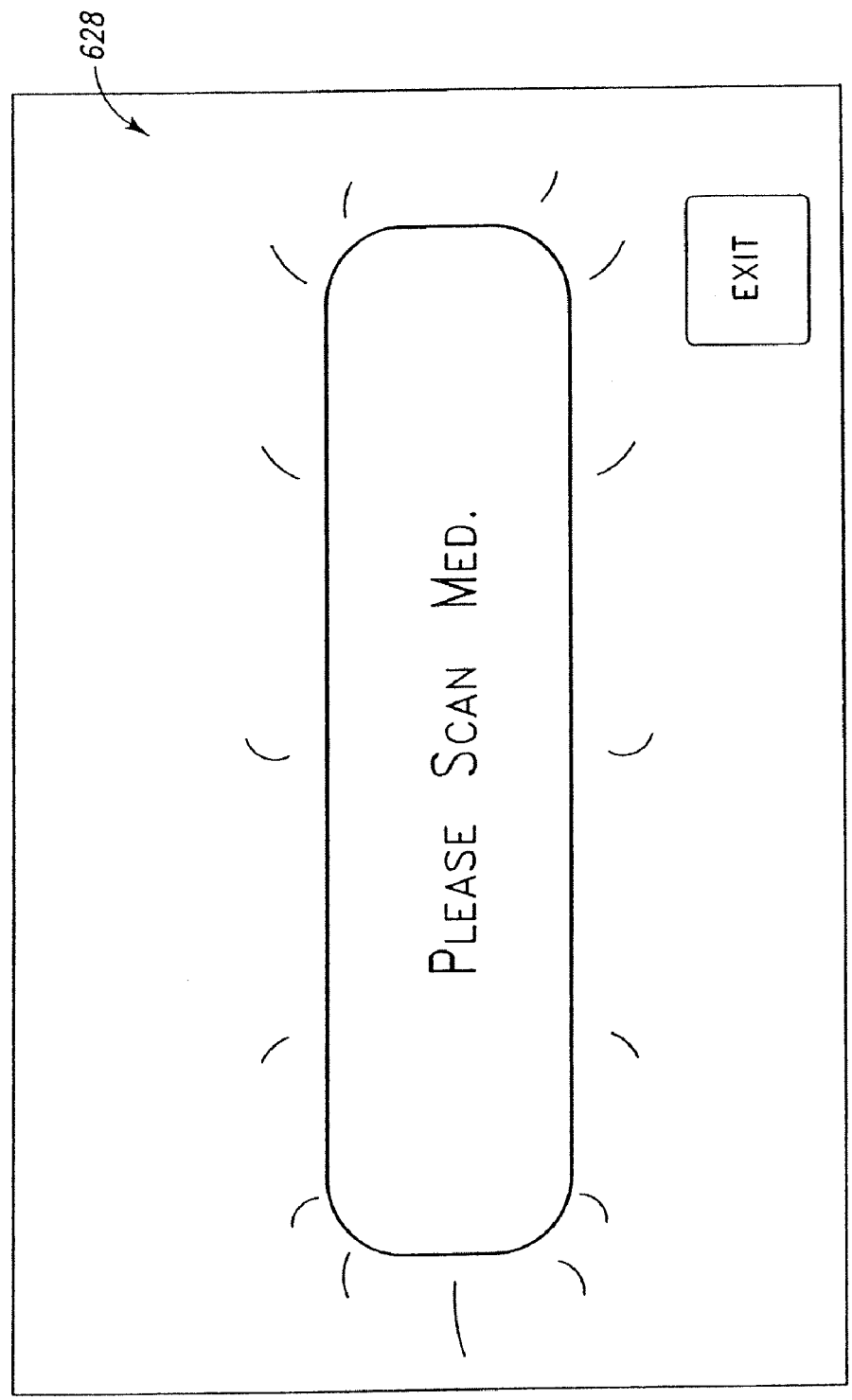
Figure 51:
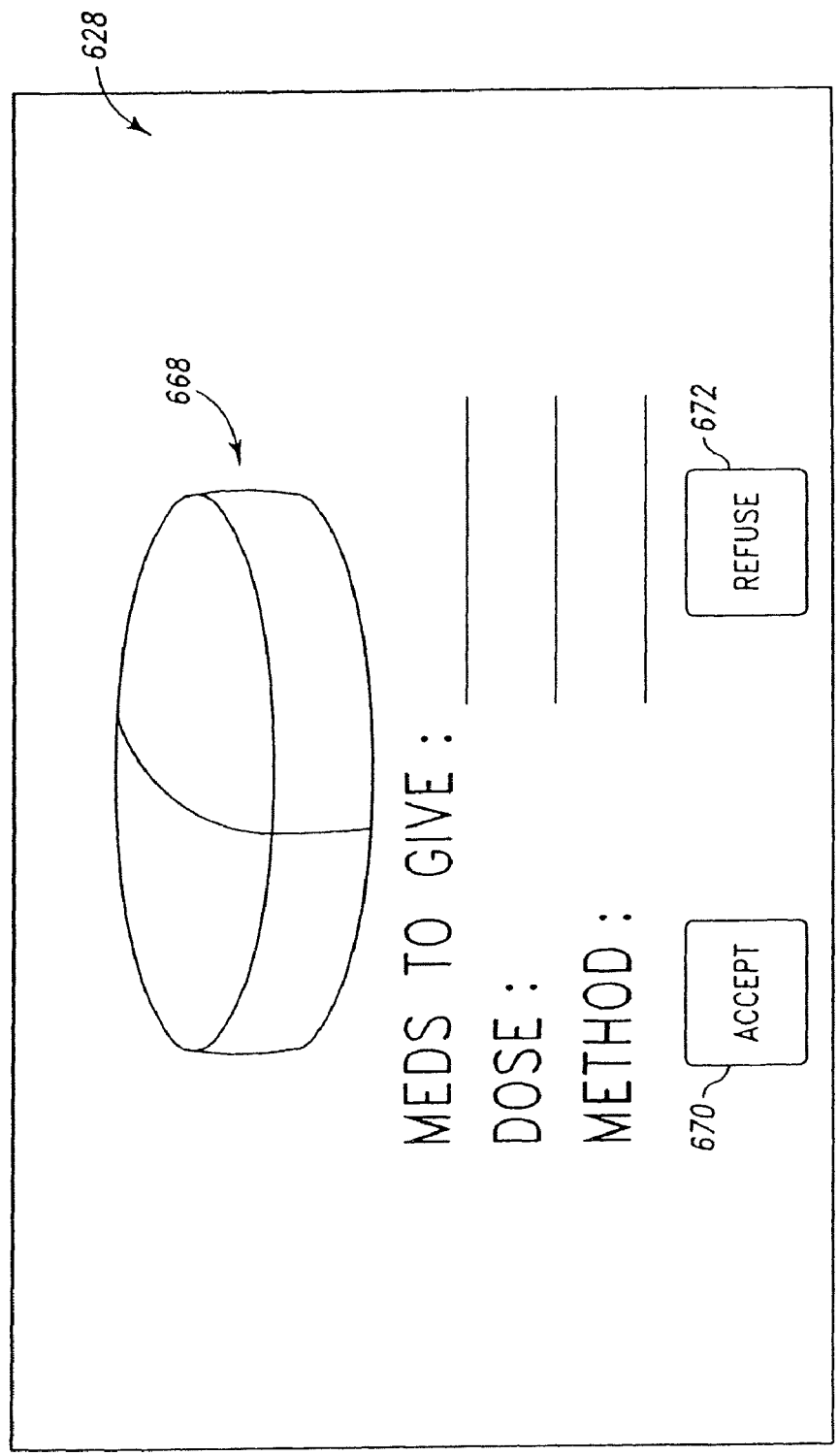
Figure 52:
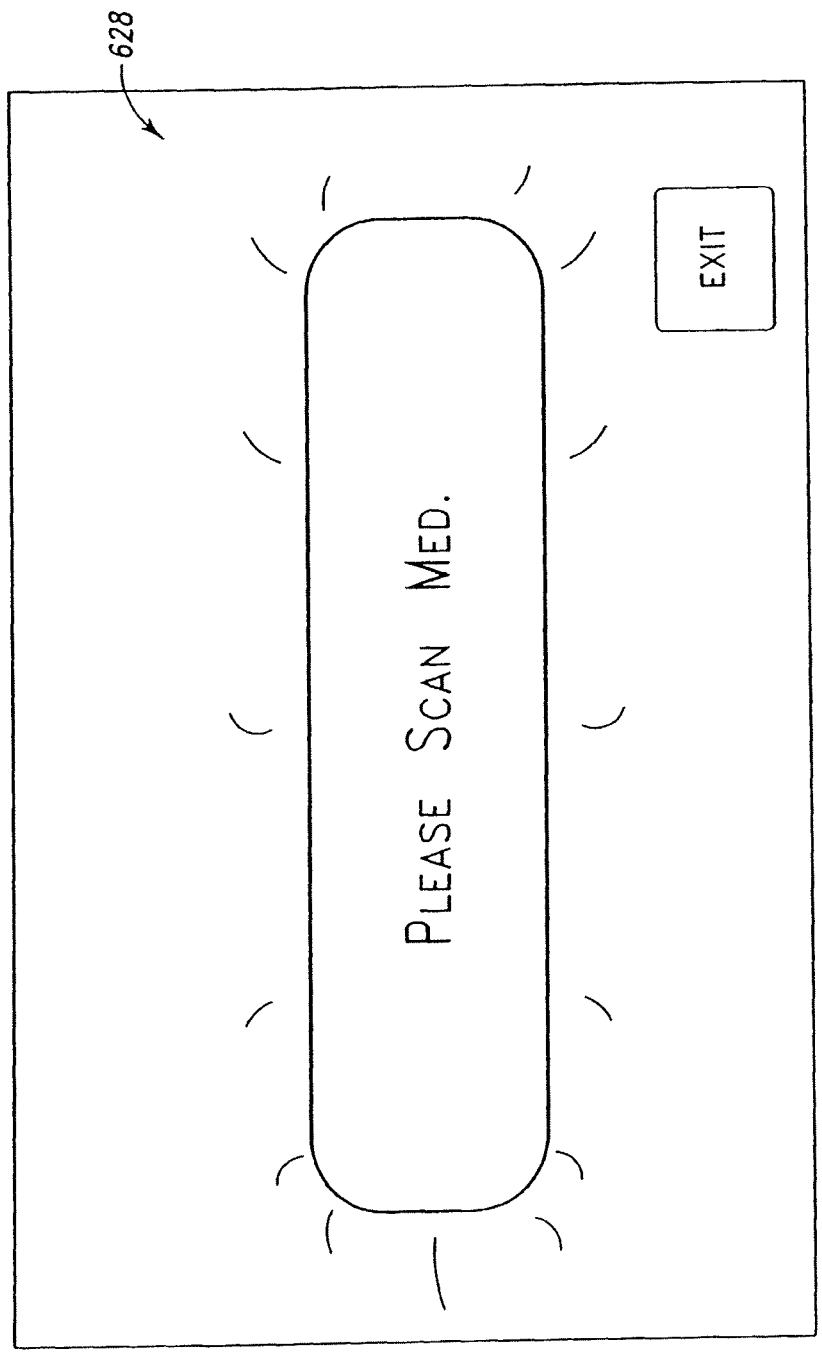
Figure 53:
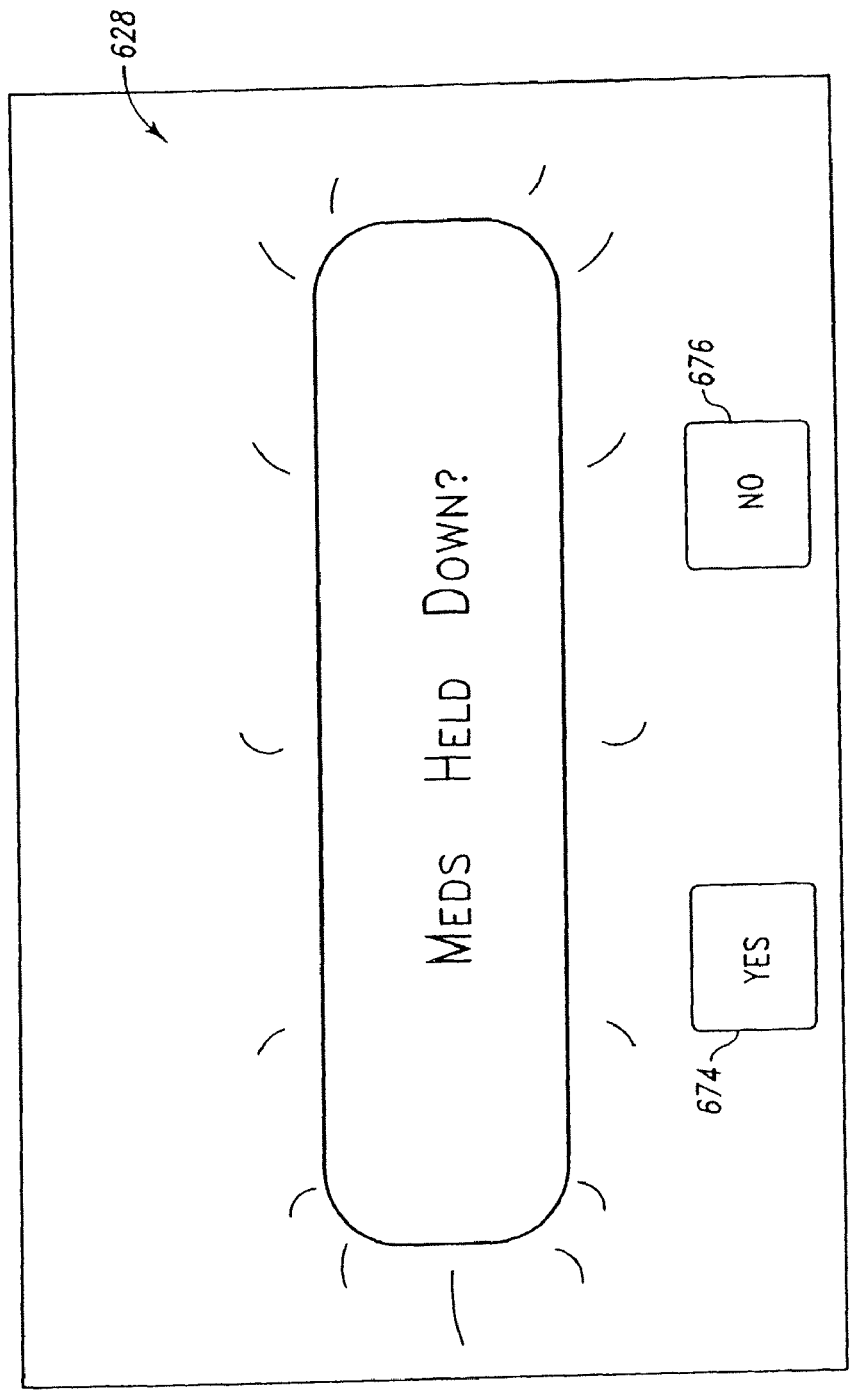

Next, computer 12 displays an image similar to that shown in FIG. 50 on screen 628 advising the caregiver to scan medication 42. The caregiver can use a bar code scanner or a receiver can automatically receive input from a transmitter associated with medication 42. Next, computer 12 generates the screen shown in FIG. 51 including an image 668 on screen 628 of the detected medication. In addition, information such as the medication name, dose, and method of administration are displayed on screen 628. The caregiver can then verify that medication 42 matches image 668 displayed on screen 628. The caregiver can either touch the accept icon 670 or the refuse icon 672 on screen 678, depending upon whether medication 42 matches. If accept icon 670 is touched, then computer 12 displays an image similar to that shown in FIG. 52 on screen 628 advising the caregiver to scan medication 42 again, which may be accomplished in the manner described above. For example, medication 42 can include a transmitter that automatically transmits information related to medication 42 to a receiver in the room or to sensor 625 (FIG. 42) of display 624. Computer 12 then automatically bills the patient for the particular dosage of medication 42. Computer 12 next displays an image similar to that shown in FIG. 53 on screen 628 to permit the caregiver to indicate whether medication 42 given to the patient was held down. If the yes icon 674 is touched, then computer 12 charts the dosage of medication 42 given to the patient. If medication 42 was not held down and the no icon 676 is touched, then computer 12 does not chart medication 42 on the patient's record. However, the patient is still billed for medication 42.

Figure 54:
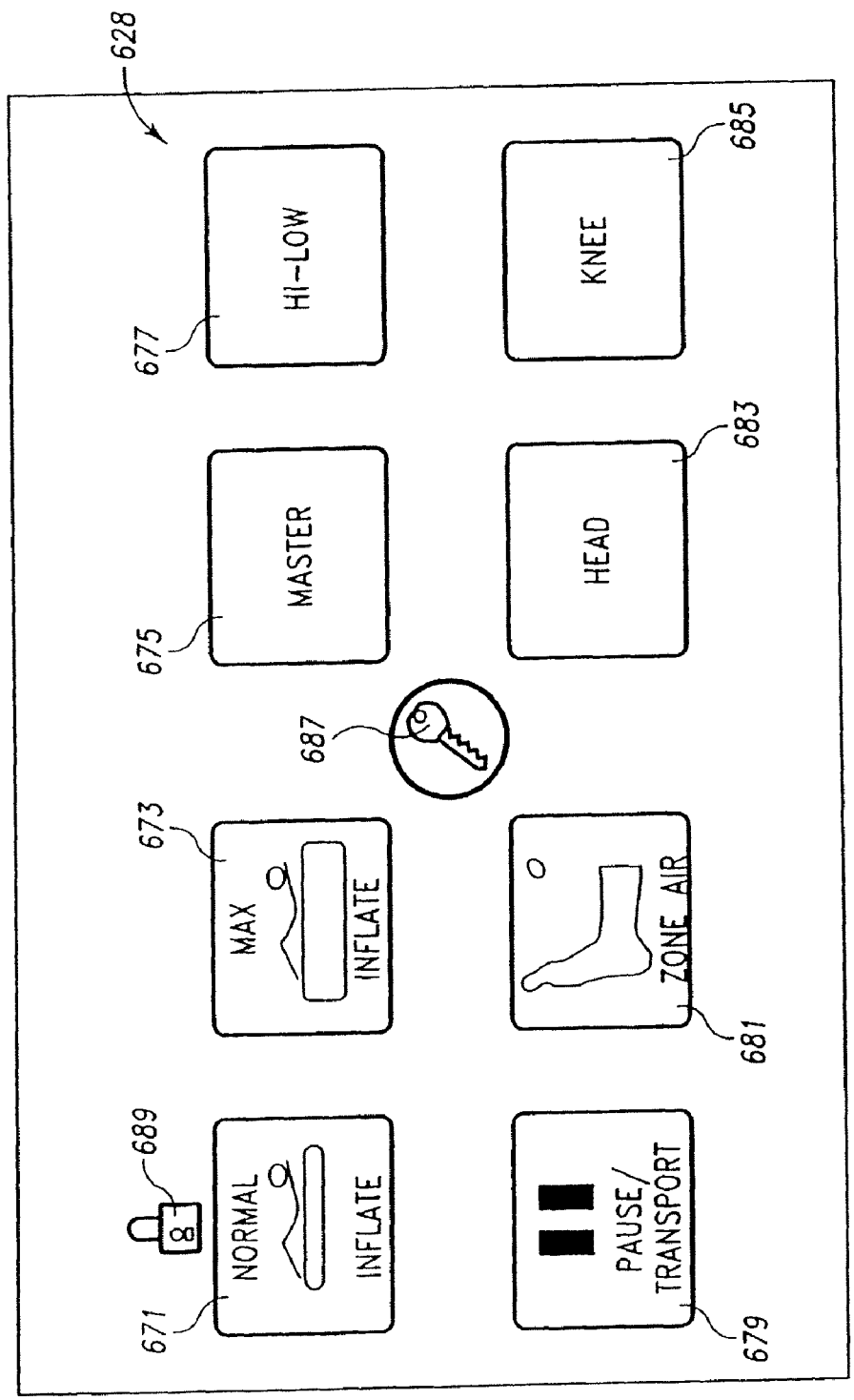

FIG. 54 illustrates a screen showing various lock out icons available to the caregiver by manipulating appropriate icons on screen 628. When an authorized caregiver is detected at display 624, for example, by sensor 625, a lock out icon (not shown) may be displayed to the caregiver. By touching the lock out icon, the caregiver may be presented with the screen of FIG. 54. This lock out screen includes a normal inflate icon 671, a max inflate icon 673, a master icon 675, a hi-low icon 677, a pause/transport icon 679, a zone air icon 681, a head icon 683, a knee icon 685, and a key icon 687. The caregiver can prevent patient access to any of the functions associated with the above-mentioned icons by touching the corresponding icon. For example, by touching normal inflate icon 671, the caregiver can prevent the patient from operating the normal inflate function of the bed. A lock indicator 689 is displayed near the icon associated with a locked out function. The caregiver can unlock the function by first touching key icon 687, and then touching the icon associated with the function the caregiver wishes to unlock.

Figure 56:
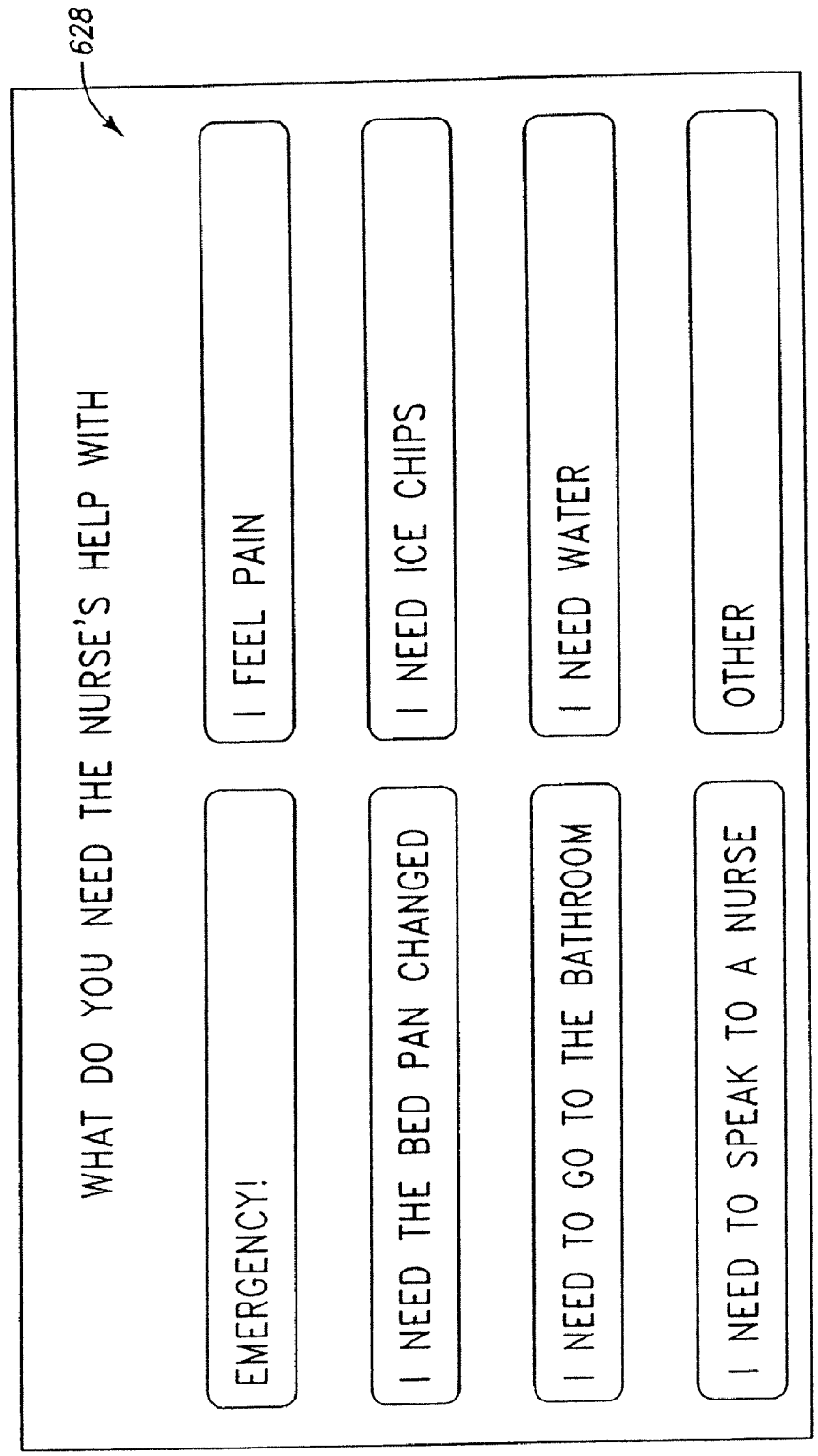
Figure 57:
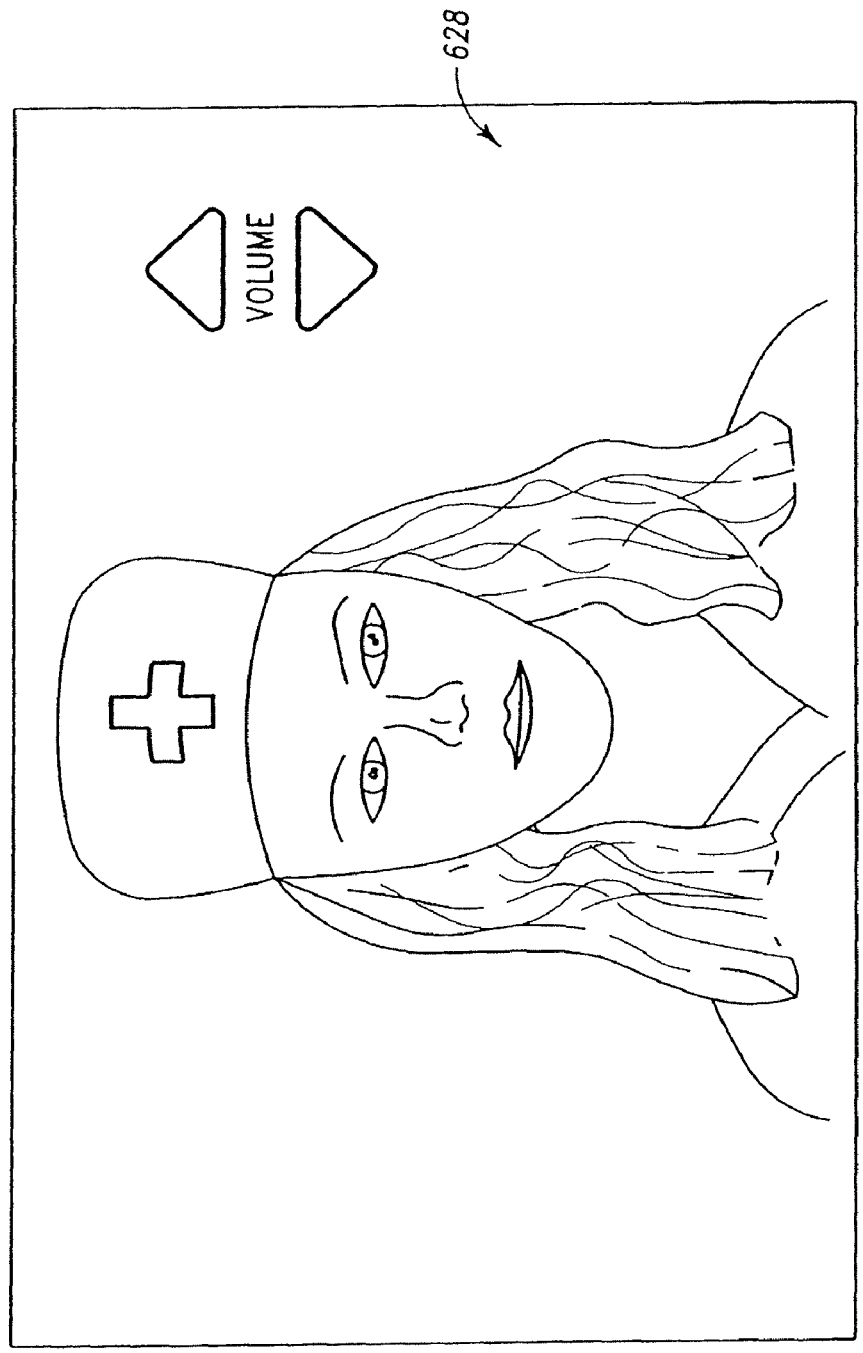

If nurse call icon 650 of FIG. 43 is activated, then a screen such as that shown in FIG. 56 is displayed to permit the patient to more specifically communicate the patient's need to the nurse. When the patient touches any of the displayed icons, computer 12 provides a message to the appropriate nurse via nurse call system 36 that includes an indication of the patient need associated with the icon pressed by the patient. Alternatively, screen 628 of FIG. 57 may be generated for providing a video conference and volume control.

Figure 58:
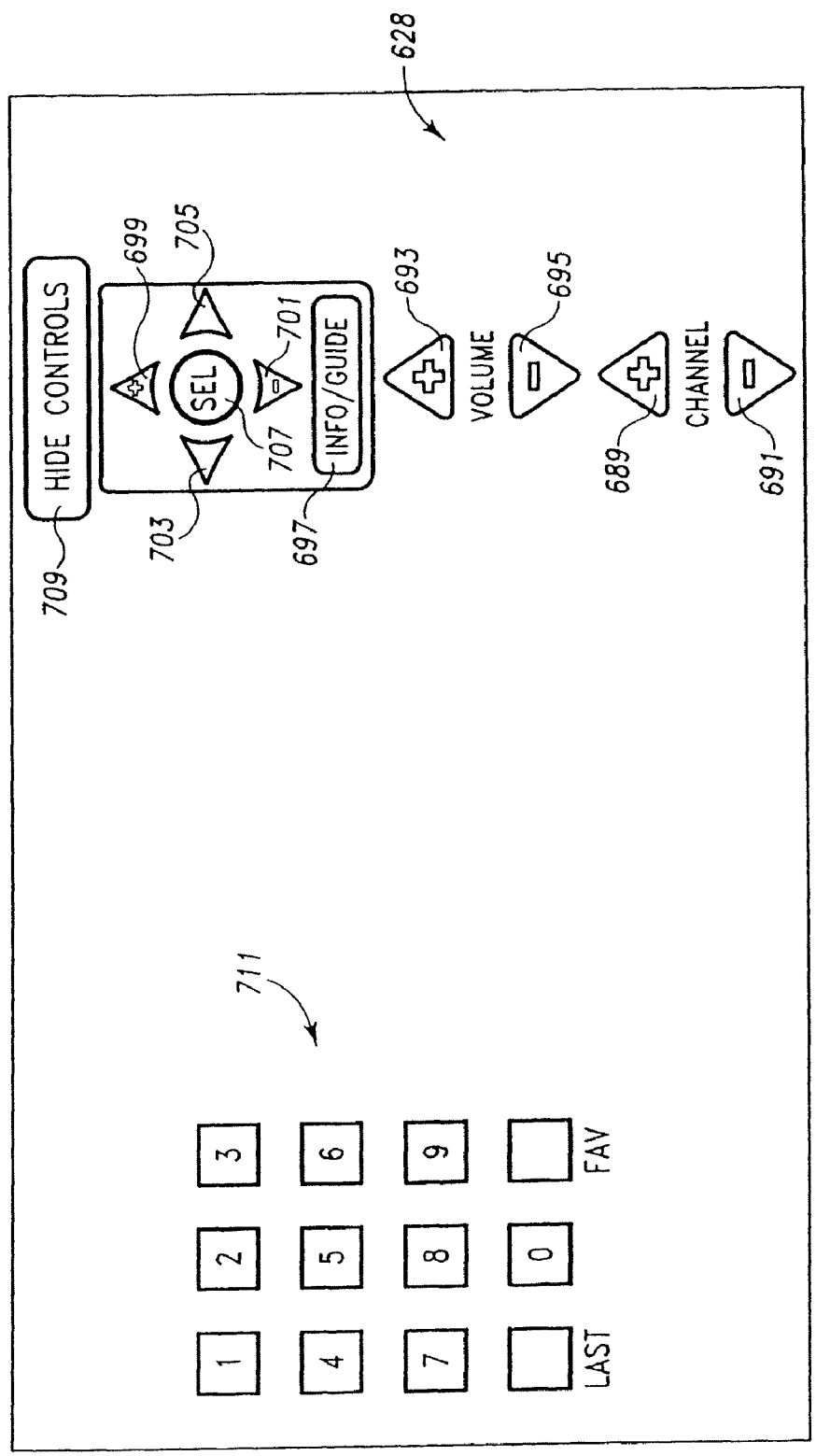
Figure 59:
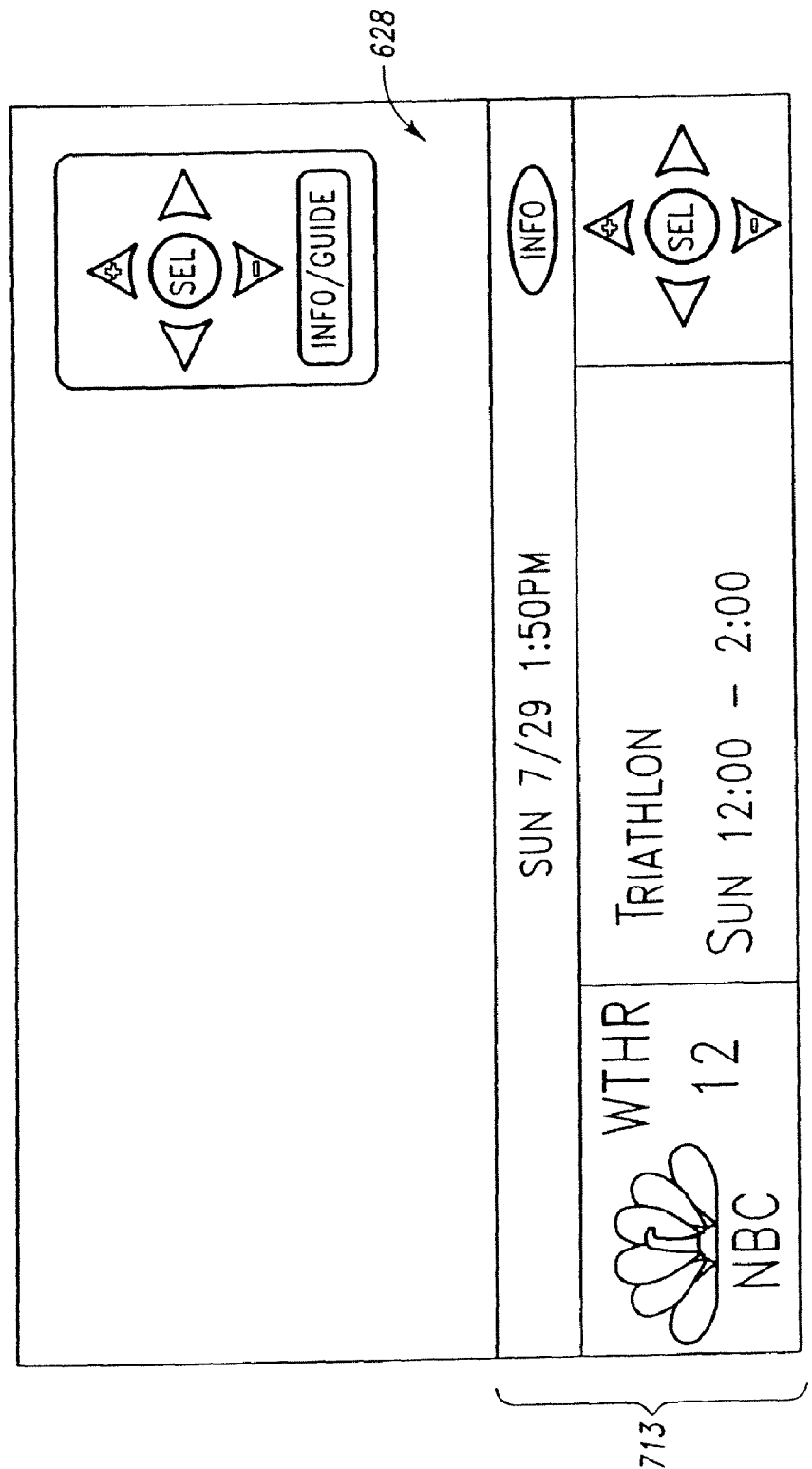

Referring now to FIG. 58, if television control icon 652 is touched, a screen is generated including channel up/down icons 689, 691, volume up/down icons 693, 695, a TV guide icon 697 with up/down icons 699, 701, next/previous icons 703, 705, and a select icon 707, a hide controls icon 709, and a number pad 711. The patient may use screen 628 as an interface to control the channel and volume of the hospital room television by manipulating icons 689, 691, 693, 695 or number pad 711. The patient may activate hide controls icon 709 to remove the above-described television controls from screen 628, or computer 12 may automatically hide the controls after a predetermined period of non-use. When the patient touches TV guide icon 697, a screen such as that shown in FIG. 59 is generated on screen 628 to provide a listing of channels and programming (not shown) and additional information relating to channels and programs in information area 713.

Figure 60:
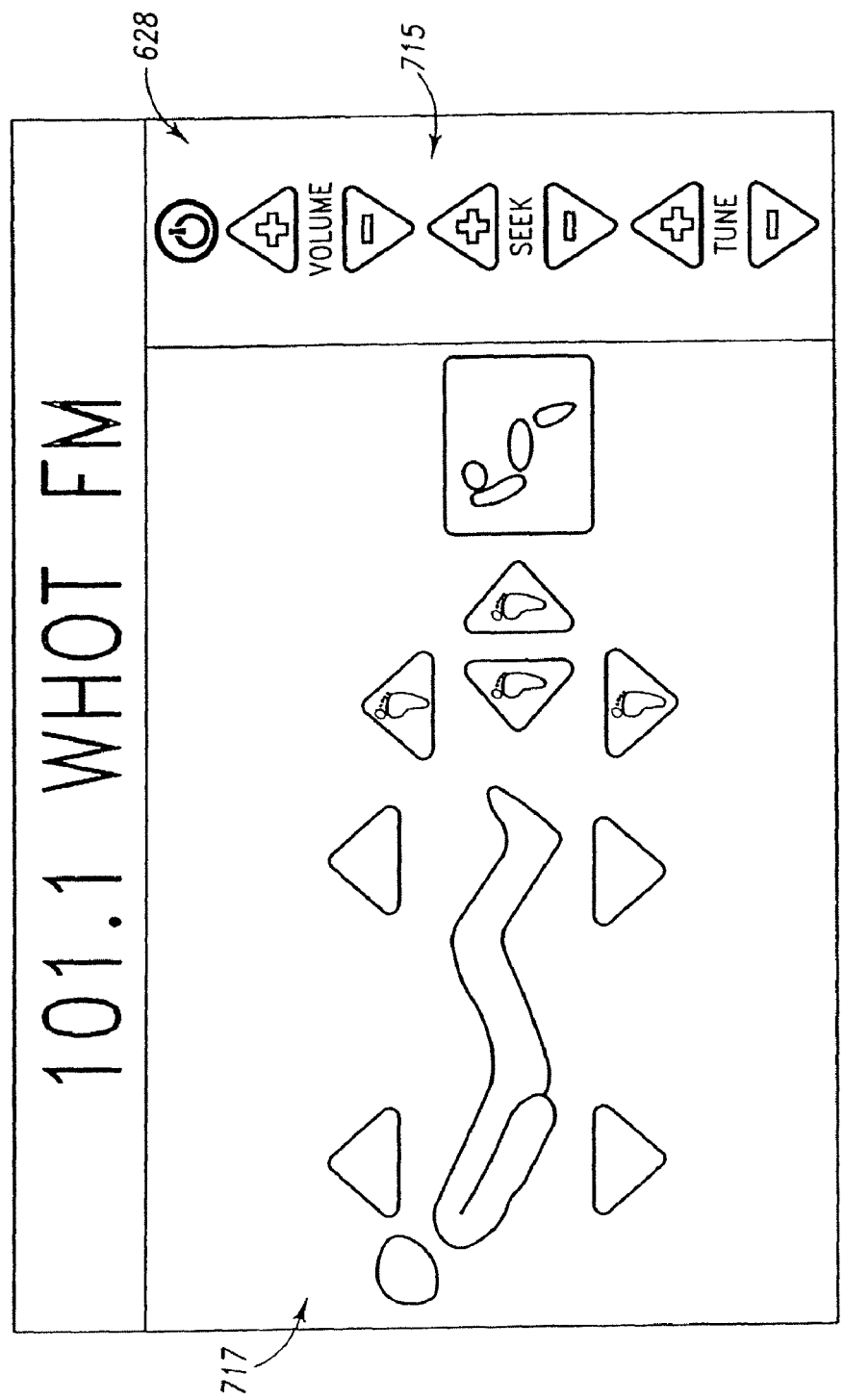

Referring to FIG. 60, when music control icon 654 is touched, the screen shown in FIG. 60 is generated to permit the user to control a radio or other music device coupled to computer 12. The music control screen of FIG. 60 includes a music control area 715 having seek/up/down icons, tune-up/down icons, and volume up/down icon, and a bed control area 717 having various bed controls. For digital audio signals, channel up/down, volume up/down, and song information icons may also be provided on screen 628.

Figure 61:
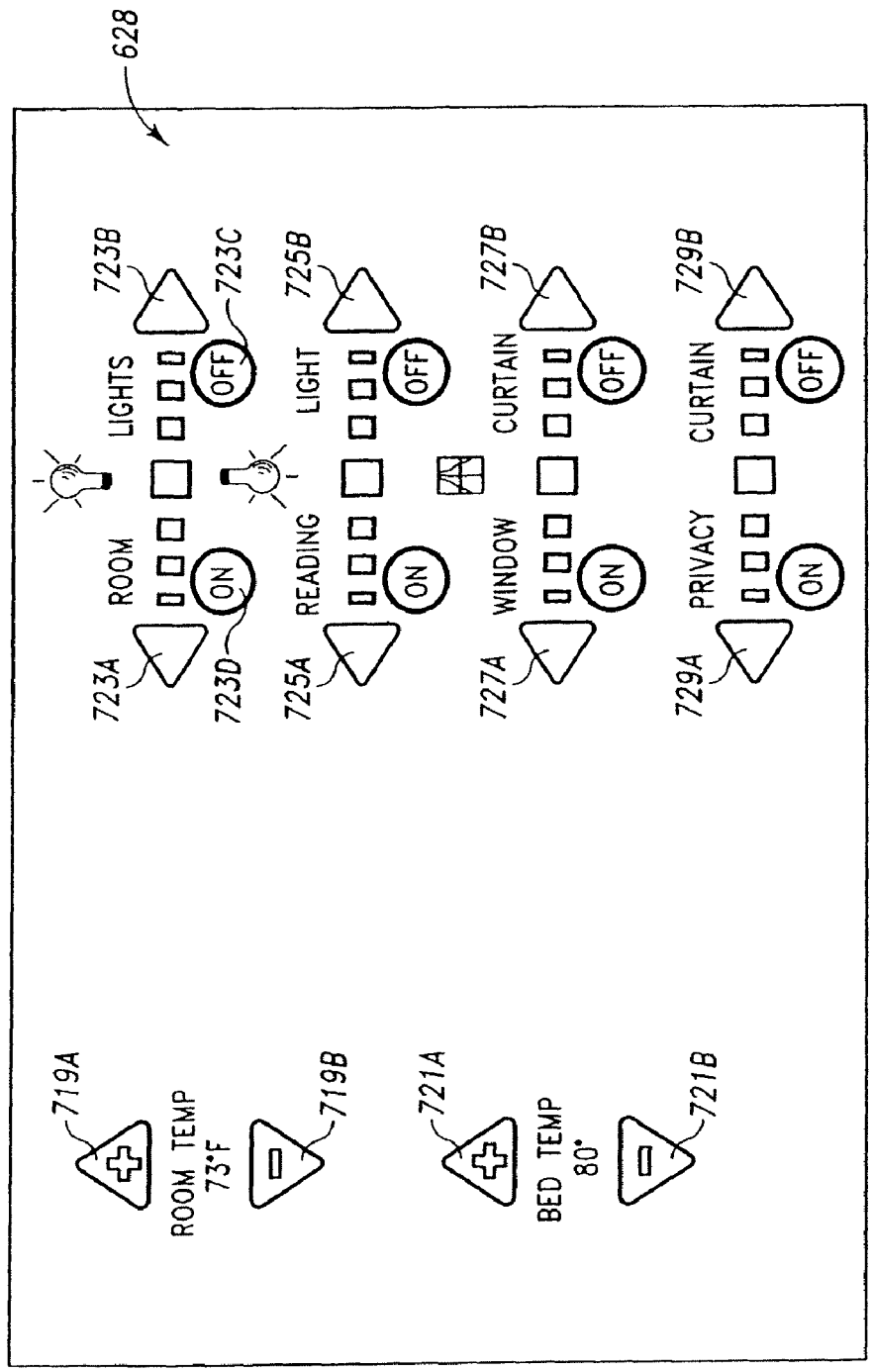

When environment control icon 656 of FIG. 43 is touched, a room environment control screen is displayed on screen 628 as shown in FIG. 61. The room environment control screen includes room temperature up/down icons 719A, B, bed temperature up/down icons 721A, B, lighting up/down icons 723A, B, reading light up/down icons 725A, B, window curtain open/close icons 727A, B, and privacy curtain open/close icons 729A, B. Accordingly, the patient or caregiver can adjust the room temperature using room temperature up/down icons 719A, B, and adjust the bed temperature using bed temperature up/down icons 721A, B. Similarly, the lights and curtains in the room may be adjusted using the various light and curtain control icons mentioned above. When a light is turned off or a curtain is fully closed, an off indicator 723C positioned on screen 628 adjacent the corresponding light or curtain control is activated. Similarly, when a light is adjusted to maximum brightness or a curtain is fully opened, an on indicator 723D is activated.

Figure 62:
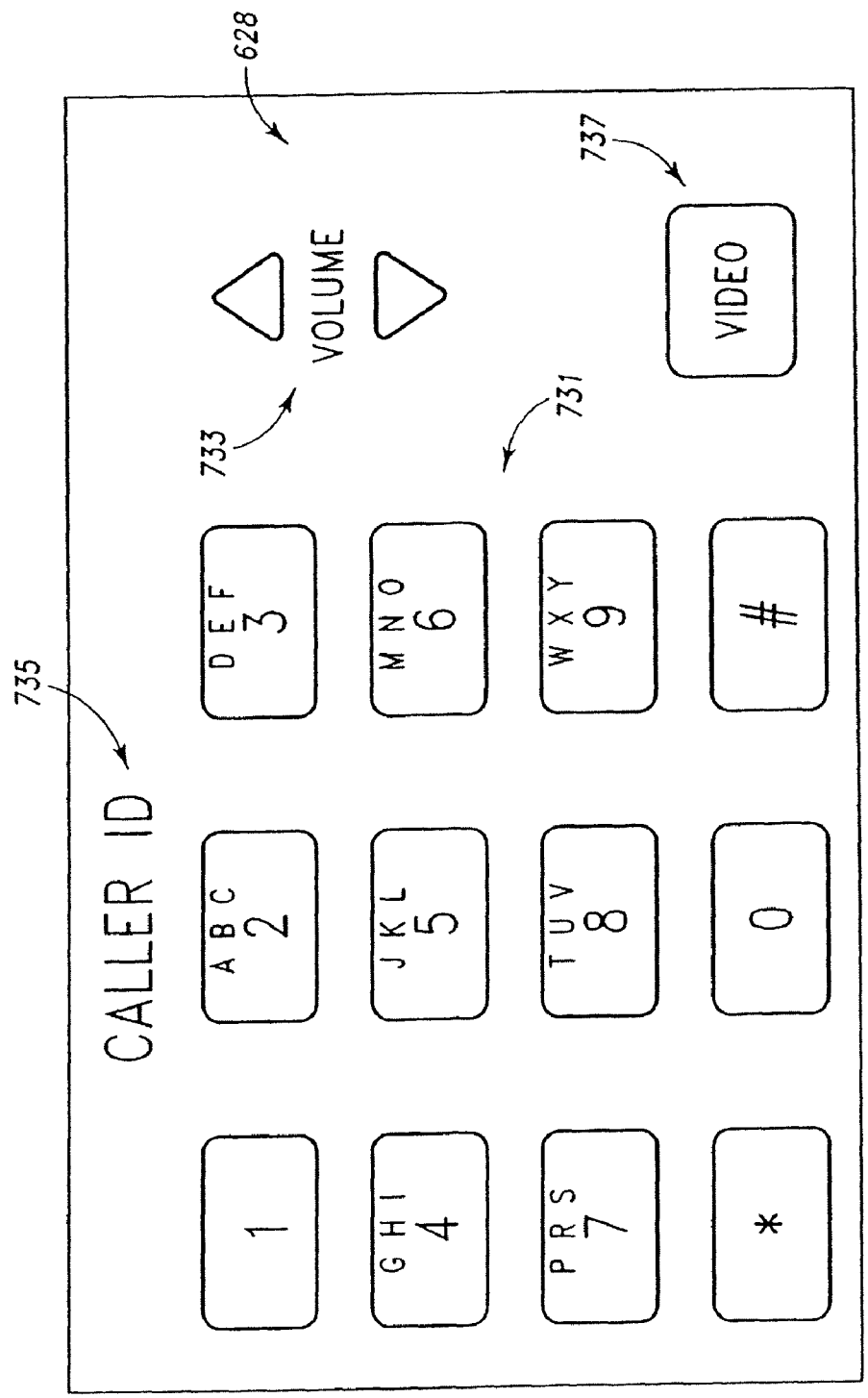

When Internet icon 658 is touched, a customized home page or other Internet connection is made. When telephone control icon 660 icon is touched, large numeric dialing icons 731 appear on screen 628 as shown in FIG. 62. The telephone control screen further includes volume control icons 733, a caller ID area 735, and a video icon 737 that enables a video screen if the system is equipped with a video telephone capability.

Figure 63:
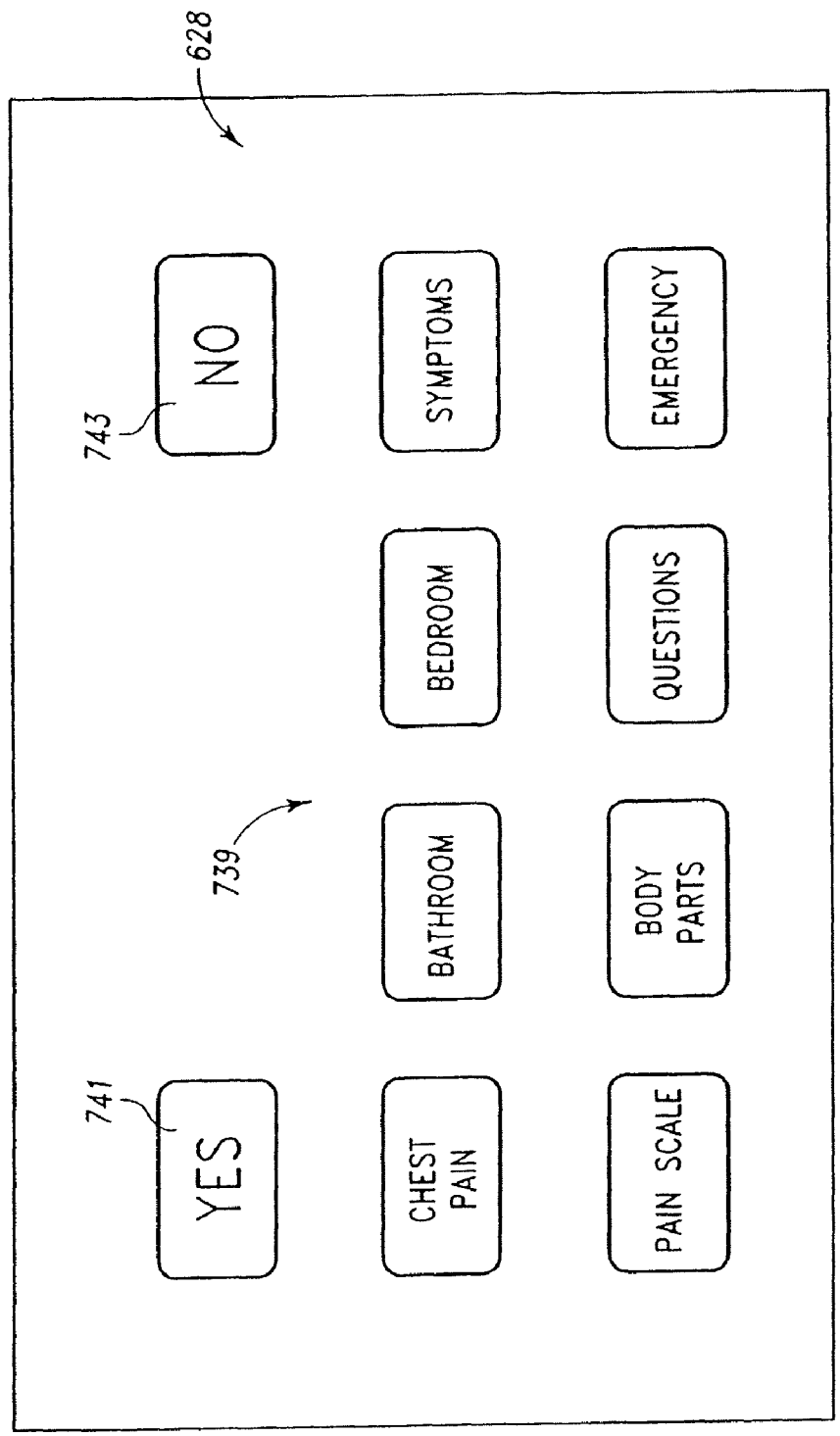

FIG. 63 illustrates a patient voice simulator displayed on screen 628 in accordance with the present invention. The patient can touch the various icons 739 to indicate conditions or symptoms and can respond to questions using "yes" icon 741 or "no" icon 743. When an icon 739 is activated, a speaker in the room or in a remote location generates a simulated voice to pose a question or make a statement relating to the subject matter of the icon 739.

As described in greater detail below, additional icons may include game icons for activating games that can be played using display 628. Moreover, the principles of the present invention may be applied to enable the patient to access the hospital Intranet to learn about illnesses, order meals, order from the gift shop, provide discharge planning (what to do once the patient is at home), document their care, view advertisements related to products and services, check the bill, complete surveys, access doctors, nurses, and religious material, investigate alternative treatments, plan diets, and schedule doctor visits and lab tests after discharge. In addition, the patient can review the schedule for the day including bath, meals, surgery, and tests, access a tutorial to explain how procedures will work, access information and pictures of caregivers, send messages to caregivers, access hospital maps and navigation systems, access fire exit information which is automatically connected to the fire alarm, access a required rights sign off indicating who can visit the patient, and access reference material including a medical dictionary and pharmaceutical references.

Figure 65:
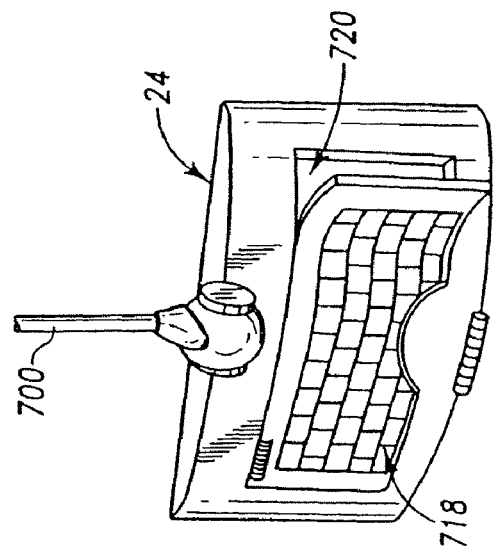
FIGS. 64 and 65 are perspective views of another embodiment of a point-of-care computer display mounting configuration of the present invention.
Figure 64:
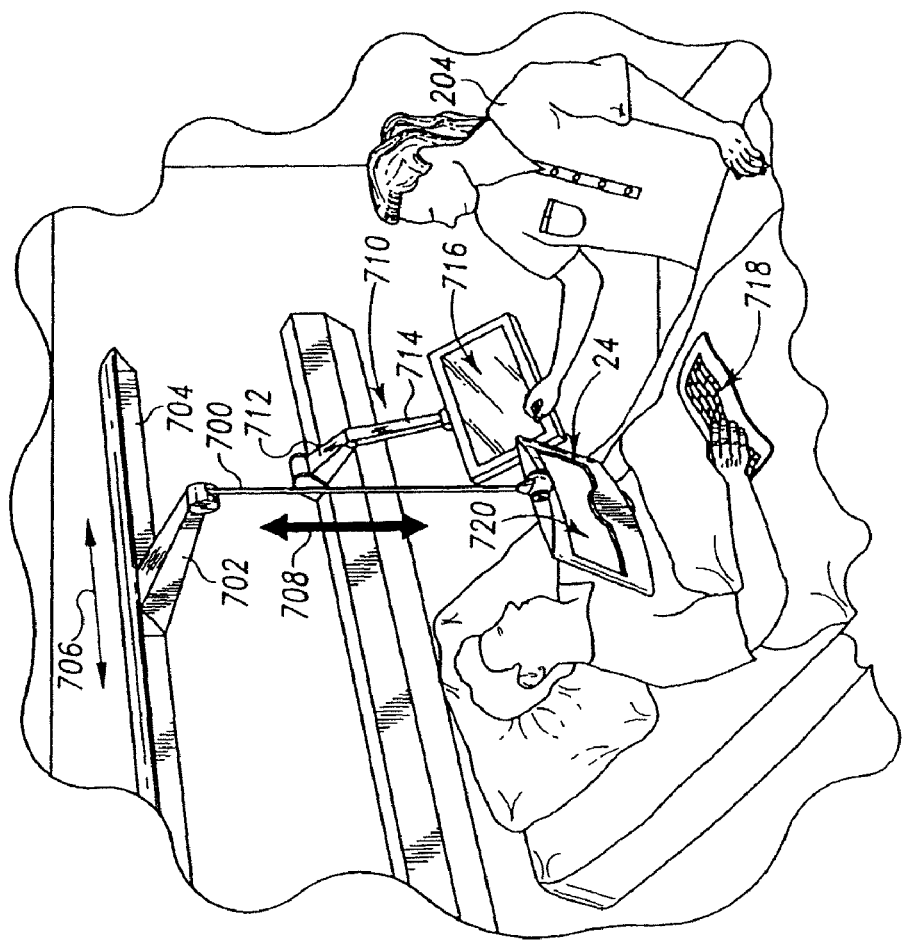

FIGS. 64 and 65 illustrate another embodiment of the present invention in which display 24 is coupled to a retracting cable 700 supported by an arm 702. Arm 702 is coupled to a support 704 on a wall. In an illustrated embodiment, arm 702 can pivot relative to support 704. In another embodiment, arm 702 can slide back and forth in the direction of double headed arrow 706. Cable 700 is retractable and extendable (manual or motorized) from arm 702 in the direction of double headed arrow 708 to adjust the height of display 24. A second arm assembly 710 including first and second adjustable arms 712 and 714 supports another display 716 for use by caregiver 204. As shown in FIG. 65, a flexible keyboard 718 is illustratively stored in a pocket or receptacle 720 on the back of display 24. Illustratively, the flexible keyboard may be a Flexboard keyboard available from Starcover GmbH located in Teltow, Germany. The patient can remove flexible keyboard 718 to enter information into computer 12. In addition, the patient 212 can use touch screen control panel 628 to enter information as described above.

Figure 67:
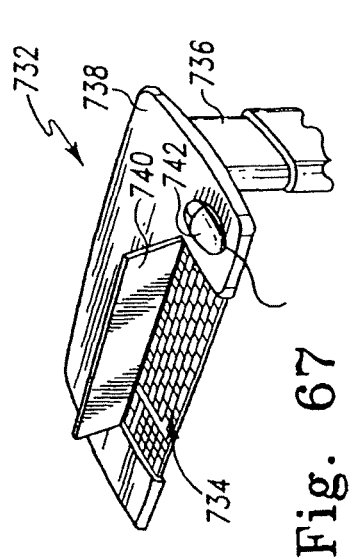
FIGS. 66-68 are perspective views of yet another embodiment of a mounting configuration.
Figure 68:
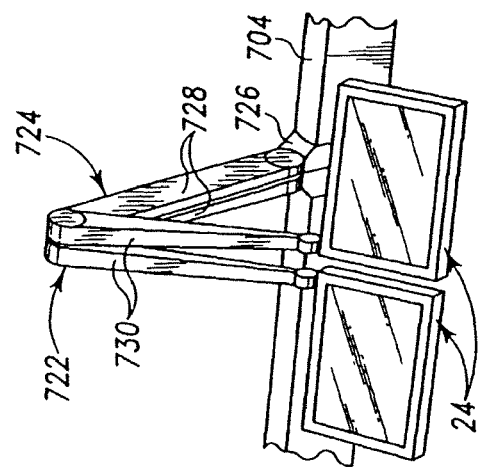
Figure 66:
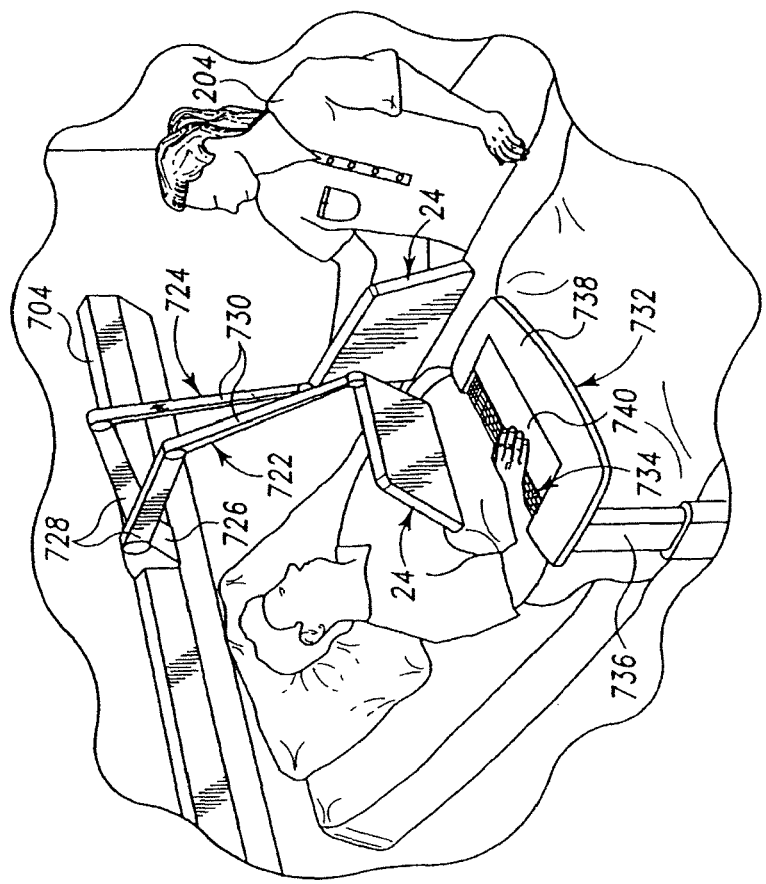

FIGS. 66-68 illustrate another embodiment of the present invention in which first and second arm assemblies 722 and 724 are coupled to support 704 by a coupler 726. Each arm assembly 722, 724 includes a first arm 728 that is pivotally coupled at one end to coupler 726 and pivotally coupled at another end to a second arm 730. Each of second arms 730 is movably coupled to a display 24. The movable connections between support 704, couplers 726, arms 728, 730, and displays 24 permit positioning of displays 24 at various locations for viewing by caregiver 204 or a patient. FIG. 66 depicts displays 24 positioned for simultaneous viewing by both caregiver 204 and the patient. FIG. 68 shows displays 24 positioned side-by-side. This embodiment further includes a table 732 having a table top 738, a keyboard 734 and a pivotable lid 740. An adjustable pedestal 736 supports table top 738. Keyboard 734 is coupled (wirelessly or with wires) to computer 12 (not shown) and functions as an input device for the user. A mouse 742 is also shown in FIG. 67 as an additional input device.

Figure 70:
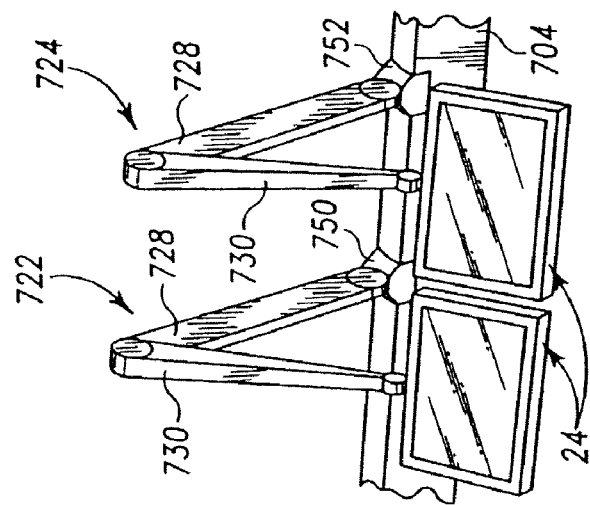
FIGS. 69 and 70 are perspective views of another embodiment of a mounting configuration.
Figure 69:
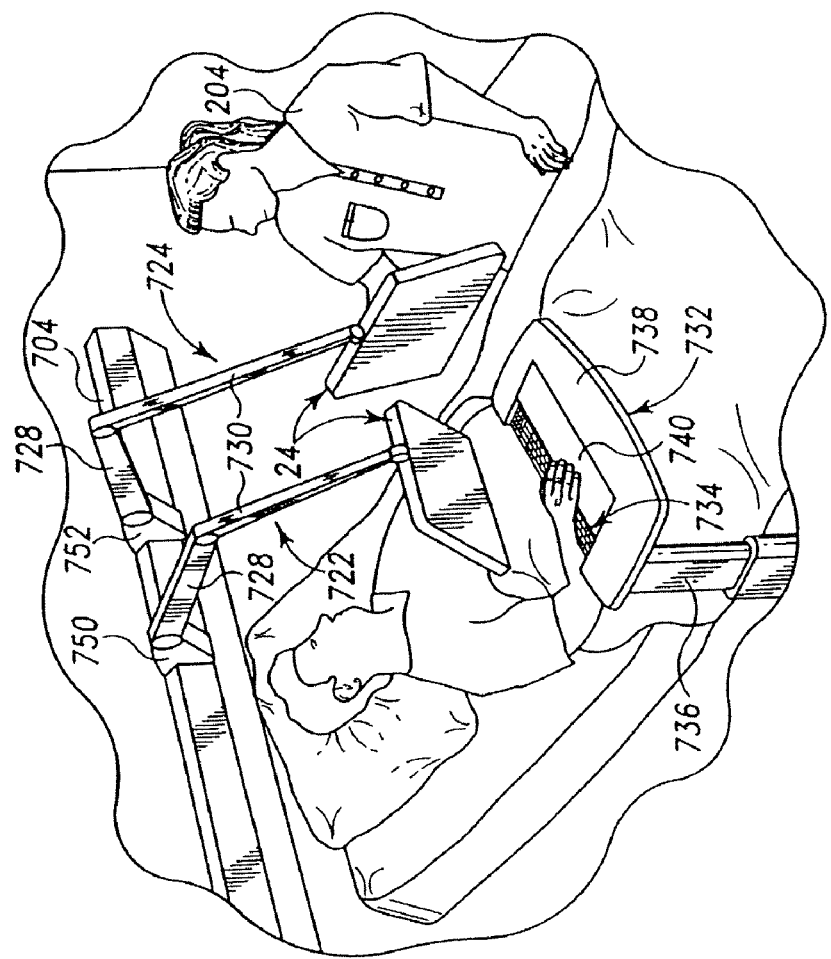

FIGS. 69 and 70 are similar to FIGS. 66 and 68, respectively, except that arm assemblies 722, 724 are coupled to separate supports 750 and 752, respectively.

Referring now to FIGS. 71-73, another embodiment of the invention is shown wherein display 24 is coupled to a cable 754. Cable 754 is coupled to arms 756, 758 which extend and retract, for example, telescopically, as indicated by arrow 760. Arm 758 is coupled to a coupler 762 that is movable along support 704 in the direction of double headed arrow 764. Cable 754 is retractable and extendable into and out of a spool 755 coupled to one end of arm 756. Extension and retraction of cable 754 may be accomplished either manually or by a motor drive (not shown). As best illustrated in FIG. 72, display 24 can be inserted into a support track 780 on an over bed table 782. Support track 780 is a lid that pivots down to cover a keyboard 784. Display 24 can be inserted into track 780 in the direction of arrow 786 to facilitate use by the patient.

In this embodiment, another arm assembly 766 is coupled to another support 757 that is attached to the wall. Arm assembly 766 includes a coupler 759 movably attached to support 757, a first arm 768 that is pivotally coupled to coupler 759, and a second arm 770 that is pivotally coupled at one end to first arm 768 and movably coupled at the other end to a support 772. Support 772 includes grip handles 774 and an input device such as a keyboard 776. A second display 778 is coupled to support 772. FIG. 73 depicts display 24 being moved into position on support 772 adjacent display 778.

Figure 74:
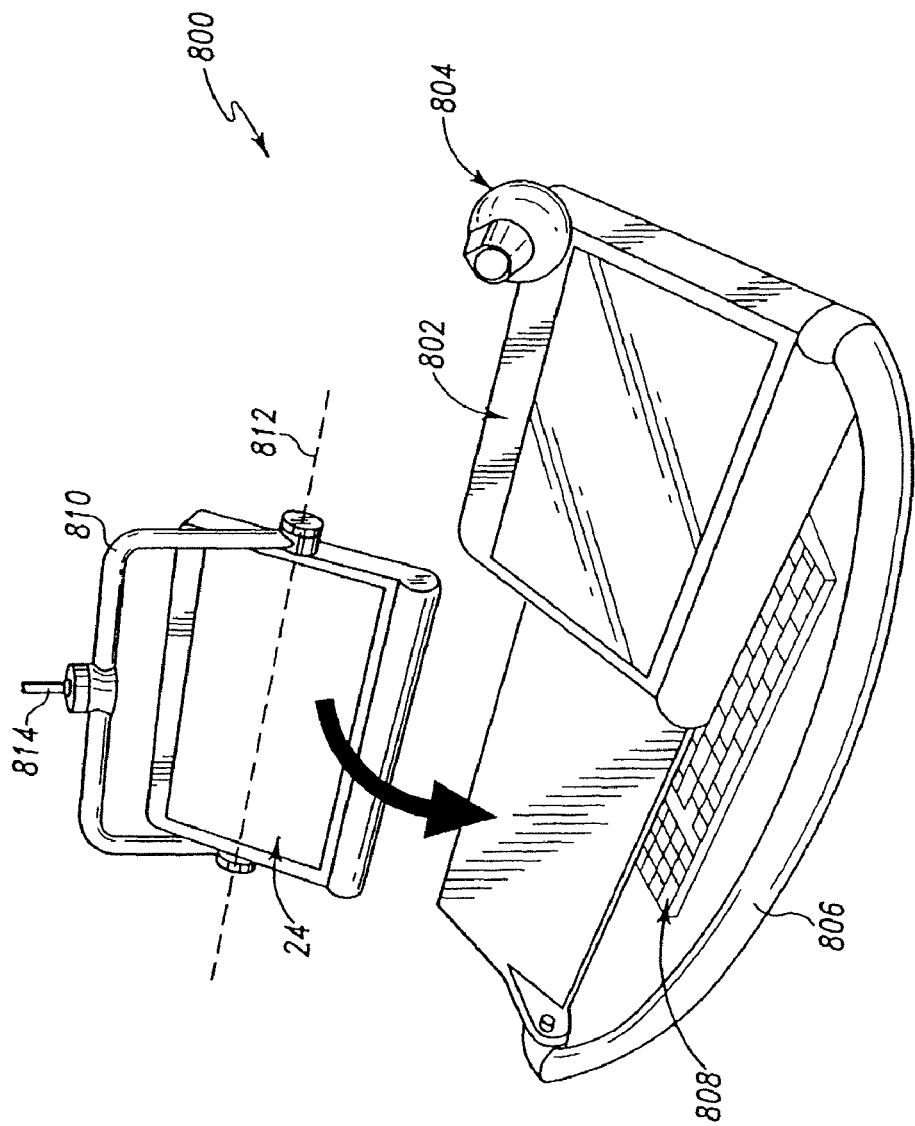
FIG. 74 is a perspective view of a display support according to one embodiment of the present invention.

FIG. 74 illustrates another embodiment of the present invention including a display support 800. Display support 800 may be attached to a wall by an arm assembly, mounted to an over bed table, mounted to the bed, or supported in any other manner disclosed herein. Support 800 includes a fixed display 802 including a controller or input device 804. A grip handle 806 extends along the front of support 800. Another input device such as keyboard 808 may be located adjacent to handle 806. Additionally, a second display 24 is provided. Display 24 is coupled to a U-shaped support 810 to pivot about axis 812. Display 24 is suspended from a cable 814 as described above with reference to FIGS. 64 and 65. As indicated in FIG. 74, display 24 may be installed on support 800 adjacent to fixed display 802.

Figure 75:
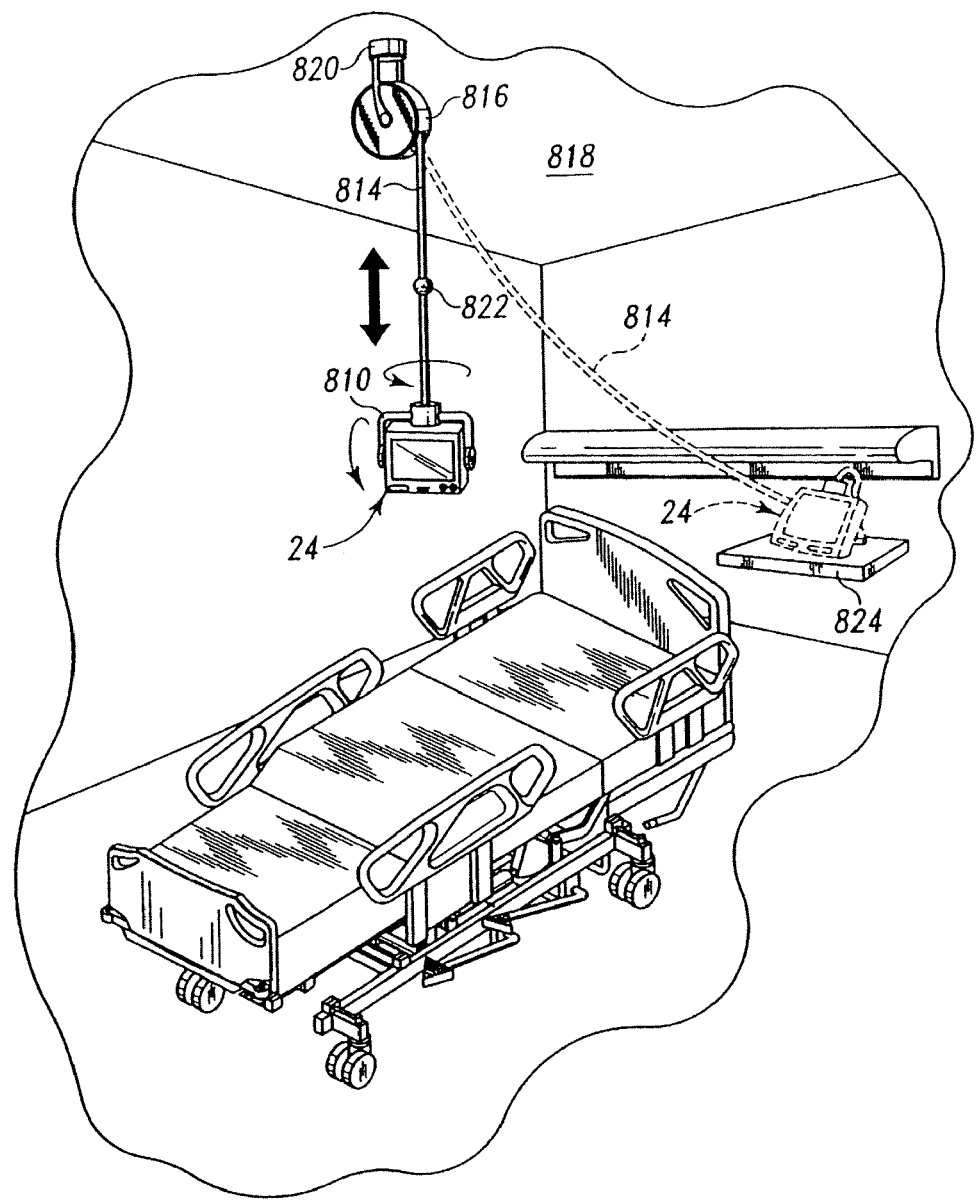
FIG. 75 is a perspective view of yet another embodiment of a mounting configuration.

Another embodiment of the present invention is illustrated in FIG. 75. In this embodiment, display 24 is coupled to U-shaped support 810 as described with reference to FIG. 74. Cable 814 is retractable into and extendable from a spool 816 suspended from ceiling 818 by a connector 820. Connector 820 permits spool 816 to pivot or rotate to facilitate positioning of display 24 at various locations within the room. Spool 816 may be a conventional self-retracting cable spool or it may be motor driven to automatically extend and retract cable 814. A stop 822 is coupled to cable 814 to prevent cable 814 from retracting too far into spool 816 for display 24 to be reached. Cable 814 can be extended to position display 24 on a support or table 824 (as shown in dotted lines in FIG. 75), or any other location within the room.

Figure 76:
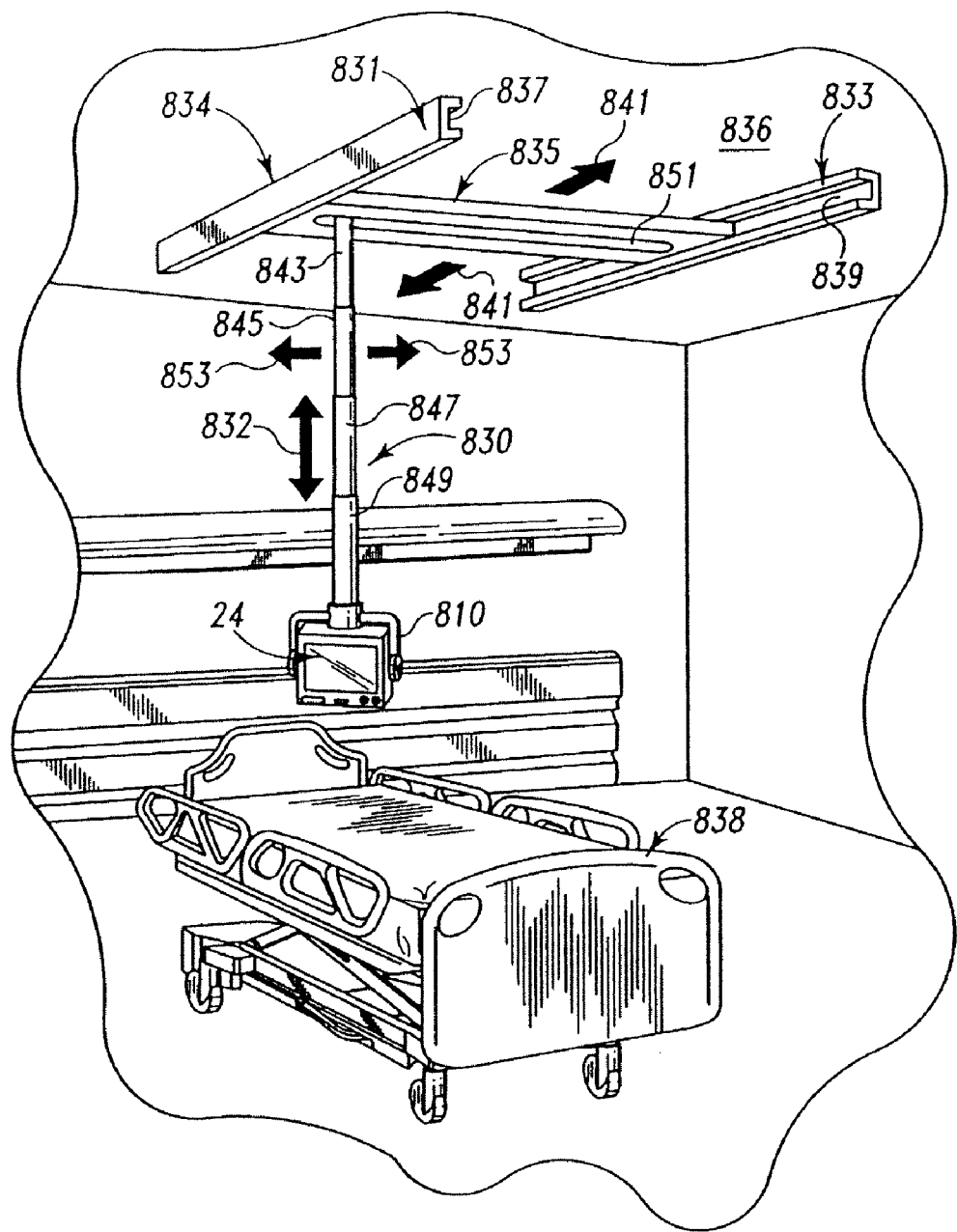
FIG. 76 is a perspective view of another embodiment of a mounting configuration of the present invention.

Another embodiment of the present invention is illustrated in FIG. 76. This embodiment is similar to that of FIG. 75, except that display 24 is supported by an arm assembly 830 that is attached to an H-shaped support 834. Support 834 includes tracks 831, 833 and movable member 835. Tracks 831, 833 define channels 837, 839, respectively, for receiving an end of movable member 835. Accordingly, movable member 835 can slide or move back and forth in the direction of arrows 841. Movable member 835 supports arm assembly 830, which illustratively includes a plurality of telescopic members 843, 845, 847, 849 that permit adjustment of the position of display 24 in the direction of arrow 832. Telescopic member 843 is received by a channel 851 formed in movable member 835. Thus, arm assembly 830 is movable back and forth in the direction of arrows 853. Telescopic member 849 is coupled to support 810, which permits adjustment of the position of display 24 in the manner described above. Accordingly, arm assembly 830 and display 24 may be moved to a plurality of different orientations over bed 838.

Figure 77:
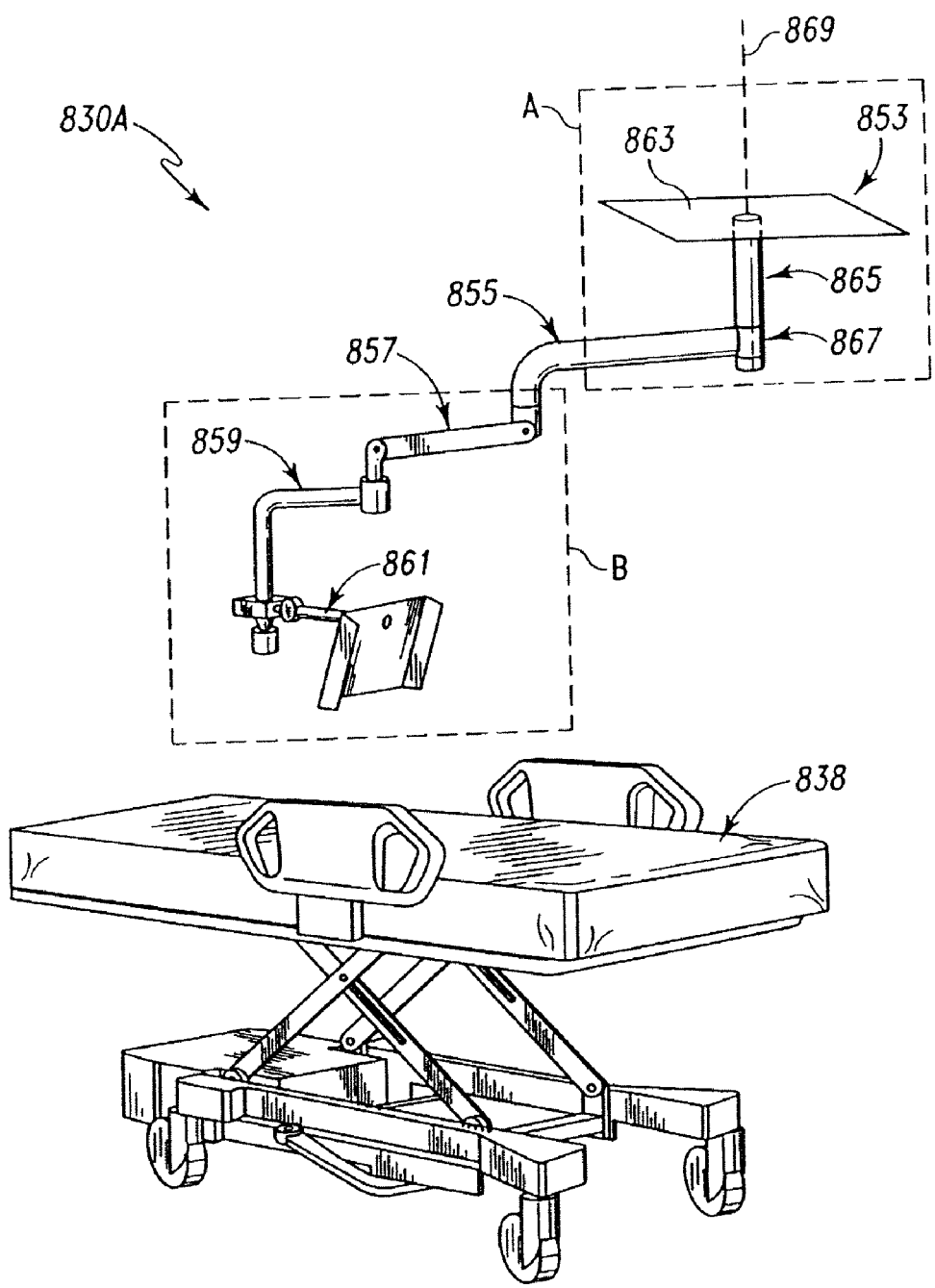
FIG. 77 is a perspective view of another embodiment of a mounting configuration of the present invention.
Figure 78:
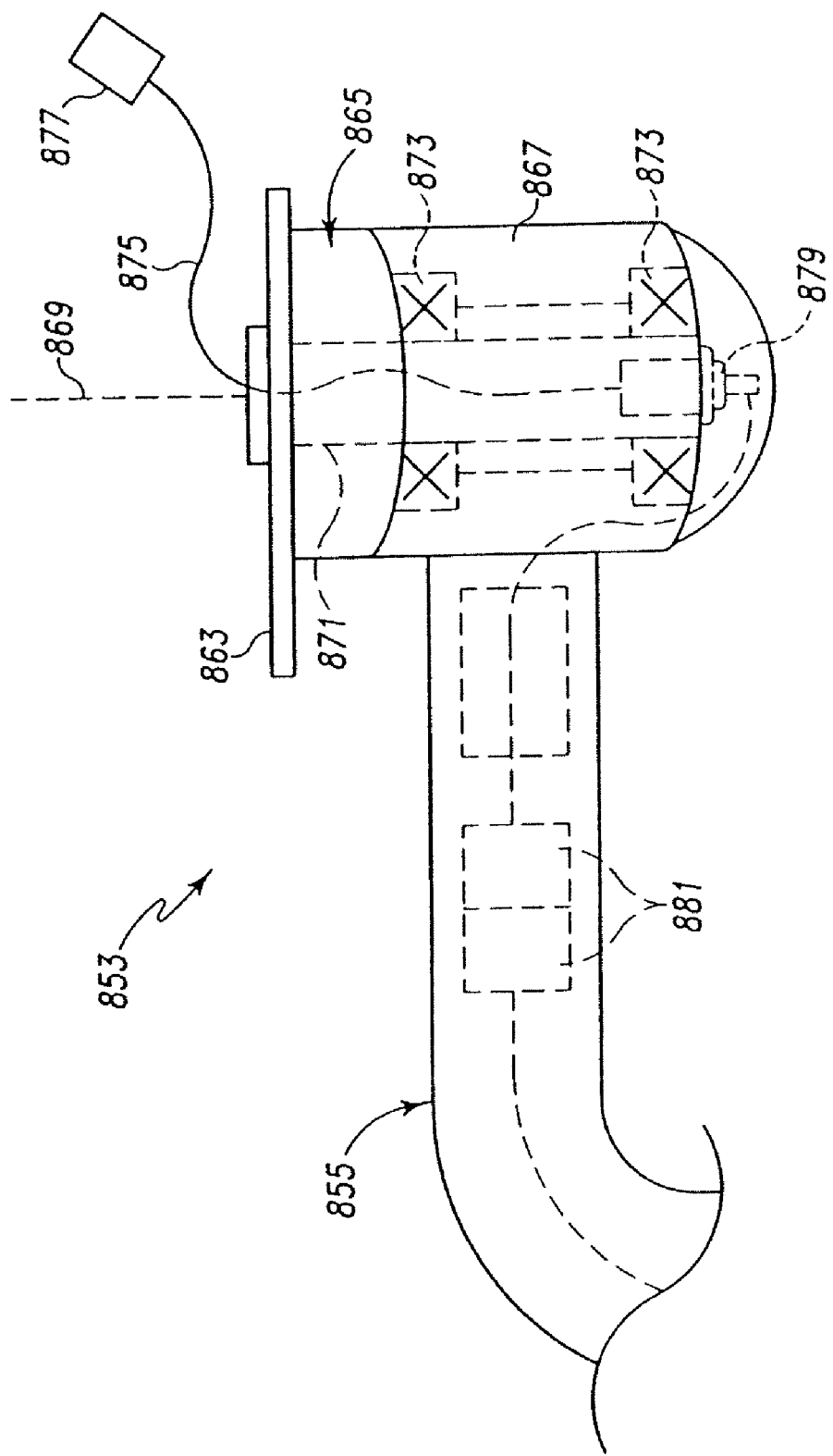
FIGS. 78 and 79 are perspective views of components of the mounting configuration depicted in FIG. 77.
Figure 79:
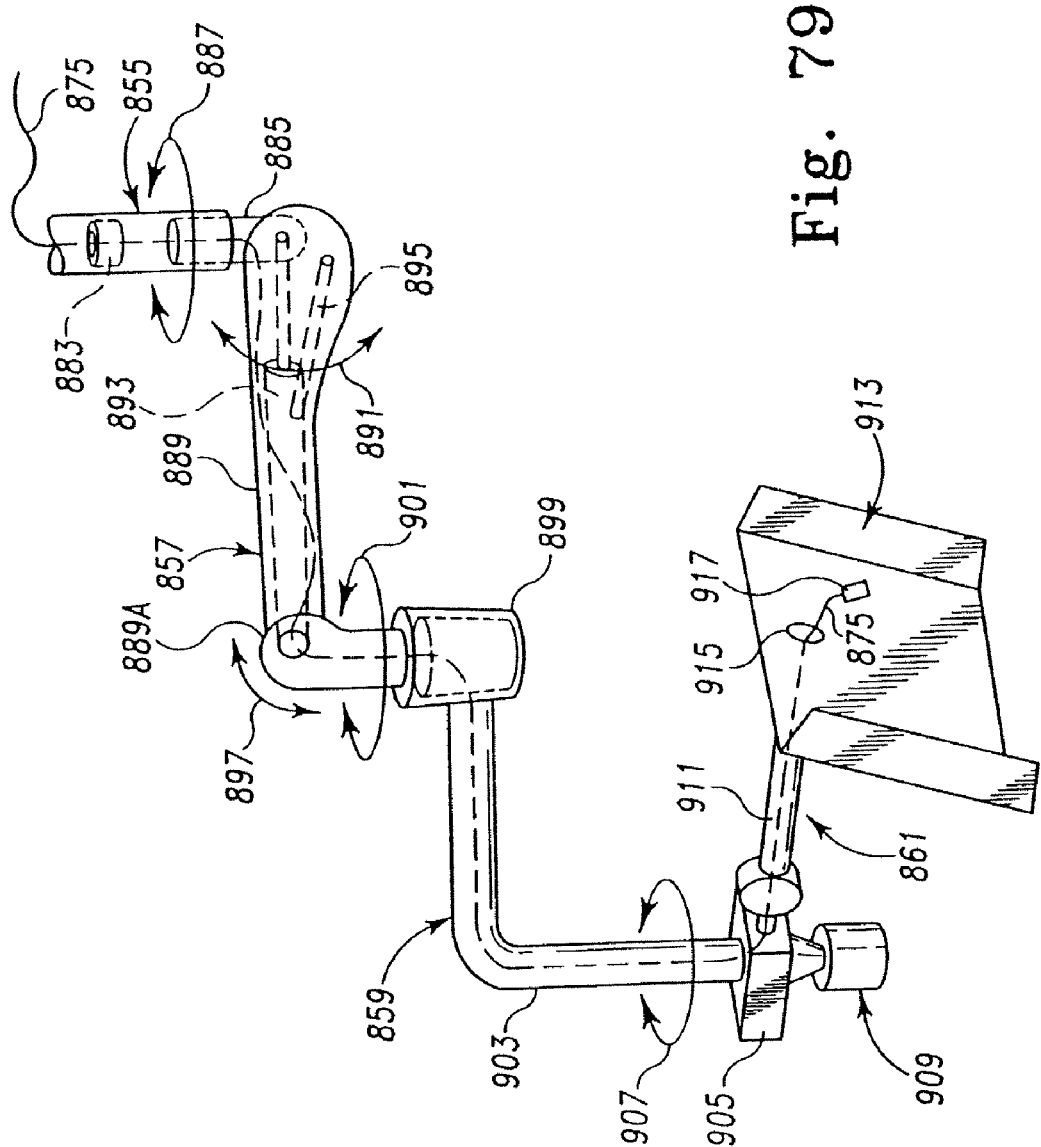
Figure 80:
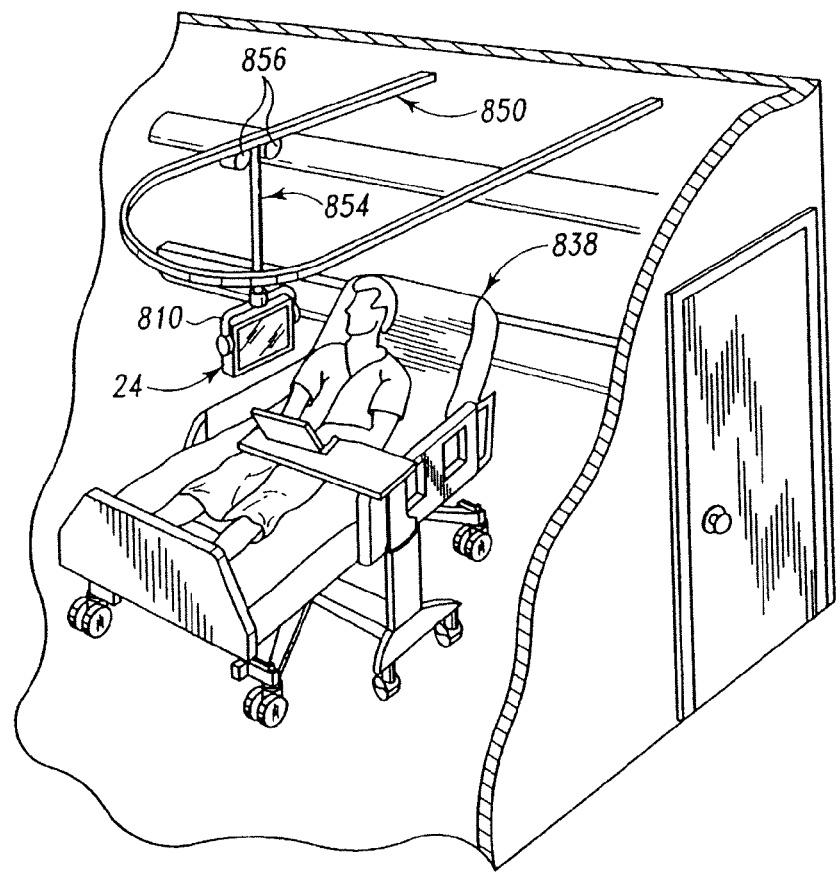
FIG. 80 is a perspective view of yet another embodiment of a mounting configuration of the present invention.

An alternative embodiment of arm assembly 830 is illustrated in FIGS. 77-79. As best shown in FIG. 77, arm assembly 830A generally includes a mount assembly 853 for attachment to the room ceiling, a first arm 855 coupled to mount assembly 853, a second arm 857 coupled to first arm 855, a third arm 859 coupled to second arm 857, and a display support 861 coupled to third arm 859. As described below, the various components of arm assembly 830A are movably connected to one another to permit adjustment of the position over bed 838 of a display 24 (not shown) mounted in display support 861.

Referring now to FIG. 78, mount assembly 853 includes a plate 863 that is attached to the room ceiling, a housing 865 that is coupled to plate 863, and a ring 867 that is coupled to housing 865 in an annular groove for rotation about axis 869. As shown, first arm 855 is attached to ring 867. Housing 865 further includes a central bore 871 and internal bearings 873 to facilitate rotational movement of ring 867 on housing 865. A wire 875 (one shown) is routed through central bore 871 from a connector 877 to a slip ring 879. While only one wire 875 is shown, it should be understood that multiple wires may be routed in the manner described herein. Wire 875 is further routed from slip ring 879 to a pair of connectors 881 and through first arm 855.

As shown in FIG. 79, first arm 855 further includes a slip ring 883 and an internal opening for receiving a stem 885 of second arm 857 to permit rotation of second arm 857 as indicated by arrow 887. Second arm 857 also includes a body 889 that is pivotally coupled at one end to stem 885 and pivotally coupled at another end to coupler 889A. Accordingly, body 889 may be pivoted relative to stem 885 as indicated by arrow 891. A locking gas spring 893 is disposed within body 889 and connected between stem 885 and coupler 889A to assist in lifting of display 24. A counter-balance arm 895 is connected between body 889 and locking gas spring 893. As also indicated in FIG. 79 by arrow 897, coupler 889A is pivotable about its connection to body 889.

Third arm 859 includes a coupler 899 that is movably connected to coupler 889A to permit rotation of coupler 899 (and third arm 859) as indicated by arrow 901. Third arm 859 further includes an L-shaped body 903 connected at one end to coupler 899 and connected at the other end to body 905 of display support 861 to permit rotation of display support 861 as indicated by arrow 907. Display support 861 includes a handle 909 and an arm 911 coupled to body 905. Arm 911 supports a mounting plate 913 for receiving display 24. As shown, wire 875 is routed through the various components of arm assembly 830A and through an opening 915 in mounting plate 913 to a connector 917. Display 24 is electrically connected to connector 917. Accordingly, arm assembly 830A permits positioning of display 24 at various locations and orientations above bed 838.

Figures 81, 82, 83:
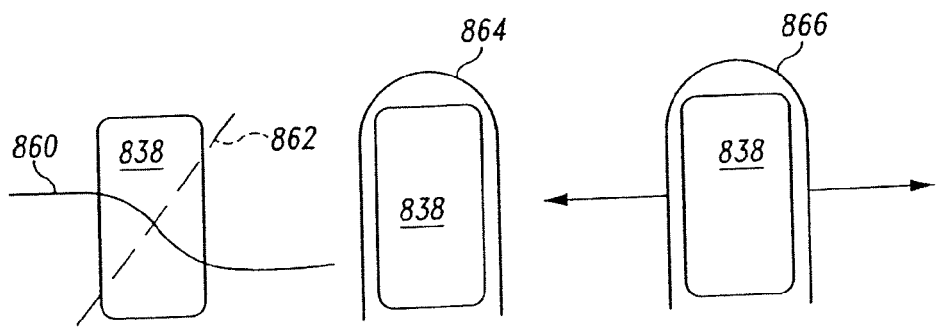
FIGS. 81-83 are top plan views of variations of the track shape of the mounting configuration of FIG. 80.

In another embodiment shown in FIGS. 80-83, display 24 is mounted on U-shaped support 810 in the manner described above. U-shaped support 810 is coupled to an arm assembly 854, which is connected to rollers 856. Rollers 856 are configured to move along a U-shaped track 850 that is attached to the ceiling of the room. Rollers 856 guide the position of display 24 around track 850. FIGS. 81-83 illustrate different orientations of tracks 860, 862, 864, and 866 relative to bed 838 in accordance with other embodiments of the present invention. It should be understood that tracks 850, 864, and 866 may also be used to support a patient support device such as a sling or harness coupled to arm assembly 854 in place of display 24. Accordingly, the patient may be assisted by the arm assembly 854 and track as the patient walks around bed 838.

Figure 86:
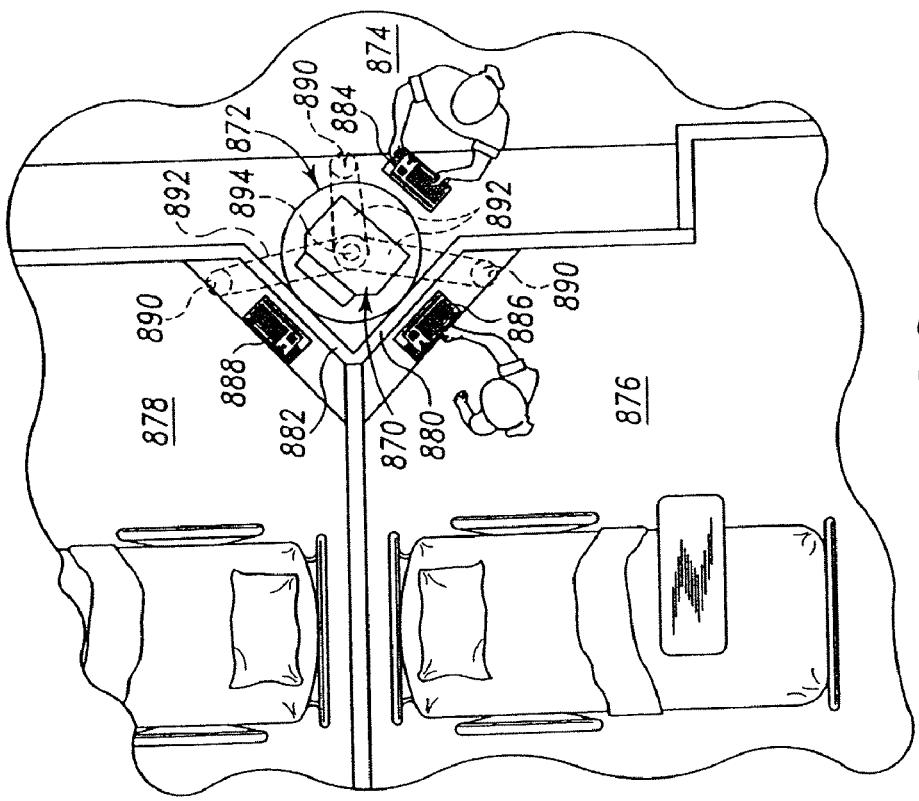
FIG. 86 is a top plan view of a portion of a hospital including the mounting configuration of FIG. 84.

FIGS. 84-86 illustrate a three-position computer turntable in accordance with another embodiment of the present invention. The computer (not shown) and display monitor 870 are mounted on a rotating turntable 872. The position of turntable 872 is controlled either manually or by a motor (not shown). FIG. 86 illustrates that monitor 870 may be positioned for viewing in the hallway 874 and in first and second rooms 876, 878 depending upon the orientation of monitor 870. Monitor 870 is visible through windows 880, 882 in rooms 876, 878, respectively. Separate keyboards or other data entry devices 884, 886 and 888 are located in hallway 874 and rooms 876, 878, respectively.

As best shown in FIG. 85, a manual drive 890 for turntable 872 may include a handle 919 rotatably connected to a disk 921 and shaft 923. Shaft 923 is rotatably connected to a table or shelf 925. Drive 890 further includes a belt 892 that extends around shaft 923 and a shaft 894 coupled to table 872. Shaft 894 is connected to a display support 927. Thus, rotation of disk 921 using handle 919 causes rotation of belt 892 and shaft 894, thereby rotating display support 927 and display 870. As shown in FIG. 86, a separate manual drive 890 may be provided in hallway 874 and each of rooms 876, 878. Therefore, monitor 870 may be rotated to the desired position for viewing.

Figure 87:
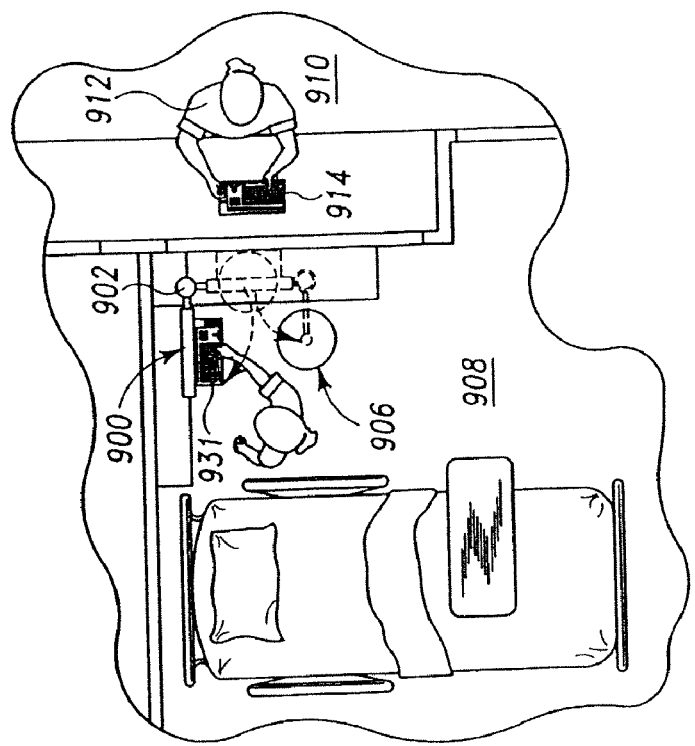
FIG. 87 is a top plan view of a portion of a hospital including another embodiment of a mounting configuration of the present invention.
Figure 89:
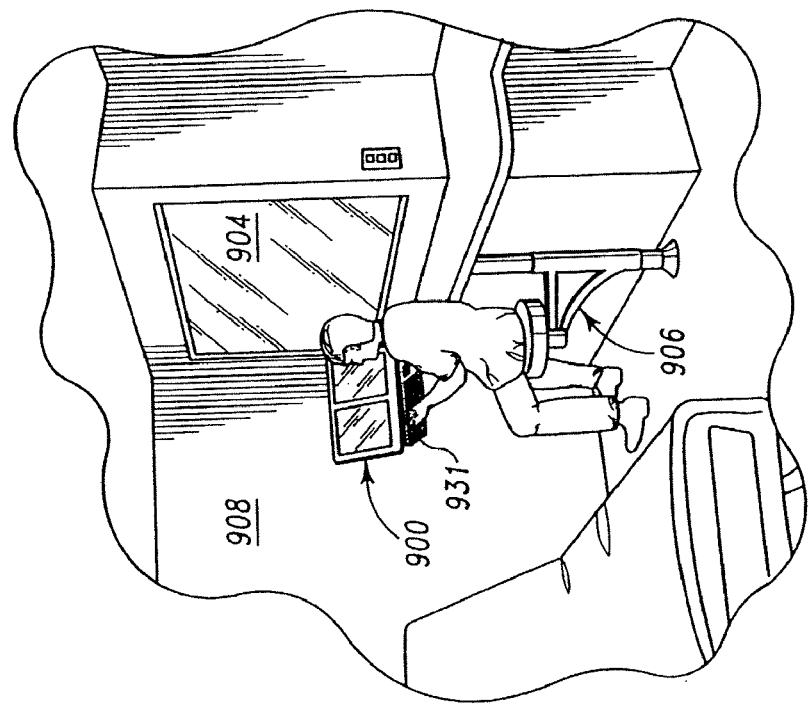
FIGS. 88 and 89 are perspective views of the mounting configuration of FIG. 87.
Figure 88:
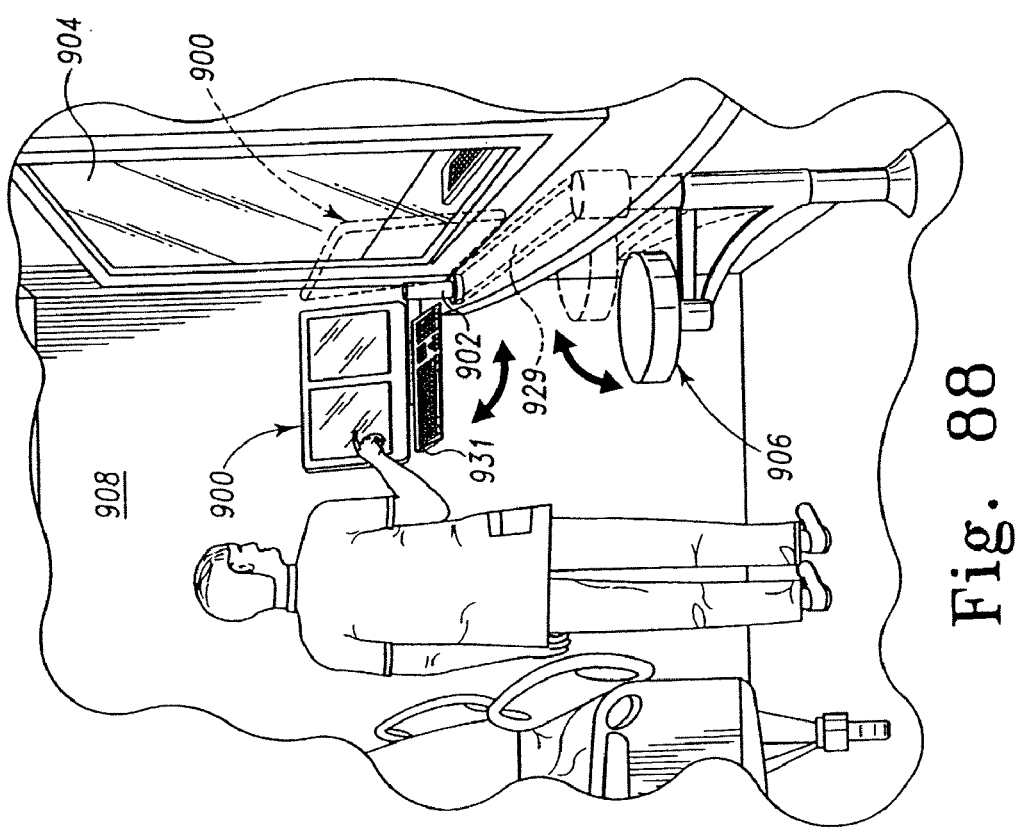

Another embodiment of the present invention is illustrated in FIGS. 87-89. In this embodiment, a dual screen display 900 is coupled to a rotatable support arm 902 located adjacent in an electronic LCD window 904. A retractable stool 906 is moveable from an extended position to a retracted position shown in dotted lines in FIGS. 87 and 88. Display 900 is also pivotable between a first position shown in FIGS. 87 and 88 for use in room 908 and a second position shown in dotted lines in FIGS. 87 and 88 so that display 900 can be viewed from hallway 910 by a user 912. As should be apparent from the drawings, movement of stool 906 from the retracted position to the extended position is translated via linkage 929 (shown as a belt) to movement of display 900 from the second position to the first position. Thus, when a user in room 908 desires to view display 900 and use user input device 931, the user may move stool 906 to the extended position. A separate keyboard or input device 914 is located in hallway 910.

Figure 91:
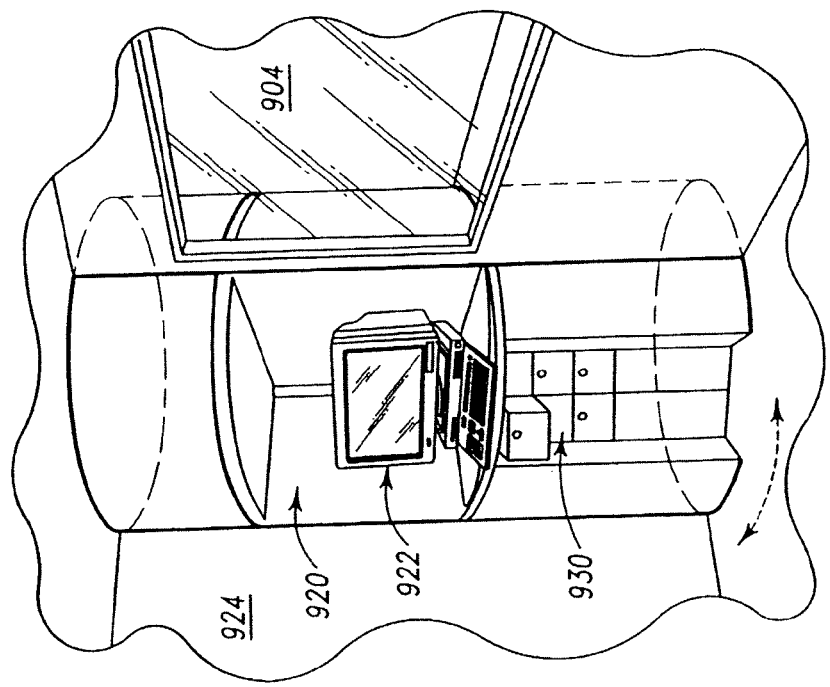
FIG. 91 is a perspective view of the mounting configuration of FIG. 90.
Figure 90:
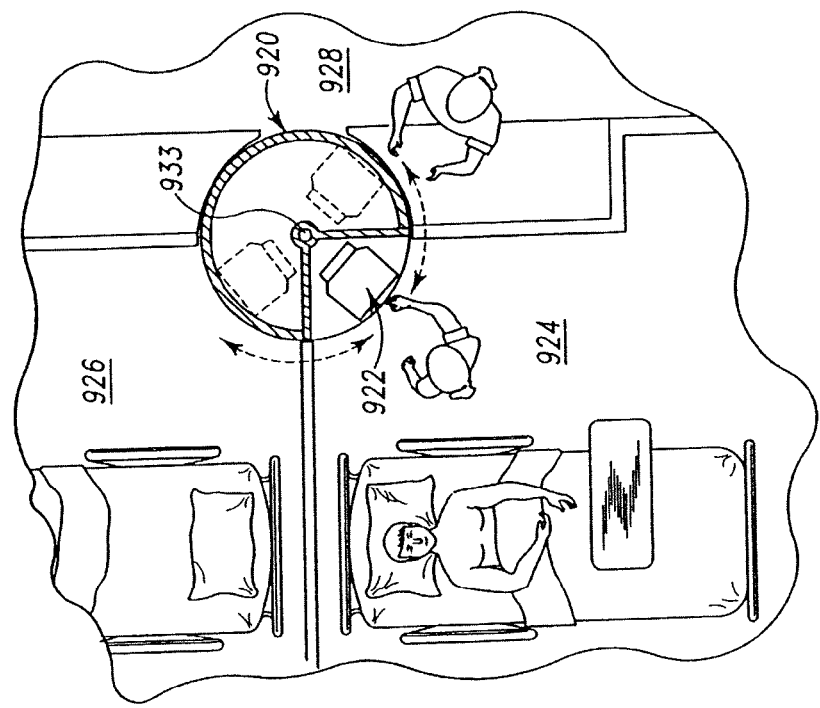
FIG. 90 is a top plan view of a portion of a hospital including another embodiment of a mounting configuration of the present invention.

Another embodiment of the present invention is illustrated in FIGS. 90 and 91. In this embodiment, a rotatable carousel 920 is configured to support a computer/monitor 922 for access in room 924, room 926 and hallway 928. Carousel 920 may be moved manually or moved by a motor (not shown). Carousel 920 is configured to be supported on and rotate about a shaft 933. As shown in FIG. 91, a supply container 930 is also rotatable with carousel 920.

Figure 92:
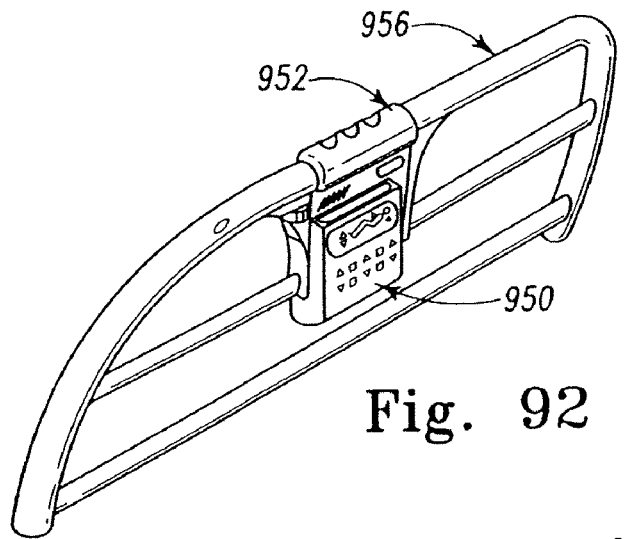
FIGS. 92-94 are perspective views of another mounting configuration for a display of the present invention.
Figure 93:
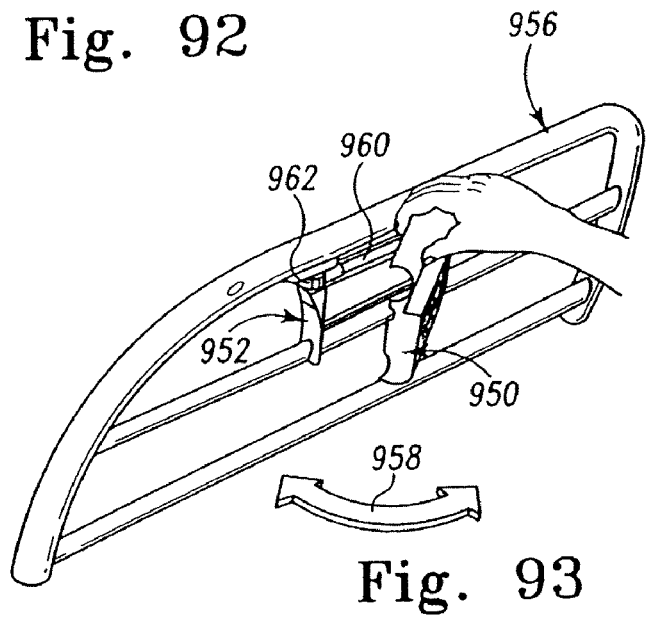
Figure 94:
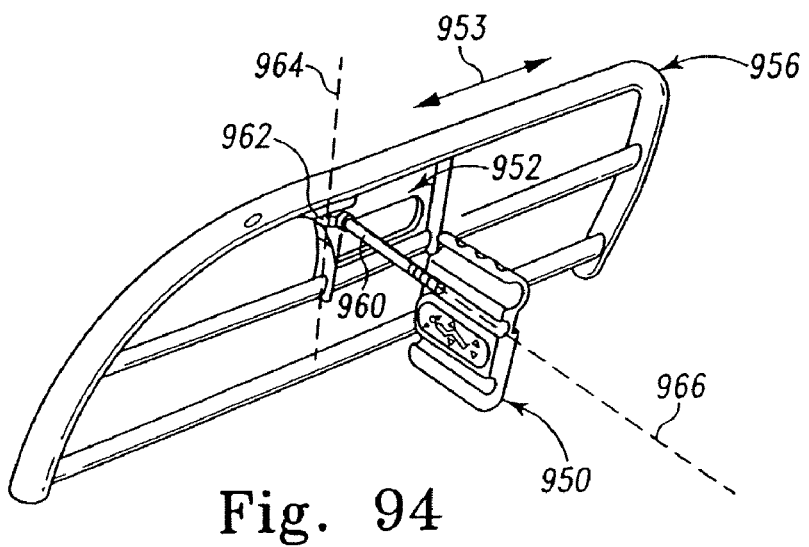

FIGS. 92-94 illustrate another embodiment of the present invention in which a display 950 is coupled to a moveable support 952 mounted to a siderail 956. Display 950 performs the function of display 24 discussed above. Display 950 is pivotable outwardly from support 952 in the direction of arrow 958 of FIG. 93 to an extended position. As shown, support 952 includes an arm 960 secured to support 952 by joint 962. Therefore, arm 960 (and display 950) can move along siderail 956 in the direction of arrow 953, and pivot about first and second axes 964 and 966.

Figure 98:
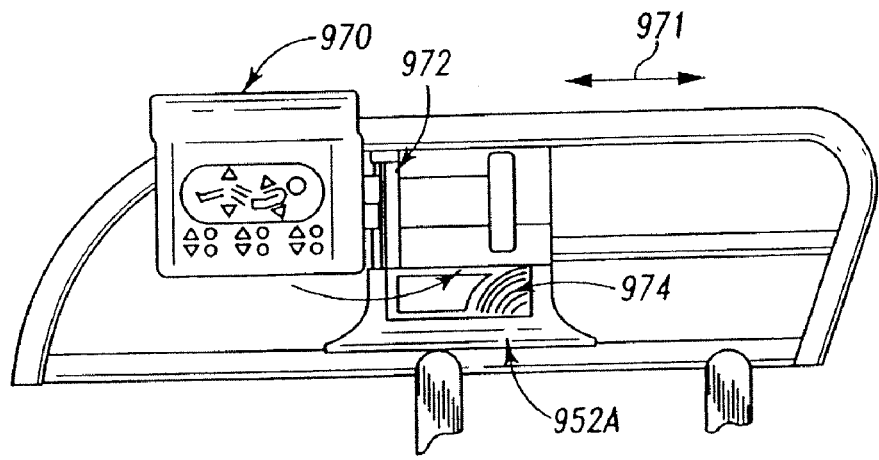
FIGS. 98 and 99 are side elevational views of the mounting configuration of FIG. 95.
Figure 99:
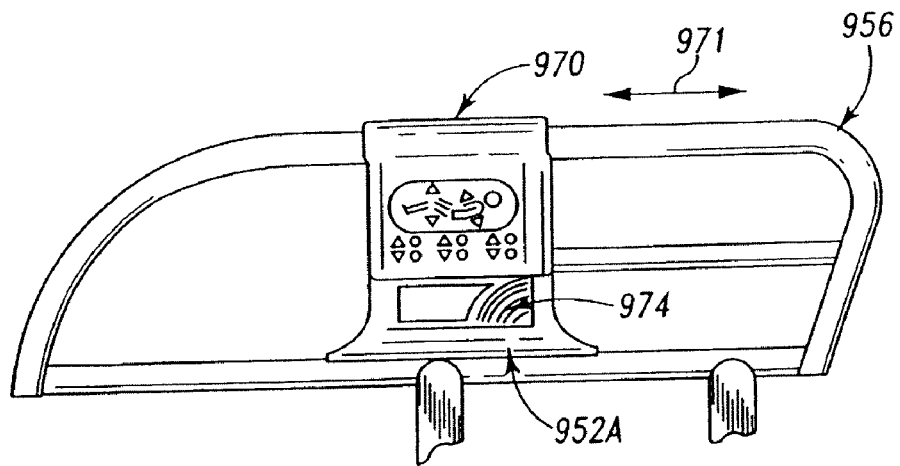

Another embodiment of the present invention is illustrated in FIGS. 95-99. In this embodiment, a display 970 is coupled to siderail 956 by a linkage 972. As best shown in FIG. 96, linkage 972 includes a pair of arms 935 that are pivotally coupled to movable support 952A at pins 937 and pivotally coupled to display 970 at pins 939. Thus, display 970 is movable vertically relative to siderail 956 as indicated by arrow 941. Additionally, pins 937 are mounted in a housing 937A that is pivotally coupled to movable support 952A at pins 943, and pins 939 are mounted to a bracket 945 that is pivotally coupled to display 970 at pins 945A. Thus, linkage 972 may also be pivoted in the direction of arrow 947, and display 970 may also be pivoted in the direction of arrow 949. Display 970 may also be moved along siderail 956 in the direction of arrow 971. FIGS. 95 and 98 show display 970 in an extended position. FIG. 99 shows display 970 in a retracted position within movable support 952A. A speaker 974 is also shown as a component of movable support 952A.

Figure 100:
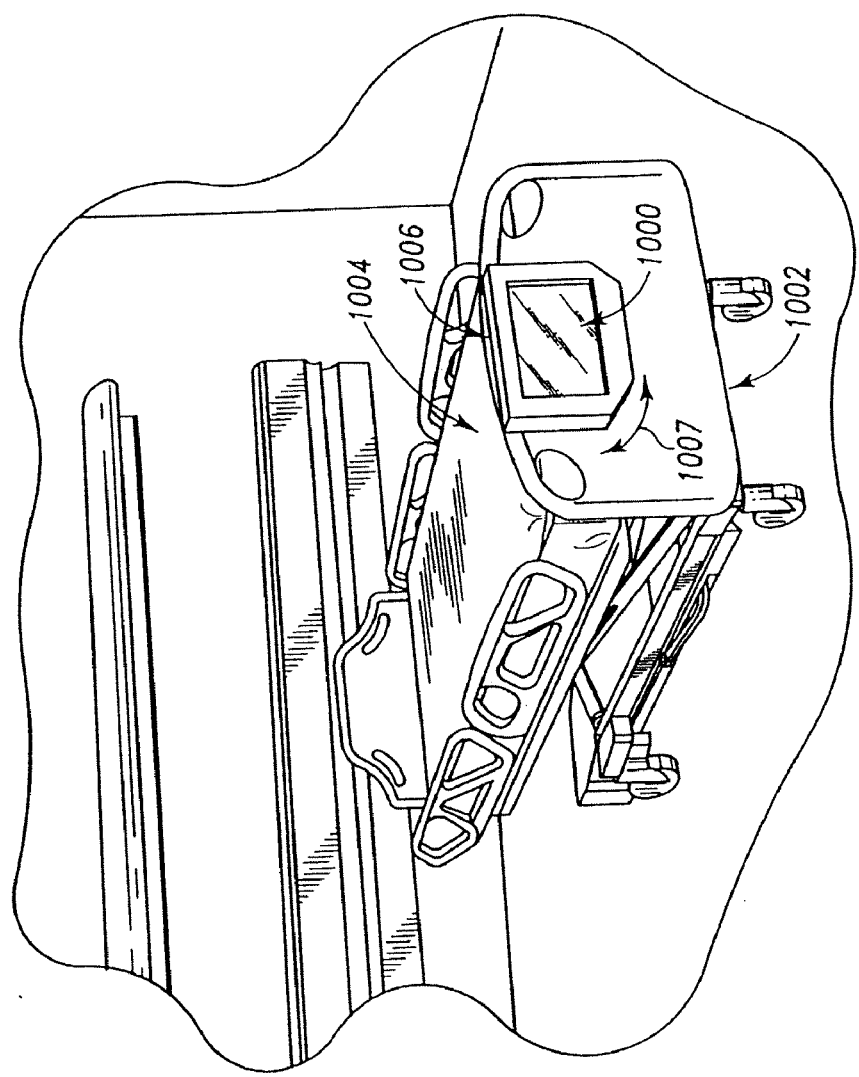
FIGS. 100-102 are perspective views of another embodiment of a mounting configuration of the present invention.
Figure 101:
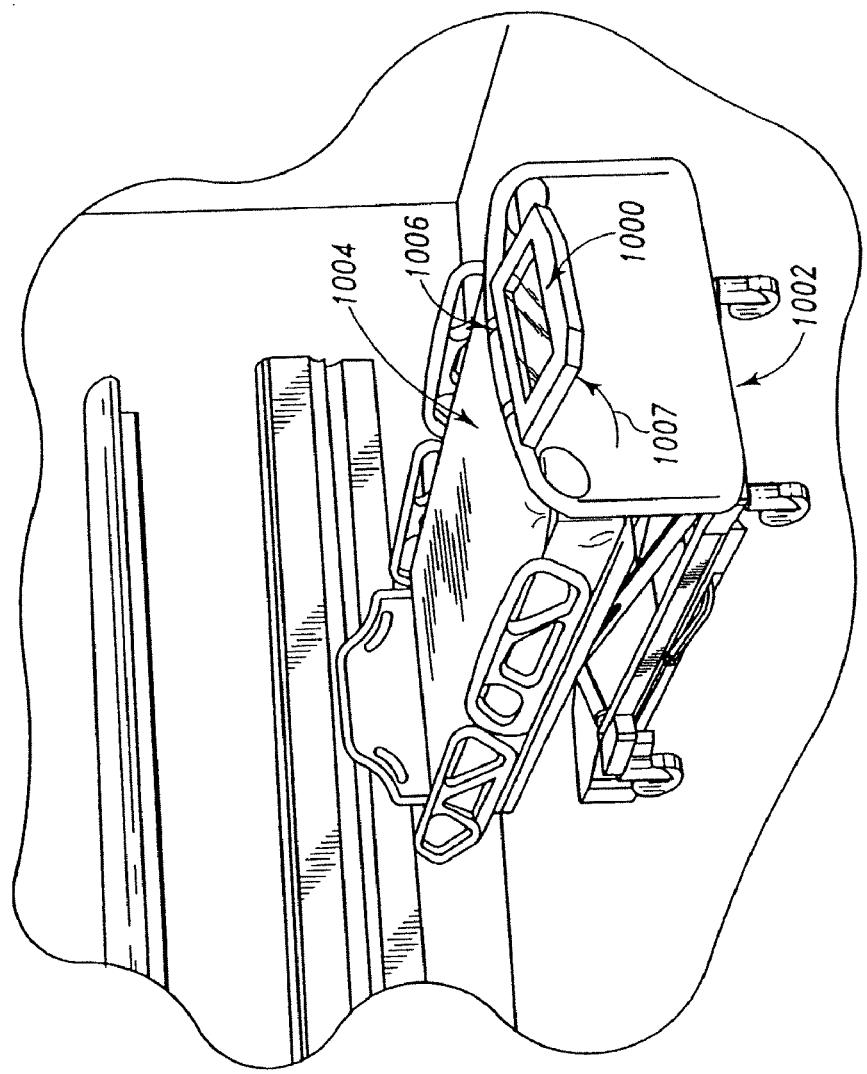
Figure 102:
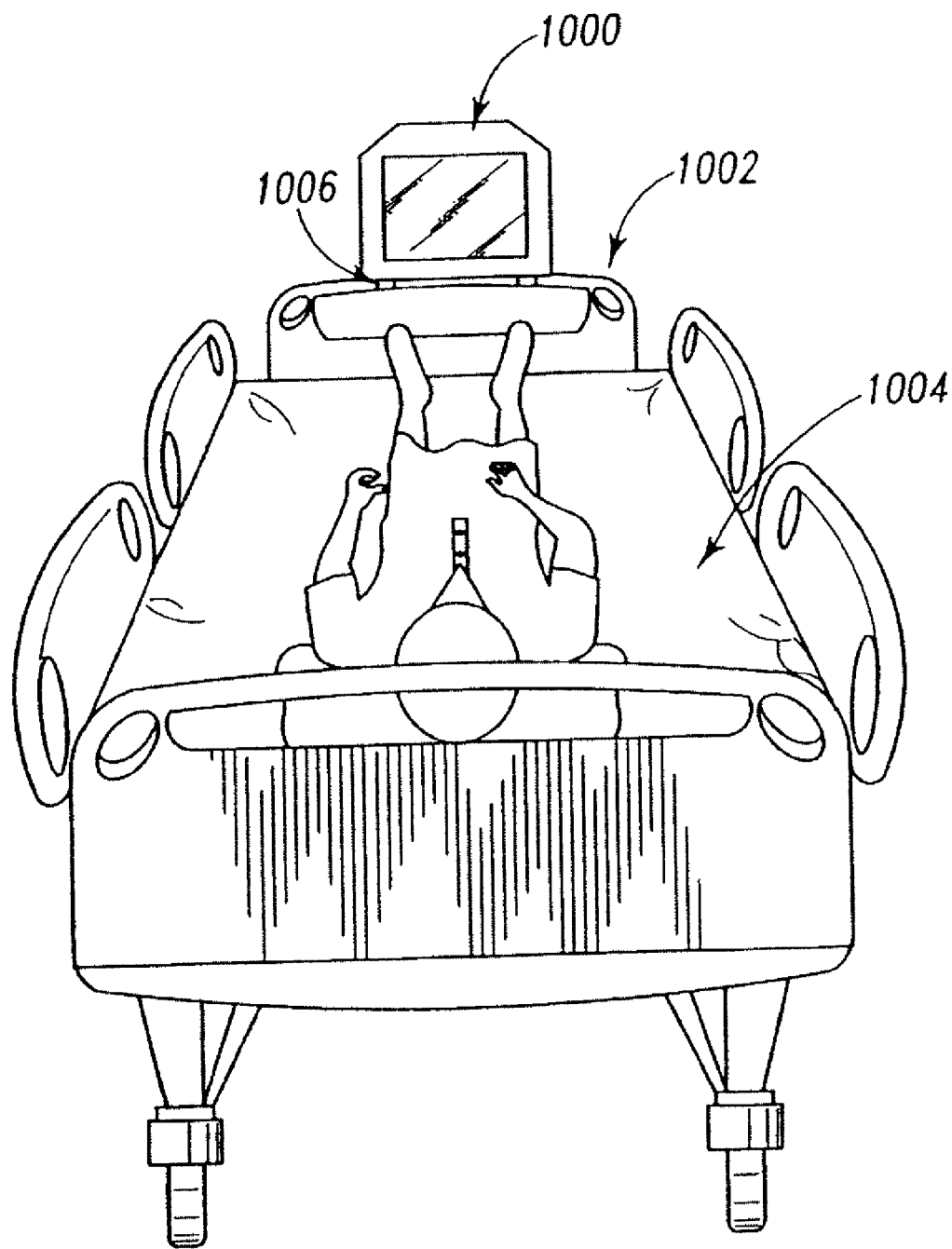
Figure 103:
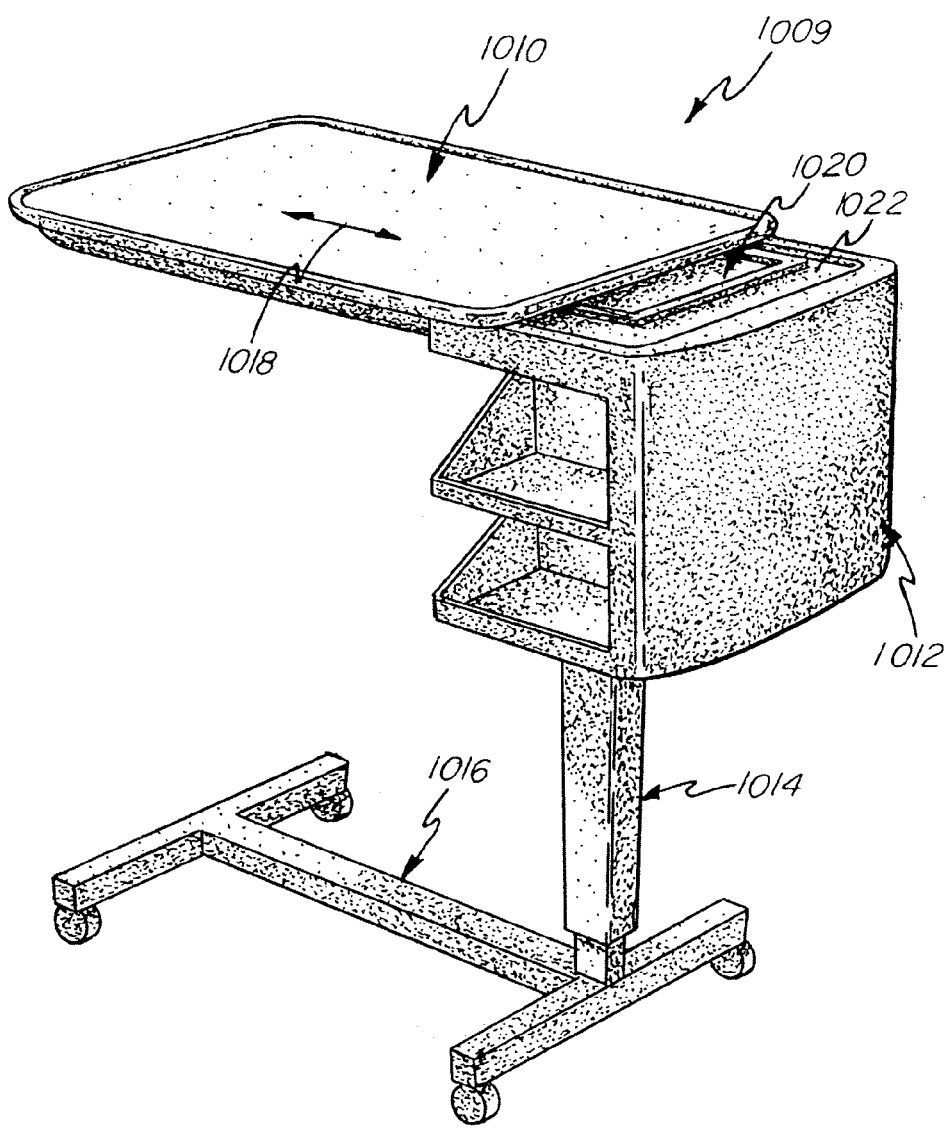
FIGS. 103-108 are perspective views of another embodiment of a mounting configuration of the present invention.

Another embodiment of the present invention is illustrated in FIGS. 100-102. In this embodiment, a display 1000 is coupled to a footboard 1002 of a bed 1004 by a support 1006. Support 1006 is pivotable from a first position shown in FIG. 100 upwardly as indicated by arrow 1007 to a vertical position shown in FIG. 102 for viewing by the patient. When display 1000 is moved from the position shown in FIG. 100 to the position shown in FIG. 102, the software in computer 12 (not shown) inverts the image on display 1000 so that is readable by the patient. Support 1006 is also moveable to any of a plurality of intermediate positions such as that shown in FIG. 101 to facilitate viewing and/or data entry by a caregiver. Support 1006 is coupled to footboard 1002 by suitable fasteners that include a locking mechanism such as detents or other clutch mechanisms to hold support 1006 in the desired position relative to footboard 1002.

Figure 104:
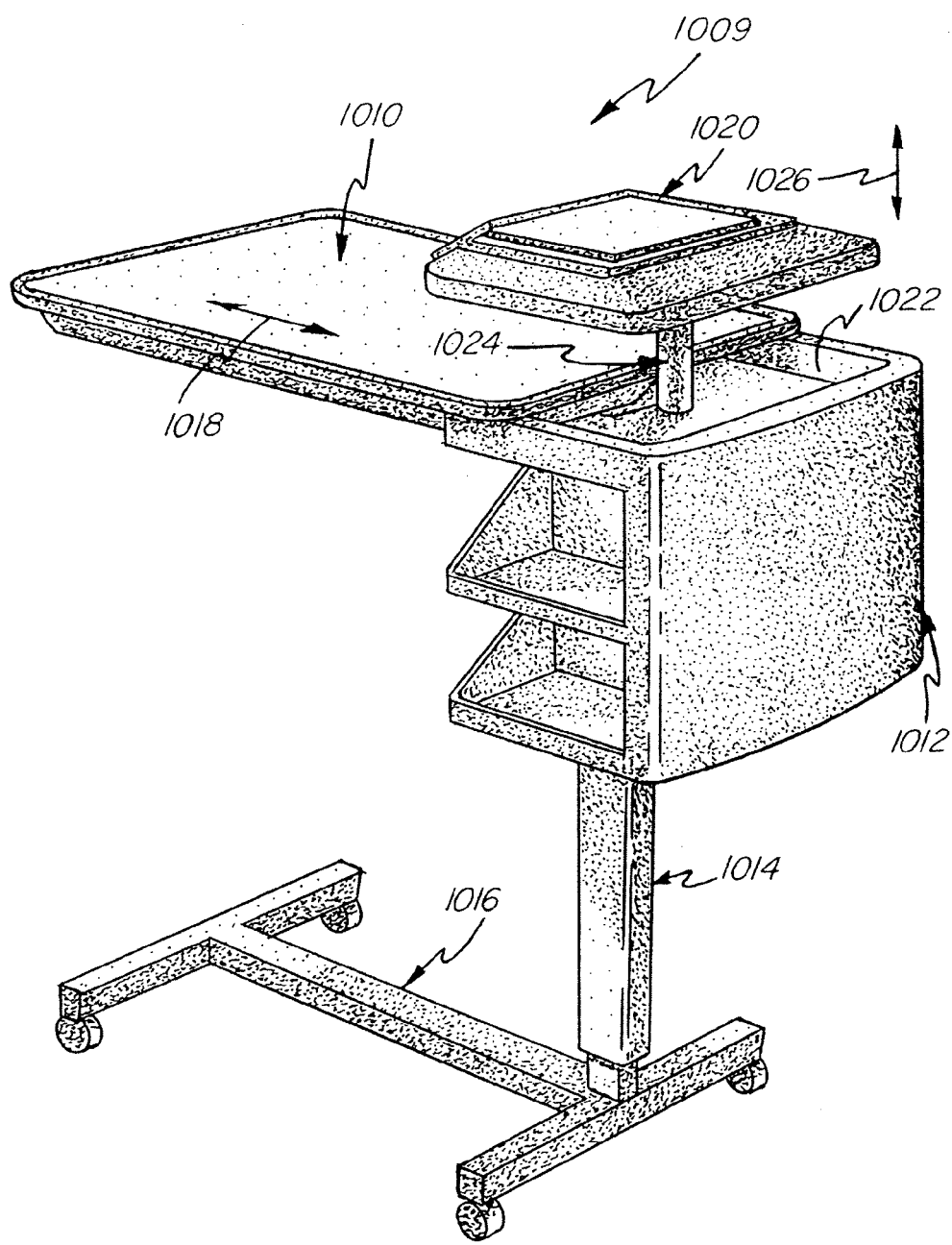
Figure 105:
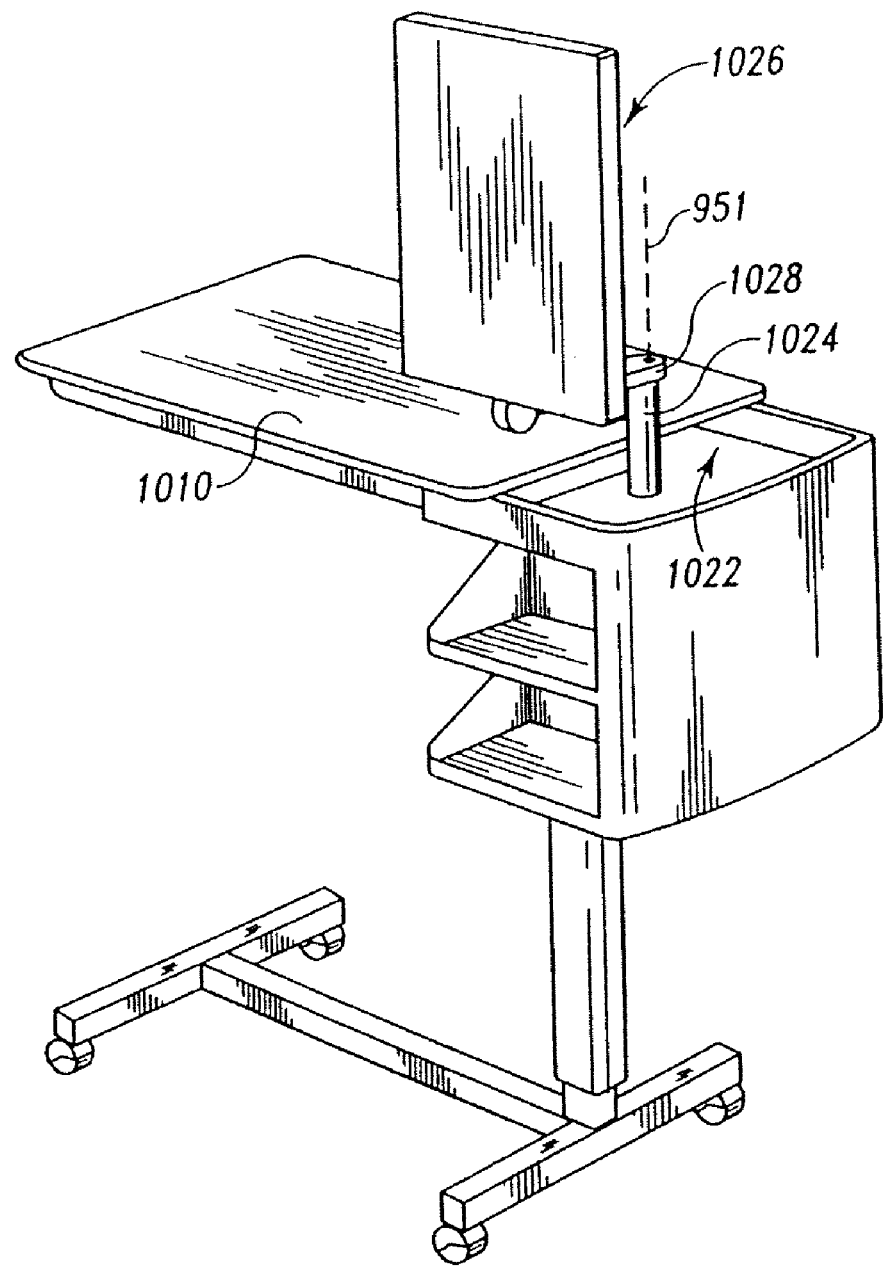
Figure 106:
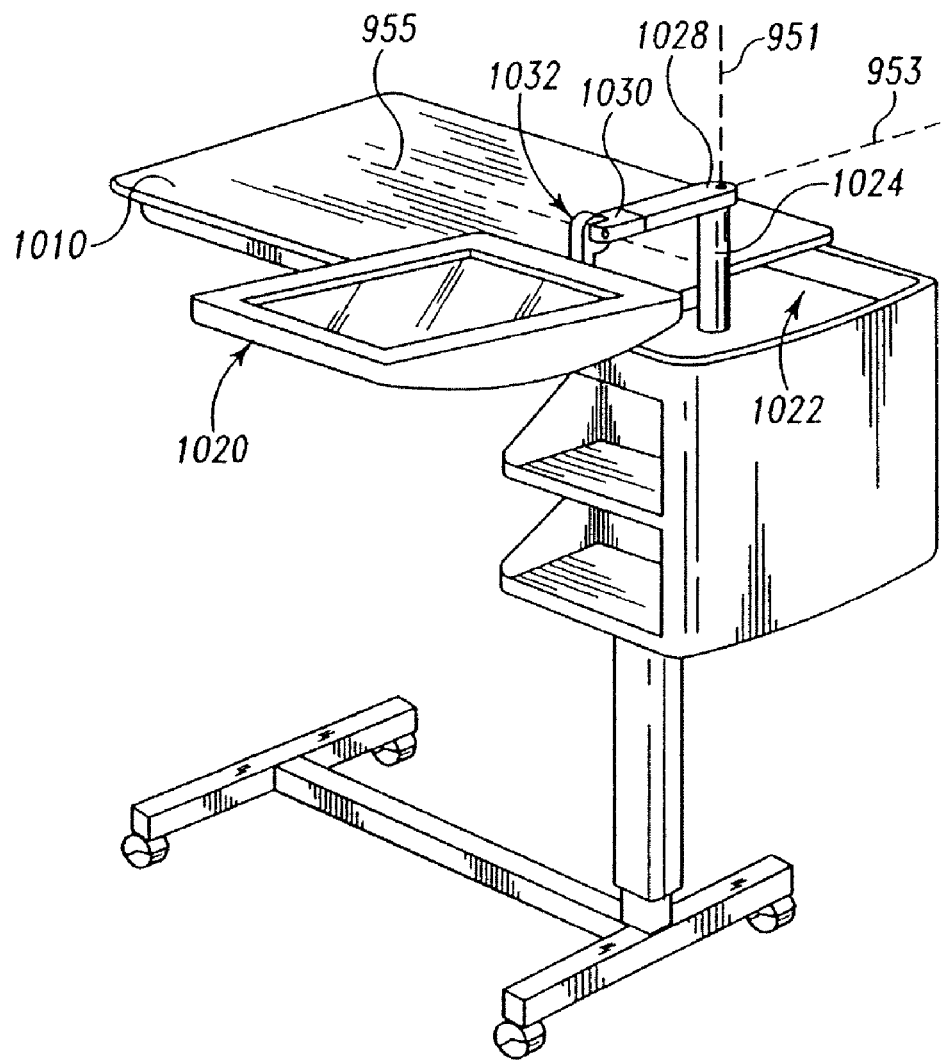
Figure 107:
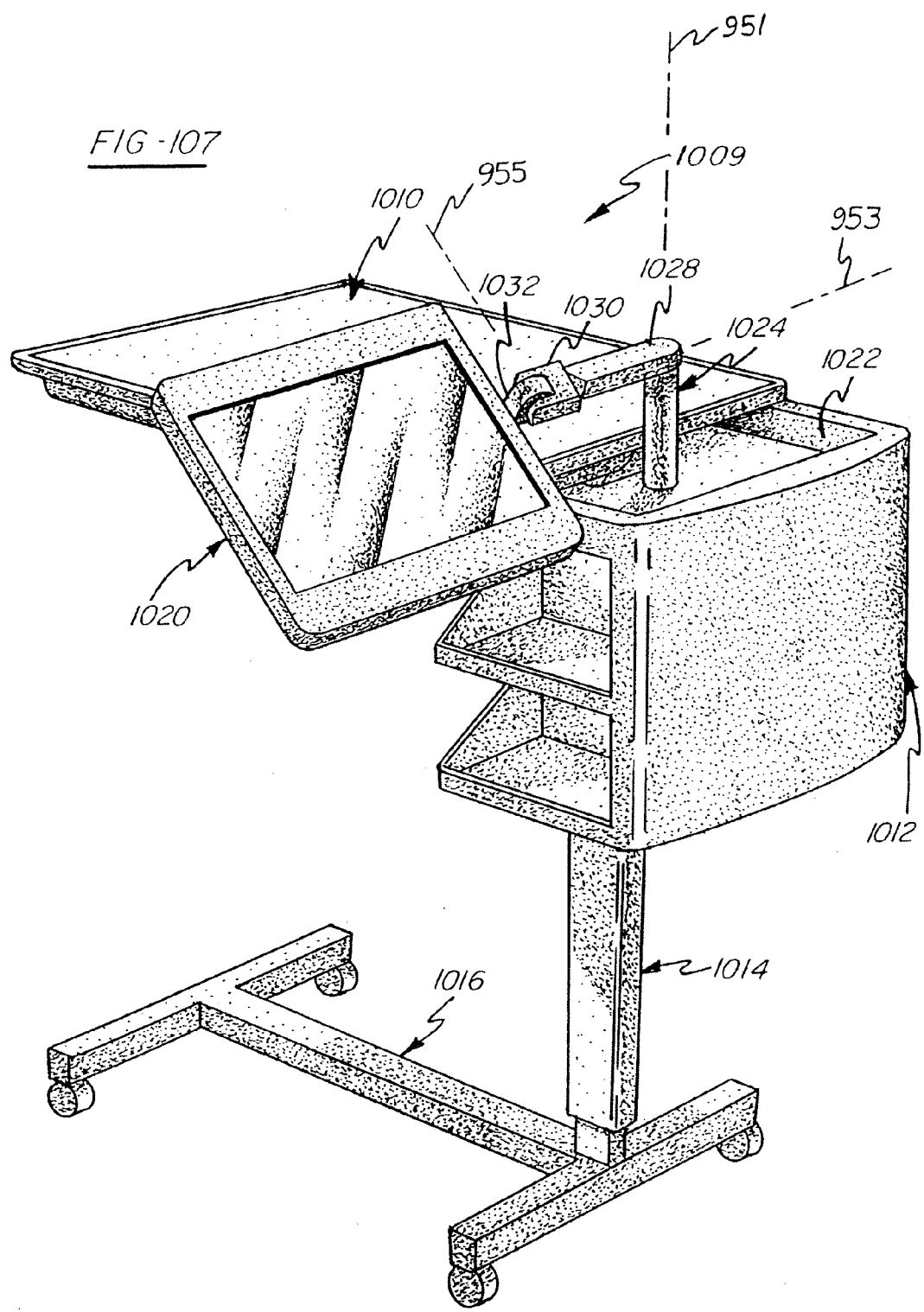
Figure 108:
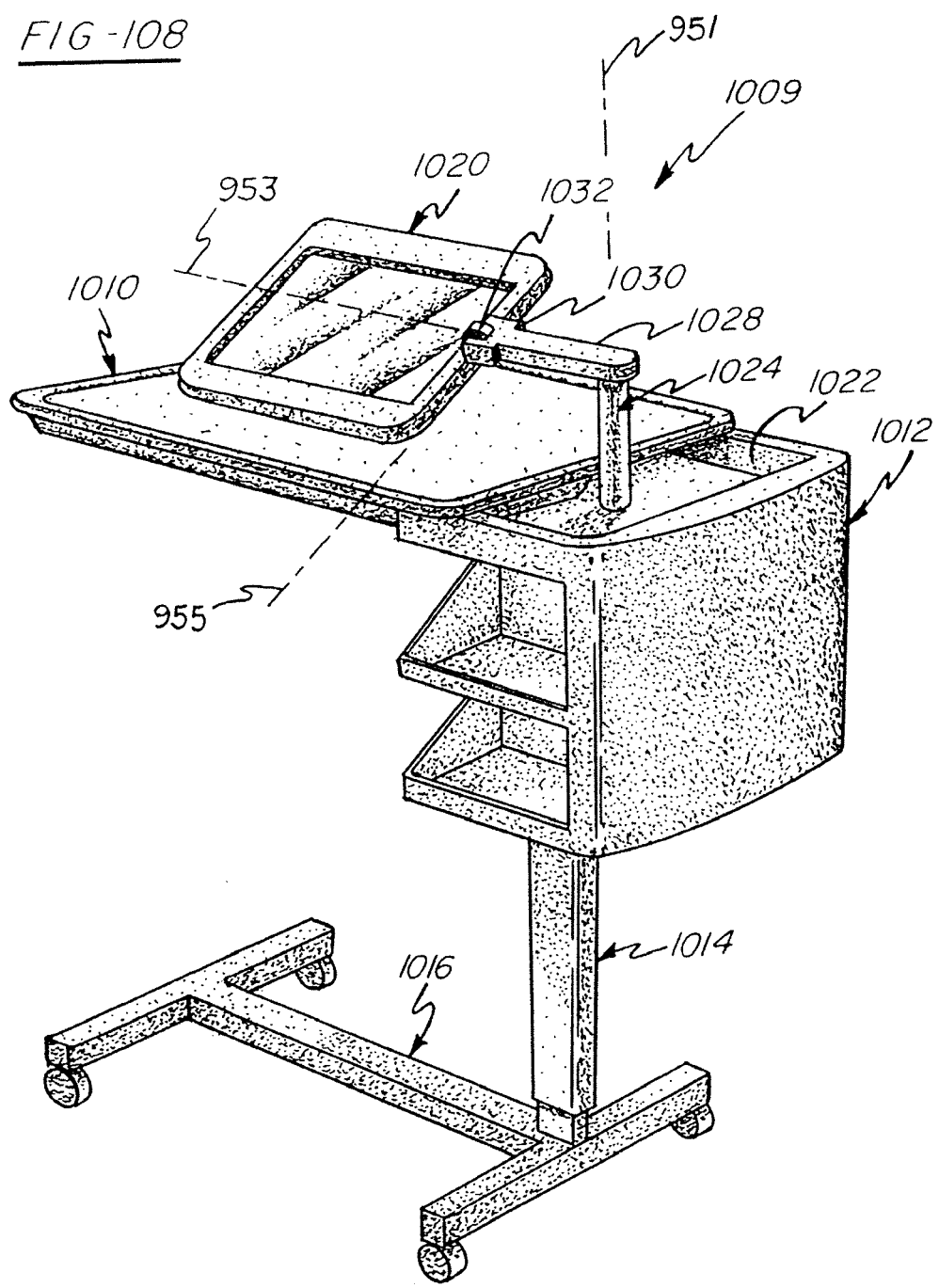

Another embodiment of the present invention is illustrated in FIGS. 103-108. In this embodiment, an overbed table 1009 includes a sliding tabletop 1010 coupled to a base support 1012. Support 1012 is coupled to an adjustable height pedestal 1014 supported by a base 1016. Tabletop 1010 can move back and forth in the direction of double headed arrow 1018 to expose a display 1020 located in a recess 1022 of base support 1012. As shown in FIG. 104, display 1020 is supported by a retractable arm assembly 1024 which can move into and out of recess 1022 in the direction of arrow 1026. As shown in FIGS. 105-108, another arm 1028 is rotatably coupled to arm assembly 1024. Display 1020 is coupled to arm 1028 by an arm segment 1030 and a coupler 1032 so that display 1020 can be moved to a plurality of different positions as shown in FIGS. 105-108. More specifically, arm 1028 may be rotated about axis 951, arm segment 1030 may be rotated about axis 953, and coupler 1032 may be rotated about axis 955.

Figure 109:
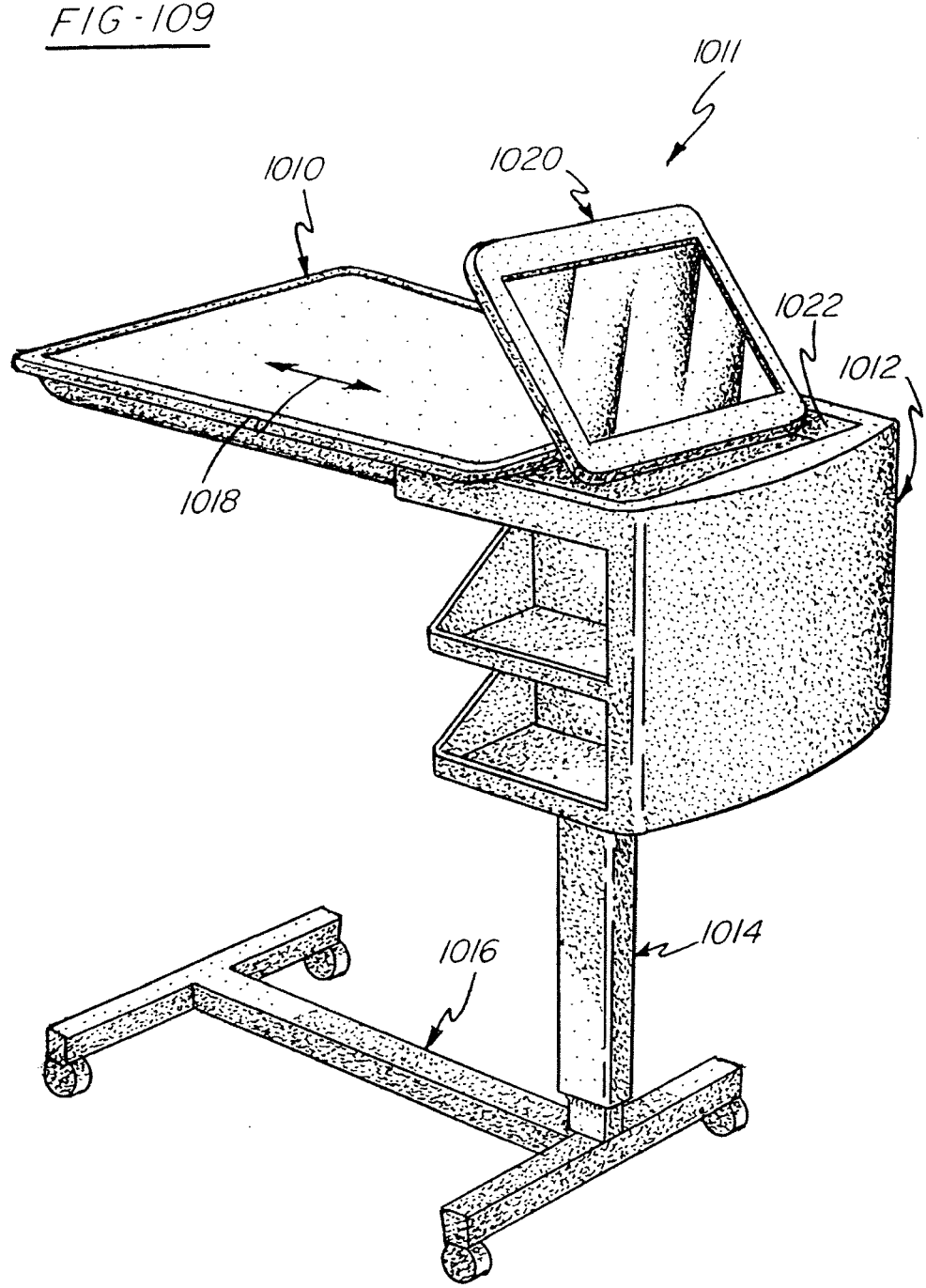
FIGS. 109-111 are perspective views of yet another embodiment of a mounting configuration similar to that of FIGS. 103-108.
Figure 110:
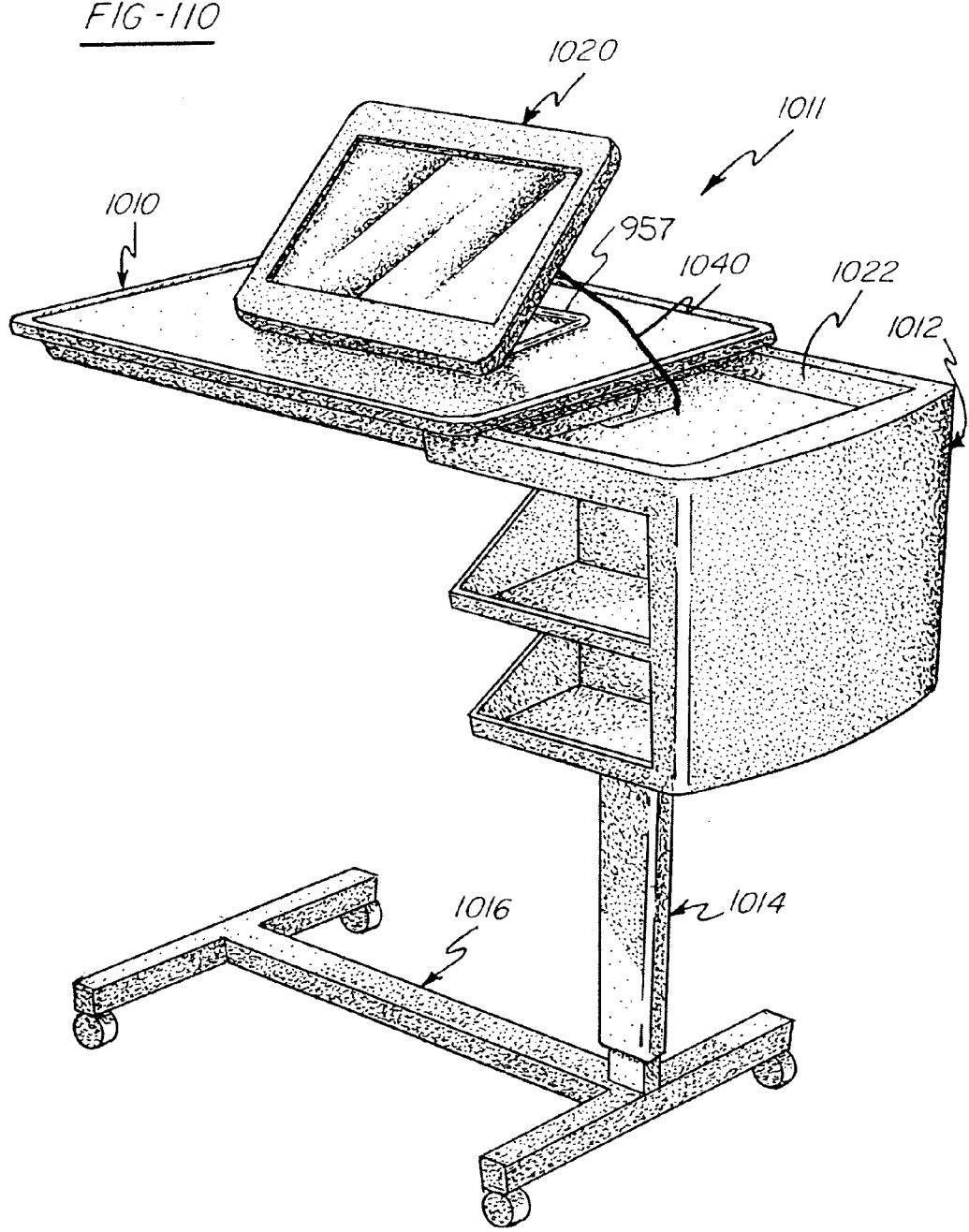
Figure 111:
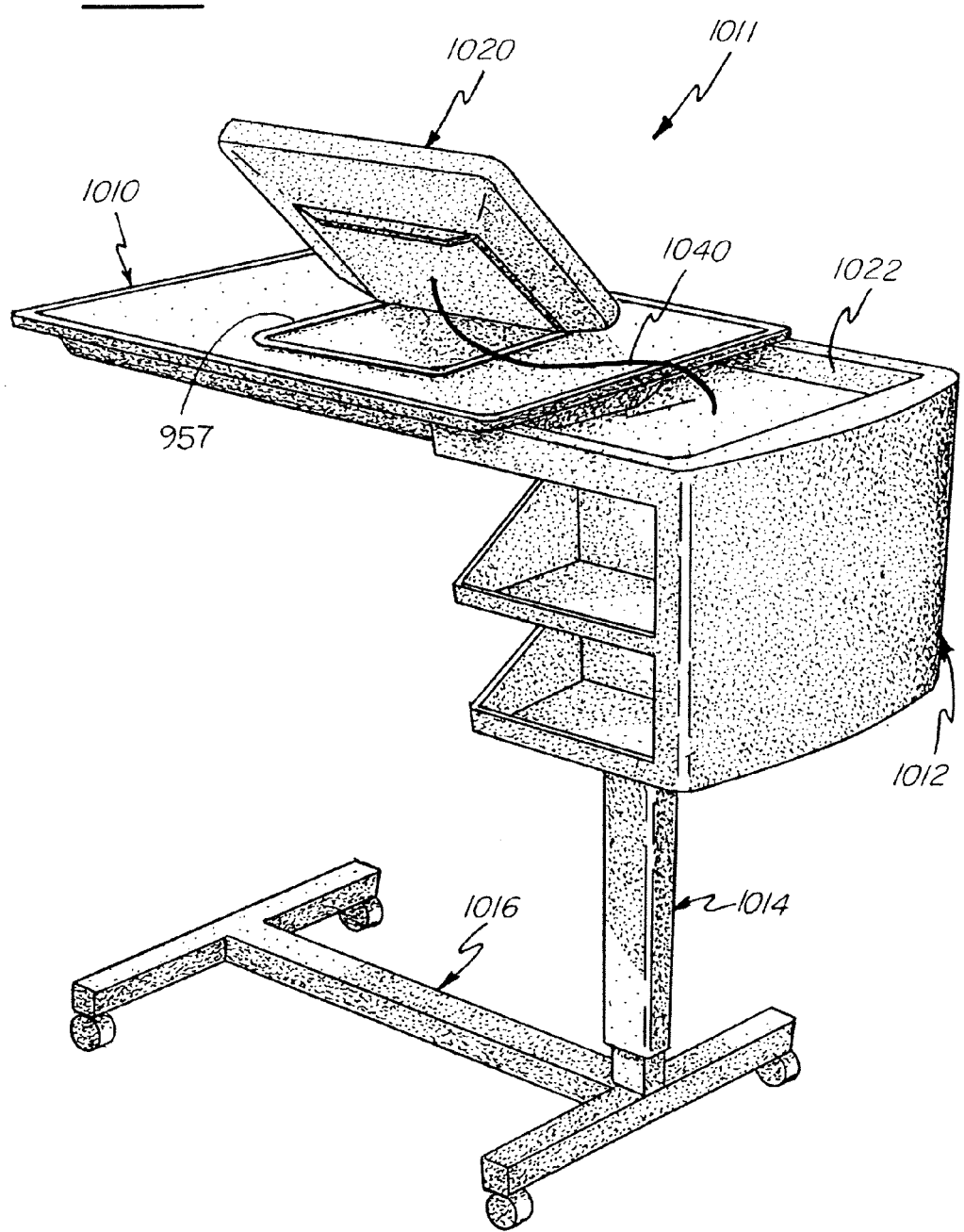

Another embodiment of the present invention is illustrated in FIGS. 109-111. In this embodiment of an overbed table 1011, display 1020 is coupled to a retractable cable 1040 so that display 1020 can be moved between a storage position to various different positions shown in FIGS. 109-111. As shown in FIGS. 110 and 111, a collapsible support 957 may be connected to the back of display 1020 to support display 1020 in a tilted position on, for example, overbed table 1011 for viewing.

Figure 112:
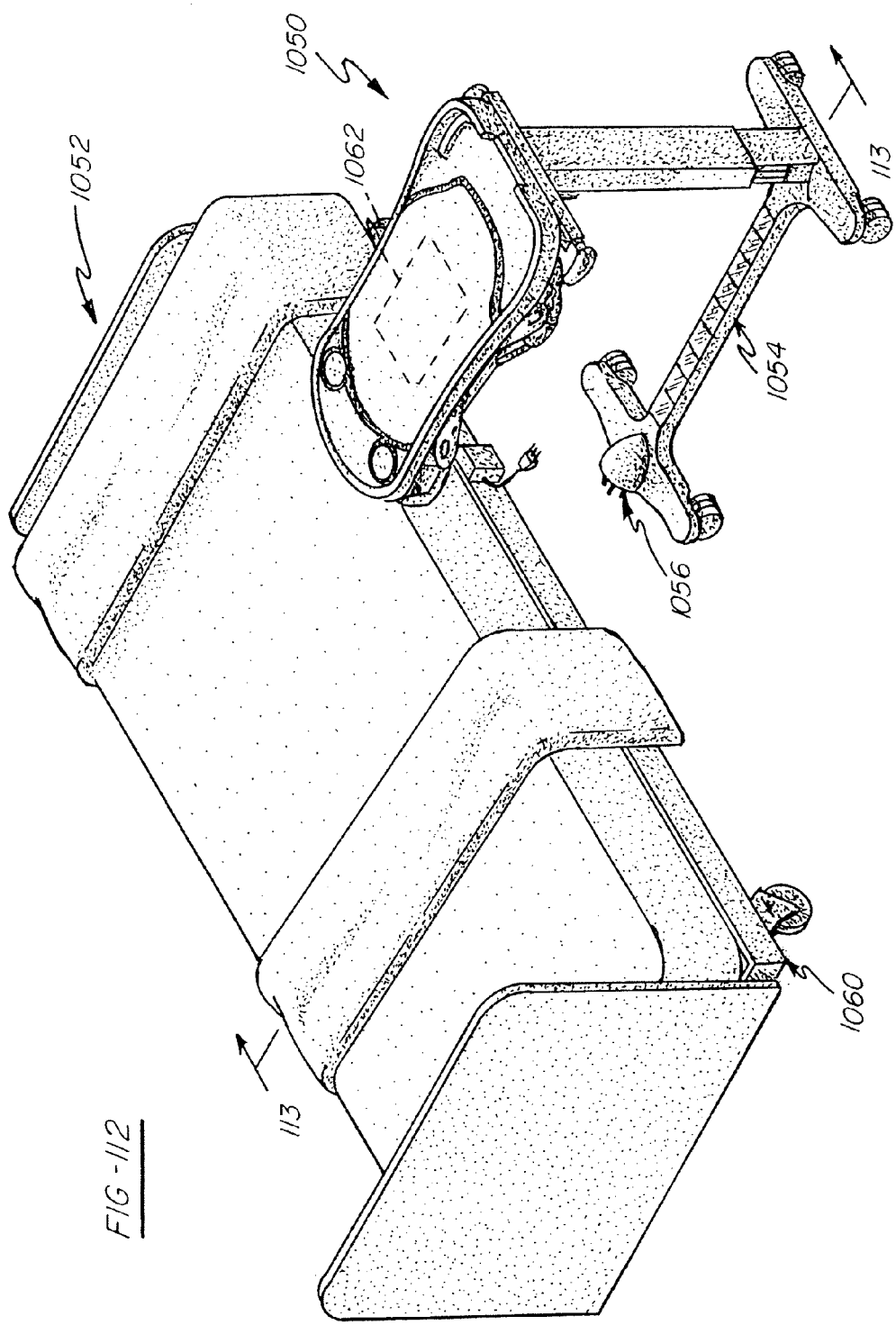
FIG. 112 is a perspective view of an overbed table including a point-of-care computer display according to the present invention.
Figure 113:
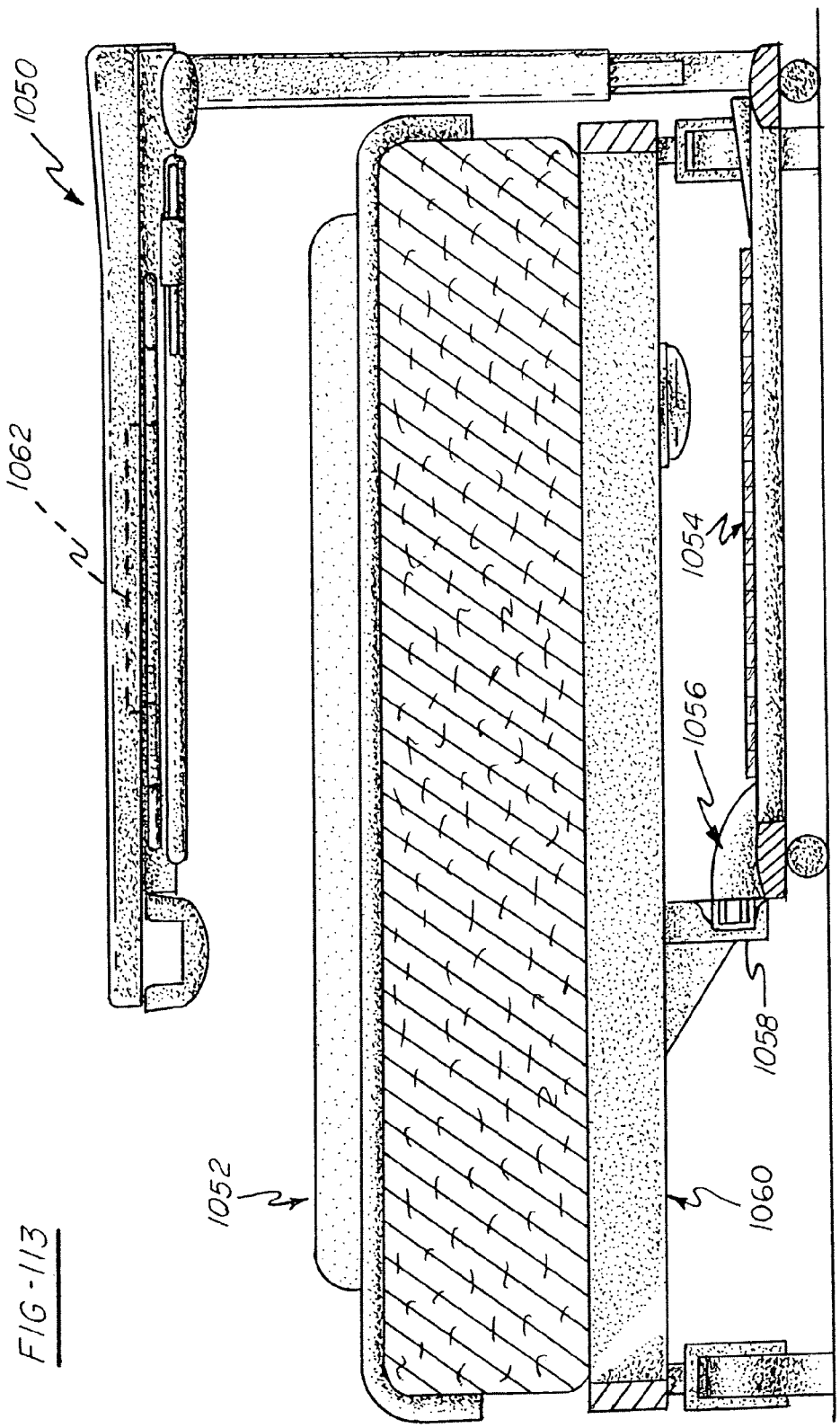
FIG. 113 is a side elevational view of the overbed table of FIG. 112.

Another embodiment of the present invention is illustrated in FIGS. 112 and 113 wherein an overbed table 1050 is shown docked to a bed 1052. A base 1054 of overbed table 1050 includes a connector 1056 that mates with a connector 1058 (FIG. 113) mounted to bed 1052 under bed base frame 1060 to supply electrical power and/or route other electrical signals to and from a display 1062 in overbed table 1050. In another embodiment, a retractable cord (not shown) is coupled to overbed table 1050 to supply power from bed 1052 to display 1062.

Figure 114:
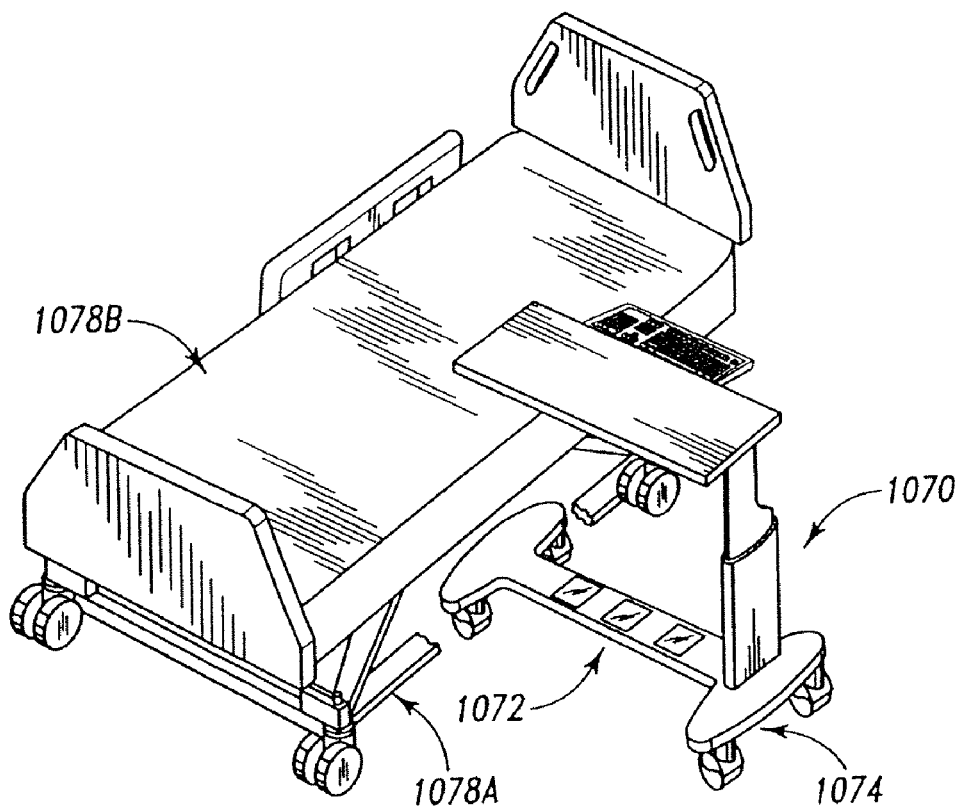
FIG. 114 is a perspective view of another embodiment of an overbed table of the present invention.
Figure 115:
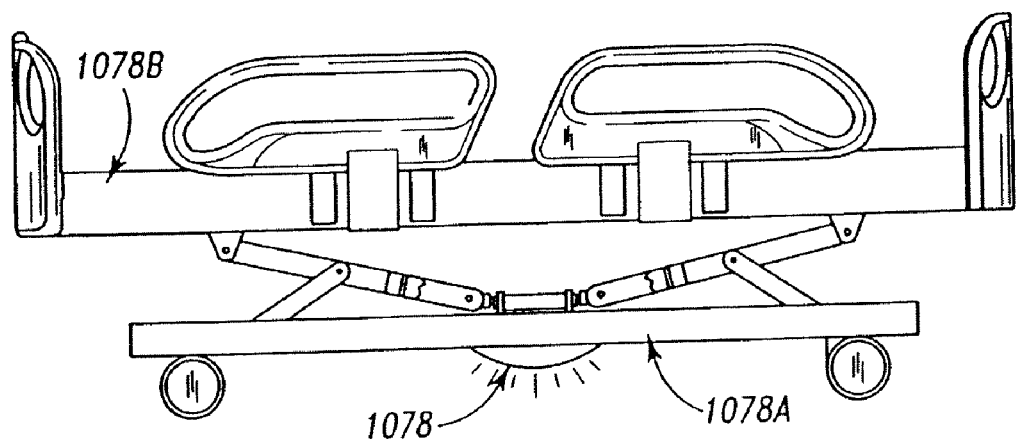
FIG. 115 is a side elevational view of the overbed table of FIG. 114.

In another embodiment shown in FIGS. 114 and 115, an overbed table 1070 includes a plurality of solar cells 1072 on a base 1074. Solar cells 1072 are used to power a wireless keyboard 1073 or a monitor (not shown) on table 1070. A battery (not shown) may be charged by solar cells 1072 using a trickle charge. At night, a light 1078 (FIG. 115) mounted to a frame 1078A of a bed 1078B may be used to provide light for solar cells 1072.

Figure 116B:
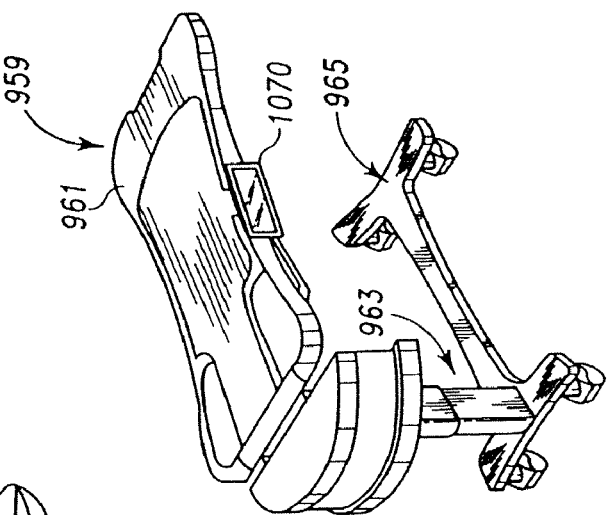
FIG. 116B is a perspective view of the overbed table of FIG. 116A.
Figure 116A:
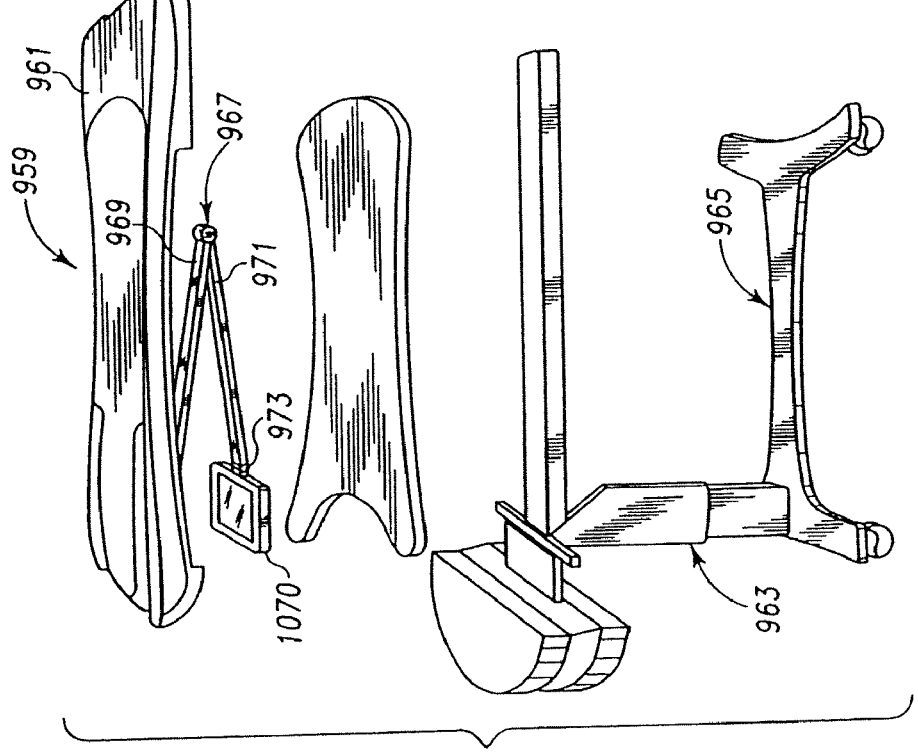
FIG. 116A is an exploded, perspective view of another overbed table including a point-of-care computer display of the present invention.

Another embodiment of a computer in an overbed table is shown in FIGS. 116A, B. In this embodiment, an overbed table 959 includes a top 961 attached to an adjustable height support 963 supported by a base 965. A linkage 967 is connected to top 961. Linkage 967 includes a first arm 969, a second arm 971, and a bracket 973. First arm 969 is movably connected at one end to top 961 and movably connected at the other end to second arm 971. Second arm 971 is connected to bracket 973 such that display 1070 attached to bracket 973 may be rotated from a horizontal position to a vertical position. By manipulating linkage 967, a patient may position display 1070 for private viewing.

Figure 117:
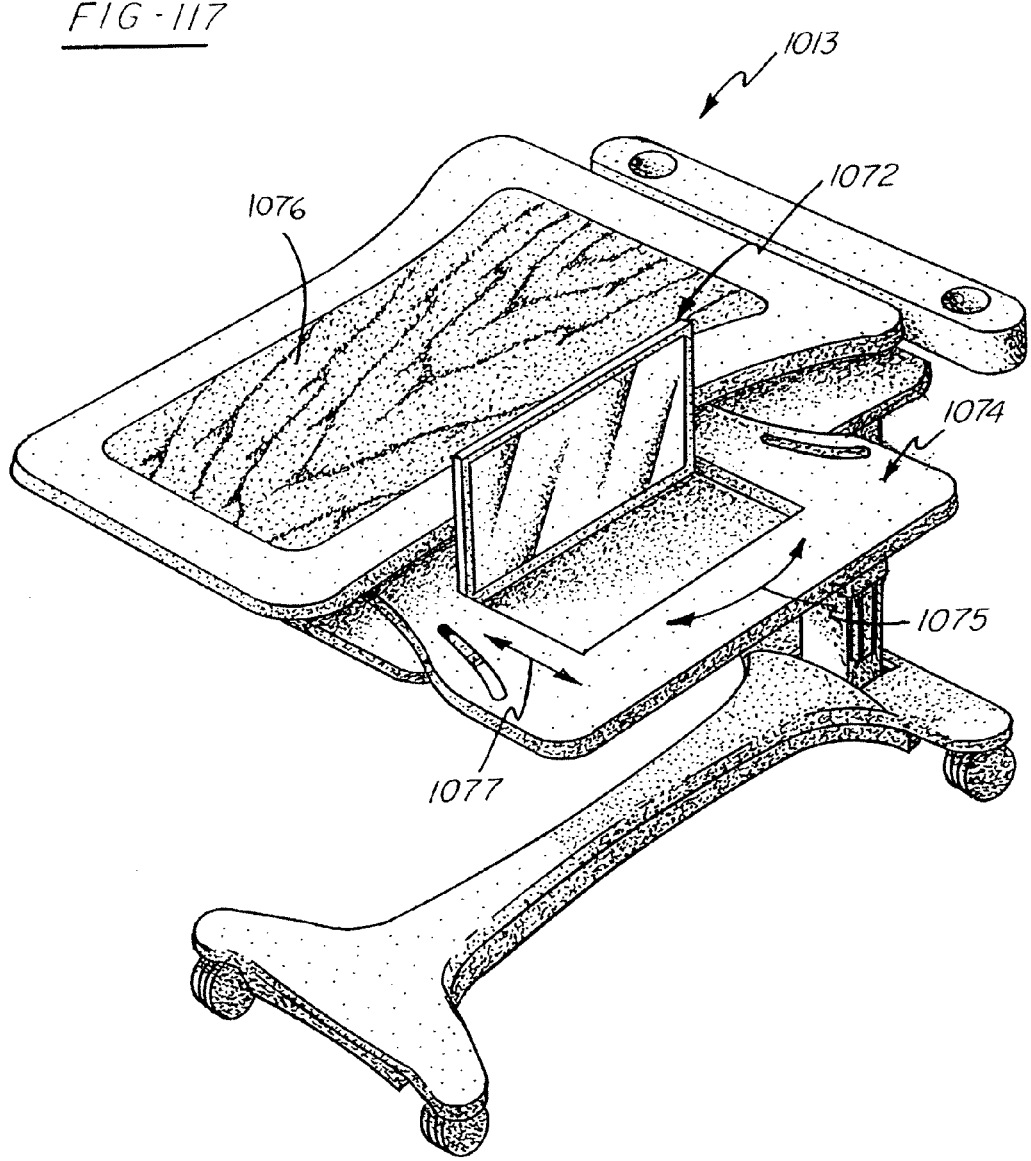
FIG. 117 is a perspective view of yet another overbed table including a point-of-care computer display of the present invention.

Another embodiment of a computer in an overbed table is shown in FIG. 117. In this embodiment of an overbed table 1013, a display 1072 is movable from a folded down, storage position in a tray 1074 to a deployed viewing position. In one embodiment, tray 1074 is pivotable in the direction of arrow 1075 under table top 1076 for storage. In another embodiment, tray 1074 slides in the direction of arrow 1077 between a storage and an in-use position. Additional details of overbed tables, including those described herein, are disclosed in a patent application owned by the applicant entitled "OVERBED TABLE FOR USE WITH A PATIENT SUPPORT," filed concurrently with this application, the disclosure of which is hereby expressly incorporated herein by reference.

Figure 118:
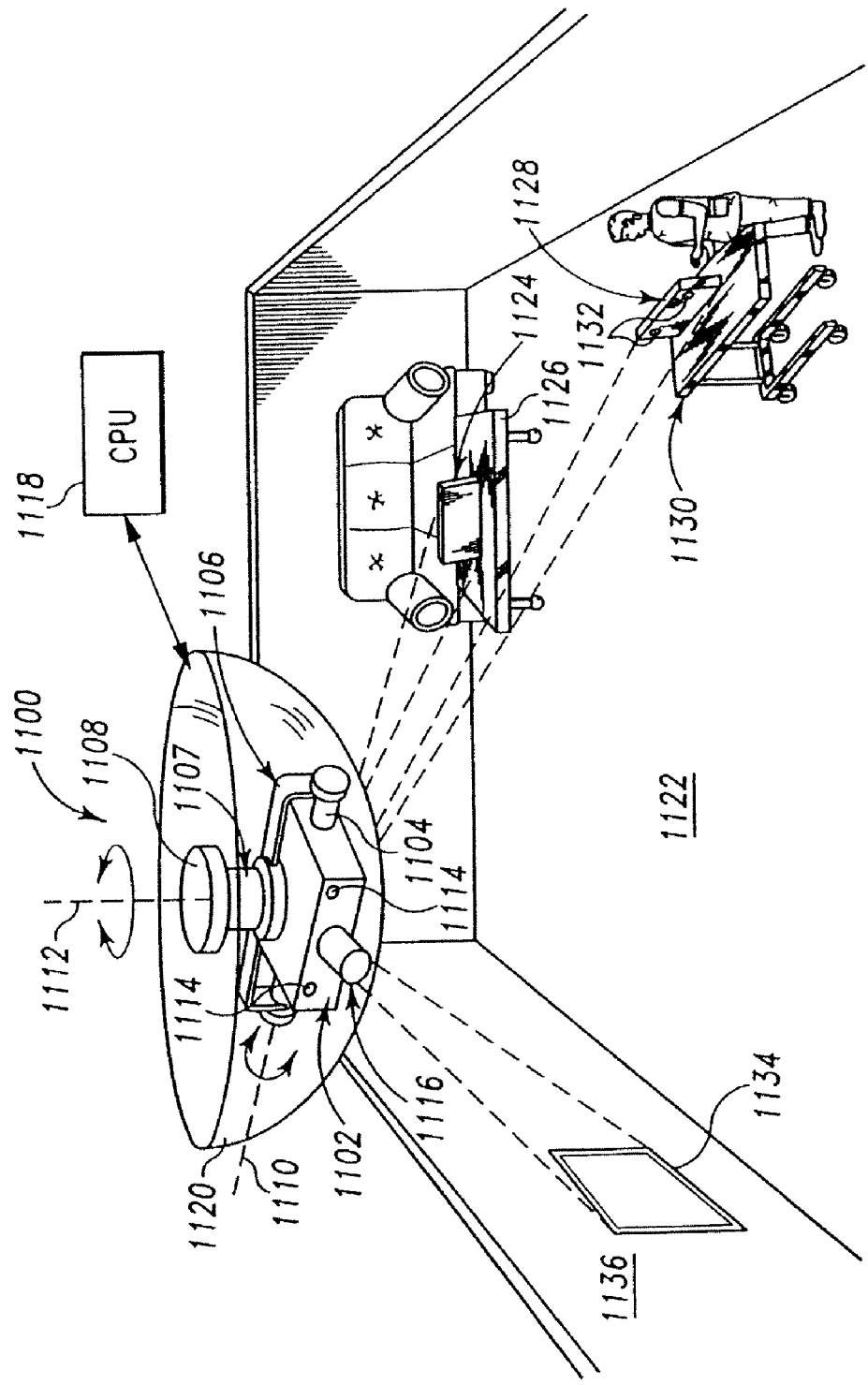
FIG. 118 is a perspective view of a projection system for use in a point-of-care computer system of the present invention.

FIG. 118 illustrates another embodiment of the present invention including a projector assembly 1100 for projecting an image on a screen or digitizer. Projector assembly 1100 generally includes a projector 1102, a first motor 1104 connected to a U-shaped bracket 1106 for supporting projector 1102, a second motor 1107 connected between bracket 1106 and a mounting plate 1108 for mounting assembly 1100 to a ceiling. First motor 1104 permits rotation of projector 1102 about axis 1110, and second motor 1107 permits rotation of projector 1102 about axis 1112. Projector 1102 further includes a pair of IR receivers 1114 for tracking movement of a screen as further described below, and a lens 1116, such as an auto-focus lens. As indicated in FIG. 118, projector 1102 is coupled to a CPU 1118, which controls the position of projector 1102 and the content of the projected image. Projector assembly 1110 also includes a clear protective dome 1120 made from plastic or another suitable material.

Also shown in FIG. 118 are displays or screens 1124, 1128 mounted at various locations in room 1122. It should be understood that additional screens may be mounted at additional locations such as on a bed, a medication cart, a wall, etc. Specifically, screen 1124 is mounted to a table 1126 located, for example, in a family area of room 1122. Screen 1128 is mounted to an overbed table 1130 such as any of the plurality of overbed tables described herein, and includes a pair of IR transmitters 1132. One or more than two transmitters 1132 may alternatively be used. FIG. 118 also shows an image 1134 projected onto a wall 1136. Screens 1124, 1128 include a translucent lens and a touch screen mounted to the lens. Accordingly, projector 1102 may project images onto back surfaces of screens 1124, 1128 such that the images are visible from the front of screens 1124, 1128. Thus, the user does not obstruct or interfere with the projection of images onto screens 1124, 1128. It should be understood that CPU 1118 includes angle compensation software to permit projection of images onto tilted surfaces that may otherwise not suffice as projection surfaces. A user can then actuate areas or icons displayed on the touch screen surface of screens 1124, 1128. Such actuation causes the system to send a signal from the screen 1124, 1128 to CPU 1118, and may result in a different image or other action by the system in the manner described above.

Projector 1102 may automatically track the location of screen 1128 mounted to movable overbed table 1130. Transmitters 1132 provide signals to receivers 1114 of projector 1102. Tracking software of CPU 1118 permits CPU 1118 to detect movement of screen 1128, and adjust the position of projector 1102 by operating motors 1104, 1107 to compensate for the movement and continuously project an image or series of images onto screen 1128 while overbed table 1130 is in motion. The motion tracking function described above may be activated when screen 1128 is raised to an in-use position such as that shown in FIG. 118. In another embodiment, when screen 1128 is powered via a power switch (not shown), CPU 1118 is signaled to activate the motion tracking function.

Projector 1102 may also be used to provide a big screen television as indicated by image 1134 projected onto wall 1136. Of course, image 1134 could also be displayed on a curtain or other acceptable surface available in room 1122. By providing image 1134 in a very large format, caregivers could select displays of charts or other information intensive material for easy viewing.

Figure 119:
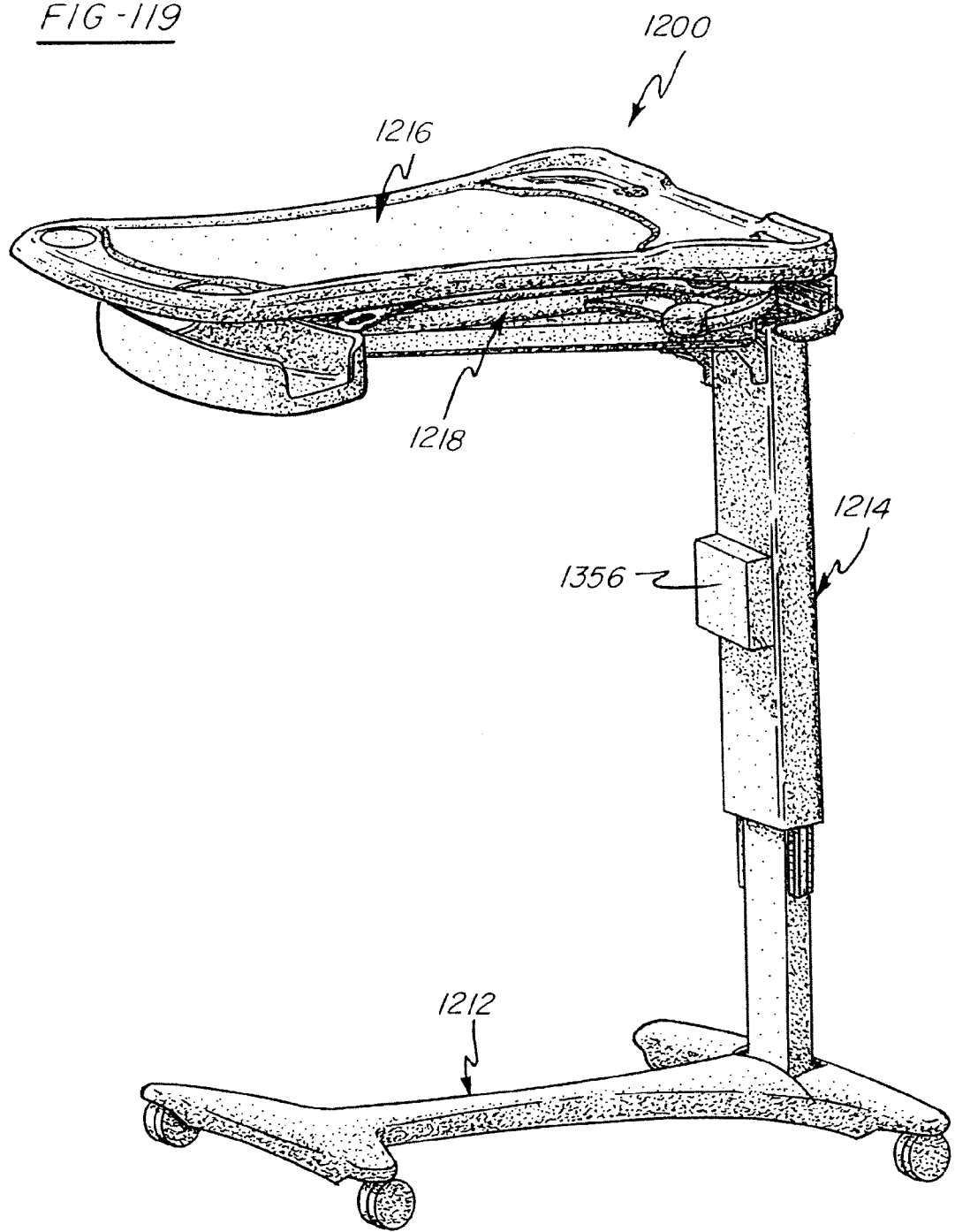
FIG. 119 is a perspective view of yet another embodiment of an overbed table including a point-of-care computer display of the present invention.

Referring now to FIG. 119, an overbed table 1200 according to another embodiment of the present invention includes a base 1212 and a telescoping support column 1214 that supports first and second table sections 1216, 1218. In the following description, first table section 1216 may also be referred to as an upper table, and second table section 1218 may also be referred to as a food tray. First and second table sections 1216, 1218 are mounted in vertically spaced relation at an upper end of support column 1214. Illustratively, first table section 1216 is positioned in spaced relation above second table section 1218, thereby defining a vertical space or an open region therebetween.

In a storage position, as illustrated in FIG. 120, second table section 1218 is positioned below first table section 1216. In the use position, as illustrated in FIGS. 121 and 122, second table section 1218 is moved at least partially out from under first table section 1216.

Second table section 1218 illustratively includes a pair of handles 1292 and 1294 to facilitate pivoting movement of second table section 1218 about a pivot post (not shown). Handles 1292, 1294 are configured to extend outwardly from beneath opposing side edges 1298, 1299, respectively, of first table section 1216 when second table section 1218 is in the storage position as shown in FIG. 120.

Table 1200 further includes a support arm 1304 that is supported within the open region between first and second table sections 1216, 1218 in vertically spaced relation to both first and second table sections 1216, 1218. Arm 1304 is supported for pivoting movement within a substantially horizontal plane about a pivot post 1306 (FIG. 120). Arm 1304 moves pivotally about pivot post 1306 between a storage position (FIGS. 119 and 120) and a use position (FIG. 122).

Arm 1304 illustratively includes a substantially U-shaped portion 1316 and a connecting portion 1318. U-shaped portion 1316 supports a pair of handles 1320, 1322 to facilitate pivoting movement of arm 1304 by a patient. Handles 1320, 1322 are configured to extend outwardly from beneath the opposing side edges of first table section 1216. A display screen or device 1324 is supported by U-shaped portion 1316 of arm 1304 by a coupler 1326.

Figure 123:
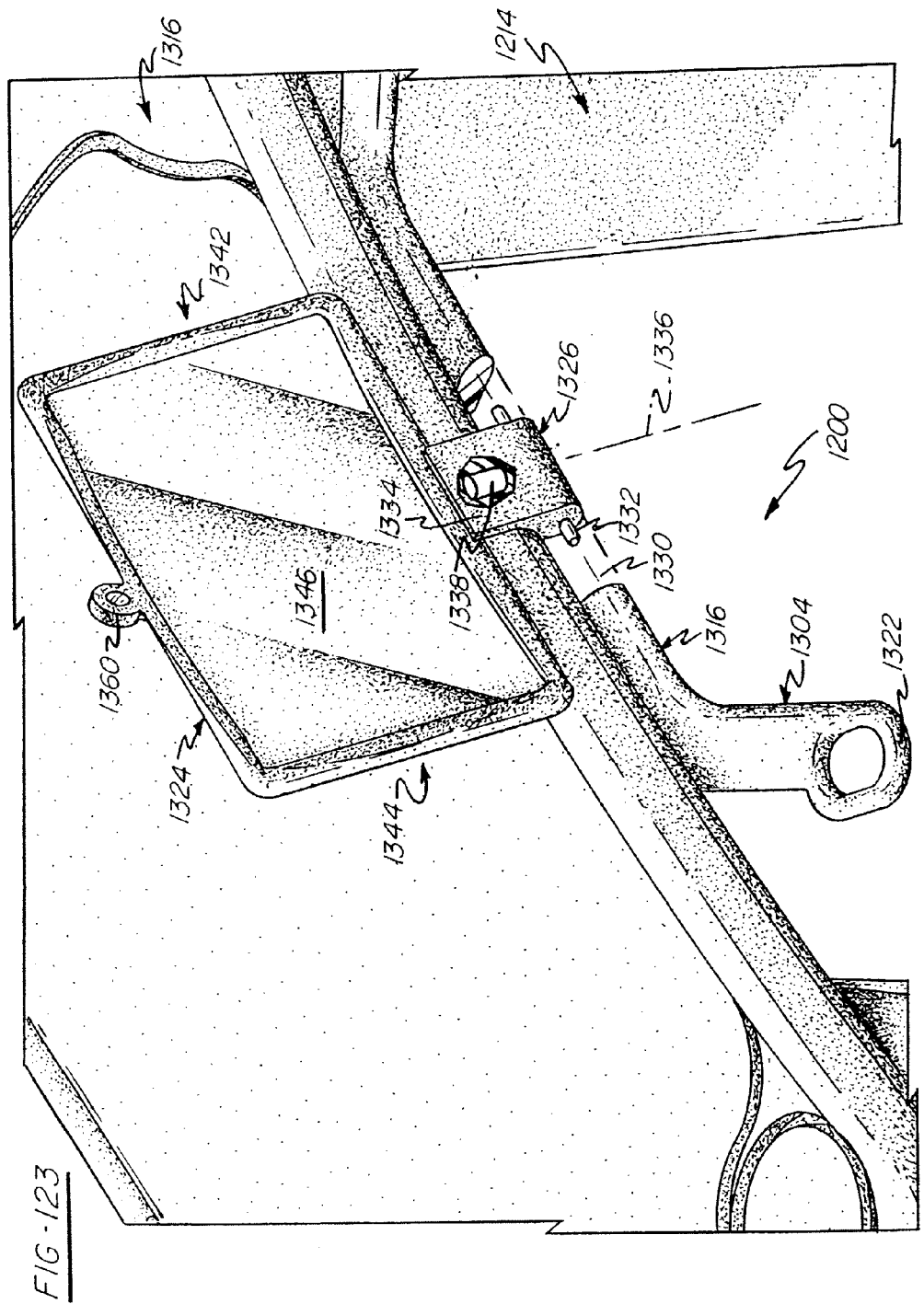
FIG. 123 is a perspective view, partly in section, of components of the overbed table of FIG. 119.

With reference to FIG. 123, coupler 1326 includes a first body portion 1328 supported for pivoting movement about a substantially horizontal first axis 1330. A first pin 1332 couples first body portion 1328 to U-shaped portion 1316 of arm 1304. A second body portion 1334 is supported by first body portion 1328 for pivoting movement about a second pivot axis 1336 disposed substantially perpendicular to first pivot axis 1330. A second pin 1338 couples second body portion 1334 to first body portion 1328. In turn, display device 1324 is fixed to second body portion 1334.

Display device 1324 includes first and second sides 1342, 1344, with first side 1342 supporting a viewable surface 1346 and configured to face a head end of a bed. Display device 1324 illustratively comprises a conventional computer monitor wherein viewable surface 1346 comprises an electronic display. A conventional mirror 1352 may be supported by second side 1344 of display device 1324 (FIG. 120). As may be appreciated, the user may alternatively use the electronic display and mirror 1352 by simply rotating display device 1324 about second pivot axis 1336 by moving second body portion 1334 around second pin 1338. In an illustrated embodiment, viewable surface 1346 of display device 1324 may be defined by other conventional screens including, but not limited to, a television screen, or a projection screen such as screens 1124, 1128 of FIG. 118, or a conventional mirror. If viewable surface 1346 is a projection screen, then images may be projected from a remote location onto the viewable surface 1346 in the manner described above with reference to FIG. 118.

A processor (not shown) is supported by table 1200 and is in communication with display device 1324 through conventional transmission means, which may include wires or a wireless transmitter and receiver (not shown). A power source in the form of a battery 1356 (FIG. 119) may likewise be secured to support column 1214 and provide power to the processor and display device 1324.

A camera 1360, such as a video or digital still image camera, is illustratively supported by display device 1324. Camera 1360 is in communication with the processor and may have power supplied by battery 1356. In one illustrative embodiment, camera 1360 provides images to the processor which are then transmitted to viewable surface 1346. As such, viewable surface 1346, the processor, and camera 1360 define an electronic mirror. In other words, the patient facing camera 1360 will see his or her image electronically generated on viewable surface 1346.

Figure 124:
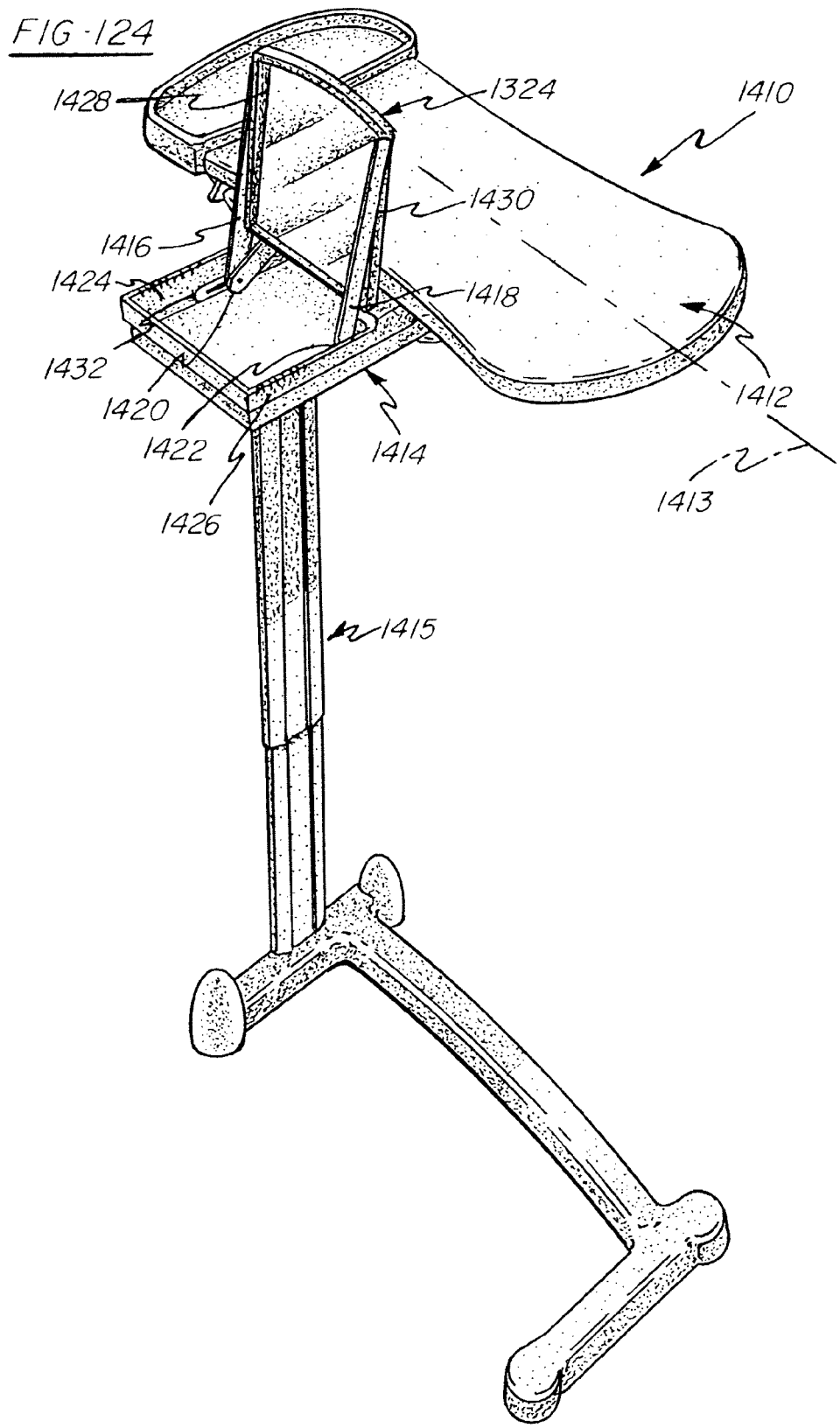
FIG. 124 is a perspective view of yet another embodiment of an overbed table including a point-of-care computer display of the present invention.

Another embodiment of an overbed table 1410 is shown in FIG. 124. Table 1410 includes a frame 1415 supporting a first table section 1412. A storage tray 1414 is supported in vertical spaced relation below first table section 1412 and is configured to move within a substantially horizontal plane in a direction generally perpendicular to a longitudinal axis 1415 of table section 1412. Display device 1324 is coupled to first and second spaced apart arms 1416 and 1418 which provide for pivoting movement of display device 1324 from an open or use position wherein display device 1324 is extending upwardly out of storage tray 1414 to a closed or storage position wherein display device 1324 is received within storage tray 1414 below the horizontal plane defined by first table section 1412. As illustrated in FIG. 124, first ends 1420, 1422 of arms 1416, 1418, respectively, are pivotally connected to longitudinally extending side walls 1424, 1426 of storage tray 1414, while opposing second ends 1428, 1430 of arms 1416, 1418, respectively, are pivotally connected to an upper portion of display device 1324. First ends 1420, 1422 of arms 1416, 1418 may be slidably received within channels 1432 extending within side walls 1424,1426 to facilitate folding of display device 1324 into storage tray 1414.

In operation, display device 1324 may be moved between an open position and a closed position by folding arms 1420, 1422 downwardly into storage tray 1414 such that display device 1324 is nested intermediate side walls 1424, 1426. Storage tray 1414 may then be slidably moved in a direction toward first table section 1412 and into the storage position wherein storage tray 1414 is located in vertically spaced relation below first table section 1412.

Figure 125:
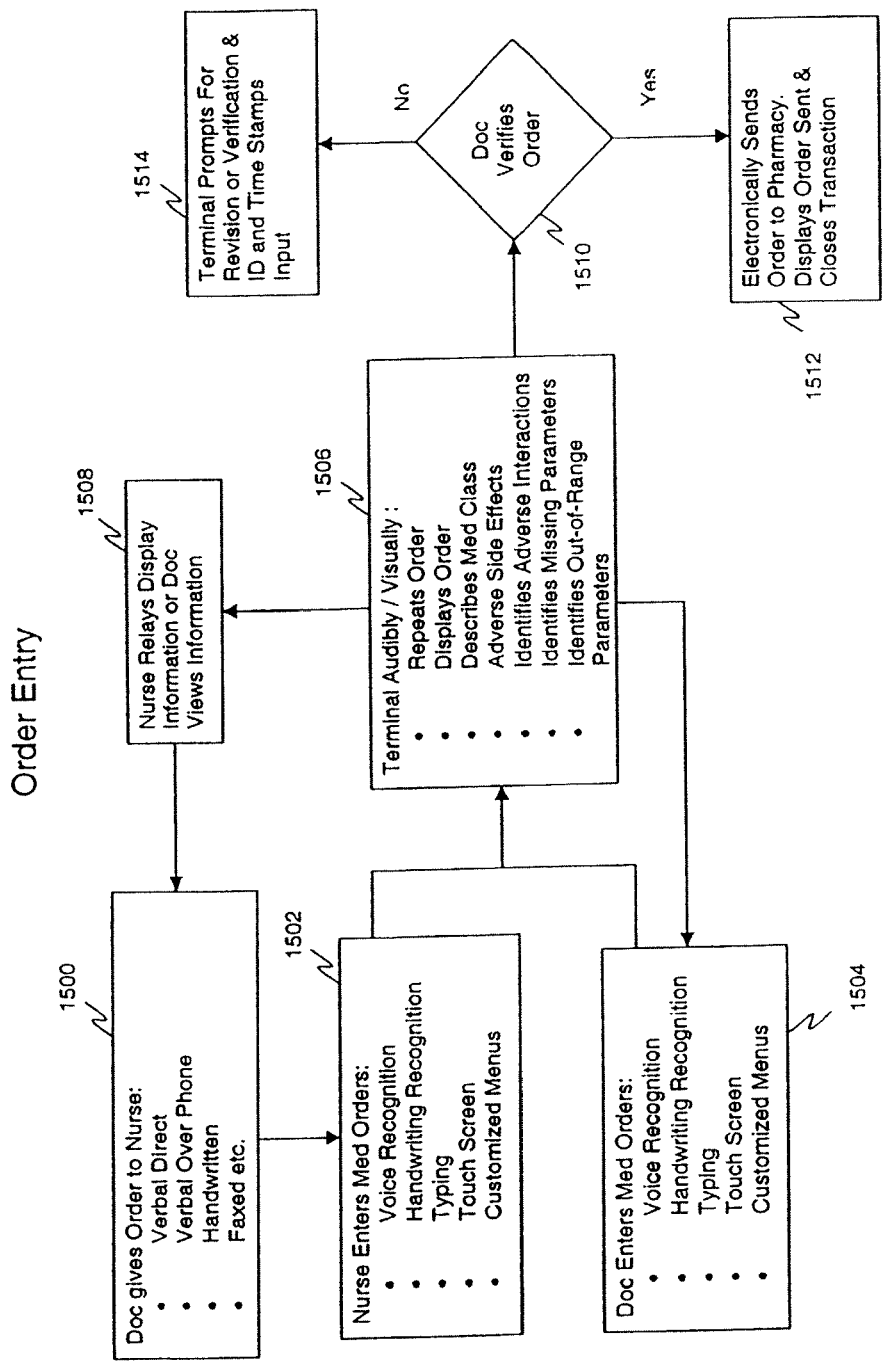
FIGS. 125-128 are block diagrams of processes facilitated by the point-of-care computer system of the present invention.

Referring now to FIGS. 125-128, various processes that are facilitated by the present invention for ordering and dispensing medication are depicted in flow diagram format. In FIG. 125, a process for ordering medication is depicted wherein a doctor provides an order to a nurse through some form of communication as illustrated by block 1500. The nurse then enters the order into a system according to the present invention such as by using one of the various input devices described above, or other means as listed in block 1502. Alternatively, the doctor may enter the order into the system as illustrated in block 1504. The terminal or point-of-care computer system then provides information about the entered order to either the doctor or the nurse, whichever entered the order. As indicated at block 1506, the order may be displayed or repeated audibly, and additional information regarding the order and/or the patient may be provided by the system upon accessing the hospital network. If the nurse entered the order, then (at block 1508), the nurse relays the information displayed at block 1506 to the doctor either directly, or by sending a message to the doctor as described herein. At block 1510, the doctor is provided the option of verifying the entered order. If the doctor verifies the order, then the point-of-care system transmits the order information to a pharmacy, displays a message that the order was transmitted, and closes the transaction as indicated by block 1512. If the doctor does not verify the order, then the system prompts the doctor to revise the order, and associates information identifying the doctor, as well as a time-stamp for the revision, with the revised order information as indicated by block 1514. If the order is revised and verified, it may be sent to the pharmacy in the manner described above.

Figure 126:
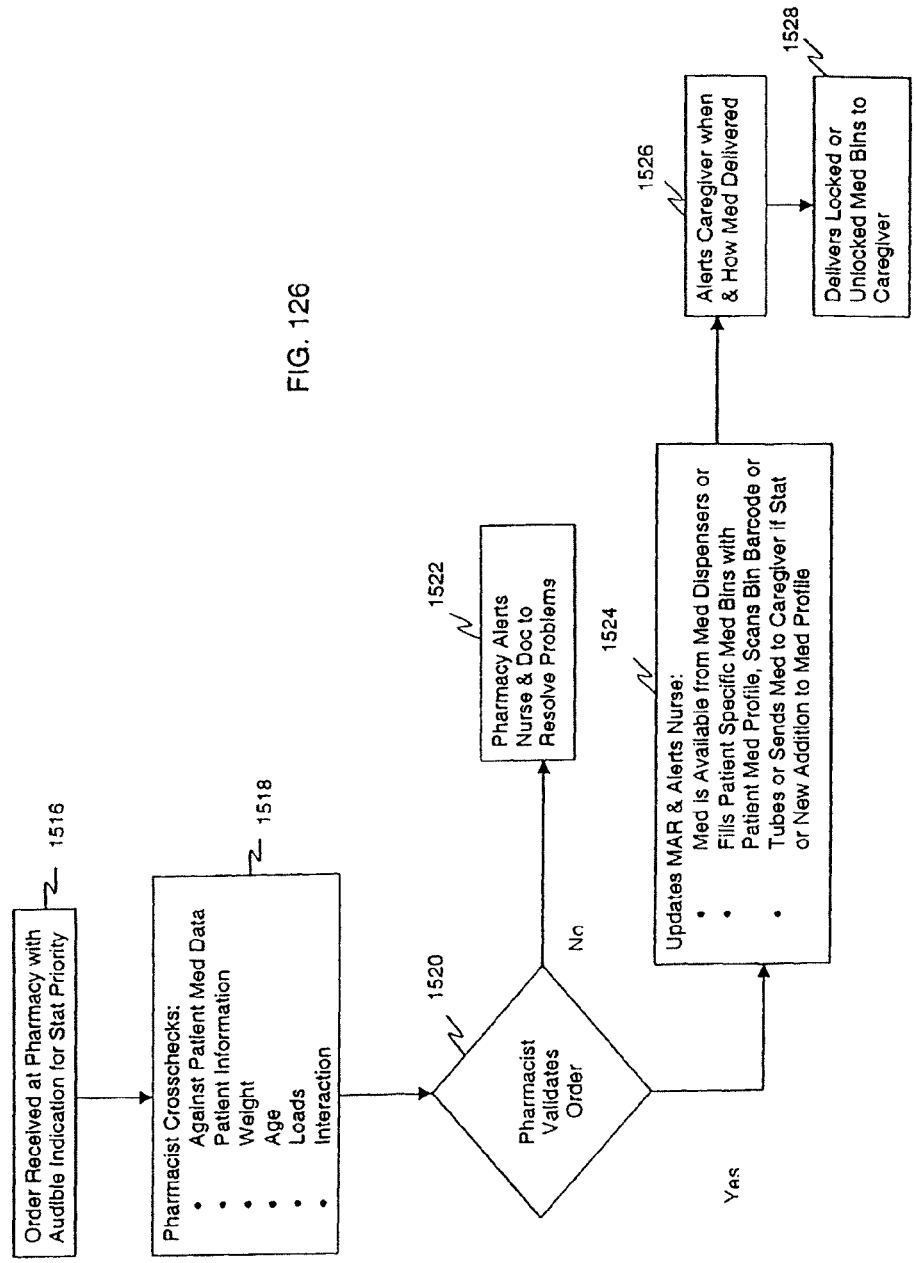

As shown in FIG. 126, the order is then received at the pharmacy (or other fulfillment center) along with an audible indication for priority orders (block 1516). At block 1518, the pharmacist crosschecks the order against other medications ordered for the patient, the patient's health information, and other types of information relating to the patient and/or the ordered medication to ensure that the medication is appropriate for the patient. At block 1520, the pharmacist either validates the order or does not validate the order. If the pharmacist does not validate the order, then the pharmacy alerts the nurse and/or doctor via some communication means to resolve any problems the pharmacist identified. If the pharmacist validates order, then any one or more of a variety of actions occur as indicated by block 1524. For example, the pharmacist may have a computer coupled to the hospital network so that when the pharmacist validates the order, the network automatically updates the patient's medication administration record (MAR) and alerts the nurse that the medication order has been validated. The pharmacist may manually fill medication bins (scanning or otherwise entering information describing the medication for transmission to the point-of-care system) and have them transported to the nurse, or activate an "unlock" function via the hospital computer network to unlock a locked medication box such as any of those described herein. At block 1526, the pharmacy alerts the nurse or doctor (via any of a variety of communication means, including those described herein) of the time and method of delivery of the medication. Block 1528 represents the actual delivery of the medication (either in a locked medication box or unlocked medication bins) to the caregiver.

Figure 127:
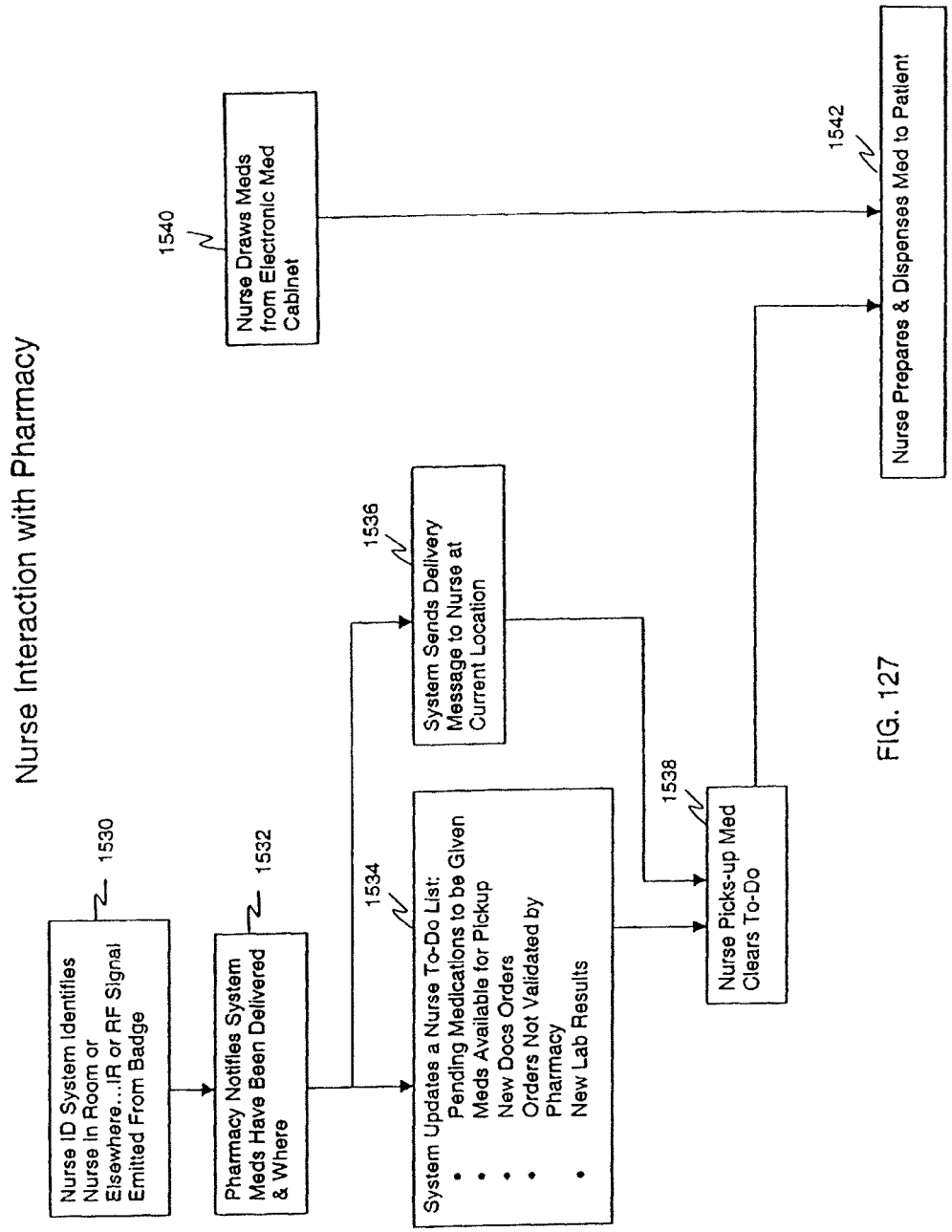

Referring now to FIG. 127, one method of arranging for the delivery of the ordered medication by the nurse is shown. According to the depicted procedure, a personnel locating and tracking system (at block 1530) may identify the nurse when the nurse enters the room of the patient requiring medication. This identification is described in detail herein and further described in U.S. Pat. No. 6,344,794, the disclosure of which is hereby expressly incorporated herein by reference. At block 1532, the pharmacy may provide the system with the time and delivery method of the medication. At block 1534, the system may post a message to the nurse that is displayed when the nurse is detected in the patient's room, thereby updating the nurse's to-do list. The message may include delivery information relating to the ordered medication as indicated at block 1536. At block 1538, the nurse picks up the medication and clears the associated entry on the nurse's to-do list. As indicated by block 1540, the nurse may also remove the validated medication from an electronically controlled medication box or cabinet. Finally, at block 1542, the nurse dispenses the medication to the patient. The process of dispensing the medication is described in greater detail with reference to FIG. 128 below.

Figure 128:
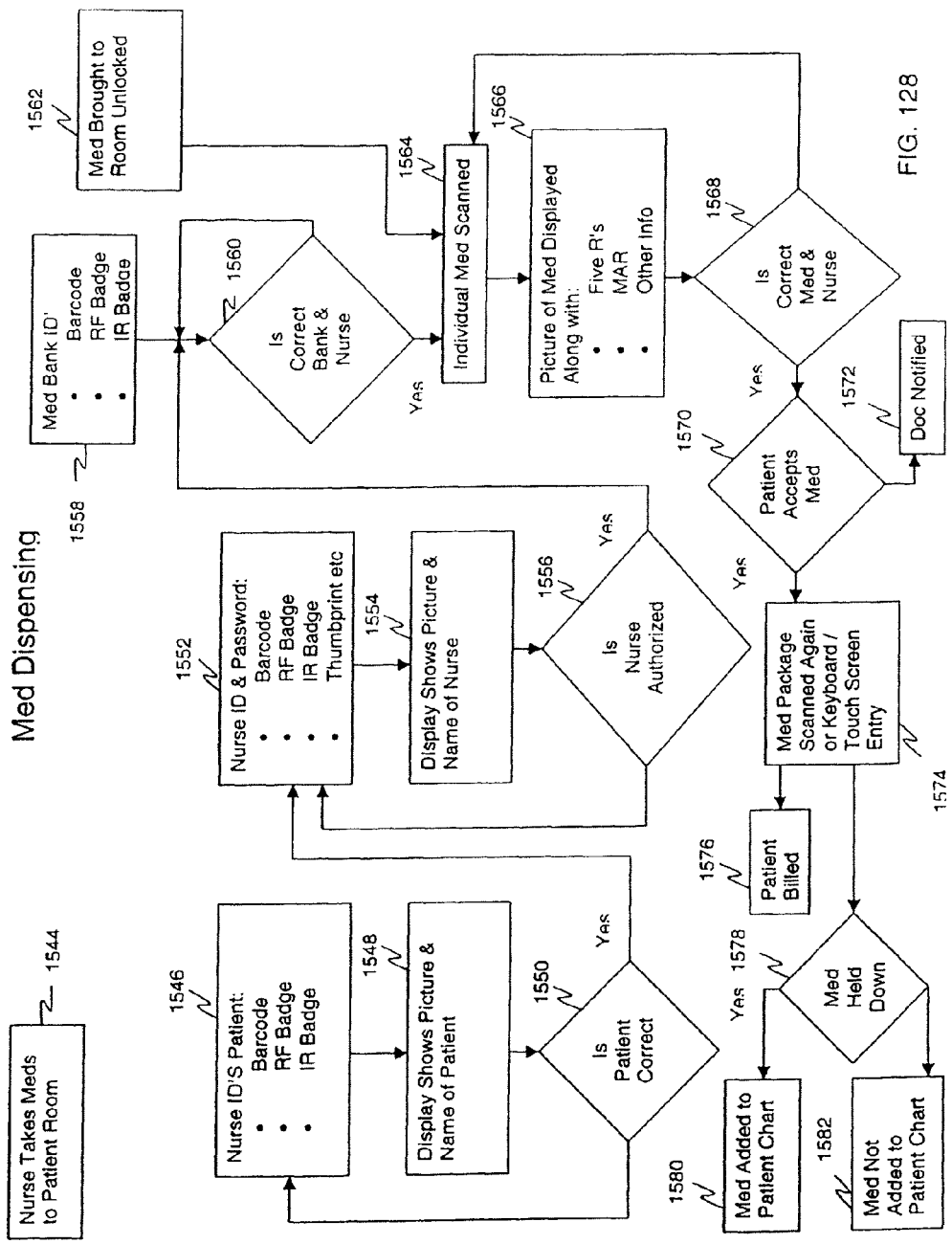

The process of FIG. 128 is similar in certain respects to that of FIG. 3B. According to this process, the nurse may either take the ordered medication to the patient's room (block 1544), the medication may be delivered in a locked medication box (block 1558), or the medication may be delivered in an unlocked medication box (block 1562). At block 1546, the system identifies the patient according to any of the various sensing and/or detection techniques described herein. A display of the point-of-care computer generates an image of the patient along with a display of the patient's name for viewing by the nurse. Thus, the nurse can verify that the patient being attended to is in fact the patient maintained in the hospital main database. If the correct patient is identified (block 1550), then the nurse identification information is entered into the system as indicated by block 1552. If the correct patient is not identified, then the step of identifying the patient is repeated.

The system may identify the nurse using any of the techniques described herein. Alternatively, the nurse may manually enter identification and password information into the point-of-care computer. The computer display generates an image of the nurse along with the nurse's name as indicated by block 1554. If the nurse is authorized to dispense the medication, then the process proceeds to step 1560. If not, new nurse identification information is required.

At block 1560, the system determines whether the medication bank or box delivered to the room is the correct box. In other words, the system checks the orders for the nurse to determine whether the nurse has been scheduled to dispense medication of the kind contained in the box as detected, scanned, or sensed at block 1558. If the correct box and nurse are identified, then the system receives input (block 1564) identifying the individual medication as it is removed from the box according to the principles described herein. Similarly, information regarding individual medication removed from an unlocked medication container is entered into or received by the system. After the individual medication is identified, the system generates an image on the point-of-care computer display of the medication's physical appearance, along with other information relating to the patient's medication records as indicated at block 1568. If the correct medication is displayed, then the nurse may dispense the medication to the patient, and enter information into the system indicating that the medication has been administered (block 1570). At block 1572, the doctor may automatically be notified when the medication is dispensed (e.g., a message may be sent to the doctor). As indicated by block 1574, the medication package may again be scanned or otherwise sensed to indicate that the medication was dispensed, or the nurse may manually enter the dispensation information via an input device such as a keyboard or touch screen. After the medication is dispensed, the patient is billed as indicated by block 1576.

Additionally, as indicated by block 1578, the nurse may be prompted via the point-of-care computer display to enter whether or not the patient held down the medication. If the patient held down the medication, then the medication is added to the patient's chart at block 1580. If not, the medication is not added to the patient's chart as indicated by block 1582.

Figure 129:
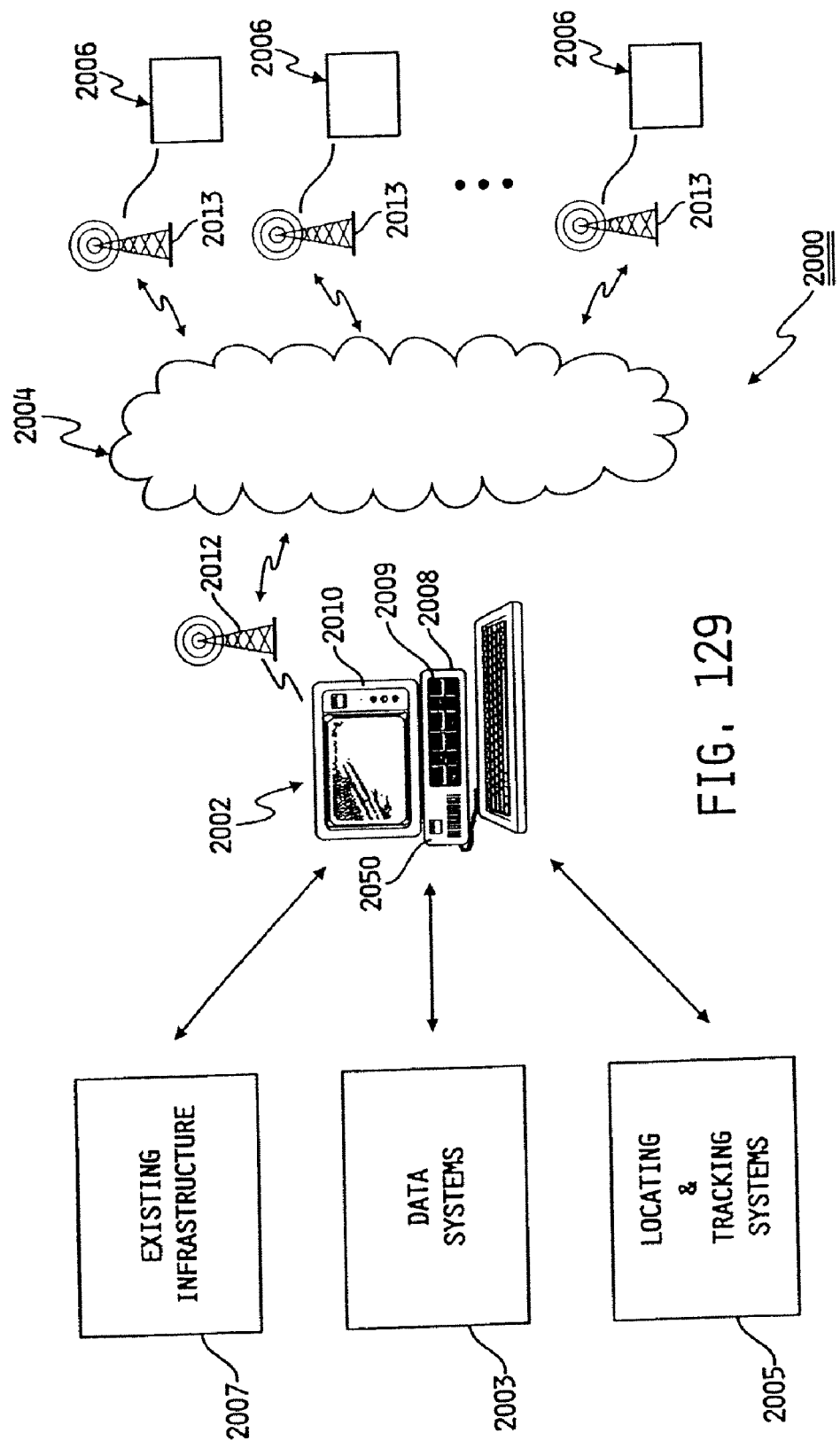
FIG. 129 is a conceptual view of another embodiment of a point-of-care computer system of the present invention.

Another embodiment of the invention is shown in FIGS. 129-143. As best shown in FIG. 129, system 2000 generally includes a central server 2002, a network 2004, and a plurality of client devices 2006. Server 2002 includes a processor 2008, a memory 2009, and a monitor 2010 such as a wall-mounted flat screen display. Server 2002 may be implemented on a standard PC or workstation having processing, memory, and other characteristics sufficient to carry out the functions described below. Server 2002 may be ethernet compatible, and memory 2009 may include a minimum of 512 Megabytes of memory space. Server 2002 is coupled to a transceiver 2012 that communicates with network 2004 to transmit signals to and receive signals from a plurality of transceivers 2013 connected to client devices 2006. Server 2002 is further coupled to any of a variety of health care data systems (generally referred to by the numeral 2003), a locating and tracking system 2005 of the type disclosed herein and further described in U.S. Pat. No. 6,344,794, and other hospital infrastructure (generally referred to by the numeral 2007) as will be further described below.

Network 2004 is shown as a wireless network. It is within the scope of the invention, however, to implement network 2004 as a wired network or any combination of wired and/or wireless networks. Transceiver 2012 and transceivers 2013 may include any type of transceiver that is compatible with the selected implementation of network 2004.

Client devices 2006 may include any of a variety of different types of computer consoles, including any of the various point-of-care computer systems/displays described herein. In one embodiment, shown in FIGS. 130 and 131, client device 2006 includes a monitor 2014 coupled to an overbed table assembly 2016. It should be understood that the principles of the present invention are equally applicable to a client device 2006 coupled to other objects commonly found in a healthcare setting such as a chair, a wheel chair, a walker, an IV stand, a headwall, a ceiling, or other furniture and structural features. Additionally, client device 2006 may be a stand-alone component, or coupled to the bed 2020 at locations other than that described herein (e.g., headboard, footboard, siderail, etc.).

Figure 130:
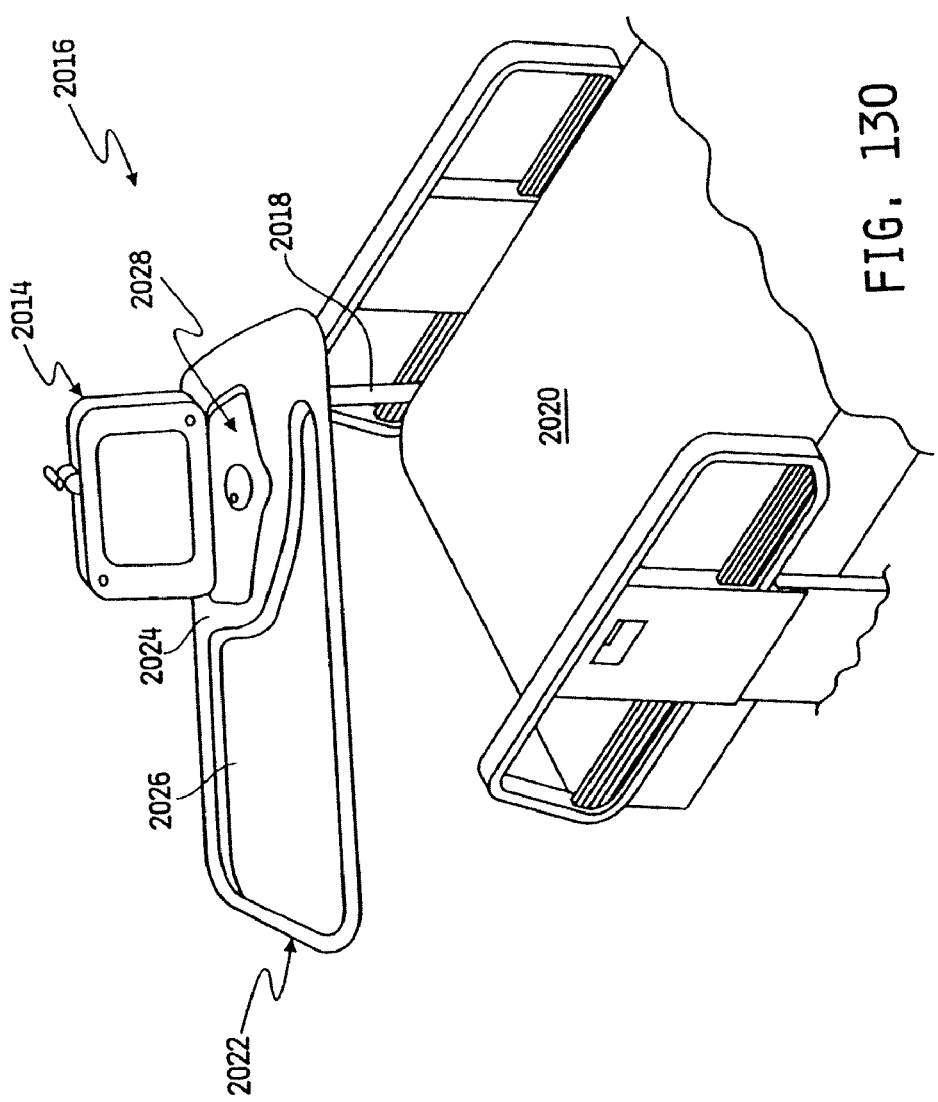
FIGS. 130 and 131 are perspective views, partly in section, of a client device of the system of FIG. 129.

Referring to FIG. 130, table assembly 2016 includes a mounting pole 2018 that provides electrical connection to a receptacle (not shown) on bed 2020. Pole 2018 may be configured according to the principles disclosed in U.S. provisional patent application Ser. Nos. 60/333,387 and 60/314,483, the disclosures of which are hereby expressly incorporated herein by reference. In this manner, wiring (not shown) internal to pole 2018 may provide power to client device 2006 where a wireless data transfer network is employed, or may provide both power and facilitate data transfer to and from client device 2006 where a wired network is employed. Pole 2018 may be vertically adjustable relative to bed 2020, as well as pivotable about a longitudinal axis of pole 2018. One end of pole 2018 is connected to a table 2022 of table assembly 2016 by a bracket (not shown) that may permit rotation of table 2022 about the longitudinal axis of pole 2018 or other form of adjustment of the position of table 2022 relative to bed 2020.

Table 2022 includes an outer edge 2024 that defines a work surface 2026 and a recessed area 2028. Outer edge 2024 may form a raised lip around the perimeter of work surface 2026 to prevent objects from falling off work surface 2026. Work surface 2026 may be covered by or formed from any of a variety of durable materials to provide a suitable writing surface. Such material may also be stain resistant or otherwise liquid repellant.

Figure 131:
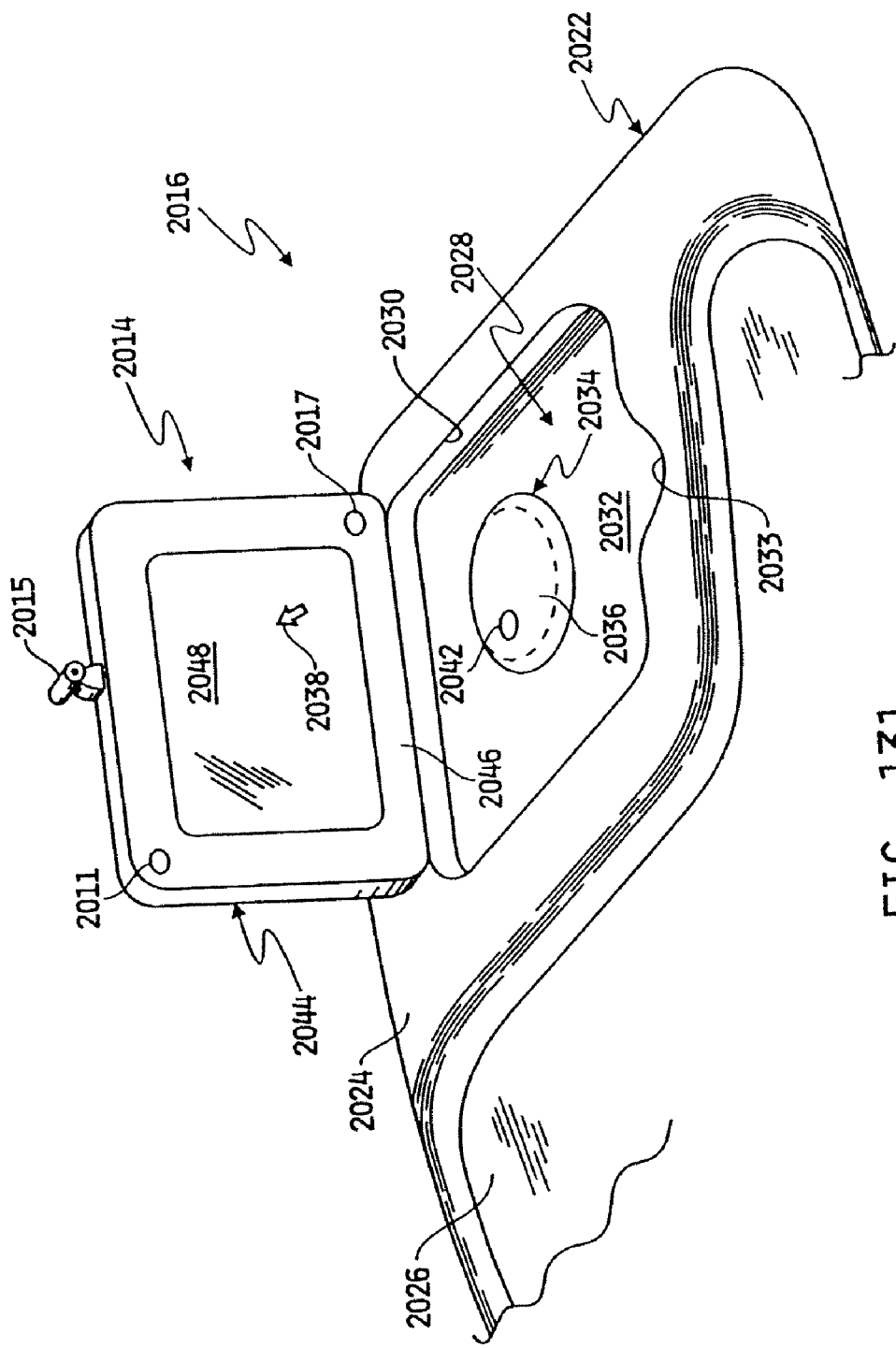

Referring now to FIG. 131, recessed area 2028 includes a sidewall 2030 and a bottom wall 2032, and is sized to receive monitor 2014 when monitor 2014 is folded to an inactive position. The depth of recessed area 2028 may be such that when monitor 2014 is in the inactive position, the back surface of monitor 2014 is substantially flush with the upper surface of outer edge 2024. Sidewall 2030 may be formed to permit access to monitor 2014 when in the inactive position such as by providing a curved portion 2033. When monitor 2014 is in the inactive position, a user can reach an edge of monitor 2014 by placing a hand into recessed area 2028 at curved portion 2033, thereby permitting the user to raise monitor 2014 to the active position.

In the illustrated embodiment, a hand pad 2034 is located at bottom wall 2032 of recessed area 2028. Hand pad 2034 functions as an input device for client device 2006. More specifically, hand pad 2034 includes a control mechanism (not shown) mounted to bottom wall 2032. The control mechanism is electrically coupled to the processor (not shown) for controlling monitor 2014 in a manner similar to a roller ball, rocker switch, joystick, or the like, and is covered by a membrane 2036. Membrane 2036 is sufficiently flexible to permit the user to move, rock, or otherwise actuate the control mechanism, which, according to well-known principles, causes corresponding movements of a cursor 2038 on monitor 2014. The control mechanism of hand pad 2034 also includes a select button situated below a portion 2042 of membrane 2036. When the user depresses portion 2042, the select button is actuated, thereby causing the control mechanism to send a select signal to the processor (not shown). Alternatively, the select button associated with portion 2042 could be implemented as an electrical, optical, magnetic or other type of switch or device for indicating a user selection. Thus, using hand pad 2034, the user can move cursor 2038 on monitor 2014 and select items displayed on monitor 2014 to activate different functions of client device 2006 as is further described below.

The above-described configuration of hand pad 2034 may be especially suitable for providing an easy to operate input device for users having limited manual dexterity or mental ability due to illness or advanced age. The entire perimeter of membrane 2036 may be attached to bottom wall 2032 to facilitate cleaning of table 2022 and prevent debris from collecting under membrane 2036, potentially interfering with the operation of the control mechanism or causing a risk to the health of patients.

It should be understood that other types of input devices may readily be adapted for use with client device 2006. For example, a conventional mouse or keyboard could be used. Additionally, monitor 2014 may employ touch screen technology and provide input areas that are sensitive to pressure, capacitance, resistance, magnetic fields, optical interference, etc. It should further be understood that other embodiments of the invention may exclude recessed area 2028 of table 2022 such that monitor 2014 is positioned on top of outer edge 2024 when folded to the inactive position. Moreover, any of the various displays and mounting configurations described herein (or in any of the disclosures incorporated herein) may be adapted for use with table assembly 2016.

Monitor 2014 generally includes a housing 2044 having a hinge 2046 connected to one edge of monitor 2014. Hinge 2046 connects monitor 2014 to recessed area sidewall 2030 for pivoting movement between the inactive and active positions as described above. Housing 2044 may enclose the processor and other control electronics (not shown) that control the operation of client device 2006. Alternatively, housing 2044 may enclose wiring for connection to the processor and control electronics which may be inconspicuously mounted elsewhere on table assembly 2016. Housing 2044 further includes a screen 2048 such as a LCD type color screen for displaying information to the user. Monitor 2014 also includes a sensor 2011 (or plurality of sensors 2011) for detecting badges or tags worn by caregivers, patients, etc., or mounted to equipment, supplies, files, etc., as well as a camera 2015 to provide video input to client device 2006. In such an embodiment, client device 2006 can detect and identify, via locating and tracking system 2005, individuals as they come within the range of sensor 2011. Moreover, client device 2006 may provide on-screen messages to identified individuals. For example, if a member of the cleaning staff enters a room including client device 2006, monitor 2014 may display a message on screen 2048 requiring the member to activate a displayed icon to indicate that the room cleaning procedure is complete. Client device 2006 may then upload this information to server 2002, which may update the cleaning status of the room. Alternatively, client device 2006 may employ business logic that assumes that if the member of the cleaning staff remains within a range of the monitor sensor 2011 for at least a pre-determined time period (e.g., 15 minutes), that the room cleaning procedure is complete. Also, monitor 2014 may include a position sensor 2017 (mechanical, electrical, optical, magnetic, etc.) for determining when monitor 2014 is in the inactive position or the active position. Alternatively, position sensor 2017 may be mounted to table 2022.

The software 2050 (FIG. 129) of system 2000 includes a conventional operating system such as Microsoft Windows® or Linux®, and application software operated by server 2002 and client devices 2006. Software 2050 facilitates communications with between server 2002 and client devices 2006, health care data systems 2003, locating and tracking system 2005, and hospital infrastructure 2007, processes inputs from the user, and provides information on monitor 2014, in addition to other functions described herein. In general, software 2050 is stored on server 2002 and portions of software 2050 are uploaded to particular client devices 2006 over network 2004 when needed by client devices 2006 (according to standard thin client architectures). Data is also stored in memory 2009 of server 2006, including patient records data, equipment maintenance data, facilities processes data, billing information data, data associating each client device 2006 with a particular location such as a hospital room, a particular person such as a patient, or both a location and a person, and other data as described herein.

Figure 132:
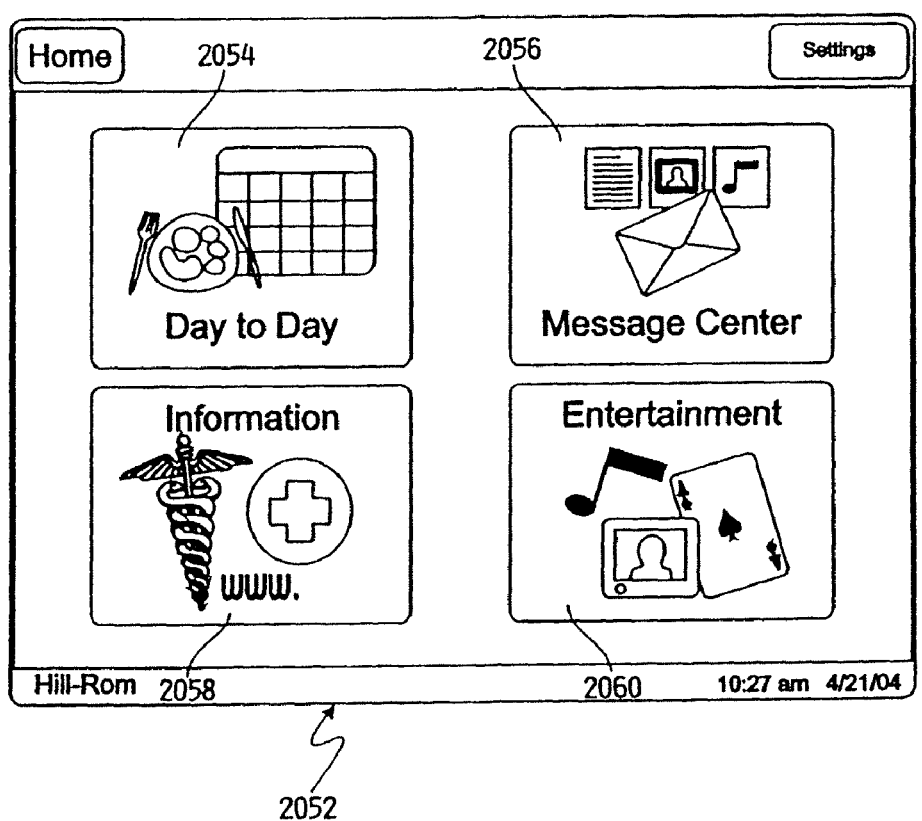
FIGS. 132-143 depict various screens generated on a client device display of the present invention.

Software 2050 functions with client device 2006 to generate a plurality of screens such as the home screen 2052 shown in FIG. 132. Home screen 2052 is shown including a day-to-day icon 2054, a message center icon 2056, a medical information icon 2058, and an entertainment icon 2060. As is described below, activation of any of these icons causes software 2050 to initiate various functions and generate various screens. During any of these various operations (or any of the other operations described below with reference to FIGS. 133-143), software 2050 may be configured to turn off or otherwise suspend operation of monitor 2014 when position sensor 2017 associated with monitor 2014 indicates that monitor 2014 is in the inactive position. When the user moves monitor 2014 to the active position, software 2050 may automatically activate or enable monitor 2014 and generate the same screen as was displayed when monitor 2014 was last moved to the inactive position.

Medical information icon 2058 is associated with a medical information application of software 2050 wherein patients may view information relating to symptoms or parts of the human anatomy. Upon activation of icon 2058, software 2050 generates the screen 2062 shown in FIG. 133. Screen 2062 generally includes a status bar 2063, an image area 2065, and an information area 2067. Status bar 2063 includes a home button 2064, an information indicator 2066, and a medinfo indicator 2068 to indicate to the user that the user is currently running the medical information application provided by software 2050. Image area 2065 includes an image 2070 of a human body, a head button 2072, a chest button 2074, a pelvis button 2076, a limbs button 2078, a systemic button 2080, a child button 2088, an adult button 2090, a female button 2092, and a male button 2094. Information area 2067 includes a list 2069 of topics, a search button 2084, and a more button 2086.

Figure 133:
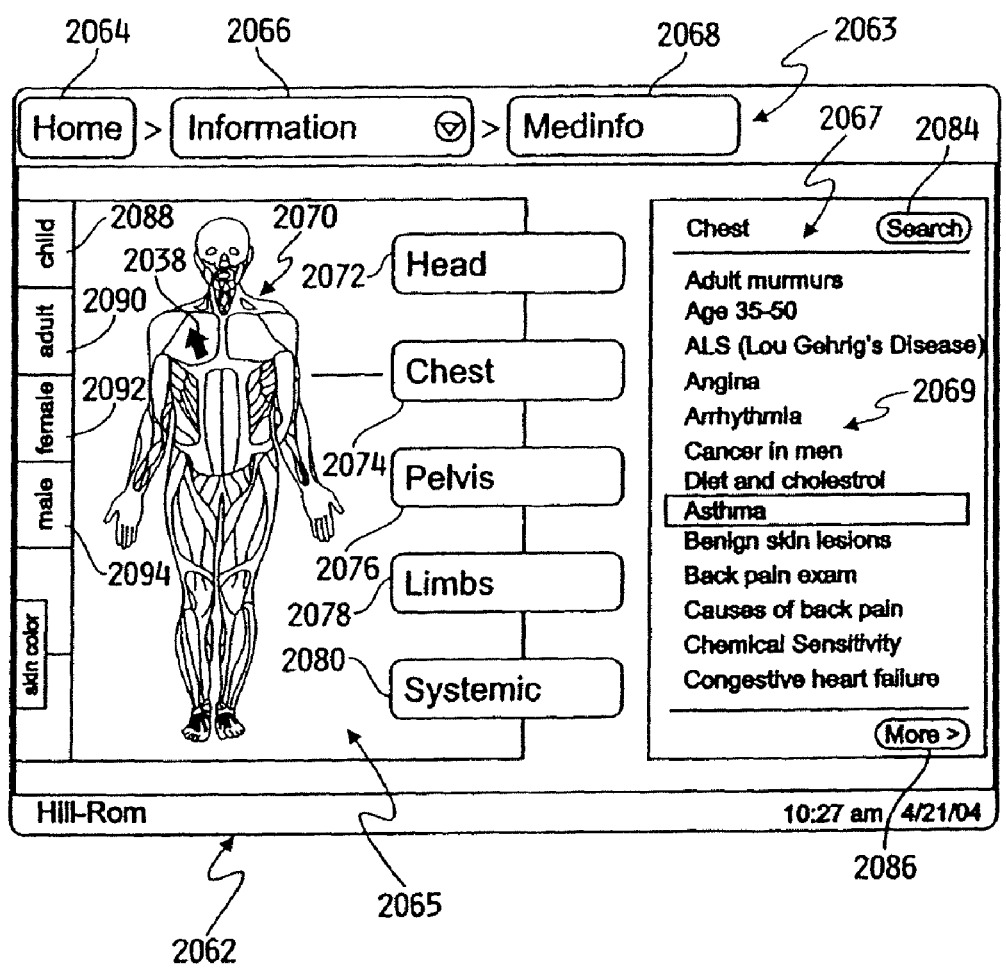

In operation, the user selects a part of image 2070 (such as the chest region as shown in FIG. 133) by touching the portion of screen 2048 on which the image part is displayed. For the remainder of this description, it is assumed that screen 2048 of monitor 2014 is touch sensitive or otherwise able to be actuated by the user. As such, hand pad 2034 may be used as an additional input device. When the user touches a portion of image 2070, software 2050 generates a list 2069 in information area 2067 of a variety of topics including symptoms and medical subjects relating to the corresponding part of the human anatomy. Alternatively, the user may directly activate one of buttons 2072, 2074, 2076, 2078, or 2080 to obtain the desired list. In the event that list 2069 includes more items than can be simultaneously displayed in information area 2067, the user can view additional items by activating more button 2086. The user may select a symptom or subject by highlighting the desired symptom or subject in list 2069 and activating the list item using hand pad 2034. When the user activates search button 2084, software 2050 accesses additional information relating to the selected item from server 2002, and displays the additional information in information area 2067. In an alternate embodiment, by activating a medical dictionary button (not shown), the user can access an electronic medical dictionary database stored on server 2002. In such an embodiment, the user can toggle between the anatomical information searching described above and the medical dictionary by activating an appropriate button displayed on screen 2062. The user can return to home screen 2052 of FIG. 132 by activating home button 2064. Additionally, the user can select a type of human anatomy by activating a desired one of child button 2088, adult button 2090, female button 2092, and male button 2094 to obtain medical information and topic options specific to the selected anatomy. Thus, the user may switch between different types of anatomy during navigation of the application.

According to one embodiment, the medical data accessed by the application is stored on server 2002 in a database organized in a tree data structure. Each leaf on the tree of the tree structure contains a pointer to a list of pointers in the database. The pointers ultimately direct the application to information pages contained in the database. The information pages may include collections of text pages providing the selected medical information for display in information area 2067.

Figure 134:
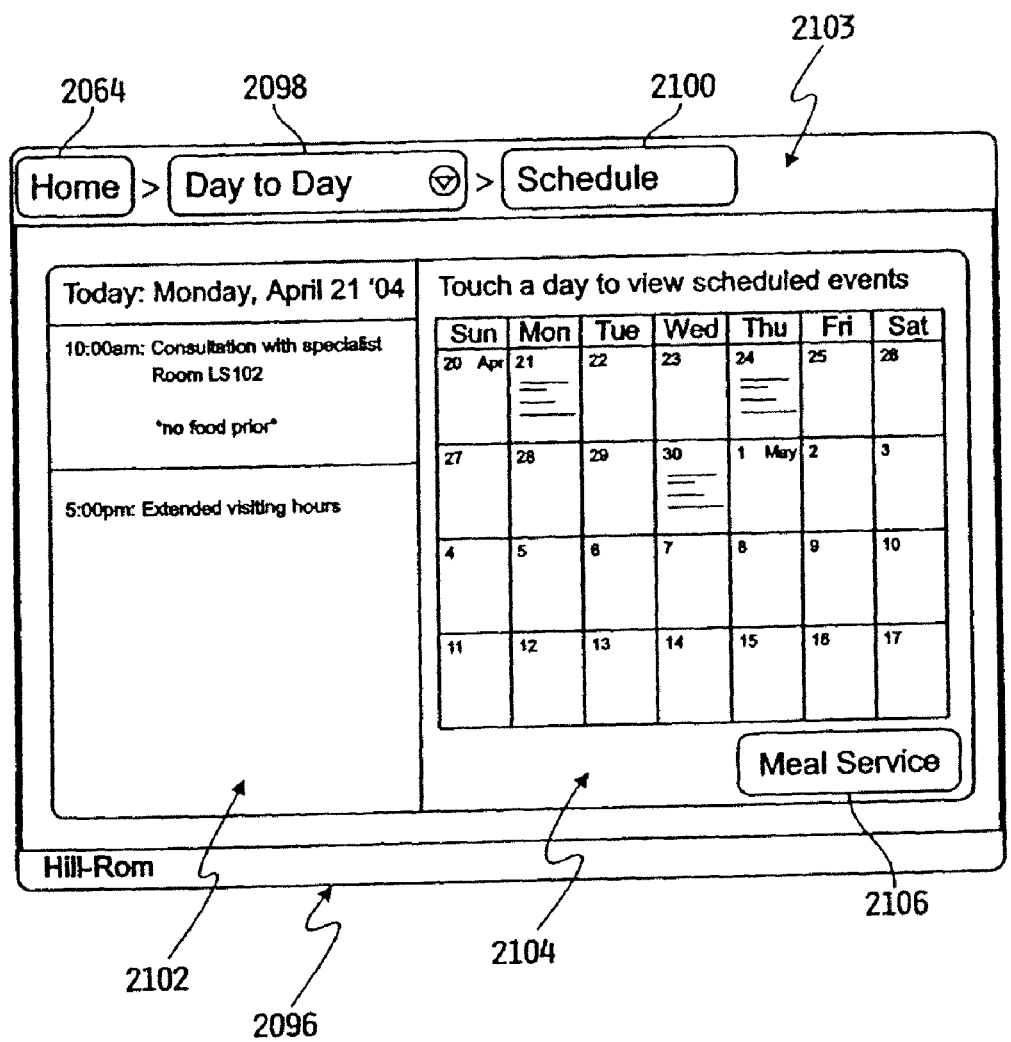

Software 2050 also includes a schedule and meal ordering application wherein patients may view scheduled items and order meals from bed 2020. Upon activation of icon day-to-day icon 2054, software 2050 generates screen 2096 as shown in FIG. 134. Screen 2096 generally includes an information area 2102, a status bar 2103, and a calendar area 2104. Status bar 2103 includes home button 2064, a day-to-day button 2098, and a schedule indicator 2100. Calendar area 2104 includes a display of a calendar representing, for example, four weeks including the current week, and a meal service button 2106. The calendar days having scheduled items are indicated in some manner, such as by shading. As indicated in calendar area 2104, the user may view any scheduled items associated with a particular day by touching the displayed day. When the user touches a day, the scheduled items for that day are displayed in information area 2102. In this manner, the user (or patient) is provided with reminders of visits, consultations, etc., and can plan accordingly.

Figure 135:
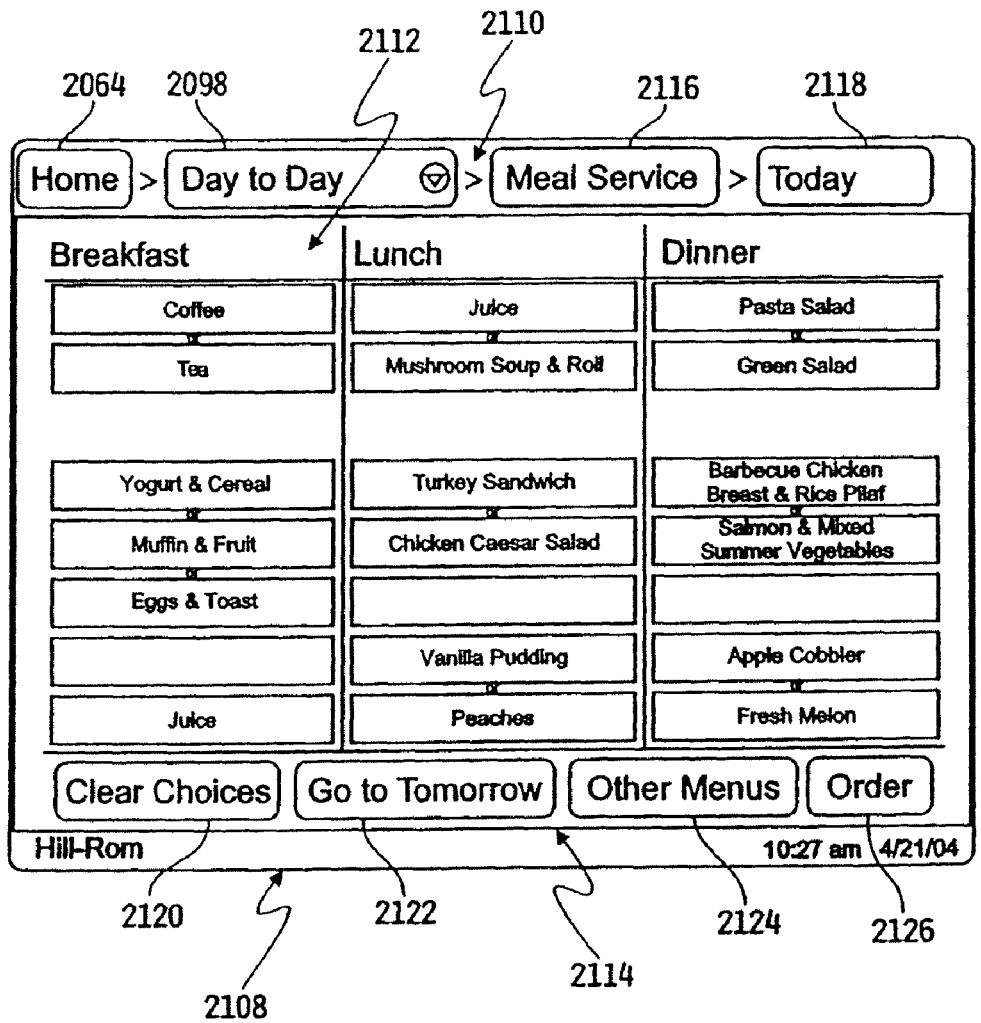

Upon activating meal service button 2106 (or selecting a meal service option (not shown) displayed along with a scheduling option (not shown) in a pull-down menu (not shown) upon activation of day-to-day button 2098), software 2050 causes client device 2006 to generate and display on display 2048 the screen 2108 shown in FIG. 135. Screen 2108 generally includes a status bar 2110, a menu area 2112, and a command bar 2114. Status bar 2110 includes home button 2064, day-to-day button 2098, a meal service indicator 2116, and a today indicator 2118. Menu area 2112 includes a display of menu items arranged in three columns corresponding to breakfast, lunch, and dinner. The menu items listed may be selected and entered into system 2000 by hospital personnel to correspond to available menu items and conform to any specific dietary needs or restrictions of the user. It should be understood that screen 2108 could also include information or links to information relating to the nutritional characteristics of the listed menu items. Command bar includes a clear choices button 2120, a go-to-tomorrow button 2122, an other menus button 2124, and an order button 2126.

Figure 136:
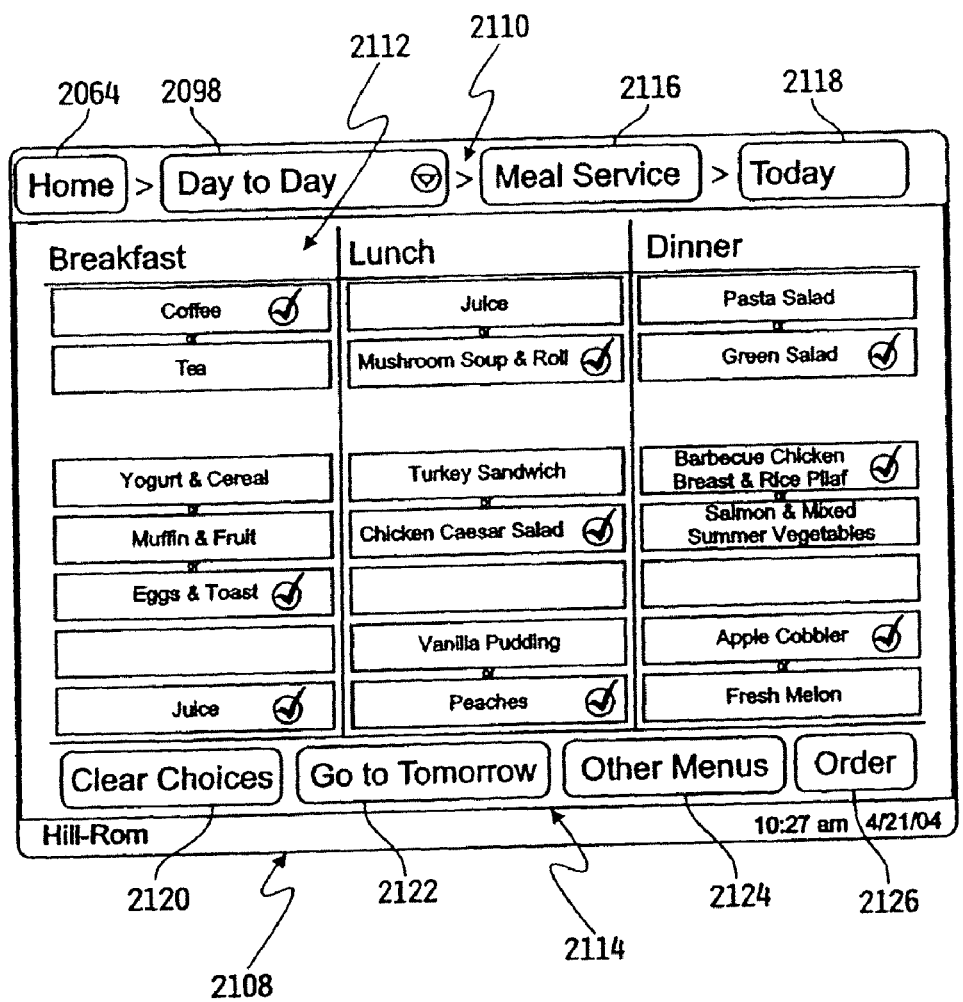
Figure 137:
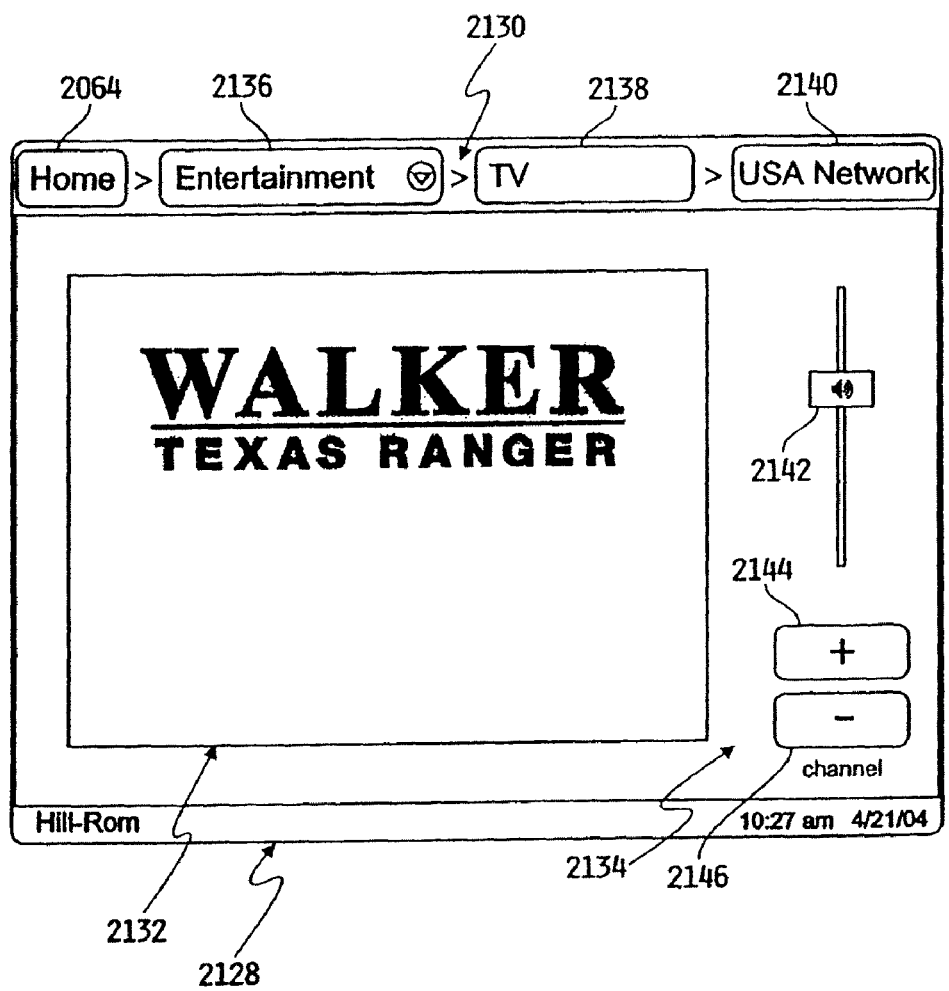

As shown in FIG. 136, the user may select items for each of the displayed meals by touching the selected items, thereby causing software 2050 to display a checkmark near the selected item or otherwise indicate its selection. The user may submit the order (i.e., a list of selected items) to a fulfillment location (such as a food preparation/meal assembly center) by touching order button 2126. In one embodiment, when order button 2126 is activated, software 2050 generates a verify selections message (not shown), and provides the user with the ability to edit the selections. If the selections are verified, then client device 2006 transmits signals via network 2004 to server 2002, which may subsequently route the order to an appropriate fulfillment location.

The clear choices button 2120 enables the user to reset his or her selections and begin the selections process again. Activation of the go-to-tomorrow button 2122 causes software 2050 to display the menu selections for meals to be served one day in the future. When the user touches the other menus button 2124, software 2050 may generate a display (not shown) of menu options for special meals, links to local restaurants, or some other menu related options. The user may return to home screen 2052 of FIG. 132 by activating home button 2064, or return to scheduling screen 2096 of FIG. 134 by selecting the scheduling option (not shown) displayed in the pull-down menu (not shown) generated upon activation of day-to-day button 2098.

According to one embodiment of the present invention, when the user touches entertainment icon 2060 of home screen 2052, software 2050 invokes an entertainment control application that enables the user to control power, channel selection, volume, and other functions associated with entertainment equipment typically found in a hospital room such as a television or radio. Specifically, software 2050 generates screen 2128 shown in FIG. 137. Screen 2128 is, in this embodiment, the default entertainment screen that is initially displayed when entertainment icon 2060 is selected. Screen 2128 includes a status bar 2130, a video area 2132, and a control area 2134. Status bar 2130 includes home button 2064 (activation of which returns the user to home screen 2052 of FIG. 132), an entertainment button 2136, a TV indicator 2138, and a channel indicator 2140. Video area 2132 displays the video content of the selected television channel. It should be understood that system 2000 may, instead, be coupled to conventional hospital television controls such that system 2000 functions simply as a control interface, without providing content output. In other words, the television video may, in other embodiments, be displayed on the hospital television.

The accompanying audio may be provided through a speaker connected to system 2000, through the conventional radio speaker provided with bed 2020, or through any other suitable sound system.

Control area includes volume slider 2142, channel-up button 2144, and channel-down button 2146. By touching volume slider 2142 and moving it vertically, the user can adjust the volume of the audio accompanying the video content of the selected television channel. The user may change channels to an adjacent channel by activating one of channel-up button 2144 or channel-down button 2146 according to principles that are well known in the art. When a new channel is selected, channel indicator 2140 may display an identification of the selected channel.

Figure 138:
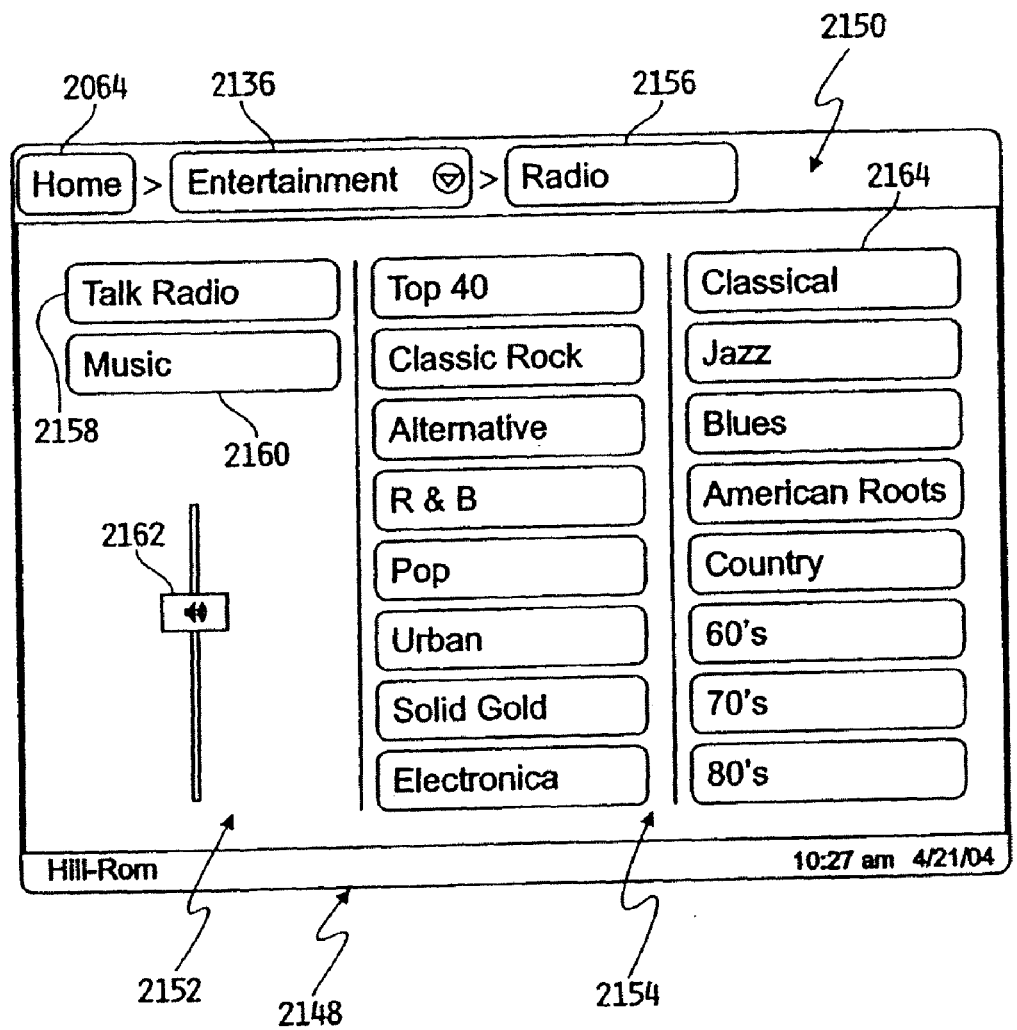

When entertainment button 2136 is activated, software 2050 generates a pull-down menu (not shown) for display on screen 2128 that lists as options TV, radio, and games. The user may navigate between these various entertainment control functions using entertainment button 2136 and the displayed options. When the user selects the radio option (not shown), software 2050 causes client device 2006 to display screen 2148 on monitor 2014 as shown in FIG. 138. Screen 2148 generally includes a status bar 2150, a control area 2152, and a channel selection area 2154. Status bar 2050 includes home button 2064 (for returning to home screen 2052), entertainment button 2136, and a radio indicator 2156. Control area 2152 includes a talk radio button 2158, a music button 2160, and a volume slider 2162. When initially displayed, screen 2148 may default to music radio as shown in FIG. 138. Accordingly, channel selection area 2154 includes a plurality of channel icons 2164 that correspond to different music formats. Activation of any channel icon 2164 causes client device 2006 to send appropriate signals to a radio receiver (not shown), thereby causing the receiver to tune to a predetermined channel corresponding to the selected music format. The user may adjust the volume of the music by manipulating volume slider 2162 in the manner described above with regard to volume slider 2142.

Figure 139:
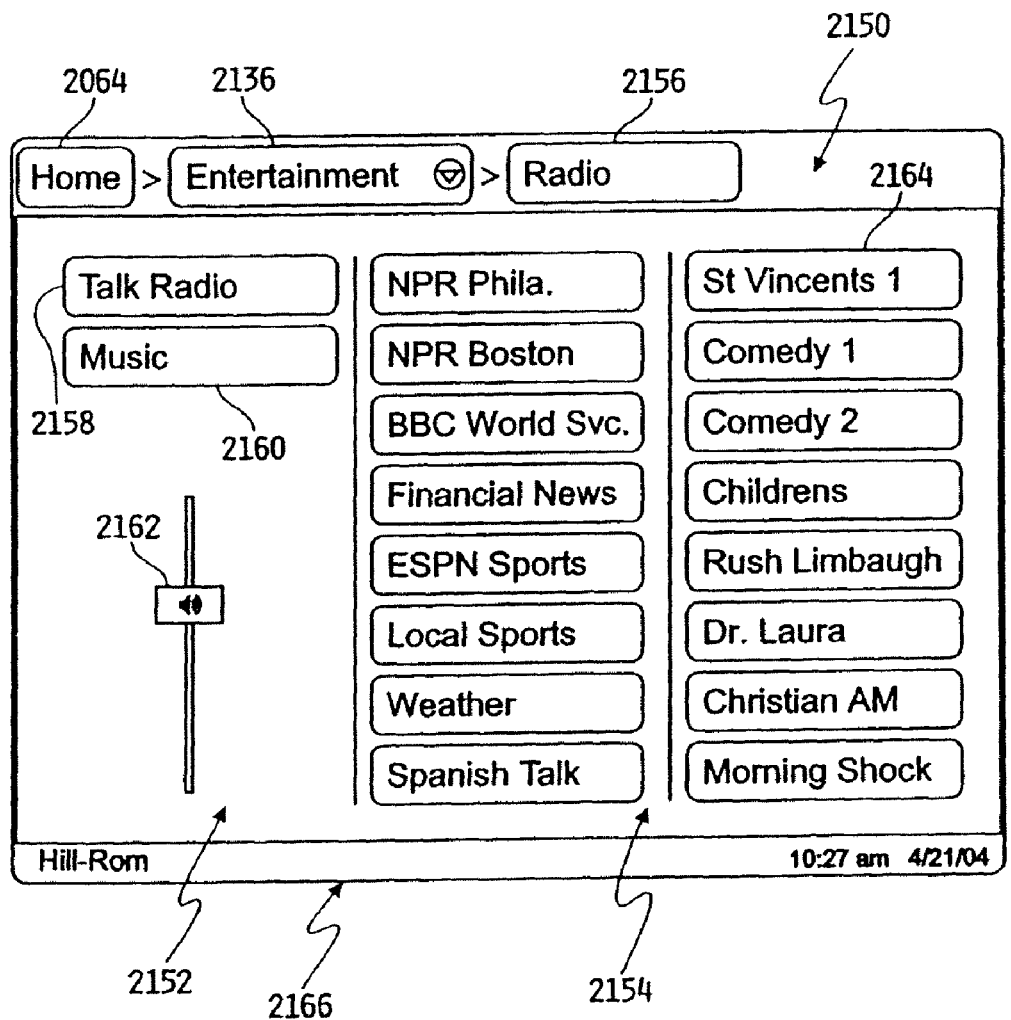

When the user activates talk button 2158, software 2050 causes client device 2006 to generate screen 2166 as shown in FIG. 139. Screen 2166 is identical to screen 2148, except that a plurality of talk radio formats are displayed in channel icons 2164 instead of music formats as shown in FIG. 138. The user may select a particular talk radio format by touching the corresponding channel icon 2164 in the manner described above.

As should be understood from the foregoing, when the user activates a television or radio channel or volume control function, client device 2006 transmits the appropriate signal(s) to carry out the selected function either to the entertainment equipment directly via a wired or wireless connection, or to other control equipment connected to the entertainment equipment. For example, client device 2006 may readily be configured to provide input to a television control device such as that disclosed in co-pending U.S. patent application Ser. No. 10/025,934, which is hereby expressly incorporated herein by reference. Alternatively, or in addition to the functions described above, the entertainment control application could serve as an interface for ordering pay-per-view programming, the cost of which could be tracked by system 2000 and stored on server 2002 for billing to the user. Applying the principles disclosed herein, system 2000 could further readily be configured to function as a control interface for a DVD player, VCR, cassette player, or any other type of entertainment device.

Similarly, software 2050 may provide a phone service interface application that enables the user to place telephone calls via monitor 2014. More specifically, client device 2006 may be connected to the hospital phone system via a wired or wireless connection. Software 2050 may cause client device 2006 to generate screens (not shown) presenting the user with options of placing a phone call, accessing a directory, etc. The user may input a telephone number (or select a number from a directory), and command client device 2006 to call the number via the hospital phone system.

Figure 140:
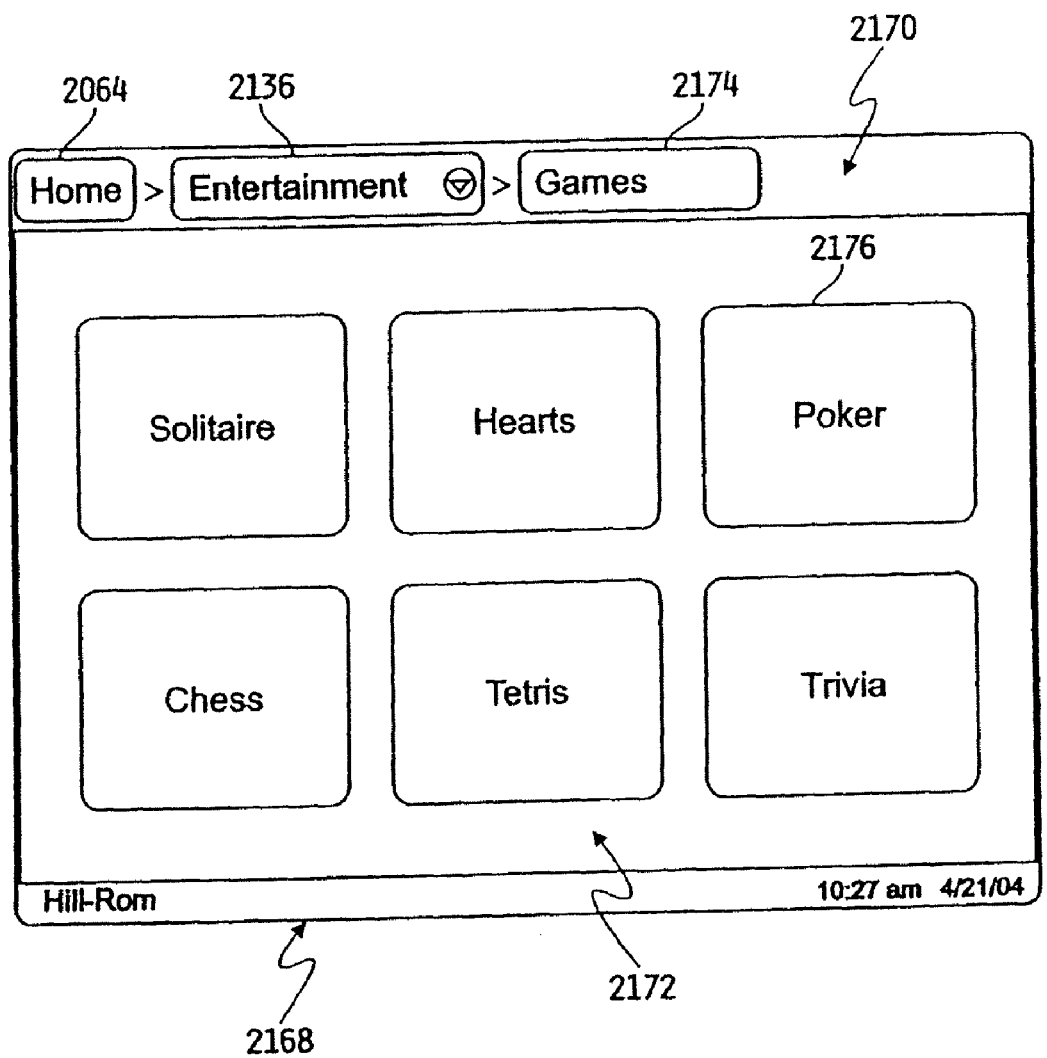

Referring now to FIG. 140, when the user activates entertainment button 2136 to access the resulting pull-down menu (not shown) that provides television, radio, and games options, and selects the games option, software 2050 causes client device 2006 generate screen 2168. As shown, screen 2168 generally includes a status bar 2170 and a games selection area 2172. Status bar 2170 includes home button 2064, entertainment button 2136, and a games indicator 2174. By touching one of the plurality of games icons 2176 displayed in games selection area 2172, the user causes software 2050 to invoke a software application corresponding to the selected game. The user may return to home screen 2052 or return to television control or radio control using home button 2064 or entertainment button 2136, respectively.

Software 2050 also includes a messaging application that enables users and hospital personnel to send and receive messages. Upon activating message center icon 2056 displayed on home screen 2052 (FIG. 132), the user causes software 2050 to display screen 2178 shown in FIG. 141. Screen 2178 generally includes a status bar 2180, a message area 2182, and a command area 2184. Status bar 2178 includes home button 2064, a message center button 2186, and a compose indicator 2188. Message area 2182 includes an intended recipient field 2190, a subject field 2192, a message field 2194, and a scroll bar 2195. Command area 2184 includes a send button 2196, a +voice button 2198, and a +video button 2200.

A user may compose a message and input the recipient name(s) and subject of the message using, for example, a wireless keyboard (not shown) coupled to client device 2006. Alternatively, software 2050 may generate a keyboard overlay (not shown) on screen 2178 to enable the user to touch portions of the screen corresponding to the desired letters and/or numbers. When the message is composed, the user may review the message (i.e., scroll up or down) by manipulating scroll bar 2195 as is well known in the art. It is within the scope of the present invention to configure software 2050 to provide a variety of message editing and distribution functions similar to functions typically provided by conventional internet browser software. Upon activation of send button 2196, software 2050 forwards the message to a destination location corresponding to the recipient(s). For example, server 2002 may access locating and tracking system 2005 (FIG. 129) to determine the current location of a recipient, and forward the message over network 2004 to a monitor 2014 associated with or otherwise in proximity of the recipient. Alternatively, server 2002 may store the message until locating and tracking system 2005 detects the presence of the recipient in a particular area. At the time of detection, server 2002 may transmit the message to a monitor 2014 in proximity of the recipient. It should be understood that messages so transmitted may also include an access screen that requires the recipient to comply with a security provision (e.g., enter a password) before accessing the content of the message if automatic detection of user identification via sensors and badges/tags is not used.

The message described above is a text message, generated, for example, by manipulating an on-screen keyboard. By activating +voice button 2198, the user causes software 2050 to begin recording an audio message provided by the user through a microphone (not shown) connected to monitor 2014 or a telephone handset of a conventional, in-room telephone electrically coupled to monitor 2014. The resulting audio file is associated with the text file (if one was created) and forwarded to the recipient(s) in the manner described above. By activating +video button 2200, the user causes software 2050 to display screen 2216 of FIG. 143 (as further described below) to enable the user to record an audio-visual message through use of an audio input as described above and camera 2015 of monitor 2014.

Figure 141:
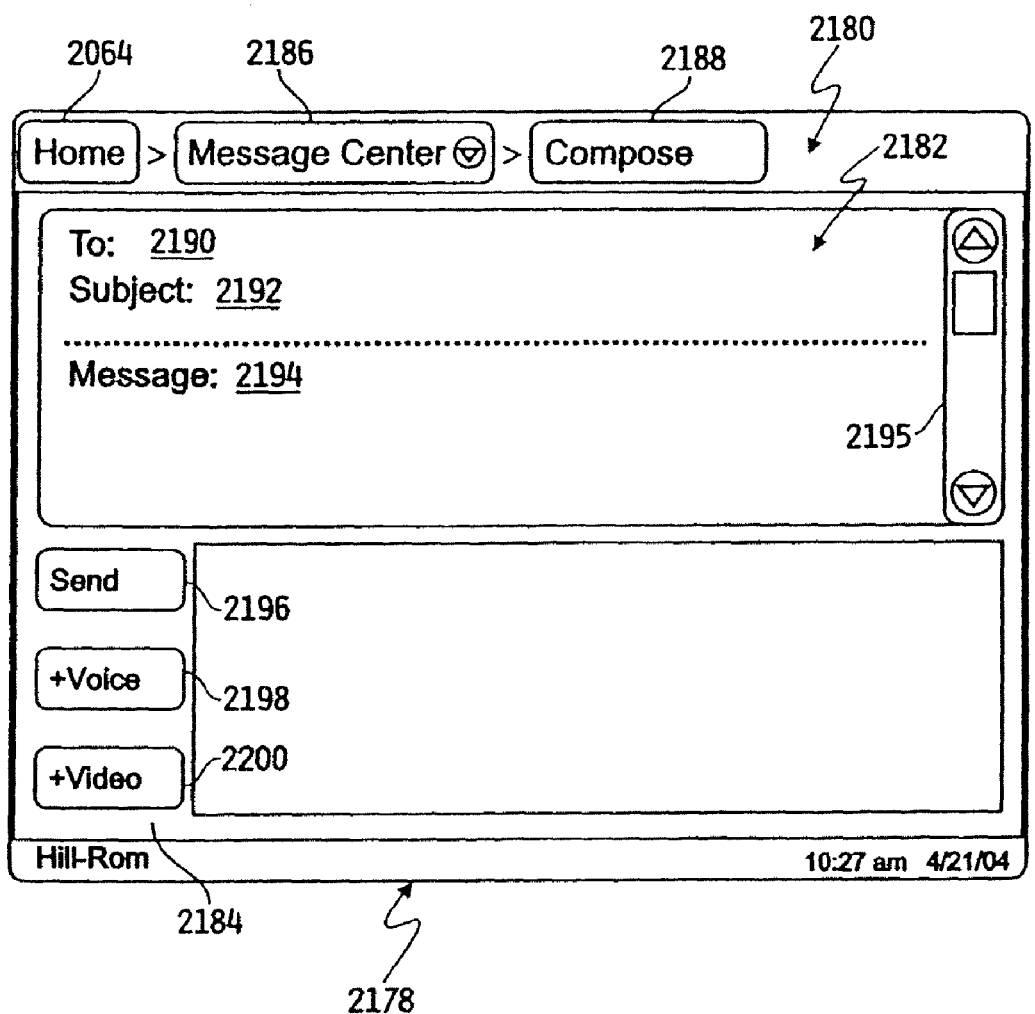
Figure 142:
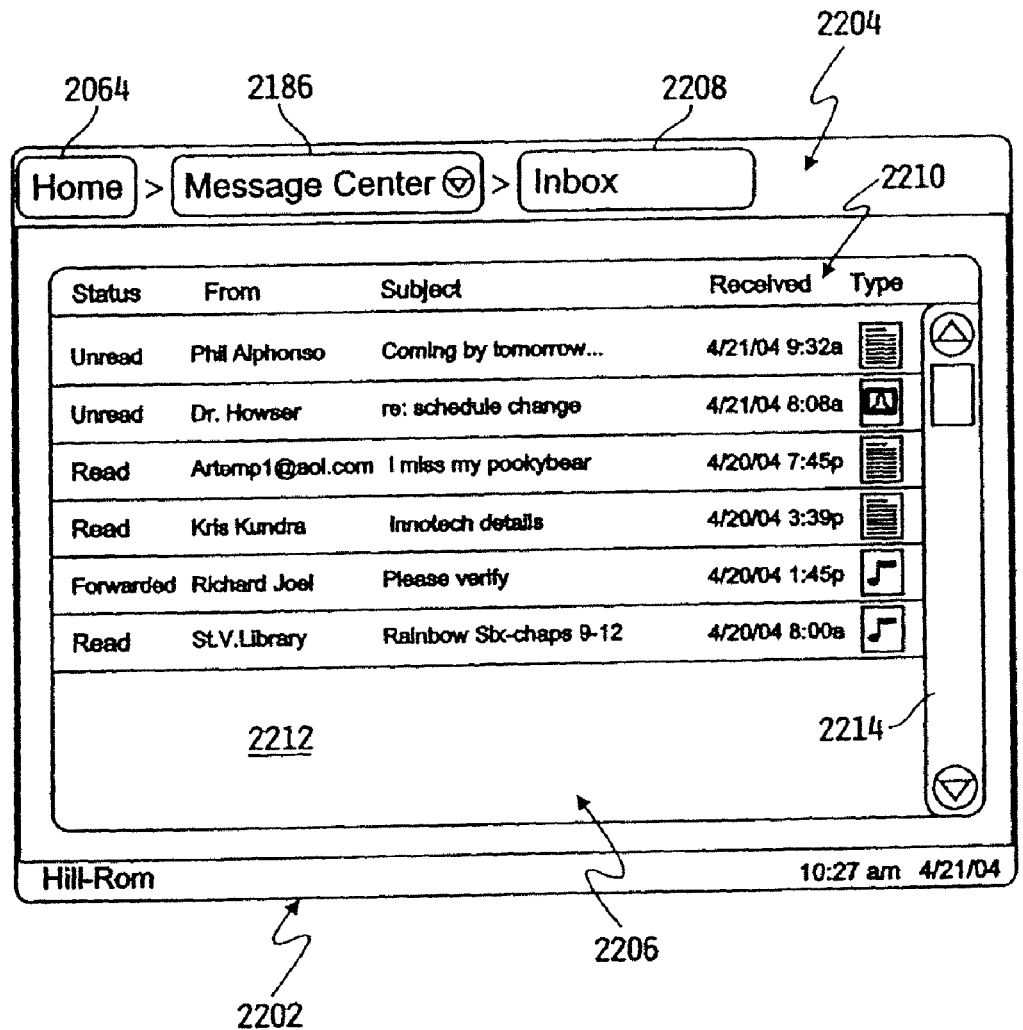

When the user touches message center button 2186, software 2050 generates a pull-down menu (not shown) that displays a compose option and an inbox option. When the compose option is selected, screen 2178 is generated as shown in FIG. 141. When the user selects the inbox option, software 2050 causes client device 2006 to display screen 2202 on monitor 2014 as shown in FIG. 142. Screen 2202 generally includes a status bar 2204 and a message box 2206. Message status bar 2204 includes home button 2064, message center button 2186, and an inbox indicator 2208. Message box 2206 includes a heading bar 2210, a message listing area 2212, and a slider bar 2214. As shown, heading bar 2210 provides labels such as "Status," "From," "Subject," "Received," and "Type," to organize the messages listed in message listing area 2212 in column format. Thus, under the "Status" label, message listing area 2212 provides an indication of whether a listed message has been read, forwarded, etc. The message sender is listed under the "From" label, the subject matter of the message is listed under the "Subject" label, the date and time the message was received is listed under the "Received" label, and the type of message (i.e., text, audio, video) is indicated under the "Type" label. The user can scroll through the messages listed in the message listing area 2212 by manipulating slider bar 2214.

As should be apparent from the foregoing, utilizing client device 2006, the user may access the internet and send and receive e-mail messages with other internet users. In such an embodiment, network 2004 is connected to the internet, and software 2050 includes a browser for interfacing with server 2002 and the internet. Software 2050 may be configured (using conventional techniques) to provided limited internet access, restricting user access to certain websites. Since client device 2006 utilizes thin client type architecture, client device 2006 is inherently resistant to infection by computer viruses of the type transmitted over the internet. An overlay text application may function in cooperation with the browser to provide an on-screen keyboard, thereby permitting text entry into the browser. Alternatively, as indicated above, a wireless keyboard may be used as an input device.

When the user activates a text message listed in the message listing area 2212 to select the message, software 2050 generates a text box (not shown) including the content of the message. When the user activates an audio message, software 2050 generates a control box (not shown) on monitor 2014 including buttons that correspond to conventional control functions for a piece of audio equipment such as a tape player similar to the control box described below in connection with the selection of a video message.

Figure 143:
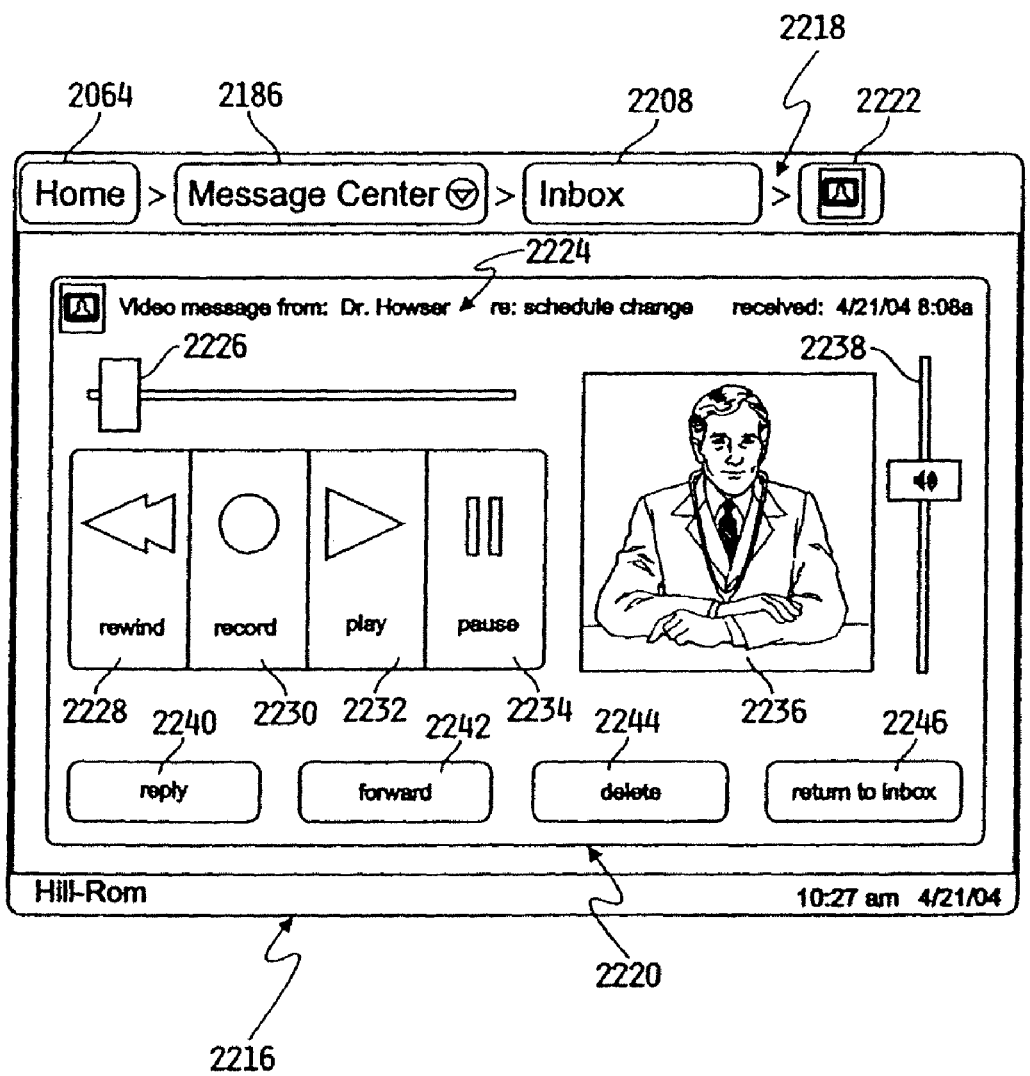

Referring now to FIG. 143, when the user selects a video message from the message listing area 2212 (or touches +video button 2200 of FIG. 141), software 2050 generates screen 2216. Screen 2216 generally includes a status bar 2218 and a control box 2220. Status bar 2218 includes home button 2064, message center button 2186, inbox indicator 2208, and a video message indicator 2222. Control box 2220 includes an information area 2224 that lists the message sender, subject matter, and date and time received, a video slider 2226, a rewind button 2228, a record button 2230, a play button 2232, a pause button 2234, a video area 2236, an audio slider 2238, a reply button 2240, a forward button 2242, a delete button 2244, and a return to inbox button 2246. When the user touches play button 2232, software 2050 causes client device 2006 to communicate with server 2002 over network 2004. Specifically, client device 2006 requests server 2002 to access data stored in memory 2009 corresponding to the selected video message. This data is provided to client device 2006, which generates or recreates the stored video message in video area 2236. Associated audio is provided through a speaker (not shown) or other sound system coupled to client device 2006. The playback of video and audio may be manipulated by the user via rewind button 2228 and pause button 2234. Also, the user can move to specific parts of the playback using video slider 2226, and adjust the volume of the audio portion of the playback using audio slider 2238. The user may compose a video message (e.g., after activating the +video button 2200 of FIG. 141) by touching record button 2230. Delete button 2244 enables the user to remove the selected message from the user's inbox. Return to inbox button 2246 enables the user to return to the user's inbox (i.e., screen 2202 of FIG. 142 is displayed). The user can forward the message to another person by touching forward button 2242, which causes software 2050 to generate a screen similar to screen 2184 of FIG. 141, showing the selected video message as an attachment. Similarly, when the user activates reply button 2240, software 2050 causes client device 2006 to generate a screen similar to screen 2184 of FIG. 141, showing the message sender as the recipient of the reply message.

As an example of the foregoing messaging application, a doctor could leave a message for a nurse at a monitor 2014 coupled to bed 2020 of a patient being treated by the doctor. The doctor's badge could be sensed by sensor 2011 coupled to client device 2006, thereby giving the doctor access to the messaging application and the doctor's inbox. The doctor could then generate an audio-visual message according to the principles described above. The message could be stored on server 2002 until the nurse visits the patient. When the nurse approaches the patient, the nurse's badge is sensed by sensor 2011, causing client device 2006 to generate a message on monitor 2014 notifying the nurse that a message is waiting. The nurse could then access the message content as described above.

Finally, it is within the scope of the invention to configure client device 2006 such that the user can control the position of bed 2020 via client device 2006. In such an embodiment, client device 2006 responds to user activation of bed control icons displayed on screen 2048 by generating appropriate signals for transmission (either over a wired connection or wirelessly) to actuators controlling various conventional bed functions.

In addition to providing the above-described "client-centric" features, system 2000 may be configured to provide a variety of "caregiver-centric" features and functions including equipment and personnel locating, patient record retrieval and input, patient physiological monitoring, medication management, and doctor's order management as is further described below. Using the principles described above, client device 2006 may display to authorized personnel the status and location of equipment and personnel based on information obtained from locating and tracking system 2005. Again, with appropriate authorization, hospital personnel such as doctors and/or nurses, may use client device 2006 as an interface to a hospital records database accessible by server 2002 to access the health records and other records of a patient. In this manner, hospital personnel may access health related information for patient at the point of care. Moreover, hospital personnel may add information to the patient's records or files using client device 2006 as an interface to the central records database. Also, as indicated above, client device 2006 may be electrically coupled to any of a variety of types of physiological monitoring equipment and display data corresponding to the monitored parameter(s). For example, a conventional EKG interface box could readily be coupled to monitor 2014 such that monitor 2014 functions as a user interface (and power supply) for the EKG equipment. Alternatively, client device 2006 could directly couple to existing physiological monitoring equipment via a communications port (e.g., an RS-232 port) and function as a common interface. Client device 2006 may also function as computer 12 described in U.S. patent application Ser. No. 60/310,092, the disclosure of which is hereby expressly incorporated herein by reference. Finally, client device 2006 may, in conjunction with server 2002, function as an input and retrieval device for creating, storing, and accessing doctor's orders. For example, a doctor could create a message for another caregiver in the manner described above, ordering, for example, continuous lateral rotation therapy for a patient. The caregiver could receive the message and activate the appropriate bed equipment to administer the therapy. Client device 2006 may be in communication with the bed equipment to monitor the therapy, detect completion of the therapy, and generate a record of compliance with the doctor's orders. Moreover, client device 2006 could readily be configured to log regulatory compliance based upon the occurrence of certain events such as maintenance of equipment.

System 2000 further enables a plurality of "administration-centric" features and functions including care process improvement, room status and/or availability, billing information input, and equipment maintenance. For example, process data collected, for example, employing the technology described in U.S. patent application Ser. No. 10/154,644 (hereinafter, "the '644 application"), the disclosure of which is hereby expressly incorporated herein by reference, may be accessed using client device 2006 as an interface. Moreover, client device 2006 may include a detector such as those described in the '644 application to passively obtain data regarding the movement of people, equipment, supplies, etc. for use in care process modeling, forecasting, and improvement. By detecting patient discharges or transfers either directly through sensing patient movements or patient movements in conjunction with other activities associated with discharge or transfer (e.g., room cleaning), or indirectly by accessing a hospital occupancy database, client device 2006 may display room status and availability information, or function as an interface for authorized personnel to update room status and availability data. Also, as indicated above, client device 2006 may permit authorized personnel to input or access patient billing information, or may directly modify a patient's bill by detecting billable events (e.g., usage of medication, purchase of pay-per-view entertainment, or the usage of equipment). Finally, via communication with locating and tracking system 2005, system 2000 may provide information to authorized personnel regarding the maintenance status of various pieces of equipment. For example, bed 2020 may provide a signal to client device 2006 indicating the hours of use bed 2020 has provided since its last scheduled maintenance. Client device 2006 and software 2050 may be configured to send a message or signal to appropriate personnel (such as maintenance personnel) when maintenance is required. The maintenance personnel may use monitor 2014 as an interface to locating and tracking system 2005 to determine the location of bed 2020.

Figure 144:
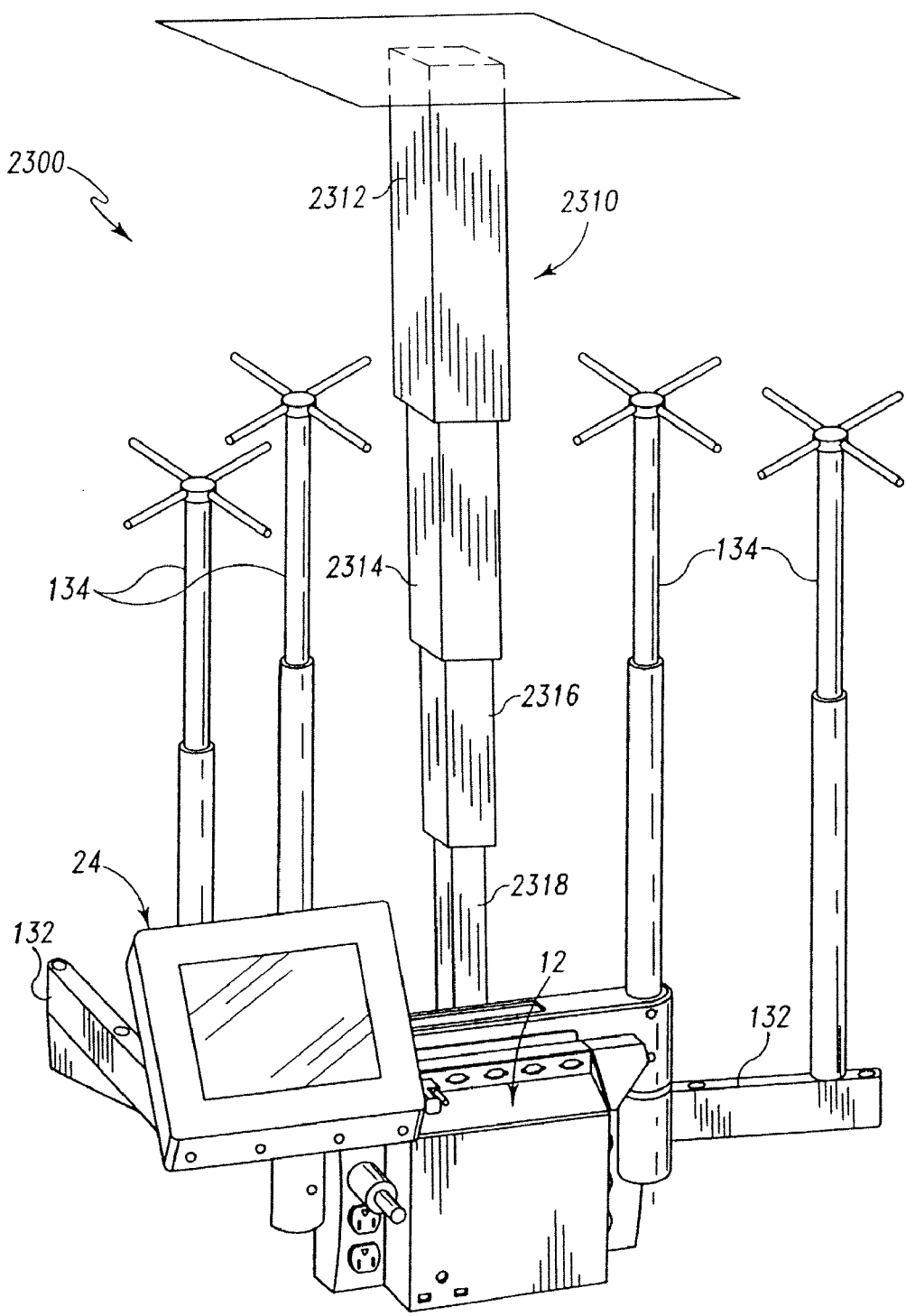
FIGS. 144-147 are perspective views of another embodiment of a mounting configuration for a point-of-care computer display.

Another plurality of variations of another embodiment of the present invention are shown in FIGS. 144-147. Referring to FIG. 144, a point-of-care computer mounting configuration 2300 includes a computer 12 and display 24 supported by a telescopic support 2310. A pair of moveable support arms 132 that support IV poles 134 also supported by telescopic support 2310. Telescopic support 2310 includes a first member 2312 that is connected at one end to the ceiling of the room. A second member 2314 is telescopically received by first member 2312, and telescopically receives a third member 2316. Third member telescopically receives a fourth member 2318, which is connected to the housing to which computer 12 and display 14 are attached. Thus, telescopic support 2310 permits adjustment of the vertical position of display 24, computer 12, and IV poles 134 relative to the ceiling. Power and other signals are provided to computer 12 and display 24 by wiring (not shown) routed from the ceiling through telescopic support 2310. It should be understood that fourth member 2318 may include a rotatable coupling such that display 24 and computer 12 may be rotated about a longitudinal axis of telescopic support 2310.

Figure 145:
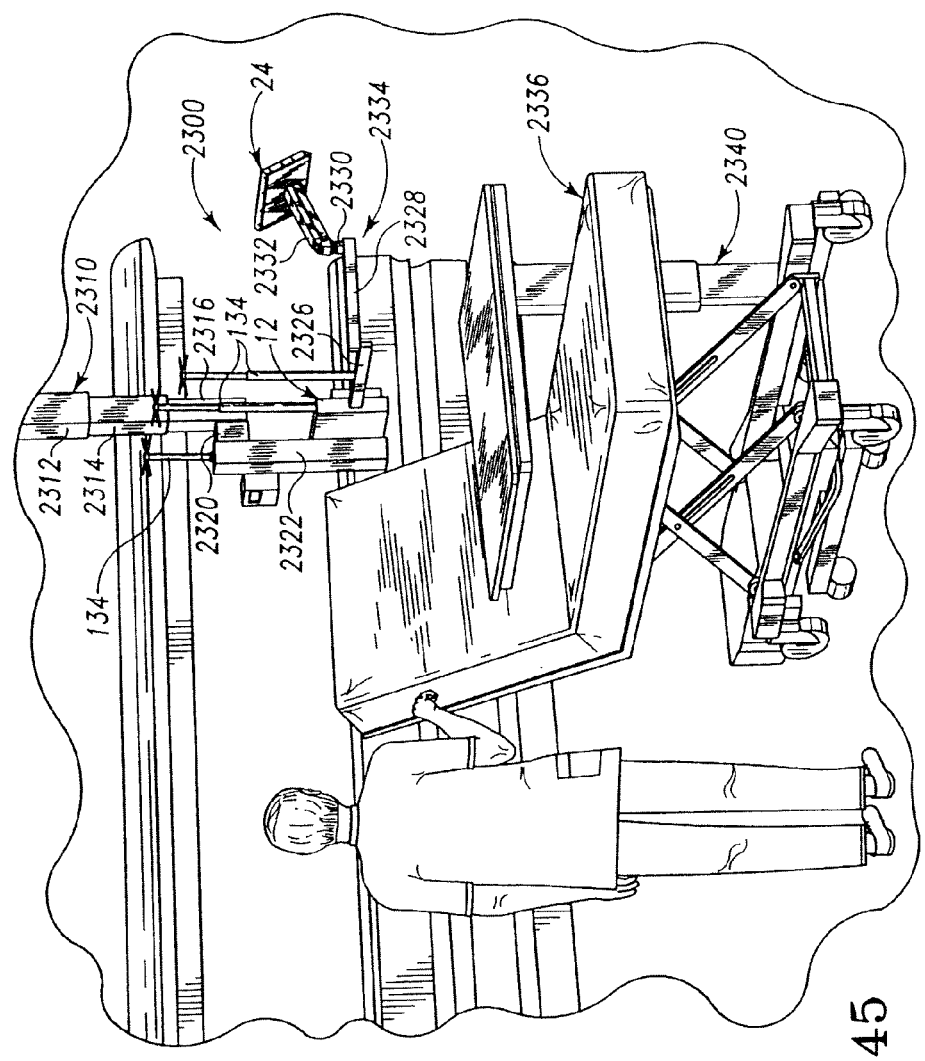

FIG. 145 shows a variation of point-of-care computer mounting configuration 2300. In this embodiment, third member 2316 of telescopic support 2300 is coupled to a bracket 2320 that is connected to a support column 2322 coupled to computer 12. Additionally, display 24 is mounted to an arm assembly 2324, including a first arm 2326, a second arm 2328, a coupler 2330, and a third arm 2332. First arm 2326 is pivotally connected at one end to computer 12, and pivotally connected at the other end to second arm 2328. Arm 2328 is also pivotally connected to coupler 2330, which in turn is pivotally connected to third arm 2332. Thus, as with many other mounting configurations described herein, arm assembly 2330 permits adjustment of the position of display 24 relative to bed 2336. The power and other signals routed to computer 12 and display 24 are routed as described with reference to FIG. 144, except that an additional input connector (not shown) is provided at the lower end of support column 2322. In this embodiment, mounting configuration 2300 may be detached from third member 2316 and docked to another power and signal input source as shown in FIGS. 146 and 147.

Figure 146:
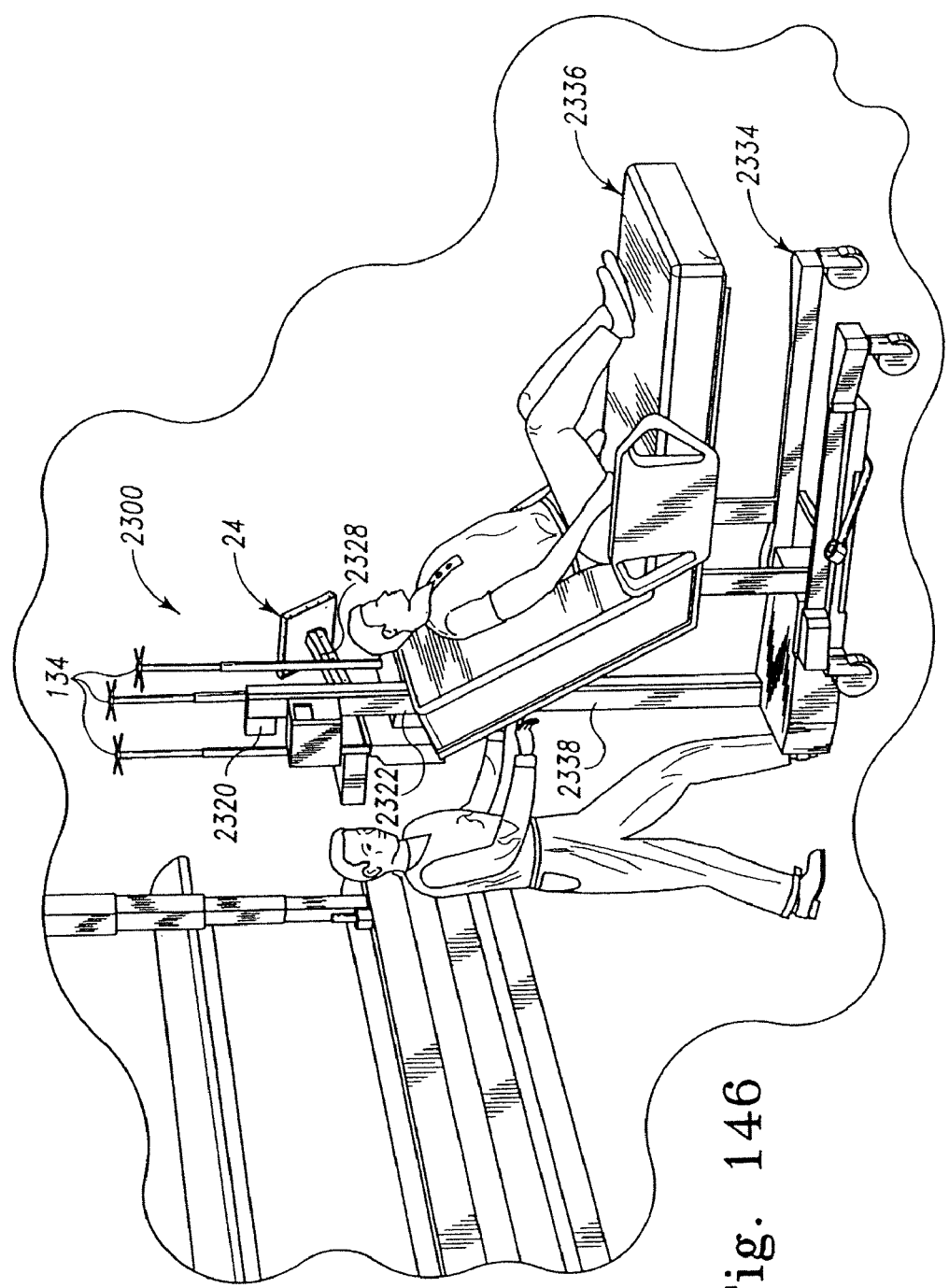

As shown in FIG. 146, mounting configuration 2300 may be docked to a bed mover 2334 that supports bed 2336 for movement of bed 2336 to various locations within the facility. Bed mover 2334 includes a docking column 2338 that includes a connector (not shown) for mating with the connector at the lower end of support column 2322. A battery (not shown) may be provided in bed mover 2334 and wired to the connector of docking column 2338 for powering computer 12 and display 24 during transportation of bed 2336.

Figure 147:
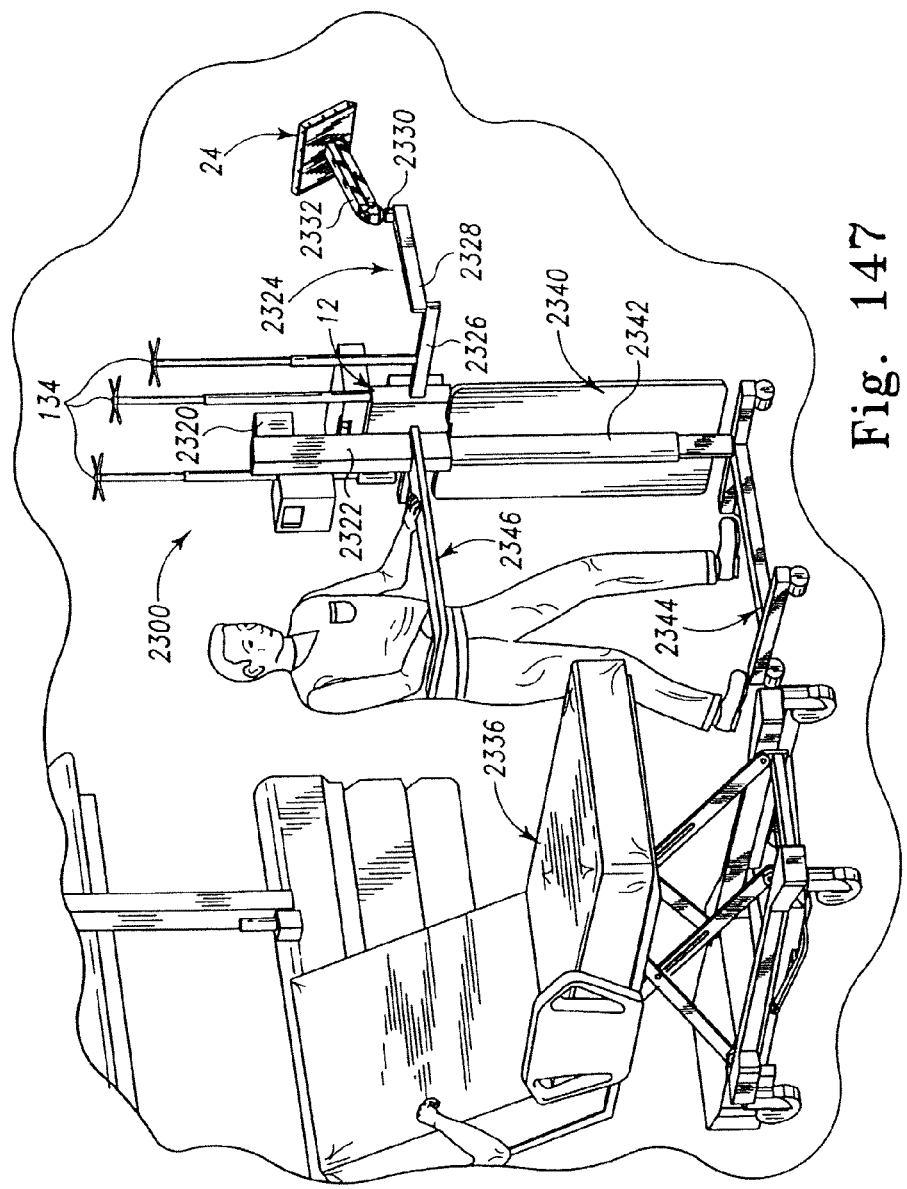

In FIG. 147, mounting configuration 2300 is shown docked to the overbed table 2340 shown in FIG. 145. In this variation, overbed table 2340 includes a docking column 2342 and a push handle 2346 for moving table 2340. Docking column 2342 includes a connector (not shown) at its upper end that mates with the connector (not shown) of support column 2322 in the manner described above. A battery (not shown) may also be provided on overbed table 2340 to power computer 12 and display 24.

Figure 148:
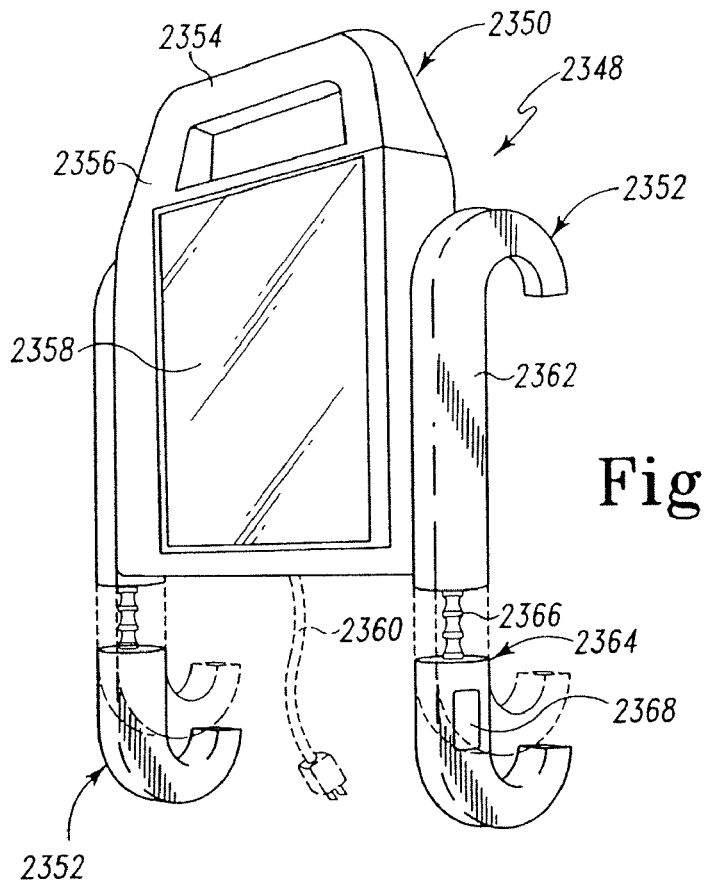
FIGS. 148-150 are perspective views of another embodiment of a mounting configuration according to the present invention.
Figure 149:
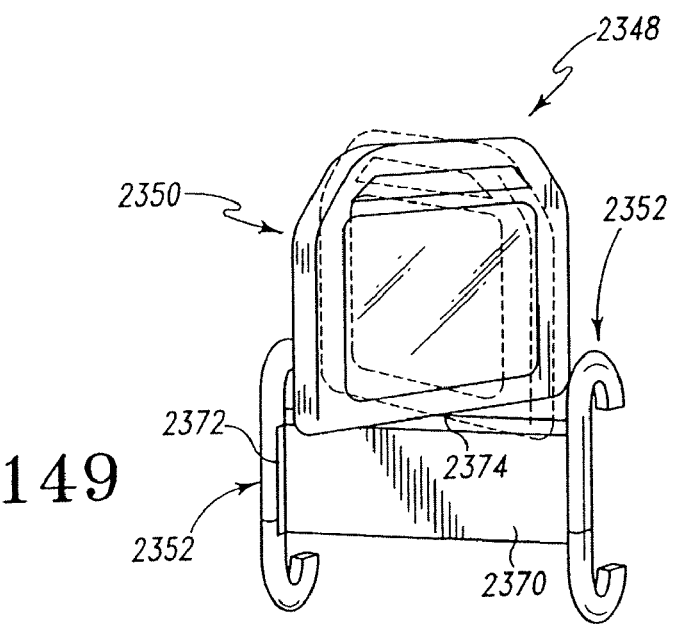
Figure 150:
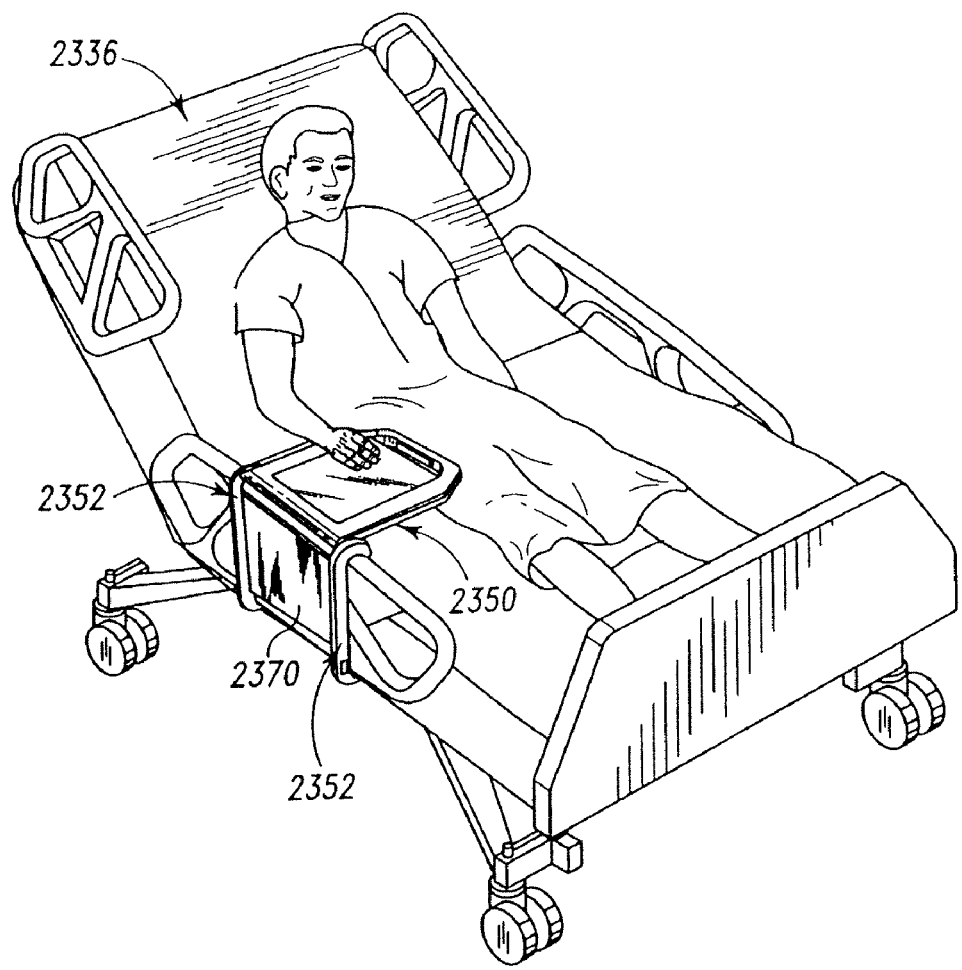

FIGS. 148-150 depict yet another embodiment of the present invention. In mounting configuration 2348, a point-of-care display 2350 is movably mounted on a clamp assembly including a pair of adjustable clamps 2352. Display 2350 includes a handle 2354, a housing 2356 connected to handle 2354, and a screen 2358 mounted in housing 2356. Display 2350 may receive power and other signals from the computer 12 (not shown) wirelessly. Alternatively, display 2350 may include a cord 2360 for connection to computer 12 or another interface device. Each adjustable clamp 2352 includes a J-shaped upper clamp 2362 having a segmented post 2366 extending therefrom, and a J-shaped lower claim 2364 having a bore (not shown) for receiving post 2366 and a release button 2368. Adjustable clamps 2352 are configured for mounting to a siderail, a headboard, or a footboard of bed 2336 as shown in FIG. 150. Clamps 2362, 2364 are first extended apart from one another to fit over, for example, a siderail. Then, release buttons 2368 are depressed to retract stops (not shown) that normally engage one of the segments of segmented posts 2366, thereby permitting movement of lower clamps 2364 upwardly toward upper clamps 2362. When clamps 2364, 2362 securely engage lower and upper portions of the siderail, respectively, release buttons 2368 are released, thereby permitting the stops (not shown) to engage a segment of segmented posts 2366 to lock adjustable clamps 2352 onto the siderail.

As shown in FIGS. 149 and 150, adjustable clamps 2352 are connected together by a plate 2370. In one embodiment as shown in FIG. 149, display 2350 is movable within vertical grooves 2372 formed in the opposing surfaces of adjustable clamps 2352. Display 2350 may also be removed from grooves 2372 and positioned on a post 2374 for rotation about post 2374. In this manner, display 2350 may be viewed from a variety of different viewing angles. Additionally, as shown in FIG. 150, when display 2350 is moved to an uppermost position relative to plate 2370, display 2350 may be rotated to a perpendicular position relative to plate 2370 to simultaneously function as an overbed table and a display. It should be understood that display 2350 may be rotated to any of a plurality of different positions relative to plate 2370. It should also be understood that software operated by computer 12 (not shown) may include code for rotating or otherwise adjusting the images displayed on screen 2358 to compensate for the position of display 24 and correct the viewing angle for the viewer.

The foregoing description of the invention is illustrative only, and is not intended to limit the scope of the invention to the precise terms set forth. Although the invention has been described in detail with reference to certain illustrative embodiments, variations and modifications exist within the scope and spirit of the invention as described and defined in the following claims.

The invention claimed is:

1. A hospital bed comprising
 a frame including at least one movable frame portion,
 circuitry coupled to the frame, and
 a touch screen coupled to the frame and coupled to the circuitry, the touch screen being operable to display a plurality of screens for controlling bed functions, including displaying a frame control screen having at least one icon which is touched by a user to command the circuitry to actuate movement of the movable frame portion of the frame, wherein the circuitry includes a receiver that detects wireless information from an object and the circuitry operates to disable or enable at least one of the bed functions based on the wireless information from the object.

2. The hospital bed of claim 1, wherein the at least one icon includes a plurality of icons, the at least one movable frame portion includes a plurality of deck sections, and the plurality of icons are touchable by the user to control movement of the plurality of deck sections.

3. The hospital bed of claim 2, wherein the plurality of icons include a head up icon and a head down icon.

4. The hospital bed of claim 2, wherein the plurality of icons include a knee up icon and a knee down icon.

5. The hospital bed of claim 2, wherein the plurality of icons include a chair position icon that is touchable to move the frame into a chair position.

6. The hospital bed of claim 2, wherein the plurality of icons include a flat position icon that is touchable to move the frame into a flat position.

7. The hospital bed of claim 1, wherein the at least one icon includes icons that are touchable to raise and lower the movable frame portion relative to another portion of the frame.

8. The hospital bed of claim 1, wherein the at least one icon includes icons that are touchable to tilt the movable frame portion relative to another portion of the frame.

9. The hospital bed of claim 1, wherein the at least one icon includes icons that are touchable to move the frame to Trendelenburg and reverse Trendelenburg positions.

10. The hospital bed of claim 1, wherein the movable frame section comprises a foot section and the at least one icon includes a foot adjust icon that is touchable to adjust a position of the foot section.

11. The hospital bed of claim 1, wherein the frame further includes at least one barrier including at least one of a siderail and a footboard and the touch screen is carried by the at least one barrier.

12. The hospital bed of claim 1, wherein the frame has a weigh scale system and the plurality of screens for controlling bed functions includes a weigh scale screen having at least one icon which is touched by the user to control a function of the weigh scale system.

13. The hospital bed of claim 1, wherein the frame has a patient position monitoring (PPM) system and the plurality of screens for controlling bed functions includes a PPM screen having at least one icon which is touched by the user to control a function of the PPM system.

14. The hospital bed of claim 1, further comprising a mattress supported on the frame, the mattress having at least one inflatable bladder, and the plurality of screens for controlling bed functions includes a mattress control screen having at least one mattress control icon which is touched by the user to control inflation of the at least one air bladder.

15. The hospital bed of claim 14, wherein the at least one air bladder comprises a turn assist bladder and the at least one mattress control icon is touched by the user to control the inflation of the turn assist bladder.

16. The hospital bed of claim 14, wherein the at least one air bladder comprises a continuous lateral rotation therapy (CLRT) bladder and the at least one mattress control icon is touched by the user to control the inflation of the CLRT bladder.

17. The hospital bed of claim 14, wherein the at least one air bladder comprises percussion and vibration (P&V) bladder and the at least one mattress control icon is touched by the user to control the inflation of the P&V bladder.

18. The hospital bed of claim 14, wherein the at least one mattress control icon is touched by the user to inflate the at least one air bladder to a maximum firmness level.

19. The hospital bed of claim 1, wherein the touch screen is also operable to display a reminder message to the user.

20. The hospital bed of claim 19, wherein the reminder message relates to entering information regarding at least one of a patient and medication.

21. A hospital bed comprising
a frame including at least one movable frame portion,
a mattress supported by the frame and including at least one movable mattress portion,
circuitry coupled to the frame, and
a touch screen coupled to the frame and coupled to the circuitry, the touch screen being operable to display a plurality of screens for controlling bed functions, including displaying a frame control screen having at least one icon which is touched by a user to command the circuitry to move at least one of the movable mattress portion and the movable frame portion, wherein the icon depicts the movable portion that is commanded to move when it is touched, wherein the circuitry includes a receiver that detects wireless information from an object and the circuitry operates to disable or enable at least one of the bed functions based on the wireless information from the object.

22. The hospital bed of claim 21, wherein the at least one icon includes a plurality of icons, the at least one movable frame portion includes a plurality of deck sections, and the plurality of icons are touchable by the user to control movement of the plurality of deck sections.

23. The hospital bed of claim 21, wherein the movable mattress portion comprises at least one of a support bladder, a continuous lateral rotation therapy bladder, and a percussion and vibration bladder.

* * * * *